US010620187B2

(12) United States Patent
Ayyub et al.

(10) Patent No.: US 10,620,187 B2
(45) Date of Patent: Apr. 14, 2020

(54) DEVICE AND METHODS OF USING DEVICE FOR DETECTION OF HYPERAMMONEMIA

(71) Applicants: University of Maryland, College Park, College Park, MD (US); Children's National Medical Center, Washington, DC (US); The United States Of America, As Represented By The Secretary, Dept. Of Health And Human Services, Bethesda, MD (US)

(72) Inventors: Omar Bilal Ayyub, Potomac, MD (US); Adam Michael Behrens, Olney, MD (US); Peter Kofinas, North Bethesda, MD (US); Marshall Lynn Summar, Washington, DC (US); Juan Manuel Cabrera-Luque, Rockville, MD (US); Gary Cunningham, Washington, DC (US); Anton Simeonov, Bethesda, MD (US); Juan Marugan, Gaithersburg, MD (US)

(73) Assignees: University of Maryland, College Park, College Park, MD (US); Children's National Medical Center, Washington, DC (US)

( * ) Notice: Subject to any disclaimer, the term of this patent is extended or adjusted under 35 U.S.C. 154(b) by 0 days.

(21) Appl. No.: 15/933,834

(22) Filed: Mar. 23, 2018

(65) Prior Publication Data
US 2018/0284099 A1    Oct. 4, 2018

Related U.S. Application Data

(62) Division of application No. 14/915,602, filed as application No. PCT/US2014/053756 on Sep. 2, 2014, now Pat. No. 9,952,199.
(Continued)

(51) Int. Cl.
*C12Q 1/26* (2006.01)
*G01N 33/49* (2006.01)
(Continued)

(52) U.S. Cl.
CPC ....... *G01N 33/4925* (2013.01); *G01N 27/327* (2013.01); *G01N 27/3275* (2013.01);
(Continued)

(58) Field of Classification Search
CPC ...................................................... C12Q 1/26
See application file for complete search history.

(56) References Cited

U.S. PATENT DOCUMENTS 4,963,814 A    10/1990    Parks et al.
4,999,582 A    3/1991    Parks et al.
(Continued)

FOREIGN PATENT DOCUMENTS

IN    1871/DEL/2008    4/2010
JP    S57086053 A    5/1982
(Continued)

OTHER PUBLICATIONS

Office Action dated May 8, 2019 by the Japanese Patent Office for JP Application No. 2016537941, filed on Sep. 2, 2014 and published as JP2016529515, on Sep. 23, 2016 (Applicant—University of Maryland) (Original—3 pages/Translated—3 pages).
(Continued)

*Primary Examiner* — Rosanne Kosson
(74) *Attorney, Agent, or Firm* — Ballard Spahr LLP

(57) ABSTRACT

The present disclosure relates to a biosensor capable of measuring the total concentration of one or a plurality of ammonia or ammonium ions with the use of indophenol reagents in the presence of an ionomer. In some embodiments, the biosensor comprises a perfluorinated membrane that comprises an ionomer in contact with an alkali buffer in
(Continued)

a vessel configured to receive a sample, such as whole blood. The disclosure also relates to a method of detecting or quantifying the ammonia or ammonium ion concentration in whole blood in a point of care bio sensor without reliance on gas chromatography or any measurement that takes more than about twenty minutes.

5 Claims, 29 Drawing Sheets

Specification includes a Sequence Listing.

Related U.S. Application Data

(60) Provisional application No. 61/872,149, filed on Aug. 30, 2013.

(51) Int. Cl.
  *G01N 27/327* (2006.01)
  *G01N 33/84* (2006.01)
  *G01N 33/68* (2006.01)
  *G01N 21/78* (2006.01)

(52) U.S. Cl.
  CPC ......... *G01N 33/6893* (2013.01); *G01N 33/84* (2013.01); *G01N 21/78* (2013.01); *G01N 2800/04* (2013.01)

(56) References Cited

U.S. PATENT DOCUMENTS

| | | | |
|---|---|---|---|
| 4,999,632 | A | 3/1991 | Parks |
| 5,128,015 | A | 7/1992 | Szuminsky et al. |
| 5,243,516 | A | 9/1993 | White |
| 5,352,351 | A | 10/1994 | White et al. |
| 5,366,609 | A | 11/1994 | White et al. |
| 5,405,511 | A | 4/1995 | White et al. |
| 5,438,271 | A | 8/1995 | White et al. |
| 5,624,537 | A | 4/1997 | Turner et al. |
| 5,670,031 | A | 9/1997 | Hintsche et al. |
| 5,698,083 | A | 12/1997 | Glass |
| 5,762,770 | A | 6/1998 | Pritchard et al. |
| 5,981,203 | A | 11/1999 | Meyerhoff et al. |
| 6,645,359 | B1 | 11/2003 | Bhullar et al. |
| 6,662,439 | B1 | 12/2003 | Bhullar |
| 6,720,164 | B1 | 4/2004 | Shinozuka et al. |
| 7,150,975 | B2 | 12/2006 | Tamada et al. |
| 2004/0186359 | A1 | 9/2004 | Beaudoin et al. |
| 2005/0245844 | A1 | 11/2005 | Mace et al. |
| 2007/0161113 | A1 | 7/2007 | Ash |

FOREIGN PATENT DOCUMENTS

| | | |
|---|---|---|
| JP | H02091574 A | 3/1990 |
| JP | H02104272 A | 4/1990 |
| JP | H09271398 A | 10/1997 |
| JP | 2006126092 A | 5/2006 |
| JP | 2010160134 A | 7/2010 |

OTHER PUBLICATIONS

Weatherburn, "Phenol-hypochlorite reaction for determination of ammonia," Anal Chem 39(8);971-974, 1967.

Xu Huahua et al., "Determination of Trace Ammonium Ion by Using Flow Injection Analysis with Membrane", Shanghai Environment Sicence, Dec. 2000, vol. 19, No. 12, p. 577-578.

Martina Baumgartner et al: "Evaluation of flow injection analysis for determination of urea in sheep's and cow's milk". Acta Veterinaria Hungarica .• vol. 50. No. 3. Jul. 1, 2002 (Jul. 1, 2002). pp. 263-271. XP055354034. HU ISSN: 0236-6290. 001: 10.1556/AVet.50.2002.3.2.

Ayyub Omar B et al: "Simple and inexpensive quantification of ammonia in whole blood", Molecular Genetics and Metabolism, vol. 115, No. 2, 2015, pp. 95-100, XP029130368, ISSN: 1096-7192, 001: 10.1016/J.YMGME.2015.04.004.

EP Extended Search report dated Mar. 3, 2017.

Eggenstein et al., A desposable biosensor for urea determination in blood based on an ammonium-sensitive transducer, Biosensors & Bioelectronics 1999 14:33-41.

Eijgelshoven et al., The time consuming nature of phenylketonuria: a cross-sectional study investigating time burden and costs of phenylketonuria in the Netherlands, Mol Genet Metab 2013 109(3):237-242.

Poordad, Review article: the burden of hepatic encephalopathy, Aliment Pharmacol Ther 2007 52(Supp1):3-9.

Summar et al., The incidence of urea cycle disorders, Mol Genet Metab 2013 110(1-2):179-180.

Ayyub Omar B et al: "Simple and inexpensive quantification of ammonia in whole blood", Molecular Genetics and Metabolism, vol. 115, No. 2, (2015), pp. 95-100.

Baumgartner et al: "Evaluation of flow injection analysis for determination of urea in sheep's and cow's milk", Acta Veterinaria Hungarica., vol. 50, No. 3, (2002), pp. 263-271.

Eggenstein C et al: "A Disposable Biosensor for Urea Determination in Blood Based on an Ammonium-Sensitive Transducer", Biosensors and Bioelectronics,vol. 14, No. 1, (1999), pp. 33-41.

European Search Report dated May 29, 2019, by the European Patent Office for EP Application No. 19150428.1, which was filed on Sep. 2, 2014 (Applicant—University of Maryland) (9 Pages).

SEQUENCE LISTING

<160> NUMBER OF SEQ ID NOS: 24

<210> SEQ ID NO 1
<211> LENGTH: 378
<212> TYPE: PRT

<213> ORGANISM: Artificial Sequence
<220> FEATURE:
<223> OTHER INFORMATION: Dehydrogenase mutant 1

<400> SEQUENCE: 1

```
Met Asn Thr Val Thr Asn Gln Trp Lys Ala Val Asp Ile Phe Thr Gln
1               5                   10                  15

Ile Arg Asp His Glu Gln Val Val Phe Cys Asn Asp Lys Asn Thr Gly
            20                  25                  30

Leu Lys Ala Ile Ile Ala Ile His Asp Thr Thr Leu Gly Pro Ala Leu
        35                  40                  45

Gly Gly Cys Arg Met Tyr Pro Tyr Ala Thr Val Glu Asp Ala Leu Phe
50                  55                  60

Asp Val Leu Arg Leu Ser Lys Gly Met Thr Tyr Lys Cys Leu Ala Ala
65                  70                  75                  80

Asp Val Asp Phe Gly Gly Gly Lys Ala Val Ile Ile Gly Asp Pro His
                85                  90                  95

Lys Asp Lys Thr Pro Glu Leu Phe Arg Ala Phe Gly Gln Phe Val Glu
            100                 105                 110

Ser Leu Asn Gly Arg Phe Tyr Thr Gly Thr Asp Met Gly Thr Thr Pro
        115                 120                 125

Asp Asp Phe Val His Ala Met Lys Glu Thr Asn Cys Ile Val Gly Val
130                 135                 140

Pro Glu Glu Tyr Gly Gly Ser Gly Asp Ser Ser Val Pro Thr Ala Leu
145                 150                 155                 160

Gly Val Ile Tyr Gly Ile Gln Ala Thr Asn Lys Val Ile Trp Gly Ser
                165                 170                 175

Asp Glu Leu His Gly Lys Thr Tyr Ala Ile Gln Gly Leu Gly Lys Val
            180                 185                 190

Gly Arg Lys Val Ala Glu Arg Leu Leu Lys Glu Gly Ala Asp Leu Tyr
        195                 200                 205

Val Cys Asp Ile His Pro Thr Ala Ile Glu Ala Ile Val Ser Tyr Ala
210                 215                 220

Lys Lys Leu Gly Ala Asn Val Lys Val Val Gln Gly Thr Glu Ile Tyr
225                 230                 235                 240

Arg Thr Asp Ala Asp Ile Phe Val Pro Cys Ala Phe Gly Asn Val Val
                245                 250                 255

Asn Asp Asn Thr Ile His Val Leu Lys Val Lys Ala Ile Val Gly Ser
            260                 265                 270

Ala Asn Asn Gln Leu Leu Asp Val Arg His Gly Gln Leu Leu Lys Glu
        275                 280                 285

Lys Gly Ile Leu Tyr Ala Pro Asp Tyr Ile Val Asn Ala Gly Gly Leu
290                 295                 300

Ile Gln Val Ala Asp Glu Leu Tyr Gly Leu Asn Lys Glu Arg Val Leu
305                 310                 315                 320

Gln Lys Thr Lys Ala Ile Tyr Ser Thr Leu Leu His Ile Tyr Ser Arg
                325                 330                 335

Ala Glu Ala Asp His Ile Thr Thr Ile Glu Ala Ala Asn Arg Phe Cys
            340                 345                 350

Glu Glu Arg Leu Gln Gln Arg Ser Arg Arg Asn Asp Phe Phe Thr His
        355                 360                 365

Arg Lys Gln Pro Lys Trp Asp Ile Arg Arg
370                 375
```

```
<210> SEQ ID NO 2
<211> LENGTH: 366
<212> TYPE: PRT
<213> ORGANISM: Artificial Sequence
<220> FEATURE:
<223> OTHER INFORMATION: Mutant Enzyme 2

<400> SEQUENCE: 2

Met Arg Asp Val Phe Glu Met Met Asp Arg Tyr Gly His Glu Gln Val
1               5                   10                  15

Ile Phe Cys Arg His Pro Gln Thr Gly Leu Lys Ala Ile Ile Ala Leu
            20                  25                  30

His Asn Thr Thr Ala Gly Pro Ala Leu Gly Gly Cys Arg Met Ile Pro
        35                  40                  45

Tyr Ala Ser Thr Asp Glu Ala Leu Glu Asp Val Leu Arg Leu Ser Lys
    50                  55                  60

Gly Met Thr Tyr Lys Cys Ser Leu Ala Asp Val Asp Phe Gly Gly Gly
65                  70                  75                  80

Lys Met Val Ile Ile Gly Asp Pro Lys Lys Asp Lys Ser Pro Glu Leu
                85                  90                  95

Phe Arg Val Ile Gly Arg Phe Val Gly Gly Leu Asn Gly Arg Phe Tyr
            100                 105                 110

Thr Gly Thr Asp Met Gly Thr Asn Pro Glu Asp Phe Val His Ala Ala
        115                 120                 125

Arg Glu Ser Lys Ser Phe Ala Gly Leu Pro Lys Ser Tyr Gly Gly Lys
    130                 135                 140

Gly Asp Thr Ser Ile Pro Thr Ala Leu Gly Val Phe His Gly Met Arg
145                 150                 155                 160

Ala Thr Ala Arg Phe Leu Trp Gly Thr Asp Gln Leu Lys Gly Arg Val
                165                 170                 175

Val Ala Ile Gln Gly Val Gly Lys Val Gly Glu Arg Leu Leu Gln Leu
            180                 185                 190

Leu Val Glu Val Gly Ala Tyr Cys Lys Ile Ala Asp Ile Asp Ser Val
        195                 200                 205

Arg Cys Glu Gln Leu Lys Glu Lys Tyr Gly Asp Lys Val Gln Leu Val
    210                 215                 220

Asp Val Asn Arg Ile His Lys Glu Ser Cys Asp Ile Phe Ser Pro Cys
225                 230                 235                 240

Ala Lys Gly Gly Val Val Asn Asp Asp Thr Ile Asp Glu Phe Arg Cys
                245                 250                 255

Leu Ala Ile Val Gly Ser Ala Asn Asn Gln Leu Val Glu Asp Arg His
            260                 265                 270

Gly Ala Leu Leu Gln Lys Arg Ser Ile Cys Tyr Ala Pro Asp Tyr Leu
        275                 280                 285

Val Asn Ala Gly Gly Leu Ile Gln Val Ala Asp Glu Leu Glu Gly Phe
    290                 295                 300

His Glu Glu Arg Val Leu Ala Lys Thr Glu Ala Ile Tyr Asp Met Val
305                 310                 315                 320

Leu Asp Ile Phe His Arg Ala Lys Asn Glu Asn Ile Thr Thr Cys Glu
                325                 330                 335

Ala Ala Asp Arg Ile Val Met Glu Arg Leu Lys Lys Leu Thr Asp Ile
            340                 345                 350

Arg Arg Ile Leu Leu Glu Asp Pro Arg Asn Ser Ala Arg Arg
        355                 360                 365
```

<210> SEQ ID NO 3
<211> LENGTH: 1068
<212> TYPE: DNA
<213> ORGANISM: Artificial Sequence
<220> FEATURE:
<223> OTHER INFORMATION: nucleic acid encoding enzyme 3

<400> SEQUENCE: 3

| | | | | | |
|---|---|---|---|---|---|
| atggaaatct | tcgaggaaat | caaacggcgg | ggacacgagc | aaattctgtt | caattatgat | 60 |
| cgggcttccg | gtttgaaagc | aattatcgcc | attcacaata | ctacgttggg | gccggcgttg | 120 |
| ggcgggtgcc | gaatgttacc | gtatcaaacg | gaagaggcgg | ccctcgagga | tgcgctgcgg | 180 |
| ttgtcggaag | ggatgaccta | taaagcggcc | gccgccgggc | tcgatttcgg | cggggggcaaa | 240 |
| acggtgatta | tcggggatcc | gatgaaagac | aagtccgagg | ccctgtttcg | tgcgctcggg | 300 |
| cgttttatcg | agaccttgaa | aggccgttac | cttacgggag | aagacgtagg | aaccaacgaa | 360 |
| gaagattttg | tctgggctcg | tcgggaaacc | cgttatgttg | tcggattgcc | gccggcttat | 420 |
| ggcgggtccg | gcgatacggg | tgacaatacc | gcgcgcggcg | tcattcaagc | gatgcgcgcc | 480 |
| gcgttgatgc | accggtacgg | ttcgccggat | ctccagggcc | ggcggattgc | cgtccaaggg | 540 |
| ctgggcaaag | taggctatca | tgtggcgcga | cgggccatcg | aggccggcgc | tcgagtgatt | 600 |
| gcggccgata | tcaatccgca | tgtagtcggc | cgagtggcgt | ccgcttgggg | gattgaagcc | 660 |
| accgatccgt | gggctgtggt | ggaaaccccc | tgcgatattt | tcgcccccctg | tgcgttgggt | 720 |
| aacgtcatta | cggaacggac | cgtgtccgcc | ctccaatgtc | aggtggtggc | cggttcggcc | 780 |
| aacaatcagc | tggcggatga | tcgactggcc | gatgatttag | ctgcccgcgg | cattctctat | 840 |
| gcgccggatt | ttattgcgaa | tgccggcgga | ttgattcagg | tggcggatga | aattcgggga | 900 |
| tatcatgaag | aacgggtccg | tcatcaaata | gacgggattt | atgacgtcct | gctcgagatt | 960 |
| tttcggaagg | cggacgcctc | cggccgatca | accgtggcgg | ttgcggtaga | cgaggcgcgt | 1020 |
| cgccgtttgg | acaccattca | ggccatccac | cgcctgtacg | gatcatag | | 1068 |

<210> SEQ ID NO 4
<211> LENGTH: 3939
<212> TYPE: DNA
<213> ORGANISM: Artificial Sequence
<220> FEATURE:
<223> OTHER INFORMATION: Nucleic Acid encoding enzyme 4

<400> SEQUENCE: 4

| | | | | | |
|---|---|---|---|---|---|
| ctgcaggtca | acggatcata | ttctacacat | atataatgca | ctccaattga | cataatacat | 60 |
| aacgtgacat | atgatacatt | tattaatatt | aattgtcaca | tttacacttc | acatattaaa | 120 |
| atactctcgt | atgaatgcaa | tttgaaacat | attttaaatt | aattgattga | tatatattga | 180 |
| acaaaaccta | acaaaaatgc | accctcttgg | ttcacaaaga | aactttcttc | tatttctcac | 240 |
| ttatttctgc | tagtgtctttt | cctattcaaa | gccatcattt | ccatcaacct | tcacaatacc | 300 |
| atgtttaaaa | agtcattaaa | aatcaatttt | ttaaatagaa | aaaacaaga | agatggaaat | 360 |
| cacttggttg | gtactatata | tttagttgtt | aagtttgact | cataccgtgt | attgaccaat | 420 |
| ataaataaaa | tcttatttca | aataaattca | aaagttcaat | aaatatatat | tcgttcataa | 480 |
| cttataataa | aattgattat | acatagtcct | cccccattca | cttttactga | tcaattattt | 540 |
| ctaaaatata | ttattacttt | tacttgttat | ttttaataaa | ttaagaaaat | ataatactcc | 600 |
| cttcgttttt | aaaaaaatac | ctagtttgac | ttgaaacgga | gtttaataaa | agaaagaaga | 660 |
| cttgttaatc | ttgtgattct | aaattaaagt | tatgtcaaat | gtaccaaaat | gtcctttaat | 720 |

```
cttgtggtct taaacatgtc acatgaaaaa ttaaagtgtt tccaaaaaaa gaaagggggtc     780 aatgtcattc ttttttaaac agactaaaaa agaaataaac tcattctttt tgaaacggag     840
agagtaattt tttccacgtt ttactcatta atattaaata ttattctcta gatcatccta     900
taagatctaa tagtggacat caattaatac ctatgtcact tattattatt ttaataattg     960
tatcaagtca ataataaca agtaaaaatg gagtacctac tattaatctt caacaaccac    1020
aatttactag ttttttccta gcaacccccct ctcacatatt tcaccattta ctggttttt    1080 cctagcaacc ccctctcaca tattttgttt accaaccatc atttgttcct ctatatatac    1140
tcaccacatg atagatacat atatatacca caaccaaaac aaaaggtttt ataagttcac    1200
aacatttttt atatacatac aaataaactc taaccatttt ctcttcacta aaatttcttc    1260
attacaaatc taacaattta cttgatccaa tggcaccatc aattgcacaa aatggacata    1320
ttaatggaga agtagctatg gatttgtgca agaaatcaat caatgatcca ttgaattggg    1380
aaatggctgc tgattcttta agaggcagcc atttggatga agtgaaaaag atggtggatg    1440
aatttagaaa gccaattgtg aaacttgggg gtgaaacttt gtcagttgca caagttgcat    1500
ccattgcaaa tgttgatgac aaaagtaatg gggttaaagt ggaactttct gaaagtgcaa    1560
gggctggtgt gaaagctagt agtgattggg ttatggatag tatgagtaaa ggtacagata    1620
gttatggtgt tactgctgga tttggagcaa catctcatag aagaacaaaa aatggtggtg    1680
ctcttcaaaa agaacttatt aggtaaacaa actattttt ttcgttatat atactaacaa    1740
tgtaaagaat ttaatatttt tttgttatat atactaacaa tgtaaaaaat ttaatatttt    1800
tttgttatat atactaacaa tgtaaagaat ttaatatttt tttgttatac atagcttatc    1860
gactacttaa gtgctccatt gataaagatt ttttttgtt tttacgcgaa ggggattcgg    1920
atgaattcag ttaaaatgtg atcttaatga attatgatat tttttgtag gttcttgaat    1980 gctggagttt ttggtaatgg aatagaatca tttcacacat tgccacattc agcaacaagg    2040
gcagctatgc ttgttaggat caacactctg cttcaaggct actctggcat tagatttgag    2100
atcttggaag caatcactaa gttgatcaat agcaacatca ccccgtgttt gcctctccgt    2160
ggcacgatca ctgcctcggg tgatctcgtc cctttgtcct atattgctgg tttgctcact    2220
ggcagaccta attccaaggc tgttggaccc aatggtgaga aacttaatgc tgaggaagct    2280
ttctgcgtgg ctggtattag tggtggattt ttcgagttgc agcctaagga aggacttgca    2340
cttgtgaatg gcacagcagt tggttctgct atggcatcaa tagtcctgtt tgagtccaat    2400
atctttgctg ttatgtctga agtttttatca gcgatttta ctgaagtgat gaacggaaag    2460
cccgaattca ctgactattt gacacacaag ttgaagcatc accctggtca gattgaggct    2520
gctgctatta tggaacacat tttgatgga agctcttatg tgaaggtagc tcagaagctc    2580
catgaaatgg atcctcttca aaaaccaaag caagatcgtt atgctctccg aacatctcca    2640
caatggcttg gacctcagat tgaagtcatt cgtgctgcaa ctaagatgat cgagagggag    2700
attaactcag tgaacgacaa tccattgatc gatgtttcaa gaaacaaggc cttacatggt    2760
ggcaacttcc aaggaacccc tattggtgtc tccatggata atacaagatt ggcccttgca    2820
tcaattggta aattgatgtt tgcccaattc tcagagcttg tcaacgacta ttacaacaac    2880
gggttgccat ctaatctgac agcaggaagg aatccaagct tggactatgg tttcaagggc    2940
gctgaaatcg cgatggcttc ttactgctcg gaacttcaat tcttggcaaa tccagtgact    3000
aaccatgtct aaagtgctga gcaacacaac caagatgtga attccttggg cttaatttca    3060
gccaggaaaa cagctaaggc tgttgatatc ttgaagataa tgtcatcaac ctatctcgtg    3120
```

```
gctctttgcc aagctattga cttacgacat ttggaggaaa acttgaagag tgttgtcaag    3180
aacacagtta gccaagtagc taagagaact ttgacaatgg gtgctaatgg tgaacttcat    3240
ccagcaagat tcagcgaaaa agaattgctt cgagtcgtgg atagagaata cttgtttgcc    3300
tatgctgatg atccctgcag ctccaactac cctttgatgc agaagctgag acaagtcctt    3360
gttgatcaag caatgaagaa tggtgaaagt gagaagaatg tcaacagctc aatcttccaa    3420
aagattggag ctttcgagga cgaattaatc gctgtgttgc ctaaagaagt tgagagtgta    3480
agagctgttt ttgaaagtgg caacccttta attcgtaaca ggatcacaga atgcagatca    3540
tatccattgt acaggttggt gagagaagaa cttggaacag aattgttgac gggtgaaaaa    3600
gttcgatcac ctggtgagga gattgataaa gtgtttacag caatatgtaa tggacagatt    3660
attgatccat tgttggagtg tctgaagagc tggaatggtg ctcctcttcc aatctgctaa    3720
atgtgttatt ctttcaagtt ctttttttgt acctttttagt gaattactag aattataatg    3780
atgttatgaa cttatattaa aaaaaaatat ttttgactat aaaatttagt tttgttattg    3840
aaattaaagg ctcaatctgt gttctttcct tctgttatct gaatattata agaattcaag    3900 taatcttttta gctttgtgaa catgatgaca tgctttctt                          3939

<210> SEQ ID NO 5
<211> LENGTH: 1521
<212> TYPE: DNA
<213> ORGANISM: Artificial Sequence
<220> FEATURE:
<223> OTHER INFORMATION: Nucleic Acid seqeunce encoding enzyme 5

<400> SEQUENCE: 5
atgatcacgc ttaccccgg ccacctgacc ctcccgcaac tgcgccagat cgcgcgcgag       60
cccgtgcagc tgacgctgga tccggccagc ttcgcgaaga tcgacgcggg cgcgaaggcc     120
gtgtccgaca tcgccgcgaa gggcgagccg gcgtacggca tcaacacggg cttcggtcgt     180
ctggccagca cgcatatccc gcacgatcag ctcgaattgc tgcagaagaa cctcgtgctg     240
tcgcatgcag tcggtgtcgg cgagccgatg gcgcgttcgt cggtgcgtct gctgatcgcg     300
ctgaagctgt cgagcctcgg ccgcggccat tcgggcattc gccgcgaagt gatggacgcg     360
ctgatcaagc tgttcaacgc cgacgtgctg ccgctgattc cggtgaaggg ctcggtcggc     420
gcatcgggcg acctcgcgcc gctcgcgcac atgtcggccg tgctgctcgg cgtcggcgaa     480
gtgttcattc gcggcgagcg cgcgagcgcg gtggacgggt tgcgcgtcgc gggcctcgcg     540
ccgctgacgc tgcaggcgaa ggaaggcctc gcgctgctga acggtacgca ggcgtcgacg     600
gcgctcgcgc tcgacaacct gttcgcgatc gaagacctgt accgcacggc gctcgtcgcc     660
ggcgcgctgt cggtcgatgc ggcggccggc tcggtgaagc cgttcgacgc gcgcatccac     720
gaactgcgcg gccatcgcgg ccagatcgat gcggcggccg cgtatcgcga gctgctcgaa     780
ggctcggcga tcaacctctc gcatcgcgac tgcggcaagg tgcaggatcc gtacagcctg     840
cgctgccagc cgcaggtgat gggcgcgtgc ctggaccaga tgcgtcatgc ggccgacgtg     900
ctgctcgtcg aggcgaacgc ggtatcggac aacccgctga tcttcccgga taccggcgaa     960
gtgctgtcgg gcggcaattt ccatgcggag cccgtcgcgt tcgcggccga caacctcgcg    1020
ctcgcggctg cggaaatcgg cgcgctggcc gagcgccgca tcgcgctgct gatcgacgcg    1080
acgctgtcgg gcctgccgcc gttcctcgtg aaggatggcg gcgtgaactc gggcttcatg    1140
attgcgcacg tgacggcagc tgcgctcgca tcggagaaca agacgctcgc gcatccggcg    1200
```

| | |
|---|---|
| tcggtcgatt cgctgccgac ctcggcgaac caggaagacc acgtgtcgat ggcgacgttc | 1260 |
| gcggcacgca agctggccga catcgccgac aacacgaagc acatcctcgc gatcgaactg | 1320 |
| ctcgcggccg cgcagggcgt cgatctgcgc gagaacgaga cgagcccgaa gctcgcggaa | 1380 |
| gtgatgaaga cgattcgcag caaggtcgcg cattacgagc tcgaccacta ctttgcgccg | 1440 |
| gacatcgccg tgatcgcgaa gctcgtcgtc gagcgcgcgt tcgcgaagca ctgcccgttc | 1500 |
| gccttcgcat cggagcagta a | 1521 |

<210> SEQ ID NO 6
<211> LENGTH: 1533
<212> TYPE: DNA
<213> ORGANISM: Artificial Sequence
<220> FEATURE:
<223> OTHER INFORMATION: Nucleic Acid Sequence encoding enzyme 6

<400> SEQUENCE: 6

| | |
|---|---|
| gtgacgcagg tcgtggaacg tcaggctgat cggctcagca gcagggagta cctggcccgg | 60 |
| gtcgtgcgca gcgccgggtg ggacgccggt ctcacctcgt gcaccgacga ggagatcgtc | 120 |
| cggatgggcg cgagcgcgcg caccatcgag gagtacctga agtccgacaa gcccatctac | 180 |
| ggcctgacgc agggcttcgg tccgctggtg ctgttcgacg ccgactcgga gctggagcag | 240 |
| ggcggctcgc tgatctcgca cctgggcacc ggccagggcg cgccactggc cccggaggtg | 300 |
| tcgcggctga tcctctggct gcgcatccag aacatgcgca aggggtactc ggcggtctcg | 360 |
| ccggtgttct ggcagaagct cgccgacctg tggaacaagg ggttcacccc ggcgatcccc | 420 |
| cggcacggca cggtcagcgc gagcggcgac ctgcaaccgc tggcgcacgc cgcgctcgcc | 480 |
| ttcaccggtg tcggcgaggc gtggacccgg gacgccgacg gccggtggtc caccgtgccg | 540 |
| gccgtgacg cgctcgccgc gctggggggcg gagccgttcg actggccggt gcgcgaggcg | 600 |
| ctggcgttcg tcaacgggac cggcgcgagc ctcgcggtgg ctgtgctcaa ccaccggtcc | 660 |
| gccctgcggc tggtccgcgc ctgcgccgtg ctctccgcgc ggctggcgac cctgctgggg | 720 |
| gccaatcccg agcactacga cgtggggcac ggtgtcgcgc gcggccaggt cggtcagctg | 780 |
| accgcggcg agtggatccg gcaggggctg ccccggggca tggtgcgcga cggcagccgc | 840 |
| ccgctccagg agccgtacag cctgcggtgc gcgccgcagg tgctcggcgc ggtgctcgac | 900 |
| cagctcgacg gcgcgggcga cgtgctggcg cgggaggtcg acggctgcca ggacaacccg | 960 |
| atcacctacg agggcgagct gctgcacggc ggcaacttcc acgccatgcc ggtgggtttc | 1020 |
| gcctccgacc agatcgggtt ggccatgcac atggccgcct acctggccga cgccagctg | 1080 |
| ggtctgctgg tcagcccggt gaccaacggc gacctgccgc ccatgctcac cccgcgcgcc | 1140 |
| gggcgcggtg ccgggctggc cggggtgcag atcagcgcga cctcgttcgt ctcgcggatc | 1200 |
| cggcagctgg tgttccccgc ctcgctgacc accctgccga ccaacggctg gaaccaggac | 1260 |
| cacgtgccga tggcgctcaa cggggcgaac tcggtgttcg aggcgttgga gctcggctgg | 1320 |
| ctgacggtcg ggtcgctggc ggtgggcgtc gcgcagctcg cggccatgac cggccacgcc | 1380 |
| gcggagggcg tctgggcgga gctggccggg atctgcccgc gctggacgc cgaccgcccg | 1440 |
| ctgggcgccg aggtgcgcgc cgcgcgcgac ctgctgtccg cgcacgcgga ccaactgctc | 1500 |
| gtcgacgagg cagacgggaa ggatttcgga tga | 1533 |

<210> SEQ ID NO 7
<211> LENGTH: 721
<212> TYPE: PRT
<213> ORGANISM: Solanum lycopersicum

<400> SEQUENCE: 7

```
Met Ala Ser Ser Ile Val Gln Asn Gly His Val Asn Gly Glu Ala Met
1               5                   10                  15

Asp Leu Cys Lys Lys Ser Ile Asn Val Asn Asp Pro Leu Asn Trp Glu
            20                  25                  30

Met Ala Ala Glu Ser Leu Arg Gly Ser His Leu Asp Glu Val Lys Lys
        35                  40                  45

Met Val Asp Glu Phe Arg Lys Pro Ile Val Lys Leu Gly Gly Glu Thr
    50                  55                  60

Leu Thr Val Ala Gln Val Ala Ser Ile Ala Asn Val Asp Asn Lys Ser
65                  70                  75                  80

Asn Gly Val Lys Val Glu Leu Ser Glu Ser Ala Arg Ala Gly Val Lys
                85                  90                  95

Ala Ser Ser Asp Trp Val Met Asp Ser Met Gly Lys Gly Thr Asp Ser
            100                 105                 110

Tyr Gly Val Thr Thr Gly Phe Gly Ala Thr Ser His Arg Arg Thr Lys
        115                 120                 125

Asn Gly Gly Ala Leu Gln Lys Glu Leu Ile Arg Phe Leu Asn Ala Gly
    130                 135                 140

Val Phe Gly Asn Gly Thr Glu Ser Ser His Thr Leu Pro His Ser Ala
145                 150                 155                 160

Thr Arg Ala Ala Met Leu Val Arg Ile Asn Thr Leu Leu Gln Gly Tyr
                165                 170                 175

Ser Gly Ile Arg Phe Glu Ile Leu Glu Ala Ile Thr Lys Leu Ile Asn
            180                 185                 190

Ser Asn Ile Thr Pro Cys Leu Pro Leu Arg Gly Thr Ile Thr Ala Ser
        195                 200                 205

Gly Asp Leu Val Pro Leu Ser Tyr Ile Ala Gly Leu Leu Thr Gly Arg
    210                 215                 220

Pro Asn Ser Lys Ala Val Gly Pro Asn Gly Glu Lys Leu Asn Ala Glu
225                 230                 235                 240

Glu Ala Phe Arg Val Ala Gly Val Thr Ser Gly Phe Phe Glu Leu Gln
                245                 250                 255

Pro Lys Glu Gly Leu Ala Leu Val Asn Gly Thr Ala Val Gly Ser Gly
            260                 265                 270

Met Ala Ser Met Val Leu Phe Glu Ser Asn Ile Leu Ala Val Met Ser
        275                 280                 285

Glu Val Leu Ser Ala Ile Phe Ala Glu Val Met Asn Gly Lys Pro Glu
    290                 295                 300

Phe Thr Asp Tyr Leu Thr His Lys Leu Lys His His Pro Gly Gln Ile
305                 310                 315                 320

Glu Ala Ala Ala Ile Met Glu His Ile Leu Asp Gly Ser Ser Tyr Val
                325                 330                 335

Lys Ala Ala Gln Lys Leu His Glu Met Asp Pro Leu Gln Lys Pro Lys
            340                 345                 350

Gln Asp Arg Tyr Ala Leu Arg Thr Ser Pro Gln Trp Leu Gly Pro Gln
        355                 360                 365

Ile Glu Val Ile Arg Ala Ala Thr Lys Met Ile Glu Arg Glu Ile Asn
    370                 375                 380

Ser Val Asn Asp Asn Pro Leu Ile Asp Val Ser Arg Asn Lys Ala Leu
385                 390                 395                 400

His Gly Gly Asn Phe Gln Gly Thr Pro Ile Gly Val Ser Met Asp Asn
```

```
                405                 410                 415
Thr Arg Leu Ala Leu Ala Ser Ile Gly Lys Leu Met Phe Ala Gln Phe
            420                 425                 430

Ser Glu Leu Val Asn Asp Tyr Tyr Asn Asn Gly Leu Pro Ser Asn Leu
            435                 440                 445

Thr Ala Gly Arg Asn Pro Ser Leu Asp Tyr Gly Leu Lys Gly Ala Glu
            450                 455                 460

Ile Ala Met Ala Ser Tyr Cys Ser Glu Leu Gln Phe Leu Ala Asn Pro
465                 470                 475                 480

Val Thr Asn His Val Gln Ser Ala Glu Gln His Asn Gln Asp Val Asn
                485                 490                 495

Ser Leu Gly Leu Ile Ser Ala Arg Lys Thr Ala Glu Ala Val Asp Ile
            500                 505                 510

Leu Lys Leu Met Ser Ser Thr Tyr Leu Val Ala Leu Cys Gln Ala Ile
            515                 520                 525

Asp Leu Arg His Leu Glu Glu Asn Leu Arg Ser Ala Val Lys Asn Thr
            530                 535                 540

Val Ser Gln Val Ala Lys Arg Thr Leu Thr Met Gly Ala Asn Gly Glu
545                 550                 555                 560

Leu His Pro Ala Arg Phe Cys Glu Lys Glu Leu Leu Arg Val Val Asp
                565                 570                 575

Arg Glu Tyr Val Phe Ala Tyr Ala Asp Asp Pro Cys Ser Ser Thr Tyr
            580                 585                 590

Pro Leu Met Gln Lys Leu Arg Gln Val Leu Val Asp His Ala Met Lys
            595                 600                 605

Asn Gly Glu Ser Glu Lys Asn Val Asn Ser Ser Ile Phe Gln Lys Ile
            610                 615                 620

Val Ala Phe Glu Asp Glu Leu Lys Ala Val Leu Pro Lys Glu Val Glu
625                 630                 635                 640

Ser Ala Arg Ala Val Val Glu Ser Gly Asn Pro Ala Ile Pro Asn Arg
                645                 650                 655

Ile Thr Glu Cys Arg Ser Tyr Pro Leu Tyr Arg Leu Val Arg Gln Glu
            660                 665                 670

Leu Gly Ser Glu Leu Leu Thr Gly Glu Lys Val Arg Ser Pro Gly Glu
            675                 680                 685

Glu Ile Asp Lys Val Phe Thr Ala Met Cys Asn Gly Gln Ile Ile Asp
            690                 695                 700

Pro Leu Leu Glu Cys Leu Lys Ser Trp Asn Gly Ala Pro Leu Pro Ile
705                 710                 715                 720

Cys

<210> SEQ ID NO 8
<211> LENGTH: 1101
<212> TYPE: DNA
<213> ORGANISM: Thermoactinomyces intermedius

<400> SEQUENCE: 8
atgcgcgacg tgtttgaaat gatggaccgc tatggccacg agcaggtcat tttttgccgt      60
catccgcaaa ccgtctcaa agcgatcatc gccttgcata atacaaccgc ggggccggct     120
ttgggtggat gccgcatgat cccgtatgct tcgacggacg aagccttgga ggatgttttg     180
cggttgtcca aaggcatgac ctataaatgc agtctggcgg atgtggactt ggcgggggga     240
aaaatggtta tcatcggcga tccgaaaaaa gataaatcgc cggagttgtt tcgcgtgatc     300
```

-continued

```
ggccgttttg tgggcgggtt aaacggccgt tctataccg gaaccgacat gggaaccaat    360
ccggaagatt ttgtccatgc cgccagggaa tcgaaatctt ttgccggatt gccgaaatcg    420
tacggcggaa aggggacac atccattccc accgcgctcg gggtgtttca cggaatgcgg    480
gccaccgccc ggttttatg ggggacggat cagctgaaag gcgtgtggt tgccatccaa    540
ggagtcggca aggtgggaga cgcttgttg cagcttttgg tcgaagtggg ggcttactgc    600
aaaattgccg acatcgattc ggtgcgatgc gaacagctga agaaaagta tggcgacaag    660
gtccaattgg tggatgtgaa ccggattcac aaggagagtt gcgatatttt ctcgccttgc    720
gccaaaggcg gcgtggtcaa tgatgacacc attgacgagt ccgttgcct ggccattgtc    780
ggatccgcca acaaccaact ggtggaagac cggcatgggg cactgcttca aaaacggagc    840
atttgttatg cacccgatta tctggtgaat gccggcgggc tgattcaagt ggctgatgaa    900
ctggaaggct tccatgaaga gagagtgctc gccaaaaccg aagcgattta tgacatggtc    960
ctggatattt ttcaccgggc gaaaaatgag aatattacca cttgtgaggc agcggaccgg   1020
atcgtgatgg agcgtttgaa aaagttaacc gatattcgcc ggatcttgtt ggaggatccc   1080
cgcaacagcg caaggaggta a                                               1101
```

<210> SEQ ID NO 9
<211> LENGTH: 352
<212> TYPE: PRT
<213> ORGANISM: Caenorhabditis remanei

<400> SEQUENCE: 9

```
Met Asp Phe Lys Ala Lys Leu Leu Ala Glu Met Ala Lys Lys Arg Lys
1               5                   10                  15

Ala Val Ser Gly Leu Glu Val Lys Glu Gly Ala Lys Phe Val Arg
            20                  25                  30

Gly Ala Asp Leu Glu Ser Lys Arg Thr Gln Glu Tyr Glu Ala Lys Gln
        35                  40                  45

Glu Glu Leu Ala Ile Lys Lys Arg Lys Ala Asp Asp Glu Ile Leu Gln
    50                  55                  60

Glu Ser Thr Ser Arg Ala Lys Ile Val Pro Glu Val Pro Glu Ala Glu
65                  70                  75                  80

Phe Asp Glu Lys Thr Pro Met Pro Glu Ile His Ala Arg Leu Arg Gln
                85                  90                  95

Arg Gly Gln Pro Ile Leu Leu Phe Gly Glu Ser Glu Leu Ser Val Arg
            100                 105                 110

Lys Arg Leu His Gln Leu Glu Ile Glu Gln Pro Glu Leu Asn Glu Gly
        115                 120                 125

Trp Glu Asn Glu Met Gln Thr Ala Met Lys Phe Ile Gly Lys Glu Met
    130                 135                 140

Asp Lys Ala Val Val Glu Gly Thr Ala Asp Ser Ala Thr Arg His Asp
145                 150                 155                 160

Ile Ala Leu Pro Gln Gly Tyr Glu Glu Asp Asn Trp Lys Ser Ile Glu
                165                 170                 175

His Ala Ser Thr Leu Leu Gly Val Gly Asp Glu Met Lys Arg Asp Cys
            180                 185                 190

Asp Ile Ile Leu Ser Ile Cys Arg Tyr Ile Leu Ala Arg Trp Ala Arg
        195                 200                 205

Asp Leu Asn Asp Arg Pro Leu Asp Val Lys Lys Thr Ala Gln Gly Met
    210                 215                 220

His Glu Ala Ala His His Lys Gln Thr Thr Met His Leu Lys Ser Leu
```

```
              225                 230                 235                 240

Met Thr Ser Met Glu Lys Tyr Asn Val Asn Asn Asp Ile Arg His His
                245                 250                 255

Leu Ala Lys Ile Cys Arg Leu Leu Val Ile Glu Arg Asn Tyr Leu Glu
                260                 265                 270

Ala Asn Asn Ala Tyr Met Glu Met Ala Ile Gly Asn Ala Pro Trp Pro
                275                 280                 285

Val Gly Val Thr Arg Ser Gly Ile His Gln Arg Pro Gly Ser Ala Lys
                290                 295                 300

Ala Tyr Val Ser Asn Ile Ala His Val Leu Asn Asp Glu Thr Gln Arg
305                 310                 315                 320

Lys Tyr Ile Gln Ala Phe Lys Arg Leu Met Thr Lys Leu Gln Glu Tyr
                325                 330                 335

Phe Pro Thr Asp Pro Ser Lys Ser Val Glu Phe Val Lys Lys Ser Val
                340                 345                 350

<210> SEQ ID NO 10
<211> LENGTH: 411
<212> TYPE: PRT
<213> ORGANISM: Arabidopsis thaliana

<400> SEQUENCE: 10

Met Asn Ala Leu Ala Ala Thr Asn Arg Asn Phe Lys Leu Ala Ala Arg
1               5                   10                  15

Leu Leu Gly Leu Asp Ser Lys Leu Glu Lys Ser Leu Leu Ile Pro Phe
                20                  25                  30

Arg Glu Ile Lys Val Glu Cys Thr Ile Pro Lys Asp Asp Gly Thr Leu
                35                  40                  45

Ala Ser Phe Val Gly Phe Arg Val Gln His Asp Asn Ala Arg Gly Pro
        50                  55                  60

Met Lys Gly Gly Ile Arg Tyr His Pro Glu Val Asp Pro Asp Glu Val
65                  70                  75                  80

Asn Ala Leu Ala Gln Leu Met Thr Trp Lys Thr Ala Val Ala Lys Ile
                85                  90                  95

Pro Tyr Gly Gly Ala Lys Gly Gly Ile Gly Cys Asp Pro Ser Lys Leu
                100                 105                 110

Ser Ile Ser Glu Leu Glu Arg Leu Thr Arg Val Phe Thr Gln Lys Ile
                115                 120                 125

His Asp Leu Ile Gly Ile His Thr Asp Val Pro Ala Pro Asp Met Gly
        130                 135                 140

Thr Gly Pro Gln Thr Met Ala Trp Ile Leu Asp Glu Tyr Ser Lys Phe
145                 150                 155                 160

His Gly Tyr Ser Pro Ala Val Val Thr Gly Lys Pro Ile Asp Leu Gly
                165                 170                 175

Gly Ser Leu Gly Arg Asp Ala Ala Thr Gly Arg Gly Val Met Phe Gly
                180                 185                 190

Thr Glu Ala Leu Leu Asn Glu His Gly Lys Thr Ile Ser Gly Gln Arg
                195                 200                 205

Phe Val Ile Gln Gly Phe Gly Asn Val Gly Ser Trp Ala Ala Lys Leu
        210                 215                 220

Ile Ser Glu Lys Gly Gly Lys Ile Val Ala Val Ser Asp Ile Thr Gly
225                 230                 235                 240

Ala Ile Lys Asn Lys Asp Gly Ile Asp Ile Pro Ala Leu Leu Lys His
                245                 250                 255
```

```
Thr Lys Glu His Arg Gly Val Lys Gly Phe Asp Gly Ala Asp Pro Ile
            260                 265                 270

Asp Pro Asn Ser Ile Leu Val Glu Asp Cys Asp Ile Leu Val Pro Ala
            275                 280                 285

Ala Leu Gly Gly Val Ile Asn Arg Glu Asn Ala Asn Glu Ile Lys Ala
            290                 295                 300

Lys Phe Ile Ile Glu Ala Ala Asn His Pro Thr Asp Pro Asp Ala Asp
305                 310                 315                 320

Glu Ile Leu Ser Lys Lys Gly Val Val Ile Leu Pro Asp Ile Tyr Ala
            325                 330                 335

Asn Ser Gly Gly Val Thr Val Ser Tyr Phe Glu Trp Val Gln Asn Ile
            340                 345                 350

Gln Gly Phe Met Trp Glu Glu Lys Val Asn Asp Glu Leu Lys Thr
            355                 360                 365

Tyr Met Thr Arg Ser Phe Lys Asp Leu Lys Glu Met Cys Lys Thr His
            370                 375                 380

Ser Cys Asp Leu Arg Met Gly Ala Phe Thr Leu Gly Val Asn Arg Val
385                 390                 395                 400

Ala Gln Ala Thr Ile Leu Arg Gly Trp Gly Ala
            405                 410
```

<210> SEQ ID NO 11
<211> LENGTH: 1275
<212> TYPE: DNA
<213> ORGANISM: Artificial Sequence
<220> FEATURE:
<223> OTHER INFORMATION: Nucleic Acid Sequence encoding enzyme 11

<400> SEQUENCE: 11

```
atgtcagcaa agcaagtctc gaaagatgaa gaaaagaag ctcttaactt atttctgtct      60
acccaaacaa tcattaagga agcccttcgg aagctgggtt atccgggaga tatgtatgaa     120
ctcatgaaag agccgcagag aatgctcact gtccgcattc cggtcaaaat ggacaatggg     180
agcgtcaaag tgttcacagg ctaccggtca cagcacaatg atgctgtcgg tccgacaaag     240
gggggcgttc gcttccatcc agaagttaat gaagaggaag taaaggcatt atccatttgg     300
atgacgctca aatgcgggat tgccaatctt ccttacggcg gcgggaaggg cggtattatt     360
tgtgatccgc ggacaatgtc atttggagaa ctggaaaggc tgagcagggg gtatgtccgt     420
gccatcagcc agatcgtcgg tccgacaaag gatattccag ctcccgatgt gtacaccaat     480
tcgcagatta tggcgtggat gatggatgag tacagccggc tgcgggaatt cgattctccg     540
ggctttatta caggtaaacc gcttgttttg ggaggatcgc aaggacggga acagcgacg      600 gcacagggcg tcacgatttg tattgaagag gcggtgaaga aaaagggat caagctgcaa      660 aacgcgcgca tcatcataca gggctttgga aacgcgggta gcttcctggc caaattcatg     720
cacgatgcgg gcgcgaaggt gatcgggatt tctgatgcca atggcgggct ctacaaccca     780
gacggccttg atatccctta tttgctcgat aaacgggaca gctttggtat ggtcaccaat     840
ttatttactg acgtcatcac aaatgaggag ctgcttgaaa aggattgcga tattttagtg     900
cctgccgcga tctccaatca aatcacagcc aaaaacgcac ataacattca ggcgtcaatc     960
gtcgttgaag cggcgaacgg cccgacaacc attgatgcca ctaagatcct gaatgaaaga    1020
ggcgtgctgc ttgtgccgga tatcctagcg agtgccggcg cgtcacggtt ttcttatttt    1080
gaatgggtgc aaaacaacca aggatattat tggtcggaag aagaggttgc agaaaaactg    1140
agaagcgtca tggtcagctc gttcgaaaca atttatcaaa cagcggcaac acataaagtg    1200
```

```
gatatgcgtt tggcggctta catgacgggc atcagaaaat cggcagaagc atcgcgtttc    1260
cgcggatggg tctaa                                                     1275

<210> SEQ ID NO 12
<211> LENGTH: 1419
<212> TYPE: DNA
<213> ORGANISM: Artificial Sequence
<220> FEATURE:
<223> OTHER INFORMATION: Nucleic Acid Sequence encoding enzyme 12

<400> SEQUENCE: 12
atgtccatca aagacgctgt aaaactgatt gaagaaagcg aagcccgctt tgtcgatttg      60
cgctttaccg ataccaaagg caagcagcac cactttaccg tgcctgcgcg catcgtgttg     120
gaagaccccg aagagtggtt cgaaaacgga caggcgtttg acggttcgtc catcggcggc     180
tggaaaggca ttcaggcttc cgatatgcag cttcgccccg atcccgccac ggcgtttatc     240
gatccttttt atgatgatgt taccgtcgtc attacctgcg acgttatcga tcccgccgac     300
ggtcagggtt acgaccgcga cccgcgctcc atcgcacgcc gcgccgaagc ctatttgaaa     360
tcttccggta tcggcgacac ggcatacttc ggtcccgaac ccgagttttt cgtcttcgac     420
ggcgtagaat ttgaaaccga tatgcacaaa accgttacg aaatcacgtc cgaaagcggc      480
gcatgggcca gcgcctgca tatggacggt caaaacaccg ccaccgccc tgccgtcaaa      540 ggcggttacg cgcccgtcgc gccgattgac tgcggtcagg atttgcgttc cgcgatggta     600
aacattttgg aaggactcgg catcgaagtc gaagtgcacc acagcgaagt cggtaccggc     660
agccaaatgg aaatcggcac gcgcttcgcc accttggtca aacgcgccga ccaaacccaa     720
gacatgaaat atgtgattca aaatgtcgcc cacaacttcg gcaaaaccgc caccttcatg     780
cccaaaccca ttatgggcga caacggcagc ggtatgcacg ttcaccaatc catctggaaa     840
gacggtcaaa acctgttcgc aggcgacggc tatgccggct tgagcgacac cgcgctctac     900
tacatcggcg gcatcatcaa acacgccaaa gccctgaacg cgattaccaa tccgtccacc     960
aactcctaca aacgccttgt gccgcacttt gaagcgccga ccaaactggc atattccgcc    1020
aaaaaccgtt ccgcttccat ccgtattccg tctgtgaaca gcagcaaggc gcgccgcatc    1080
gaagcgcgtt tccccgaccc gaccgccaac ccgtacttgg cgttcgctgc cctgctgatg    1140
gcgggtttgg acggcattca aaacaaaatc catccgggcg atcctgccga taaaaatctc    1200
tacgacctgc cgccggaaga agacgcgctc gtcccgaccg tttgcgcttc tttagaagaa    1260
gccctcgccg cgctcaaagc cgaccacgaa ttcctcttac gcggcggcgt gttcagcaaa    1320
gactggatcg acagctacat cgcctttaaa gaggaagatg tccgccgcat ccgtatggcg    1380
ccgcatccgc tggaatttga aatgtattac agcctgtaa                           1419

<210> SEQ ID NO 13
<211> LENGTH: 1075
<212> TYPE: DNA
<213> ORGANISM: Artificial Sequence
<220> FEATURE:
<223> OTHER INFORMATION: Nucleic Acid Sequence encoding enzyme 13

<400> SEQUENCE: 13
aggaggtgtt ttaataatga aaggttttgc aatgctcagt atcggtaaag tcggttggat      60
tgaaaaagaa aagcctactc ccggcccttt tgacgctatt gtaagacctc tagctgtggc     120
cccttgcact tcggacgttc ataccgtttt tgaaggtgct attggcgaaa gacataacat     180
```

```
gatactcggt cacgaagctg taggtgaagt agttgaagta ggtagtgagg taaaagattt    240
taaacctggt gatcgcgttg tggtaccagc tattacccct gattggcgaa cctctgaagt    300
gcaaagagga tatcaccaac actctggtgg aatgctggca ggctggaaat tttcgaatat    360
aaaagatggt gttttggtg aattttttca tgtgaacgat gctgatatga atttagcaca     420
tctgcctaag gaaattccat tggaagctgc agttatgatt cccgatatga tgactactgg    480 cttcacgga gccgaactgg cagatataga attaggtgcg acggtagcgg ttttgggtat     540
tggcccagta ggtcttatgg cagtcgctgg tgccaaattg cggggtgctg gaaggattat    600
cgcagtaggc agtagaccag tttgtgtaga tgctgcaaaa tactatggag ctactgatat    660
tgtaaactat aaagatggtc ctatcgacag tcagattatg gatttaacgg aaggcaaagg    720
tgttgatgct gccatcatcg ctggaggaaa tgttgacatc atggctacag cagttaagat    780
tgttaaacct ggtggcacca tcgctaatgt aaaattacttt ggcgaaggag atgttttgcc    840
tgttcctcgt cttgaatggg gttgcggcat ggctcataaa actataaaag gcgggctatg    900
ccccggtgga cgtctaagaa tggaaagact gattgacctt gttgtttata agcgtgtcga    960
tccttctaag ctcgtcactc acgttttccg gggatttgac aatattgaaa agcctttat    1020 gttgatgaaa gacaaaccaa aagacctaat caaacctgtt gtaatattag cataa         1075
```

<210> SEQ ID NO 14
<211> LENGTH: 1545
<212> TYPE: DNA
<213> ORGANISM: Artificial Sequence
<220> FEATURE:
<223> OTHER INFORMATION: Nucleic Acid sequence encoding enzyme 14

<400> SEQUENCE: 14

```
atggctgact cgcaaccct gtccggtacc ccggaaggtg ccgaatattt aagagcggtg      60
ctgcgcgcgc cggtctacga agcggcgcag gtcacgccgc tacagaaaat ggaaaaactg    120
tcgtcgcgtc tcgataacgt gattctggtg aagcgcgaag atcgccagcc agttcatagc    180
tttaagttgc gcggcgcata cgccatgatg gcgggcctga cggaagaaca aaaagcacac    240
ggcgtgatta ccgcttctgc aggtaaccac gcgcagggcg tcgcgttttc ttccgcacgg    300
ttaggcgtga aggcgctgat cgtcatgcca accgccaccg ccgatatcaa agttgatgcg    360
gtgcgcggct ttggcggcga agtgctgctt cacggcgcaa atttcgatga agcgaaagcg    420
aaagcgatcg aactgtcaca gcagcagggt ttcacctggg taccgccgtt cgatcatccg    480
atggtgatcg ccgggcaagg cacgctggcg ctggaactgc tccagcagga cgcccatctc    540
gaccgcgtat ttgtaccggt cggcggcggc ggtctggcag cgggtgtggc ggtgctgatc    600
aaacaactga tgccgcaaat caaagtaatc gccgtggaag cggaagattc cgcctgcctg    660
aaagcggcgc tggatgcggg tcatcccgtt gatctgcccc gcgtgggct gtttgctgaa    720 ggcgtcgcgg taaaacgcat cggcgatgaa accttccgtt tgtgccagga gtatcttgac    780
gacatcatca ccgtcgatag cgatgccatc tgtgcggcga tgaagatct gttcgaagat    840 gtgcgcgcgg tggcggaacc ttccggcgcg ctggcgctgg cggggatgaa aaaatacatc    900
gcccagcaca acattcgcgg tgaacggctg gcgcatattc tttccggtgc taacgtgaac    960
tttcacggtc tgcgctacgt ctcggaacgc tgcgaactgg gcgaacagcg tgaagcgttg   1020
ttggcggtga ccattccgga agaaaaaggc agcttcctca aattctgcca actgcttggc   1080
gggcgttcgg tcaccgagtt caactaccgt tttgccgatg ccaaaaacgc ctgcatcttt   1140
gtcggcgtgc gcttaagccg tggcctcgaa gagcgcaaag aaattttgca gatgctcaac   1200
```

```
gacggtggct acagcgtggt tgatctctcc gacgacgaaa tggcgaagct gcatgtgcgc   1260
tatatggttg gcgggcgtcc atcgcatccg ttgcaggaac gcctatacag cttcgaattc   1320
ccggaatcac cgggcgcgct gctgcgcttc ctcaacacgc tgggtacgca ctggaacatc   1380
tcgctgttcc attatcgcag ccacggtacc gactacgggc gcgtactggc ggcgttcgag   1440
cttggcgatc atgaaccgga ttttgaaacc cggttgaatg aactgggcta cgattgccac   1500
gacgaaacca ataacccggc gttcaggttc tttttggcgg gttag                  1545
```

<210> SEQ ID NO 15
<211> LENGTH: 750
<212> TYPE: DNA
<213> ORGANISM: Artificial Sequence
<220> FEATURE:
<223> OTHER INFORMATION: Nucleic acid sequence encoding enzyme 15

<400> SEQUENCE: 15

```
atgagcggta ccatcctcat caccggcgcc acgtccggct tcggacaggc cacggcgcgg    60
cgtttcgtca aggaaggctg aaggtcatc ggcacaggtc ggcgggcgga acggctggag   120
gcgctggcgc aagaactcgg ctccgccttt cacggcgctg ccttcgatgt taccgacgaa   180
gatgccacta gaaaggcact tgcggctttg ccggaaggtt tccgggacat cgatattctc   240
gtcaacaatg cggggcttgc gctcggcacc gcacctgcac cgcaggtgcc gctgaaagac   300
tggcagacca tggtgaacac caacatcacc ggtcttttga acatcaccca ccatcttttg   360
cccacgttga tcgaccgcaa gggcattgtc atcaaccttt cctcggtagc tgcgcactgg   420
ccctatgcgg gcggcaatgt ctatgccgga cgaaagcct tcctgcggca attctcgctc   480
ggtctgcgct ccgacctgca tggcaagggc gtgcgcgtca cctcgatcga accgggcatg   540
tgcgaaacgg aattcacgct tgttcgcacc ggcggcaatc aggatgcctc ggacaatctt   600
tacaagggcg tcaatccgat cacgccgag gatatcgcca atacgatcca ttgggtcgcc   660
tcgcagccca aacatatcaa catcaacagc ctcgaactca tgccggtcaa ccagtccttt   720
gccggtttcc aagtgcatcg ggaaagttga                                    750
```

<210> SEQ ID NO 16
<211> LENGTH: 1380
<212> TYPE: DNA
<213> ORGANISM: Artificial Sequence
<220> FEATURE:
<223> OTHER INFORMATION: Nucleic Acid sequence encoding enzyme 16

<400> SEQUENCE: 16

```
atgatgacca aaacgaaat ccaaaagtgg gtaaggaat cccgctgct gaaacgatc       60 atggcggccg aagaggtatt ttggcgcaat ccaaaatatc acgcgtttgc gcaagctatt    120
cgaacgattc ctttacgcga acgcgatgtc aaggaggccg aagagcgatt gcgccgcttt    180 gcccctaca tcgcgaaagt gtttcccgag acgcgaacgg cccacggtat catcgaatcc    240
cctttagtgc ggattccgaa catgaaacag cgtttggaaa agatgtttca gaccaacatc    300 gaggggatc tgttgctaaa atgcgacagc catcttccca tctccggatc gatcaaggcg    360 agaggggaa tctacgaggt tctgaaacat gcggaagaac tcgctctggc aaaccatatg    420
atcaccatgg gggatgacta tgcggtcatg gccagcgaag aattccggca gttcttttcc    480
cgctattcgc ttgtcgttgg ttcgacggga aatttaggct tgagtatcgg catcatcggg    540
gcgcagcttg ggttccgcgt taccgttcat atgtcagccg atgcgaaaca atggaaaaaa    600
```

```
gacttgttgc gaagcaaagg ggttgcggtc atcgaacatc tcaccgacta caacaaggtg      660
gtggaagagg cgcgaagaca gtccgccgag gatccaacgt cgtattttat cgatgatgag      720
aactcgatcc atctgttttt aggctatgcg gtggcggcgt ttcggctgaa aaagcaatta      780
gaggacatga acatcacggt tgatgaaaac cacccgctct ttgtatatct tccttgcggc      840
gtcggcggcg gtccgggcgg ggtgacgttt gggctgaagc tcgtgtacgg cgatcatgtc      900
cattgctttt tcgctgagcc gacgcattcg ccttgcatgt tgctcggcct gatgacggga      960
cagcacgacc gcgtgtcggt gcaagatttt ggcctcgaca ataagaccga agcggacggg     1020
ctagcggtgg ggcggccgtc aaggttggtg ggaacatgc ttgagaacgt catcagcggc      1080
gtctatacgg tggacgatgc gacgctttac cgcttgctcg cggcgatggt ggaaacggag     1140
gaaatctatt tagagccgtc cgccttggcg ggggtggcgg ggcctgttcg gctgtttcgt     1200
gatttggcgg ggcaaacgta cgtagaggca aacggtttga agaaaagat gaaaaacgcc      1260 gtccatattg gctgggcgac aggcggaagc atggtgctaa aggatgtgat ggaggcctat     1320
tatcgggaag gcgtgcgcat cgaaacgatg acaggaacg gtttttctga aggacgataa      1380
```

<210> SEQ ID NO 17
<211> LENGTH: 1047
<212> TYPE: DNA
<213> ORGANISM: Artificial Sequence
<220> FEATURE:
<223> OTHER INFORMATION: Nucleic Acid sequence encoding enzyme 17

<400> SEQUENCE: 17

```
atgctgatgt tcgaagaaat ccaggcgcgc ggccacgaga gcgtcacgct gctgcaccac       60
gcccccagcg gcctgcgcgc cgtgctcgcc gtgcactcca ccgtgctcgg ccctgccatt      120
gccggctgcc gcctgatgcc ctgcaccgag gaacgcgccg tgcgcgacgc cctcgccctc      180
agcgagtccg tcacgctcaa ggccgccctc gcgggcctga actacggcgg gggcgcgtgc      240
gtcatgctcc ccccggaagg cggcgacatc gacgggcacg cccgcgaggc gctgttccgc      300
gcgctcggcc ggcagatccg ttaccgcggt ggccgcgtca tcctcaccga ggacgtcggc      360
gtgaccggcc gcgacatcgc cttcgccgcg caggaaaccg acagcaccat gggcatgcac      420
accgacacgc ccaccgtcac cgcgtacggc gtgtaccgcg gcatcaaggc cgccgcgcgc      480
gcctacctcg gcgcgagag catgcgcggc gtgcgcgtcg cgctgctcgg cgcgggcgca      540
gtcgggcgca ccctcgcgca gcacctgcac cgcgagggcg cgcgcctcac cgtcgcagac      600
ctgatgtctg agcgcgcgca ggccctcgcg gacgacctcg gcgagcgcgt caccgtcgtg      660
agcgccgctg acatcttcga cgtgccgtgc gacgtattcg cgccgtgcgc gttcgggcac      720
agcatcaaaa gcgccgacgt gccccgcttg cagtgccggg tgatcgccgg cagcgaacac      780
cacccgctca gccacaacgg cgagacgctc gtgcgcgaag cgggcatcac atacatcccg      840
gacttcgcca tcaacagcgc cggcctgatg agccgccgc agaacctcag catcgaaacg      900
gcggcggaac gcgtgtacga gagcgtcgcg cagatctgcg cgaccgcgca gaagtacgag      960
aagccgccgc acgtcgtcgc ccgtaaactc gcgctgcgcc gcatcgaact gatcggctcc     1020
atcagcggcc agtacgccgg ccagtaa                                         1047
```

<210> SEQ ID NO 18
<211> LENGTH: 768
<212> TYPE: DNA
<213> ORGANISM: Artificial Sequence
<220> FEATURE:
<223> OTHER INFORMATION: Nucleic Acid sequence encoding enzyme 18

<400> SEQUENCE: 18

```
tcatgtgcca acacgtatgt tatcacttaa aattttagt aaagtgactg ctgaatatgc    60
tgccaaaaca cttgttttg gatttaattc acacacagtg tttttgtta tagatttaaa   120
ctctccaaaa tctcctttaa catggacttc atggatattg tgttcaactt caggatctgc   180
aattatcttt acatccgcat ctattccaga ggctagactt aatgccgcag caacgttaat   240
attcactgga aattttttaa cagcttctga ggatttccct ttaaacacga cctcctttt   300
tttggtctta acacctaacg aagtaggtga ttttctcgtt ataagttta tttcttttat    360
cttacctaag gatgcggctt ttacaccatc taaaccaatt attgcaccgg aaggtatgta   420
tatattagct cctgattctc tagattcctt tatcaatctt cttctaactt tctcatctaa   480
tagtgcaccc acactcataa tcaaaacatc tatacctcta ctaattatat tgggcacaat   540
ttctttact gcctcttgag aagcagattc aattatcaaa tcaactccat tgaacatttc   600
ttctacctt tttacggcag tgccatttgt taaatttgct agcttcttag cttttctaaa   660
atttctgtca taaaaatatt ttaattttat ttttttgata tcttgtttta agacaaggtt   720
aactattgta tttgcaattg caccacatcc tataatccca catctcat               768
```

<210> SEQ ID NO 19
<211> LENGTH: 1425
<212> TYPE: DNA
<213> ORGANISM: Artificial Sequence
<220> FEATURE:
<223> OTHER INFORMATION: Nucleic Acid sequence encoding enzyme 19

<400> SEQUENCE: 19

```
atgtcctcgc ctgcatcatc gcgcatcgaa aaagacctgc ttggtgttct cgaagtacct    60
gccaacgcgt attacggcat ccagaccctg cgagcggtga caactttca cctctccggc   120
gtgccgcttt cgcactaccc gaaactggta gtcgcgctgg ccatggtcaa gcaggcggca   180
gcggatgcaa accatcagct cggacacctc aatgacgcca agcatgcggc gatcagcgag   240
gcctgtgccc gcctgatccg cggcgacttc cacgatcagt tcgtggtcga catgatccag   300
ggcggcgctg gcacgtcgac caacatgaat gccaacgaag tcatcgccaa catcgctctg   360
gaaaccatgg gtttcgagaa aggcgcatac aaacacctgc accccaacaa cgatgtcaac   420
atggcgcagt cgaccaacga cgcctacccc acggcgatcc gcttgggtct gctgctgggt   480
cacgacgctc tgctcgccag cctttccagc ctgattcagg ccttcgccgc caagggcgaa   540
gaattcaacc atgtgctgaa gatgggccgc acccagttgc aggacgccgt tccaatgacc   600
ctgggtcagg aattccgcgc cttcgccacc accctgacag aagacctgaa ccgcctgcgc   660
agcctggcgc cagagctgtt gaccgaagtg aacctcggcg gaaccgccat cggcaccggc   720
atcaacgccg accctggcta tcagaagctg gcagtcgatc gtctggcact catcagcggc   780
cagcctctgg tgccagcagc cgacctgatc gaagcgacct ccgacatggg cgccttcgtg   840
ttgttctcgg gcatgctcaa gcgtactgcg gtcaagctgt cgaaaatctg caacgacctg   900
cgcctgctgt ccagcggccc acgcaccggc atcaacgaaa tcaacctgcc ggcacgtcag   960
ccaggcagct cgatcatgcc cggcaaggtc aaccgggta tcccggaagc ggtcaatcag  1020
gttgccttcg aaatcatcgg caacgacctg tcgctgacca tggcagccga aggaggacaa  1080
ttgcagctca acgtgatgga gccgctgatc gcctacaaga tcttcgactc gatccgcctg  1140
ctgcagcgcg ccatggacat gctgcgcgag cactgcatcg tcggcatcac agccaacgaa  1200
```

| | |
|---|---:|
| cagcgctgcc gcgagctggt cgagcattcg atcggtctgg tcaccgccct gaacccttac | 1260 |
| atcggttacg agaactccac ccgtatcgcc cgcatcgcgc tggaaaccgg ccgcggcgtg | 1320 |
| ctggaactgg tgcgtgagga aggtctgctc gacgacgcca tgctcgacga catcctgcgc | 1380 |
| ccggaaaaca tgatcgctcc gcgtctggcc cccttgaagg cctga | 1425 |

<210> SEQ ID NO 20
<211> LENGTH: 1083
<212> TYPE: DNA
<213> ORGANISM: Artificial Sequence
<220> FEATURE:
<223> OTHER INFORMATION: Nucleic Acid sequence encoding enzyme 20

<400> SEQUENCE: 20

| | |
|---|---:|
| tcagcgaccg cgggcctcgg ccatccgctg ctcggcgatc cggtcggccg ccgcggcggg | 60 |
| cggaatgccg tccgccttcg cacgtgcgaa tatttccagc gtggtgtcga agatcttcgt | 120 |
| cgccttcgcc ttgcaccggt cgaagtcgaa cccgtgcagc tcgtcggcga cctggatcac | 180 |
| gccgccggcg ttgaccacat agtcgggtgc gtagaggacc gaccgtcgg ccaggtcctt | 240 |
| ctcgacaccc gggtgggcca gctggttgtt ggccgcgccg cacaccacct tcgccgtgag | 300 |
| caccggaacg tcgcgtcgt tgagcgcgcc gccgagcgcg cagggcgcgt agatgtcgag | 360 |
| accctcggtg cggatcagcg tctcggtgtc cgccaccacg gtgacctcgg ggtgcagatc | 420 |
| ggtgatccgg cgcaccgact cctcgcgtac gtcggtgatc acgacctcgg ccccgtcgga | 480 |
| gagcaggtgc tcgacgaggt ggtggcccac cttgccgacc ccggcgacgc cgaccttgcg | 540 |
| gccgcgcagc gtcgggtcgc cccacaggtg ctgggccgag gcccgcatgc cctggaagac | 600 |
| accgaacgcg gtgaggacgg aggagtcgcc ggcgccgccg ttctcggggg agcggccggt | 660 |
| ggtccagcgc cactccctgg cgacgacgtc catgtcggcg acgtaggtgc cgacatcgca | 720 |
| ggcggtgacg taccggccgc cgagcgaggc gacgaaccgg ccgtaggcca ggaggagttc | 780 |
| ctccgtcttg atcttctccg ggtcgccgat gatgacggcc ttgccgccac cgtggtcgag | 840 |
| tccggccagg gcgttcttgt acgacatccc gcgcgacagg ttcagcgcgt cggcgacggc | 900 |
| ctcggcctcg gtcgcgtacg ggtagaagcg ggtgccgccg aggccggggc ccagggcggt | 960 |
| ggagtggagg gcgatgacgg cccttgaggcc ggtggcacgg tcctggcaga tcacgacttg | 1020 |
| ctcgtgaccc ccctgatccg agtggaacag ggtgtgcagg acgccgttag tcacatcggt | 1080 |
| cac | 1083 |

<210> SEQ ID NO 21
<211> LENGTH: 2910
<212> TYPE: DNA
<213> ORGANISM: Artificial Sequence
<220> FEATURE:
<223> OTHER INFORMATION: Nucleic Acid sequence encoding enzyme 21

<400> SEQUENCE: 21

| | |
|---|---:|
| ctagttgtaa aagtcgaggg aggcgcaact gcacatgagg tgacgatctc cgtaaacccc | 60 |
| gtcaatgcga cccacagtcg gccagtactt ttcaacgtac gagtaaggat aagggaatgc | 120 |
| cgccaaacgc cgatcatatg gtttgtccca tttatcatcg gtgacacatc ttgccgtgtg | 180 |
| tggtgcattc ttcaaaacat tgttatccac tggttgttca ccttttttcaa tggcggcaat | 240 |
| ctcacctcga atggaaatta gtgcatctgc caagcgatcc aactcccgct gggttctga | 300 |
| ttcggtgggt tcaatcatta aagtcccggg tacaggaaac gccagtgttg gcgagtgaat | 360 |
| tccgtagtcc atcaaccgtt tggccacgtc ctccgcctca atatgagctg tcttcttgaa | 420 |

```
ccgtcgaaga tcaacgataa actcatgagc gcagtagttt tctccaccca ggaaaagaat    480
cgtataatgg ttctctaggc gcttcttcaa gtagtttgca ttcaaaacgg cgtactctgt    540
acaagttttg agcccgtgtg atccaagcat taacatcaac atgtacgata tcggaagaat    600
tgatgctgat ccgtacgctg attgtgagac ttggccgaat ggctgtgaac cgccaacttt    660
ttggttgaaa acagaatttg gcaaaaaggg ggccagatgt tgacggacag ctatagggcc    720
cattccgggg ccgccaccac catggggaat tgaaaacgtc ttgtggagat taatgtggca    780
cacgtcgcca ccgatatatc cagggcctgt atagccaacc atggcgttaa gatttgcccc    840
atcaatgtag cattgtccac cgtagtagtg cgccattgat gtaatggata aaatatcctt    900
gtcaaacaag ccatacgtac ttggatatgt tatcatgata cacgacaact cctttgcgtg    960
tttttggcaa gatttctcca ggtcattgat atcaaccctg ccgttagaca agcatttcac   1020
caagacaata ttcattcctg ccaatgttgc cgaagctgga ttcgtaccat gcgcactctc   1080
tggaatcaaa cagacgttgc ggtgtccttc cttcattgat agatggtacg cacgaataac   1140
acgaagccca gcgtattcac cttgggcgcc actattaggc tgaagcgata ccgcatccag   1200
accggtaatt tcccttaact tttgctcaag atctagacac aacgcactgt accctcgcac   1260
ttggtccact ggggcaaggg gatgcacatt ggtgaattct ggccaagaga gtggtaacat   1320
agcagcggca gggttaagct tcatggtgca agatcccaac gggacgcaac catgcgtaag   1380
gccgtaatcc tttcgttgta gacgatgaat atagcgcatc agttcacttt cactcttgta   1440
cttttgaaac gttgagtgtt tcaggaaatc agacttccgc accagatcca acggtagtac   1500
cgatttctga tcggctattt tggaaagggc tgcgacgacg ggaagcttca accctgcagc   1560
ctccaaaagt gacacaatgt gtccatccgt tgttgcctca tccacagaaa tggagacagt   1620
cccattactg taatcaacaa aaacattaat acccttctca acacatcgtg tcttgtaatc   1680
ctccgctgta atgccttta ggttcacagt aacagtgtcg aaaaatgcac tgtttaccac   1740
agagtgtcct actgattcca taccaacagc gagcactttc gccttgccgt gtatctcatt   1800
ggcaatctca tttagaccat ctggaccatg gtaggcggca taaacccac tcacgttggc   1860
caataacgct tgtgcagtac agatatttga tgtggcgcgc tcacgcttaa tatgttgttc   1920
acgtgtctgc agcgccatgc gtatggatgg ctctccggca gaatccttac tgacgccgat   1980
cacacgtccc ggcatcaacc tcttaaactg ctccttgaca gcaaagaacg cggcgtgagg   2040
acctccatat cctagtggaa caccaaaacg ctgggaggat cccacaacca catctgcatt   2100
catttcacca ggtggcttga caagaacaca agccatcaag tcggtcccac agcaactaat   2160
gacaccgtgc ttctttgcat tctcgaacag tggtgagaag tcatgaagca tgcccatcgc   2220
atctggtgtt tgtacaagga taccaaacaa ggaactgtca gtccagtcaa tcagattcgt   2280
gtcgcccacg acgacgttta tcttgagcgg ttcggctctt gtcttaacca tctcaatgca   2340
ggatggaaaa acagtttttg atacgaagaa cgtattccgc tttcgttgac catgctgaaa   2400
agcaagatgc atcgcctcgg atgatgctgt cgcttggtca agaagagatg catttgccac   2460
atccatcttt gtcaaatcca taaccatggt ttggaaattc aaaagggact ccagacgtcc   2520
ttgtgcaatc tcagcttggt atggtgtgta gggtgtgtac catccaggat tttcaatgac   2580
gttgcgaagt atgacaggag gagtaatgga ctcgtagtac ccctgaccaa tcatgctttt   2640
tagtaccttg tttcgcgcac caagagagcg cacgagtgcg agagcatcca tctcactcat   2700
agccgccacc tccgtcaagg gtgggcgtac aatatcccct ggaatagcag ccgtcatcaa   2760
```

```
atcagagaga ctctcttttc caaccgttcg aagcatcgac attgtctcag ccgttgttgg   2820
accaatatgg cggttaatat agctgtccgt ggcagtccat cgaacaaatg tcacgcatgg   2880
caaagagcca cgaaacaaac gacggtacat                                    2910
```

```
<210> SEQ ID NO 22
<211> LENGTH: 1107
<212> TYPE: DNA
<213> ORGANISM: Artificial Sequence
<220> FEATURE:
<223> OTHER INFORMATION: Nucleic Acid sequence encoding enzyme 22

<400> SEQUENCE: 22
```

```
atgatcattg gcctgccgaa agagatcaaa gttaaggaaa accgcgtggc actcacgccc     60
gggggcgtcg ccagcctcgt gcgccgcggc cacaccgtca tcgtggaacg cagcgccggc    120
gtgggcagcg gcatccagga caccgagtac gagcaggccg cgcgcagct cggcagcgcc    180 gccgaggcgt gggccgcgca gatggtcgtg aaggtcaagg agcccatcaa gagcgaatac    240
gggtacctcc gcccggacct gctgctgttc acgtacctgc acctgctgc ggaccagccc     300 ctcacggacg ccctgctgag cgccggcacg accgccgttg cgtacgagac ggtgcagctc    360
gacgaccgca gcctgccgct gctcacgccc atgagtgagg tcgcgggccg cctgagcgtg    420
caggccggcg cgtaccacct gcaaaagccc atcggcgggc gcggcgtgct gctcggcggc    480
gtgccgggcg tgcaggcggg ccacgtcgtc gtgattggcg gcggcgtcgt cggcacgaac    540
gccgcgaaaa tggccatggg cctcggcgcg aaggtcacgg tgctggacgt gaaccacggg    600
cgcctctcgt acctcgacga cgtgttcttc gggaagctca ccaccatgat gagcaacgag    660
gcgaacatcc gctccatcct gcccgaagcg gacctcgtga tcggcggcgt gctgatcccc    720
ggggcgaagg cgccgcacct tgtcacgcgc gacatgctgg cgaccatgca ggaaggcagc    780
gtcatcgtcg acgtggcggt ggaccagggc ggatgcgtgg agaccattca cgcgacgacg    840
cacgacgatc ccacgtacat cgtggacggc gtgatccact acggcgtggc gaacatgccg    900
ggcgcggtgc cgcgcaccag cacgttcgcg ctcacgaacc agaccattgg gtacgtgctg    960
cagctcgcgg acaagggcgt ggaggcactc agcgccagca agccgctgct cgtggcctg   1020 aacaccatcg gcgggaagct gacgtacgcg ggcgtcgcgg aagcgttcgg cctgacgtac   1080
accgcgcctg aagtggcgct ggcgtaa                                      1107
```

```
<210> SEQ ID NO 23
<211> LENGTH: 948
<212> TYPE: DNA
<213> ORGANISM: Artificial Sequence
<220> FEATURE:
<223> OTHER INFORMATION: Nucleic Acid sequence encoding enzyme 23

<400> SEQUENCE: 23
```

```
atggagccca ctatgagcca attcgaacag ctgtaccgcc aggtggccct cagtgtcgcc     60
ggcaacccgg tcgtggaaaa agtcttgagc aagcagggct gggcgctggc gcagcgtttt    120
gtatcgggcg agacggcgca ggacgccatc aaggccatca gcggctgga agcccagggc    180 atctccggca acctcgacct gctgggcgag ttcgtgaaca ccccggaacc cgccaatgcc    240
aacaccgaga tgattctggc gaccattgac caggtgcacg cggcgggcct cacgccctac    300
aacagcgtga aaatgtcggc gctgggccaa gggcagaccg cgccgacgg ccaggacctc    360 ggctacgtca cacccgccg cgtcgtggag cgggccaagc gctacggcgg cttcgtcaat    420
ctggacatgg aagaccacac ccgcgtggac tcgactctgc agattttccg ccgcctggtc    480
```

-continued

```
aaggagttcg gccaccagca tgtgggaacg gtgttgcagg cctacctgca ccgctcggaa    540
gacgaccgcc gcagcctgga cgacctgcgc cccaacctcc gcatggtgaa gggcgcctac    600
ctggagcccg cctccgtcgc cctgcagagc aaaaccgaca ttgacgccgc ctaccgccgc    660
ctggtctacg agcacctcaa ggccggcaac tactgcaacg tggccaccca cgaccaccac    720
atcatctacg acgtgatgca ctttgcgctg gcccacggca tccctaagga ccagttcgaa    780
ttccagctgc tgtacggcat ccgcgaggac ctgcagcgcg aattggccga ggccggctac    840
acggtgcgct cgtacattcc tttcggcaag gactggtacg gctactactc gcgccgcatc    900
gccgagcgcc cgcagaacgt gatgttcgtg ctgcgcggcc tgctgtaa                  948

<210> SEQ ID NO 24
<211> LENGTH: 1101
<212> TYPE: DNA
<213> ORGANISM: Artificial Sequence
<220> FEATURE:
<223> OTHER INFORMATION: Nucleic Acid sequence encoding enzyme 24

<400> SEQUENCE: 24
atgaaaaaca ttgtggttat cggcgcgggc aatatcggtt cggcaatcgc ctggatgctg     60
gccgcatcag gcgattatcg catcacggtt gccgatcgtt cagccgatca gctggccaat    120
gtgccggcgc atgaacgggt cgacatcgtc gacattaccg accgtcccgc tctggaagca    180
ctgctaaaag gcaaattcgc cgtgctctcc gccgccccca ccgaattcca cctgacggcg    240
ggtattgccg aagcggccgt tgccgtcggc acgcattatc tcgatctcac cgaagacgtg    300
gaatccaccc gcaaggtcaa ggcgctggcg gaaacggccg aaaccgcgct cattccgcaa    360
tgcggcctcg cccccggctt catctccatc gtcgctgccg atctcgccgt caagttcgac    420
aagctggaca gcgtgcgcat gcgcgtcggc gctctgccgc aatatccgtc caatgcgctc    480
aactacaacc tcacctggag taccgacggg ctgatcaacg aatatatcga gccctgcgaa    540
ggattcgtcg aaggccgcct caccgccgtt ccggcccttg aggagcgcga ggagttctcg    600
ctcgatggca tcacctacga ggcgttcaac acctcgggcg gtctcggtac gctttgcgcg    660
acgctggaag gcaaggtgcg gaccatgaac taccgcacta tccgttatcc cggccatgtg    720
gcgatcatga aggcgctttt gaacgacctc aacctgcgca accgccgcga tgtgctgaag    780
gacctgttcg aaaaacgccct gcccggcacc atgcaggatg tggtcatcgt cttcgtcacc    840
gtctgcggca cccgcaacgg ccgcttcctg caggaaacct atgccaacaa ggtctatgcc    900
ggcccggttt ccggccggat gatgagcgcc atccagatca ctaccgccgc cggcatctgc    960
acggttctcg acctgctcgc ggaaggcgcc ctgccgcaga agggcttcgt tcgacaggag   1020
gaagtggcgc tgccgaagtt cctcgaaaac cggtttggcc ggtattatgg ctcgcatgag   1080
ccgctggcgc gggttgggtg a                                             1101
```

DEVICE AND METHODS OF USING DEVICE FOR DETECTION OF HYPERAMMONEMIA

CROSS-REFERENCE TO RELATED APPLICATIONS

This application is a divisional application filed under 35 U.S.C. § 121, which claims priority to U.S. Ser. No. 14/915,602, filed on Feb. 29, 2016, and International Application Number PCT/US2014/053756, filed Sep. 2, 2014, which claims priority to U.S. Provisional Ser. No. 61/872,149, filed on Aug. 30, 2013, all of which are incorporated by reference herein in their respective entireties.

GOVERNMENT SUPPORT

This disclosure was made jointly by the NIH and with government support under HHSN268201200360P awarded by the NIH. The United States government has certain rights in the disclosure.

FIELD OF THE DISCLOSURE

The disclosure relates generally to devices that quantify and identify the presence or absence of ammonia or ammonimum ion in a sample of bodily fluid, water, or other environmental sample. In some embodiments, the disclosure relates to diagnosing a subject with an hyperammonemia by detecting the presence, absence, or quantity of ammonia or ammonium ion in a sample of bodily fluid. In some embodiments, the device is a biosensor only requiring a sample of whole bodily fluid for detection and/or quantification of ammonia or ammonium ion.

BACKGROUND OF THE DISCLOSURE

Elevated ammonia levels, oftentimes called hyperammonemia, is a potentially fatal symptom associated with a variety of diseases such as cirrhosis of the liver and urea cycle disorders found in neonatal infants. Left untreated, hyperammonemia can lead to cognitive developmental issues, seizures, other neurological problems, and death. The current testing methods include fluorometry and tandem mass spectroscopy performed by central laboratories, which could take multiple days to produce a reliable diagnosis. These methods involve large, cumbersome, and expensive machinery, which prevents testing of ammonia levels at the bedside or home once the disorder has been identified. Therefore, a system for a point of care testing device may be desired, as this may allow administration of treatment to occur more rapidly, in turn improving the neurological development of infants as well as making cirrhosis more manageable. Devices able to test for hyperammonemia may also be modified inexpensively to detect amino acid levels for applications in diagnosing and treating aminoacidopathies and other diseases.

SUMMARY OF DISCLOSURE

The present disclosure encompasses the recognition that hyperammonemia can be identified and/or characterized by identifying the levels or quantities of ammonia or ammonium ion in any sample, including a bodily fluid including human and non-human whole blood samples. In some embodiments, the present disclosure relates to identifying the quantity, presence, or absence of ammonia or ammonium ion in bodily fluids by contacting a bodily fluid to a device disclosed herein. In some embodiments, the methods disclosed herein do not comprise contacting the bodily fluid with any reagent or external stimuli prior to identifying or quantifying whether or how much one or more ammonia or ammonium ion are present in the bodily fluid.

According to at least one exemplary embodiment, a system, method, and apparatus for point of care hyperammonemia sensors may be disclosed. The system may utilize a phenol, 2-phenylphenol, ninhydrin, potassium tetraiodomercurate(II), nitroprusside, sodium hydroxide, similar reagents, catalysts, and buffers, or a combination thereof. The system may also utilize hyohalite, chloramine T, bleach, or similar chemical. Oftentimes called Berthelot's Reaction or an indophenol reaction, this reaction may determine ammonia levels in various mediums by changing color upon detection ammonia concentration. This may be useful for medical systems, such as in diagnosing hyperammonemia and various aminoacidopathies; for civil engineering systems, such as in determining ammonia levels of wastewater treatment plants; or for home based systems, such as ammonia detection in aquariums or pipes.

According to at least one exemplary embodiment, an apparatus for point of care hyperammonemia sensors may be disclosed. The apparatus used may have a concavity, a fossa, or any other type of well as desired for the placement of the reagents and sample to be tested. Separating the sample and reagents may be a cation exchange membrane filter, such as Nafion or similar perfluorinated ionomers, to allow the passage of ammonia between the two sections of the well. Anion exchange membranes may also be used, as well as various polymeric hydrogels such as acrylamide, poly(ethylene glycol) diacrylate, poly(2-hydroxyethyl methacrylate), or poly(vinyl alcohol). Additionally, other exemplary embodiments may include mechanisms for quantitative analysis of the color change by means of photodiodes and sensors or microfluidic devices that require smaller amounts of reagent and samples.

The present disclosure relates to a biosensor capable of measuring the total concentration of ammonia or ammonium ion in a sample with the use of a system comprising reagents for an indophenol or Berthelot reaction, such as hypchlorite, phenylphenol, a basic aqueous solution such as NaOH, and an alkali such as sodium acetate. In some embodiments, the sensor or system comprises at least a first vessel comprising a basic buffer in aqueous or dried phase. In some embodiments, comprises at least a first vessel comprises a gel or hydrogel that comprises at least one or a combination of: an indophenoal reactant or reactants in dried or aqueous phase, a basic buffer in aqueous or dried phase, a alkali solution in aqueous or dried phase, and or an enzyme that oxidizes at least one amino acid substrate. The disclosure provides an ammonia or ammonium ion biosensor for measuring the total concentration of ammonia or ammonium ion. In some embodiments, the detection or quantification of ammonia or ammonium ion is accomplished through colorimetric analysis whereby the reaction products of ammonia or ammonium ion are capable of emitting a wavelength in the visible spectrum of light. In some embodiments, the system and/or biosensor comprises a diode configured to emit light in at least one vessel and a spectrophotometer configured to receive light emitted in a vessel containing indophenol or Berthelot reaction reactant products.

In some embodiments, the system and/or biosensor also detects the absence, presence or quantity of amino acids in solution. In some embodiments, the system and/or biosensor comprises at least a first electrically conductive surface (for measuring) and at least a second electrically conductive surface (counter electrode), wherein the first electrically conductive surface having one or more indophenol reaction reagents described herein or a combination of any one or more indophenol reaction reagents described herein and any one or combination of constituent factors, mediators, one or a plurality of enzymes, wherein, if the device comprise one or more enzymes, the one or more enzymes selectively utilize one or more amino acids as substrates. In those embodiments with at least a first or second electrode, the one or plurality of enzymes produce reaction products by reacting with the specified amino acids as substrates, wherein the mediators transport electrons between the reaction products and the electrode measures amino acid concentrations, and wherein applied voltages at measuring between the first and second electrically conductive surfaces include such an applied voltage that, on a working curve representing the relationship between current value and applied voltage with respect to each of the one or plurality of specified amino acids, the distribution of current value at unchanged applied voltage as to individual amino acids. In other embodiments in which the device, system, and/or bio sensor comprise at least a first and/or second electrode, the first and/or second electrodes are positioned in, substantially adjacent to, or adjacent to at least one vessel in which an indophenol reagent described herein may react with one or more components of the reagents. In some embodiments, ammonia of ammonium ion may be the reaction product of one of the enyxmatic reactions in which the indophenol reaction, using a phenol or phenol related compound, can take place According to at least one exemplary embodiment, an apparatus, device, and/or system for point of care hyperammonemia sensors is disclosed. The apparatus comprises at least a first vessel, or a concavity, a fossa, or any other type of well as desired for the placement of the reagents and sample to be tested. The first vessel may be bifurcated by a membrane disclosed herein or the first vessel may be immediately adjacent to a second vessel in fluid communication with the second vessel via a fluid exchange opening. In some embodiments, a membrane is positioned at the fluid exchange opening. In some embodiments, the membrane is capable of transporting ions from the first vessel to the second vessel or vice versa. In some embodiments, the membrane is a cation exchange membrane filter, such as Nafion® or similar membrane comprising perfluorinated ionomers. The membrane allows the passage of ammonia between the two vessels or between the two bifurcated sections of the at least first vessel. Anion exchange membranes may also be used, as well as various polymeric hydrogels such as acrylamide, poly(ethylene glycol) diacrylate, poly(2-hydroxylethylmethacrylate), or poly(vinyl alcohol).

Other exemplary embodiments may include methods and mechanisms for quantitative analysis of ammonia or ammonium ion concentration in a sample by contacting a sample to a vessel comprising at least one indophenol reagent and/or a basic buffer, in either a solid or liquid phase, a section of the vessel exposed to at least a portion of a membrane disclosed herein. In some embodiments, the method comprises detecting or quantitating the intensity of a color change within at least the first or second vessel before and after addition of a sample to the vessel or vessel. In some embodiments, the method comprises contacting sample to at least a first vessel, a section or portion exposed or covered by at least one membrane disclosed herein, such vessel also optionally comprising at least one indophenol reagent disclosed herein and/or a basic buffer, either in solid or liquid phase. In some embodiments, if the at least first vessel comprises a buffer, the buffer may be an alkali solution such as sodium acetate or calcium acetate. In some embodiments, the disclosure relates to a method of contacting a sample to the device, biosensor or system disclosed herein comprising at least a first and second vessel, said method comprises contacting or exposing the sample to the basic buffer in the at least first vessel, allowing ammonia from the sample to transfer to the second vessel comprising the indophenol reagents disclosed herein. In some embodiments, the disclosure relates to a method of contacting a sample to the device, biosensor or system disclosed herein comprising at least a first and second vessel, said method comprises contacting or exposing the sample to the alkali solution in the at least first vessel, allowing ammonia from the sample to transfer to the second vessel comprising the indophenol reagents disclosed herein, the second vessel comprising one or a plurality of indophenol reactants, which after coming incontact with the ammonia produce a indephenol or indophenol related compound, In some embodiments, the contents of the second vessel are exposed to light measure absorbance of light by indophenol compound or indophenol related compound at specific visible wavelengths of light, the absorbance is indicative of or proportionate to a quantity of ammonia or ammonium ion in the sample and whose absorbance is detected by an individual performing the test or by a device that measures wavelengths which is incorporated in the device, biosensor, or system disclosed herein. In some embodiments, the method comprises comparing the absorbance of the color or wavelength to a standard which indicates the degree or severity of a hyperammonemia. In some embodiments, the method comprises contacting a sample to a device, biosensor, or system disclosed comprising a diode, photodiode, and/or spectrophotometer or other device capable of measuring the absorbance of wavelength by the indophenol or indophenol related compounds produced as a product of an indophenol reaction within the device and exposed to a light. In some embodiments, the device, biosensor, and/or system comprise a microfluidic circuit that comprises at least one conduit configured to receive the sample from a point external to the device, biosensor, and/or system, such microfluidic circuit comprises a conduit or series of conduits in fluid communication with at least the first and/or second vessel and the one or combination of: a spectrophotometer, diode, or other device capable of measuring the absorbance of specific wavelengths by the indophenol or indophenol related compound upon its exposure to light.

In some embodiments, the disclosure relates to contacting or exposing a sample with an alkali buffer and/or a membrane disclosed herein within a vessel attached to an electrode able to measure the electron flow produced by indophenol or an indophenol related compound or redox transformation of the metabolite being analyzed. The concentration of ammonia and or ammonium ion and/or metabolite in blood correlates with the electron flow or current measurements on the circuit that comprise the at least one electrically conductive surfaces. The disclosure relates to the reduction to practice of this concept, showing how to select the metabolite, how to choose an immobilized enzyme, how to do the immobilization (what polymer, what additives, etc), how to attach the components to the electrode, how to make a measurement and how do develop a prototype. This disclosure is used to measure ammonia or ammoniu ion and/or metabolites in blood of patients in real time. Aside from the sensor disclosed herein, there are no known sensors able to measure the proposed metabolites in real time.

The disclosure also relates to a device or system comprising at least one electrically conductive surface (such as an electrode) operably connected to a diode, a spectrophotometer, voltmeter and/or amperometer, the electrode comprises components that, when combined and in the presence of an ammonia, cause a indophenol reaction. The indophenol reaction product comprises a molecule that emits a visible or known wavelength after exposure to light. In some embodiments, the device and system disclosed herein comprise a diode, such as a photodiode, which emits light into the vessel comprising the indophenol reaction product thereby exciting the reaction product and causing the reaction product to emit a visible or known wavelength. In some embodiments, the device and system disclosed herein comprise a spectrophotometer that detects and/or quantitates the intensity of the visible or known wavelength of light emitted by the indophenol reaction product.

The disclosure also relates to a device and/or system that detects and quantifies amino acids. In some embodiments, the device and/or systems comprise a vessel or well that comprises a metabolic enzyme disclosed herein or a functional fragment thereof. In some embodiments, the enzyme or fragment thereof is immobilized to the vessel into which sample is initially place in the device, bio sensor, system, test strip, or cartridge. After contact with a sample, the enzyme or functional fragment thereof releases at least one or a series of electrons and ammonia, such that ammonia is free in solution and capable of moving between a first vessel to a second vessel through a membrane disclosed herein. In some embodiments, the device comprises at least a first and second electrically conductive surface, wherein the first electrically conductive surface comprises a hydrogel comprising an enzyme disclosed herein and the second electrically conductive surface does not comprise a hydrogel or an enzyme; wherein a voltmeter and/or amperometer are configured in a circuit such that the voltmeter can detect a voltage differential between the first and second electrodes in the presence of an amino acid and/or wherein the amperometer can detect an increased current in the first electrode as compared to the second electrode in the presence of an amino acid. The at least one or a series of electrons are released after one or more enzymes within the hydrogel catalyzes the oxidation of the amino acid in a bodily sample in the presence of the one or more amino acids.

Hydrogel formulations are used to entrap one or more enzymes (that utilizes the metabolite/analyte as a specific substrate for its reaction) along with, in some embodiments, a requisite cofactor in close proximity to the at least first electrode surface, with the hydrogel providing a simultaneous exclusion of interfering ions and macromolecules (contained within the patient's blood sample) from the electrode sensor. The coated electrode is contained within a electrochemical detection device capable of converting redox equivalents generated by the enzyme reaction into electron flow which in turn is measured as a current or voltage differential. Analyte concentration is derived using a calibration curve that correlates amperage or voltage differential to concentration of amino acid in the sample of bodily fluid. In one embodiment, a small volume of whole blood is applied to or ammonia from the whole blood diffuses to a vessel exposed to the electrode and the result is reported within minutes of the application or contact to the electrode. Depending on the exact analyte, specific enzyme(s) and cofactor(s) are incorporated into the electrode in order to achieve analyte-specific reaction and response. For example, to detect elevated phenylalanine, the enzyme phenylalanine dehydrogenase is immobilized to the at least one electrically conductive surface optionally contained within a hydrogel.

The disclosure provides a method of sorting a mixture of samples of bodily fluid comprising: contacting a plurality of bodily fluid samples to a device or system disclosed herein. In some embodiments, the method of sorting or cataloguing a mixture of samples of bodily fluid further comprises the step of determining one or more concentrations of ammonia, ammonium ion, and/or amino acid in the bodily fluid sample, if in respect to the ammonia or ammonium ion concentration, based upon the presence or quantity of indophenol reaction products in one or more vessels or a current value or voltage differential value measured by the device; and, if in respect to determining one or more concentrations of amino acid in solution, based upon a current value or voltage differential value measured by the device. In some embodiments, the method further comprises the step of comparing the one or more concentration of ammonia, ammonium ion, and/or amino acid in a sample of bodily fluid with one or more concentrations of ammonia, ammonium ion, and/or amino acid in sample of bodily fluid obtained from subject who does not have or is not suspected of having one or more aminoacidopathies or hyperammonemia, and cataloging, compiling, or identifying whether a sample of bodily fluid from a subject has an aminoacidopathy and/or hyperammonemia based upon their similarities or differences in concentration value to a sample of bodily fluid from a subject without an aminoacidopathy and/or hyperammonemia. The disclosure provides a method of diagnosing a subject with an hyperammonemia comprising: contacting at least one sample of bodily fluid from the subject to a device or system disclosed herein. In some embodiments, the method of diagnosing further comprises the step of determining one or more concentrations of ammonia and/or ammonium ion in a bodily fluid sample based upon a current value, voltage differential value, or a presence or absence of a wavelength of light emitted by an indophenol reaction product, indophenol or an indophenol related compound. In each case, the device and or system disclosed herein detects and/or measures such values. In some embodiments, the method further comprises the step of comparing the one or more concentration of ammonia, ammonium ion, and/or amino acid in the one or more samples from the subject with one or more concentrations of amino acids in sample of bodily fluid obtained from subject who does not have or is not suspected of having one or more aminoacidopathies and/or hyperammonemia, identifying whether a sample of bodily fluid from a subject has an aminoacidopathy and or hyperammonemia based upon their similarities or differences in concentration value to the sample of bodily fluid from a subject without an aminoacidopathy and/or hyperammonemia.

The disclosure also provides a method of monitoring the concentrations of ammonia or ammonium ion in subject over time in a sample of bodily fluid from a subject diagnosed or suspected as having hyperammonemia, the method comprising: contacting one or more samples of bodily fluid from a subject to a device or system disclosed herein and measuring the concentration of ammonia or ammonium ion of bodily fluid from the subject at one time point and performing a repeating of the measurement at least once at a different time point. In some embodiments, the method of monitoring the concentrations of ammonia or ammonium ion in subject over time in a sample of bodily fluid from a subject diagnosed or suspected as having hyperammonemia further comprises the step of cataloguing the concentration values of the ammonia or ammonium ion over time. In some embodiments, the method further comprises the step of comparing the one or more concentration of amino acids from the plurality of samples of bodily fluid from the subject over time and, optionally notifying a subject if the concentration of one or more ammonia or ammonium ion reaches or exceeds or drops below a threshold value that requires medical treatment or modification of diet.

In some embodiments, samples of bodily fluid are isolated from a subject having been diagnosed with or suspected as having hyperammonemia. For example, in some embodiments, a sample of bodily fluid such as a urine sample or a blood sample is isolated from the subject. The sample of bodily fluid is contacted to at least one electrode comprising at least one enzyme disclosed herein and the amino acid concentration in the sample of bodily fluid is measured based upon the magnitude of the voltage differential or current detected by the device comprising the at least one electrode. In further embodiments, method of the present disclosure comprises contacting a sample of bodily fluid to at least one electrode comprising an immobilized enzyme disclosed herein, measuring the current or voltage difference between the at least one electrode and an electrically conductive surface that does not comprise an immobilized enzyme disclosed herein, determining the concentration of one or more amino acids in the sample of bodily fluid, and optionally, providing a readout of one or more concentration values to a subject from which the sample of bodily fluid was obtained. In further embodiments, method of detecting ammonia or ammonium ion comprises contacting a sample of bodily fluid to at least one vessel comprising an hyohalite, an aqueous basic solution, and at least one compound comprising a phenyl group disclosed herein, measuring the current or voltage difference between the at least one electrode and an electrically conductive surface that does not comprise an immobilized enzyme disclosed herein, determining the concentration of ammonia or ammonium ion in the sample of bodily fluid, and optionally, providing a readout of one or more concentration values to a subject from which the sample of bodily fluid was obtained.

In some embodiments, the present disclosure provides methods comprising contacting a sample of bodily fluid from a subject to an aqueous basic solution or a basic buffer in a dried or powdered phase, exposing the sample to hyohalite and at least one compound comprising a phenyl group in the presence (or absence—to establish a control value) of a membrane comprising an ionomer, and optionally contacting a gel. In some embodiments, the gel is a hydrogel comprising alginate. In some embodiments, the present disclosure provides methods comprising detecting presence or level ammonia or ammonium ion in a sample of bodily fluid between cells in the sample. In some embodiments, provided methods comprise determining that a particular set of detected interactions defines an threshold value (or control value) that is characteristic of an increased severity of hyperammonemia in that it distinguishes them from elevated or non-elevated amino acid levels in another sample of bodily fluid from the subject or from a sample of bodily fluid that is a reference or control sample such that, if the threshold value is reached, the device or system disclosed herein provides the subject with a signal or notification that treatment or diet modification should be sought. In some embodiments, the step of detecting comprises detecting presence or level of ammonia or ammonium ion concentrations in a sample of bodily fluid that is characteristic of particular severity of disease in the sample in that it distinguishes them from a sample of bodily fluid that is a reference or control sample.

In some embodiments, the step of detecting comprises detecting presence or level of ammonia or ammonium ion concentrations in a sample of bodily fluid that is characteristic of particular severity of disease in the sample in that it distinguishes them from a sample of bodily fluid that is a reference or control sample.

In some embodiments, any of the methods disclosed herein do not comprise pre-treating the sample of bodily fluid prior to contacting the sample with the test strip, conduit, biosensor, and/or at least one electrically conductive surface. In some embodiments, any of the methods disclosed herein do not comprise using at step of treating the sample with liquid chromatography, gas chromatography, and/or electrophoresis before, simultaneously with or after contacting the sample to the test strip, conduit, biosensor, and/or at least one electrically conductive surface. In some embodiments, any of the methods disclosed herein comprise contacting the sample to at least one electrode that does not comprise an enzyme obtained from an organism other than a bacteria or a plant.

The disclosure relates to methods of detecting the levels of ammonia or ammonium ion in whole blood by exposing a whole blood sample to one of the biosensors, systems, or devices disclosed herein. The disclosure also relates to manufacturing a biosensor disclosed herein by treating the membrane with one, two, three or more washes of an acidic solution prior to placement of the membrane at a fluid exchange opening or at a vessel. The disclosure relates to manufacturing a biosensor disclosed herein by treating the membrane with one, two, three or more washes of an acidic solution from about 0.1 M to about 1 M $H_2SO_4$ prior to placement of the membrane at a fluid exchange opening or at a vessel. The disclosure also relates to manufacturing a biosensor disclosed herein by treating the membrane with one, two, three or more washes of an hydrogen peroxide solution from about 0.1 M to about 1 M $H_2O_2$ prior to placement of the membrane at a fluid exchange opening or at a vessel. The disclosure relates to manufacturing a biosensor disclosed herein by treating the membrane with one, two, three or more washes of an acid solution and/or a hydrogen peroxide solution prior to placement of the membrane at a fluid exchange opening or at a vessel. The disclosure also relates to manufacturing a biosensor disclosed herein by treating the membrane with one, two, three or more washes of an acid solution from about 0.1 M to about 1 M $H_2O_2$ prior to placement of the membrane at a fluid exchange opening or at a vessel. The disclosure also relates to manufacturing a biosensor disclosed herein by treating the membrane with one, two, three or more of an acid solution comprising from about 0.1 M to about 1 M $H_2SO_4$ and with one, two, three or more washes of an hydrogen peroxide solution comprising from about 0.1 M to about 1 M $H_2O_2$ prior to placement of the membrane at a fluid exchange opening or at a vessel.

In some embodiments, the present disclosure provides a system comprising one or more devices disclosed herein optionally in operable connection to a electronic storage medium that compiles ammonia or ammonium ion and/or amino acid concentration values of a subject. In some embodiments, the electronic storage medium comprises compiled amino acid concentration values of a subject over time. In some embodiments, the system comprises at least one electrically conductive surface that comprises an enzyme disclosed herein, a mediator, and optionally a gel or hydrogel. In some embodiments, the system comprises an electronic circuit that is in operable connection to the at least one electrodes and a diode, spectrophotometer, voltmeter and/or amperometer. In the case of a diode and/or spectrophotometer, the diode or spectrophotometer detect and wavelength of light emitted from the at least one vessel. In the case of the voltmeter and/or amperometer, the voltmeter and/or amperometer measures the respective voltage and/or amperage of the circuit across the at least one electrode when the at least one electrode is in the presence of one or more amino acids and/or ammonia concentrations. In some embodiments, system comprising one or more devices disclosed herein optionally in operable connection to a electronic storage medium that compiles amino acid concentration values of a subject determines one or a plurality of concentration values of ammonia concentration values and/ or amino acids in a sample of bodily fluid when the sample of bodily fluid is in contact with the at least one electrode and under conditions and for a time sufficient for for the indophenol reaction to take place or the one or more enzymes disclosed herein to oxidize its amino acid substrate, create a voltage differential or current change in the circuit and the device to display the concentration value on one or more displays. In some embodiments, the device, system, and/or biosensor do not comprises one or more electrodes.

In some embodiments, the disclosure provides for a method comprising steps of: contacting a sample comprising cells with an electrode. The disclosure further provides for a method comprising steps of: contacting a sample under conditions and for a time sufficient for a set of interactions to occur between ammonia in a sample and the membrane described herein. The disclosure further provides for a method comprising steps of: contacting a whole blood sample under conditions and for a time sufficient for a set of interactions to occur between ammonia in a sample and the membrane described herein. The disclosure further provides for a method comprising steps of: contacting a sample comprising bodily fluid under conditions and for a time sufficient for a set of interactions to occur between the ammonia in the sample and the one or plurality of indophenol reaction reagents described herein.

The disclosure relates to a biosensor comprising: at least one electrically conductive support, the electrically conductive support attached to a hydrogel, the hydrogel comprising at least one electron mediator, at least one reduction agent, and at least one metabolic enzyme or functional fragment thereof, wherein the hydrogel comprises alginate; and an amperometer and/or voltmeter operably connected to the at least one electrically conductive support or surface.

In some embodiments, the biosensor comprises at least three electrically conductive supports. In some embodiments, the at least one electrically conductive support is a silver and silver chloride wire. In some embodiments, the at least one electrically conductive support comprises at least one or a combination of metabolic enzymes chosen from: leucine dehydrogenase, tyrosine dehydrogenase, phenylalanine dehydrogenase, leucine oxidoreductase, tyrosine monooxygenase, alanine dehydrogenase, or glutamate dehydrogenase; or functional fragments thereof. In some embodiments, the biosensor comprises at least a first and a second electrically conductive support, wherein the first electrically conductive support is attached to a hydrogel, the hydrogel comprising at least one electron mediator, at least one reduction agent, and at least one metabolic enzyme or functional fragment thereof, wherein said first and second electrically conductive supports being operably connected to said voltmeter and/or amperometer to apply a voltage therebetween.

In some embodiments, the at least one electrically conductive support comprises an electronegative or anionic chemical component. In some embodiments, the at least one hydrogel comprises trehalose. In some embodiments, the biosensor does not comprise one or more of the following: (i) uricase or a functional fragment thereof; (ii) a hydrogel comprising dextran or a derivative thereof; (iii) a bacterial cell; (iv) an electronic dipole configured for electrophoresis; and (v) 3, 4-DHB. In some embodiments, the biosensor is at least 70% biologically active after about sixteen days in storage at 4 degrees Celsius. In some embodiments, the biosensor is at least 70% biologically active after about thirty days in storage at 4 degrees Celsius. In some embodiments, the biosensor is at least 80% biologically active after about thirty days in storage at 4 degrees Celsius In some embodiments, the biosensor is at least 90% biologically active after about thirty days in storage at 4 degrees Celsius In some embodiments, the biosensor is at least 95% biologically active after about thirty days in storage at 4 degrees Celsius. In some embodiments, the biosensor is not functionally dependent upon exposure to UV light or addition of any stimulus external to the biosensor. In some embodiments, the at least one enzyme or functional fragment thereof is derived from a bacterial species and is immobilized in the hydrogel. In some embodiments, the at least one enzyme or functional fragment thereof is derived from a thermophilic bacterial species and is immobilized in the hydrogel. In some embodiments, the at least one enzyme or functional fragment thereof comprises at least about 70% sequence identity to SEQ ID NO:1 or SEQ ID NO:2.

In some embodiments, the disclosure relates to a biosensor, device, or system disclosed herein comprise a circuit comprising at least a first and second electrode in electric communication to at least one or a combination of a diode, photodiode, spectrophotometer, or other device capable of measuring the presence, absence, or intensity of light emitted by an amount of indophenol or indophenol relate compound exposed to light. In some embodiments the circuit comprises a wire. In some embodiments, the wire comprises silver and silver chloride in operable connection to the voltmeter and/or amperometer.

In some embodiments, the biosensor, device, and/or system disclosed herein comprises a membrane optionally comprising alginate comprises a block polymer with a formula

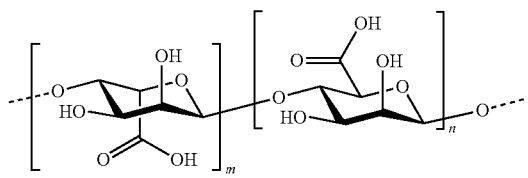

wherein m and n are any positive integer.

In some embodiments, the biosensor the at least one electrically conductive support is not covered by a membrane comprising cellulose or a derivative thereof. In some embodiments, the at least one electron mediator is selected from: thionine, o-phenylenediamine, methylene blue, and toluidine blue. In some embodiments, the at least one reduction agent is chosen from: NAD+ or FAD+.

The disclosure also relates to a biosensor comprising: at least one electrically conductive support, the electrically conductive support attached to at least one hydrogel, the hydrogel comprising at least one electron mediator, at least one reduction agent, and at least one metabolic enzyme or functional fragment thereof; wherein the at least one enzyme or functional fragment thereof is at least 70% homologous to a phenylalanine dehydrogenase from *Geobacillus thermoglucosidiasus*; and an amperometer and/or voltmeter operably connected to the at least one electrically conductive support. In some embodiments, the enzyme or functional fragment thereof is at least 70%, 80%, 85%, 90%, 95%, 96%, 97%, 98%, 99% homologous to SEQ ID NO:1 or at least 70%, 80%, 85%, 90%, 95%, 96%, 97%, 98%, 99% homologous to a functional fragment of SEQ ID NO:1. In some embodiments, the enzyme or functional fragment thereof is not derived from a species other than a bacterial cell. In some embodiments, the enzyme or functional fragment thereof is at least 70%, 80%, 85%, 90%, 95%, 96%, 97%, 98%, 99% homologous to SEQ ID NO:2 or at least 70%, 80%, 85%, 90%, 95%, 96%, 97%, 98%, 99% homologous to a functional fragment of SEQ ID NO:2.

The disclosure relates to a system comprising a bio sensor comprising at least a first and second vessel; a fluid exchange opening positioned between the at least first and second vessel; at least one conduit in fluid communication with the at least first vessel, the at least one conduit configured to receive a fluid from a point external to the biosensor; and a membrane positioned at the fluid exchange opening; wherein the membrane comprises an ionomer, and wherein the first vessel or the second vessel comprise, individually or in combination: hyohalite, an aqueous basic solution, and at least one compound comprising a phenyl group.

The disclosure also relates to a system comprising a biosensor disclosed herein optionally comprising an electric circuit comprising any one or combination of: a diode (such as a photodiode), a spectrophotometer, an amperometer and/or voltmeter operably connected to the at least one electrically conductive support or surface; wherein the bio sensor is in operable connection to at least one computer storage memory. In some embodiments, the system further comprises a sample of bodily fluid, such as whole blood. In some embodiments, the system further comprises a digital display in operable connection to the at least one electrically conductive support (or surface) by an electrical circuit capable of carrying an a electrical signal corresponding to a measurement of current and/or voltage differential from the diode, a spectrophotometer, voltmeter and/or amperometer to the digital display, wherein the digital display is a configured to display one or more concentration values of ammonia or ammonium ion and/or an amino acid in a sample over time when the at least one electrically conductive support (or surface) is in contact with the sample for a time period sufficient for the indophenol reaction to take place.

In some embodiments, the system further comprises a computer processor in operable connection with the at least one computer storage memory. In some embodiments, the metabolic enzyme is a phenylalanine dehydrogenase immobilized within the hydrogel and wherein the alginate concentration of the hydrogel is from about 1% to about 3% weight to volume of the total volume attached and/or contacted to the at least one electrically conductive support.

The disclosure also relates to a kit comprising a biosensor comprising a diode, spectrophotometer, voltmeter and/or amperometer and a display configured in an electrical circuit such that, upon contact with at least one removable electrically conductive support, the circuit becomes closed such that the diode, spectrophotometer, voltmeter and/or amperometer are in operable communication with at least one electrically conductive support.

In some embodiments, the kit comprises at least one of the following: a plurality of test strips comprising one or a plurality of vessels configured to receive a sample, such as whole blood, wherein the one or plurality of test strips further comprises at least one conduit in fluid communication with the at least first vessel. In some embodiments, the the kit comprises at least one of the following: a plurality of test strips comprising one or a plurality of vessels configured to receive a sample, such as whole blood, wherein the one or plurality of test strips further comprises at least one conduit in fluid communication with the at least first vessel and, individually or in combination: hyohalite, an aqueous basic solution, and at least one compound comprising a phenyl group. In some embodiments, the kit comprises at least one of the following: a plurality of test strips comprising one or a plurality of vessels configured to receive a sample, such as whole blood, wherein the one or plurality of test strips further comprises at least one conduit in fluid communication with the at least first vessel and a biosensor comprising a membrane disclosed herein. In some embodiments, the kit comprises at least one of the following: a plurality of test strips comprising: one or a plurality of vessels configured to receive a sample, such as whole blood, wherein the one or plurality of test strips further comprises at least one conduit in fluid communication with the at least first vessel; and a biosensor comprising a membrane disclosed herein.

In some embodiments, the membrane comprises a hydrogel layer. In some embodiments, the hydrogel layer comprises alginate. In some embodiments, the a control or reference sample of bodily fluid; a set of data comprising threshold values; and a set of instructions, wherein the set of instructions or the set of data optionally accessible remotely through an electronic medium. In some embodiments, the kit comprises a solid support that comprises at least a first and a second electrode, wherein the first electrode comprises a hydrogel, the hydrogel comprising at least one electron mediator, at least one reduction agent, and at least one metabolic enzyme or functional fragment thereof; and wherein the second electrode is a control or reference electrode. In some embodiments, the kit comprises a test strip comprising a solid support attached to a first and a second electrode described herein.

The disclosure also relates to a method of determining or identifying a concentration of an ammonia or ammonium ion in a sample of bodily fluid comprising: (a) contacting a sample of bodily fluid to: (i) a biosensor comprising at least one electrically conductive support, the electrically conductive support attached to a vessel in fluid communication with a membrane disclosed herein and, optionally an amperometer and/or voltmeter operably connected to the at least one electrically conductive support; or (ii) a system comprising a biosensor comprising: at least one electrically conductive support attached to a vessel in fluid communication with a membrane disclosed herein and, optionally an amperometer and/or voltmeter operably connected to the at least one electrically conductive support; or (iii) a test strip disclosed herein; and/or (b) determining a quantity of ammonia or ammonimum ion in the sample. In some embodiments, the sample of bodily fluid comprises blood or serum from a subject. In some embodiments, the sample consists of whole blood or consists essentially of whole blood.

The disclosure also relates to a method of quantifying a concentration of ammonia and/or an amino acid in a sample of bodily fluid comprising: (a) contacting a sample of bodily fluid to: (i) a biosensor comprising at least one electrically conductive support or surface, the electrically conductive support or surface attached to a hydrogel, the hydrogel comprising at least one electron mediator, at least one reduction agent, and at least one metabolic enzyme or functional fragment thereof, wherein the hydrogel comprises alginate; and an amperometer and/or voltmeter operably connected to the at least one electrically conductive support or surface; or (ii) a system comprising a biosensor comprising: at least one electrically conductive support or surface, the electrically conductive support or surface attached to at least one hydrogel, the hydrogel comprising at least one electron mediator, at least one reduction agent, and at least one metabolic enzyme or functional fragment thereof; wherein the at least one enzyme or functional fragment thereof is at least 70% homologous to a phenylalanine dehydrogenase from *Geobacillus thermoglucosidiasus*; and an amperometer and/or voltmeter operably connected to the at least one electrically conductive support; or (iii) a test strip disclosed herein; or (b) determining a quantity of amino acid in the sample. In some embodiments, the method further comprises comparing a concentration value obtained by the quantifying or identifying steps to a threshold value associated with one or more metabolic diseases.

The disclosure further relates to a method comprising a step of contacting a biosensor, system, or test strip disclosed herein, wherein the step of contacting a sample of bodily fluid of a subject to any of the disclosed biosensors, systems, or test strips comprises contacting the sample for a sufficient period of time to allow ammonia transport through the membrane and to expose the ammonia from the sample to reagents associated with an indophenol reaction. If amino acids are also being tested by the biosensors, systems, or test strips, such methods comprise contacting a sample for a sufficient period of time to allow oxidation of at least one amino acid in the sample of bodily fluid by the metabolic enzyme or functional fragment thereof. In some embodiments, the method does not comprise exposing the sample of bodily fluid to any external stimuli or reagent prior to contacting the sample to the at least one electrically conductive supports. In some embodiments, the method does not comprise exposing the sample of bodily fluid to iron ions and/or hydrozide ions prior to, simultaneously with, or after exposing the sample to the at least one electrode comprising a hydrogel. In some embodiments, the method does not comprise exposing the sample to a non-porous carrier, such as glass beads, contained within the device, test strip or biosensor. In some embodiments, the sample of bodily fluid contains whole blood or serum from a subject. In some embodiments, the sample of bodily fluid does not contain urine. In some embodiments, the sample of bodily fluid does not contain bodily fluid other than whole blood or blood serum.

The disclosure further relates to a method of diagnosing a metabolic disease in a subject comprising: (a) contacting a sample of bodily fluid to one or a combination of: (i) a biosensor comprising at least one electrically conductive support or surface, the electrically conductive support or surface attached to a vessel comprising an amount of indophenol or indophenol related compound; and, optionally an amperometer and/or voltmeter operably connected to the at least one electrically conductive support or surface; or (ii) a system comprising a bio sensor comprising: at least one electrically conductive support or surface, the electrically conductive support or surface exposed to the at least first vessel or second vessel comprising the indophenol and/or indophenol related compounds; and an amperometer and/or voltmeter operably connected to the at least one electrically conductive support; or (iii) a test strip disclosed herein; (b) quantifying one or more concentration values of ammonia or ammonium ion in the sample; (c) comparing the one or more concentration values of ammonia or ammonium ion in the sample to a threshold value of ammonia or ammonium ion concentration identified as being in a healthy range or not within a range or concentration indicative of hyerammonemia; and (d) identifying the subject as having hyperammonemia or a metabolic disease related to hyperammonemia if the one or more concentration values of amino acids in the sample exceed or fall below the threshold value. In some embodiments, the metabolic disease is a hyperammonemia related disorder.

The disclosure also relates to a method of determining patient responsiveness to a therapy comprising: (a) contacting a sample of bodily fluid to one or a combination of: (i) a bio sensor comprising at least one electrically conductive support or surface, the electrically conductive support or surface attached to a vessel comprising an amount of indophenol or indophenol related compound; and, optionally an amperometer and/or voltmeter operably connected to the at least one electrically conductive support or surface; or (ii) a system comprising a bio sensor comprising: at least one electrically conductive support or surface, the electrically conductive support or surface exposed to the at least first vessel or second vessel comprising the indophenol and/or indophenol related compounds; and an amperometer and/or voltmeter operably connected to the at least one electrically conductive support; or (iii) a test strip disclosed herein; (b) quantifying one or more concentration values of ammonia or ammonium ion in the sample; (c) comparing the one or more concentration values of ammonia or ammonium ion in the sample to a threshold value of ammonia or ammonium ion concentration identified as being in a healthy range or not within a range or concentration indicative of hyerammonemia; and (d) identifying the subject as having hyperammonemia or a metabolic disease related to hyperammonemia if the one or more concentration values of amino acids in the sample exceed or fall below the threshold value.

The disclosure also relates to a test strip comprising a solid support and at least a first and a second electrode attached to the solid support, wherein the first electrode comprises a membrane, the membrane comprising a perfluorinated ionomer. In some embodiments, the test strip is adapted for a portable device comprising: a diode, spectrophotometer, voltmeter and/or amperometer; and a digital display such that, when the test strip is contacted to the device, the first and second electrodes become operably connected to a closed electrical circuit comprising diode, spectrophotometer, voltmeter and/or amperometer and the digital display, and, upon contact with light emitted from an indophenol or indophenol related compound, resulting in a current on the first electrode corresponding to a concentration value of amino acid in the sample of bodily fluid, such concentration value readable on the display of the portable device. In some embodiments, the test strip comprises the at least one or combination of indophenol reagents in solid or liquid phase optionally separated from but in fluid communication with a conduit, volume, or space the at least first vessel.

The disclosure also relates to a method of manufacturing any of the disclosed biosensors, test strips, systems disclosed herein that comprises at least one electrode, the method comprising: contacting the at least one electrode with a solution comprising at least one vessel, at least one conduit in fluid communication with the at least one vessel, and at least one indophenol reagent; subsequently contacting the at least one electrode with a basic buffer with a Na+, Ca+, Cl−, and/or acetate concentration at or below about 1 M.

BRIEF DESCRIPTION OF THE DRAWINGS

Advantages of embodiments of the present invention will be apparent from the following detailed description of the exemplary embodiments. The following detailed description should be considered in conjunction with the accompanying figures in which.

DETAILED DESCRIPTION OF THE DISCLOSURE

Figure 1:
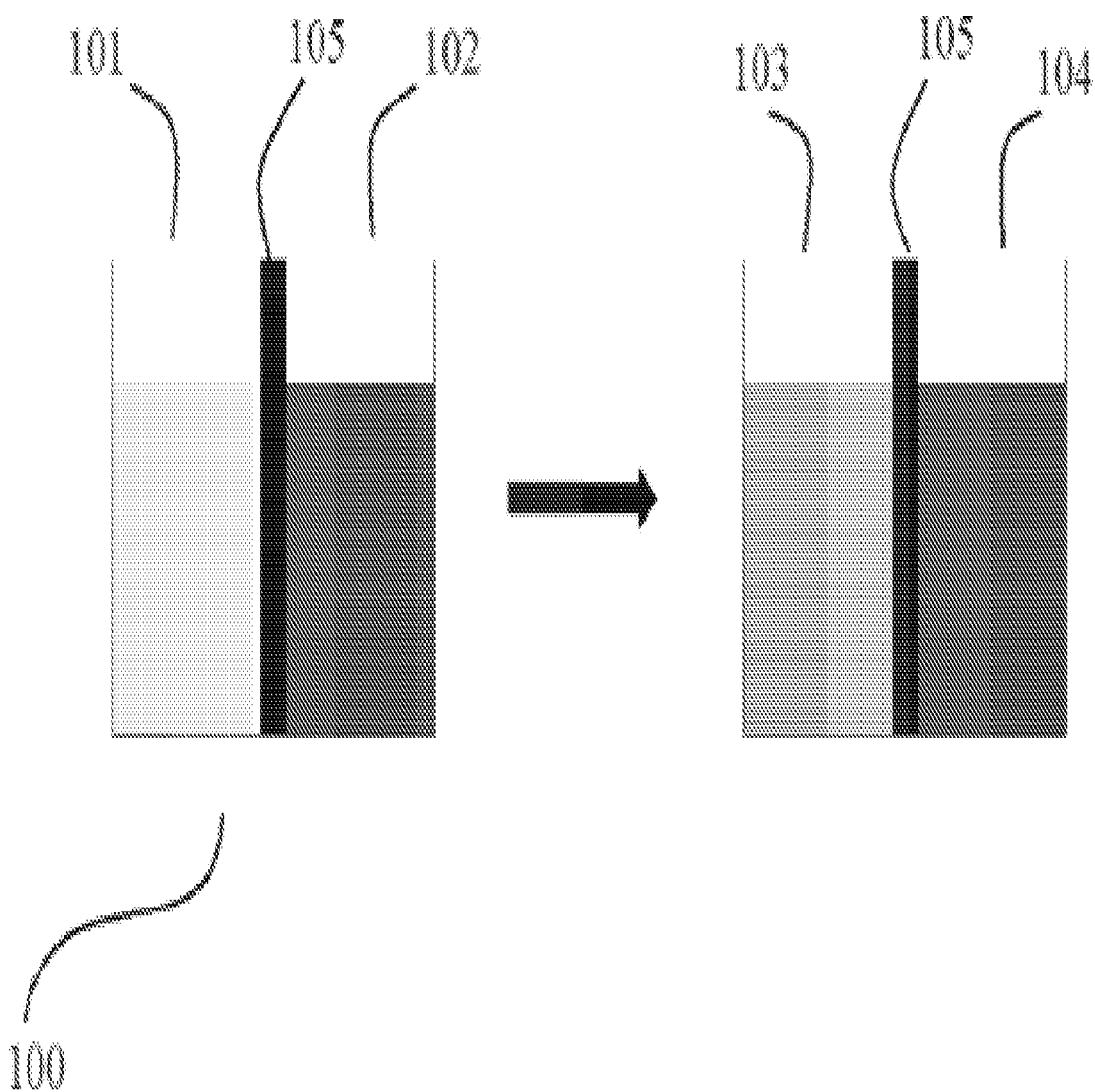
FIG. 1 is an exemplary view of a system having the ability to detect ammonia or ammonium ion levels in a given sample applied to a first and second vessel separated by a membrane positioned at an fluid exchange opening.

Various terms relating to the methods and other aspects of the present disclosure are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the terms "attach," "attachment," "adhere," "adhered," "adherent," or like terms generally refer to immobilizing or fixing, for example, a group, a compound or enzyme, to a surface, such as by physical absorption, chemical bonding, and like processes, or combinations thereof.

As used herein, the terms "biopsy" means a cell sample, collection of cells, or bodily fluid removed from a subject or patient for analysis. In some embodiments, the biopsy is a bone marrow biopsy, punch biopsy, endoscopic biopsy, needle biopsy, shave biopsy, incisional biopsy, excisional biopsy, or surgical resection.

As used herein, the terms "bodily fluid" means any fluid from a isolated from a subject including, but not necessarily limited to, blood sample, serum sample, a whole blood sample, urine sample, mucus sample, saliva sample, and sweat sample. The sample may be obtained from a subject by any means such as intravenous puncture, biopsy, swab, capillary draw, lancet, needle aspiration, collection by simple capture of excreted fluid.

As used herein the terms "electronic medium" mean any physical storage employing electronic technology for access, including a hard disk, ROM, EEPROM, RAM, flash memory, nonvolatile memory, or any substantially and functionally equivalent medium. In some embodiments, the software storage may be co-located with the processor implementing an embodiment of the disclosure, or at least a portion of the software storage may be remotely located but accessible when needed.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation. In addition, those skilled in the art may appreciate the wide variations in sizing scales that may be incorporated into the disclosed or related designs for use with samples many orders of magnitude larger or smaller than those disclosed.

As used herein, the term "aminoacidopathy" is meant to refer to those diseases and disorders characterized by dysfunction of a metabolic catalysis of amino acids that results in over production or under production of amino acids in the body of a subject. Examples of aminoaciopathies are listed in the definition of a metabolic disease, terms that are used interchangeably in this application.

As used herein, "sequence identity" is determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). To use the term "homologus to" is synonymous with a measured "sequence identity." In some embodiments, if an embodiment comprises a nucleic acid sequence or amino acid sequence with a percent sequence identity the term refers to a disclosed nucleic acid sequence or amino acid sequence possessing a homology to a disclosed sequence over its entire length.

The term "subject" is used throughout the specification to describe an animal from which a sample of bodily fluid is taken. In some embodiment, the animal is a human. For diagnosis of those conditions which are specific for a specific subject, such as a human being, the term "patient" may be interchangeably used. In some instances in the description of the present disclosure, the term "patient" will refer to human patients suffering from a particular disease or disorder. In some embodiments, the subject may be a human suspected of having or being identified as at risk to develop an aminoacidopathy. In some embodiments, the subject may be diagnosed as having at least one aminoacidopathy. In some embodiments, the subject is suspected of having or has been diagnosed with hyperammonemia. In some embodiments, the subject may be a human suspected of having or being identified as at risk to develop hyperammonemia. In some embodiments, the subject may be a mammal which functions as a source of the isolated sample of bodily fluid. In some embodiments, the subject may be a non-human animal from which a sample of bodily fluid is isolated or provided. The term "mammal" encompasses both humans and non-humans and includes but is not limited to humans, non-human primates, canines, felines, murines, bovines, equines, and porcines.

As used herein, "conservative" amino acid substitutions may be defined as set out in Tables A, B, or C below. Metabolic enzymes include those amino acid sequences wherein conservative substitutions have been introduced by modification of polynucleotides encoding polypeptides disclosed herein. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A.

TABLE A

Conservative Substitutions I

| Side Chain Characteristics | Amino Acid |
|---|---|
| Aliphatic | |
| Non-polar | G A P I L V F |
| Polar - uncharged | C S T M N Q |
| Polar - charged | D E K R |
| Aromatic | H F W Y |
| Other | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | Amino Acid |
|---|---|
| Non-polar (hydrophobic) | |
| Aliphatic: | A L I V P |
| Aromatic: | F W Y |
| Sulfur-containing: | M |
| Borderline: | G Y |

TABLE B-continued

Conservative Substitutions II

| Side Chain Characteristic | Amino Acid |
|---|---|
| Uncharged-polar | |
| Hydroxyl: | S T Y |
| Amides: | N Q |
| Sulfhydryl: | C |
| Borderline: | G Y |
| Positively Charged (Basic): | K R H |
| Negatively Charged (Acidic): | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides comprising polypeptide sequences associated with the extracellular matrix described herein are intended to include polypeptides bearing one or more insertions, deletions, or substitutions, or any combination thereof, of amino acid residues as well as modifications other than insertions, deletions, or substitutions of amino acid residues.

As used herein, the term "prognosing" means determining the probable course and/or outcome of a disease.

As used herein, the term indophenol related compound—a small chemical compound that is a reaction product of an indophenol reaction. In some embodiment, it comprises at least one carbon atom in a 4, 5, 6-membered ring and emits a visible wavelength of light upon excitation of the small chemical compound by light emitted by from light source. In some embodiments, the small chemical compound is a product of the indophenol reaction and emits a wavelength of light visible to the human eye upon excitation of the chemical compound by light emitted from a light source. In some embodiments, the small chemical compound emits a wavelength from about 400 nm to about 600 nm when it is excited by light from a light source. In some embodiments, the biosensor, device, and/or system comprises a light source and at least one diode and/or spectrophotometer, or other device capable of measuring the light emitted by the indophenol or the indophenol related compound.

The term "vessel" as used herein is any chamber, indentation, container, receptacle, or space. In some embodiments, a vessel is a well capable of holding no more than about 1,000, 900, 800, 700, 600, 500, 400, 300, 200, 100, 50, 40, 30, 20, 15, 12, 10, 9, 8, 7, 6, 5, 4, 3, 2, or 1 µL of sample. bodily fluid.

The term "membrane" means any monomer or polymer in a solid phase. In some embodiments, the membrane comprises an ionomer. In some embodiments, the membrane is incapable of gas chromatography.

The terms "point of care" disclosed herein refer to a device, biosensor, system, test strip, or cartridge, either individually or configured to function with one or more additional components, capable of analyzing the presence, absence, or quantity of a reaction product, such as ammonia, and/or a sample component, such as an amino acid, within a time period no more than about 1, 2, 3, 4, 5, 6, 7, 8, 9, 10, 15, 20, 25, or 30 minutes. In some embodiments, the terms refer to a device, biosensor, system, test strip, or cartridge, either individually or configured to function with one or more additional components, capable of analyzing the presence, absence, or quantity of ammonia and/or an amino acid within a time period no more than about 1, 2, 3, 4, 5, 6, 7, 8, 9, 10, 15, 20, 25, or 30 minutes, or capable analyzing the presence, absence, or quantity of ammonia and/or an amino acid at or substantially near the point from which the sample was taken. For instance, in some embodiments, the sample may be taken from a subject suspected of or previously diagnosed with hyperammonemia or a hyperammonemia-related disorder. Without sending and analyzing the ammonia content of a sample to a different location from the source of the sample, in some embodiments, the point of care device or biosensor or system is a point of care device which is capable of detecting the presence, absence, or quantity of ammonia or ammonium ion in a sample.

The term "fluid exchange opening" means any space or void through which a fluid may pass from one vessel to an adjacent vessel or another vessel in fluid communication with the one vessel.

The terms "individually comprise" in respect to a claimed element or elements mean that only one claimed element comprises each of the listed elements and not in combination with any other element named.

The terms "a compound comprising a phenol substituent" means any molecule comprising a phenyl group attached to a 4, 5, 6, or more-membered atomic ring comprising at least one carbon atom.

The term "ionomer" as used herein refers to any polymer comprising an ion. In some embodiments, the ionomer is a perfluorinated ionomer. In some embodiments, the ionomer comprises Formula I or a salt thereof.

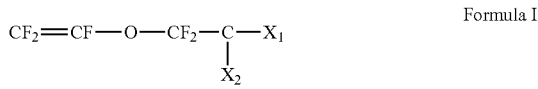

Formula I

Where $X_1=F-O-CF_2-Y$, $F_2-SO_2$, or $F_2-CF_2-CO_2CH_3$
$X_2=CF_3$, or, if $X_1$ is $F_2$, $X_2$ is null
Where $Y=CF_2-SO_2F$, $CF_2-CF-SO_2F$, or $CF_3-CO_2CH_3$
In some embodiments, the ionomer comprises one or a combination of:

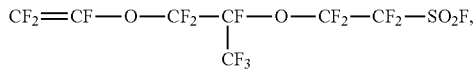

-continued $$CF_2\!=\!CF\!-\!O\!-\!CF_2\!-\!\underset{\underset{CF_3}{|}}{CF}\!-\!O\!-\!CF_2\!-\!CF_2\!-\!CF_2\!-\!SO_2F,$$

$$CF_2\!=\!CF\!-\!O\!-\!CF_2\!-\!\underset{\underset{CF_3}{|}}{CF}\!-\!O\!-\!CF_2\!-\!CF_3\!-\!CO_2CH_3,$$

$$CF_2\!=\!CF\!-\!O\!-\!CF_2\!-\!CF_2\!-\!CF_2\!-\!CO_2CH_3,$$

$$CF_2\!=\!CF\!-\!O\!-\!CF_2\!-\!CF_2\!-\!SO_2F,$$

$$[\!-\!(CF_2\!-\!CF_2)_n\!-\!\underset{\underset{O-\underset{\underset{CF_3}{|}}{CF}\!-\!CF_2\!-\!O\!-\!CF_2\!-\!SO\text{-}_3M^+,}{|}}{CF}\!-\!CF_2\!-\!]_m$$

or a salt thereof, wherein n and m are any positive integer. In some embodiments, n and/or m are 1, 2, 3, 4, 5, 6, 7, 8, 9, or 10 or more. In some embodiments, n and/or m are independently variable and any positive integer from about 1 to about 1000. In some embodiments, n and/or m are independently variable and any positive integer from about 1 to about 500.

The term "bodily fluid" means any sample taken from an animal including a human, or non-human animal.

As used herein, the term "functional fragment" means any portion of a disclosed polypeptide that is of a sufficient length to retain at least partial biological function that is similar to or substantially similar to the function of the wild-type polypeptide upon which the fragment is based. In some embodiments, a functional fragment of a polypeptide associated with the function of a metabolic enzyme is a polypeptide that comprises at least 70%, 75%, 80, 85, 90, 95, 96, 97, 98, or 99% sequence identity of any polypeptides disclosed herein and has sufficient length to retain at least partial binding affinity to one or a plurality of substrates that bind to the polypeptide. In some embodiments, the fragment is a fragment of any polypeptide disclosed herein and has a length of at least about 10, about 20, about 30, about 40, about 50, about 60, about 70, about 80, about 90, or about 100 contiguous amino acids. In some embodiments, the fragment is a fragment of any polypeptide disclosed herein and has a length of at least about 50 amino acids. In some embodiments, the fragment is a fragment of any polypeptide disclosed herein and has a length of at least about 100 amino acids. In some embodiments, the fragment is a fragment of any polypeptide disclosed herein and has a length of at least about 150 amino acids. In some embodiments, the fragment is a fragment of any polypeptide disclosed herein and has a length of at least about 200 amino acids. In some embodiments, the fragment is a fragment of any polypeptide disclosed herein and has a length of at least about 250 amino acids.

As used herein, the terms "polypeptide sequence associated with the metabolic enzyme" means any polypeptide or fragment thereof, modified or unmodified by any macromolecule (such as a sugar molecule or macromolecule), that is a metabolic enzyme as disclosed herein or a functional fragment thereof. In some embodiments the polypeptide sequence is is synthetic or recombinantly produced in any multicellular or unicellular organism. In some embodiments, a polypeptide sequence associated with the extracellular matrix is any polypeptide which sequence comprises any of the polypeptides disclosed in Table 2. In some embodiments, a polypeptide sequence associated with the metabolic enzyme is any polypeptide sequence comprising any of the polypeptides disclosed in Table 2 or a sequence that shares 85, 90, 95, 96, 97, 98, or 99% sequence identity with the polypeptides disclosed in Table 2 or a functional fragment thereof. In some embodiments, a polypeptide sequence associated with the metabolic enzyme consists of any of the polypeptides disclosed in Table 2 or a sequence that shares 85, 90, 95, 96, 97, 98, or 99% sequence identity with the polypeptides disclosed in Table 2.

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts include those formed from hydrochloric, hydrobromic, sulphuric, phosphoric, citric, tartaric, lactic, pyruvic, acetic, succinic, fumaric, maleic, methanesulphonic and benzenesulphonic acids.

In some embodiments, the device, system, membrane, or vessel, may comprise any of the disclosed reagents or formula disclosed herein or any salt. Salts may be formed by reacting the free base, or a salt, enantiomer or racemate thereof, with one or more equivalents of the appropriate acid. In some embodiments, salts of the present invention refer to salts of the disclosed reagents or formula disclosed herein having at least one basic group or at least one basic radical. In some embodiments, salts of the present invention refer to salts of the disclosed reagents or formula disclosed herein having a free amino group, a free guanidino group, a pyrazinyl radical, or a pyridyl radical that forms acid addition salts. In some embodiments, salts of the present invention refer to salts of the disclosed reagents or formula disclosed herein that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. Salts according to the present invention may be found in their anhydrous form or as in hydrated crystalline form (i.e., complexed or crystallized with one or more molecules of water).

As used herein, the term "antibody" refers to any immunoglobulin, whether natural or wholly or partially synthetically produced. In some embodiments, an antibody is a complex comprised of 4 full-length polypeptide chains, each of which includes a variable region and a constant region, e.g., substantially of the structure of an antibody produced in nature by a B cell. In some embodiments, an antibody is a single chain. In some embodiments, an antibody is cameloid. In some embodiments, an antibody is an antibody fragment. In some embodiments, an antibody is chimeric. In some embodiments, an antibody is bi-specific. In some embodiments, an antibody is multi-specific. In some embodiments, an antibody is monoclonal. In some embodiments, an antibody is polyclonal. In some embodiments, an antibody is conjugated (i.e., antibodies conjugated or fused to other proteins, radiolabels, cytotoxins). In some embodiments, an antibody is a human antibody. In some embodiments, an antibody is a mouse antibody. In some embodiments, an antibody is a rabbit antibody. In some embodiments, an antibody is a rat antibody. In some embodiments, an antibody is a donkey antibody. In some embodiments, the biosensor or system described herein comprises an antibody or plurality of antibodies.

Characteristic:

As is used herein, the term "characteristic" refers to any detectable feature of a sample of bodily fluid that allows it to be distinguished from a comparable sample of bodily fluid. In some embodiments, a characteristic is an amount or identity of ammonia or ammonium ion in bodily fluid, in an environmental sample, or water sample. In some embodiments, a characteristic is an amount, sequence of, or modification of a amino acid. In some embodiments a characteristic is an amount of a carbohydrate. In some embodiments, a characteristic is an amount of a small molecule.

Comparable:

As is used herein, the term "comparable" is used to refer to two entities that are sufficiently similar to permit comparison, but differing in at least one feature.

Metabolic Enzyme:

As is used herein, the term "metabolic enzyme" means an enzyme responsible for catalysis of at least one step in the metabolic pathway of one or more amino acids. In some embodiments, the metabolic enzyme is phenylalanine dehydrogenase, glutamate dehydrogenase, respective functional fragments or a combination thereof or a fusion protein thereof.

As used herein the terms "metabolic disease" is any one of a group of disorders caused by a defect in an enzymatic step in the metabolic pathway of one or more amino acids or in a protein mediator necessary for transport of certain amino acids into or out of cells. In some embodiments, the metabolic disease is chosen from: Argininemia (ARG, argi-nase deficiency) Argininosuccinate acidemia (ASA, argini-nosuccinase) Citrullinemia type I (CIT-I, argininosuccinate synthetase) Citrullinemia type II (CIT-II, citrin deficiency) Defects of biopterin cofactor biosynthesis (BIOPT-BS) Defects of biopterin cofactor regeneration (BIOPT-RG) Homocystinuria (HCY, cystathionine beta synthase) Hyperphenylalaninemia (H-PHE) Hypermethioninemia (MET) Maple syrup urine disease (MSUD, branched-chain ketoacid dehydrogenase) Phenylketonuria (PKU, phenylalanine hydroxylase) Tyrosinemia type I (TYR-1, fumarylacetoacetate hydrolase), Tyrosinemia type II (TYR-II, tyrosine aminotransferase), and Tyrosinemia type III (TYR-III, hydroxyphenylpyruvate dioxygenase) where the parenthetical phrases after each disease state represent an abbreviation for the disease accompanies by the enzyme that is generally defective in the subject suffering from the disease state.

Polypeptide:

The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having the complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying or significantly reducing activity. Thus, any polypeptide that retains activity and shares at least about 30-40% overall sequence identity, often greater than about 50%, 60%, 70%, 75%, 80%, or 85%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein.

As used herein, the term "threshold value" is the concentration of ammonia or ammonium ion or amino acid in a sample of bodily fluid that indicates whether the amount of ammonia or ammonium ion or amino acid in the sample is considered abnormally high or low resulting in a diagnosis or suspected diagnosis of a particular disorder, such as a metabolic disease. For instance, in the case of a blood sample, known threshold values for certain aminoacidopathies are indicated in Table 1 below:

TABLE 1

Aminoacidopathies and their associated amino acid markers detectable in a sample

| Disorder | Marker | Abnormal Range |
| --- | --- | --- |
| ARG | Arginine | >100 umol/L |
| ASA | Argininosuccinic acid | >4.0 umol/L |
|  | ASA/Arg | >0.75 |
| CIT-I and CIT-II | Citrulline | >60 umol/L |
|  | Cit/Tyr | >1.0 |
|  | Cit/Arg | >6.0 |
| HCY and MET | Methionine | >70 umol/L |
|  | Met/Phe | >1.2 |
| MSUD | Leucine | >250 umol/L |
|  | Valine | >250 umol/L |
|  | Leu/Phe | >4.0 |
|  | Val/Phe | >3.5 |
| PKU, H-PHE | Phenylalanine | >130 umol/L |
| BIOPT-BS and BIOPT-RG | Phe/Tyr | >2.0 |
| TYR-I, TYR-II, and TYR-III | Tyrosine | >250 umol/L |

In some embodiments, information about a threshold value or reference sample of bodily fluid is obtained prior to or simultaneously with information about an experimental sample of bodily fluid. In some embodiments, information about a reference cell or cell type is historical. In some embodiments, information about a threshold value or reference sample of bodily fluid is stored for example in a computer-readable storage medium. In some embodiments, comparison of a particular concentration value with a threshold value or reference sample of bodily fluid differentiates the concentration values of ammonia in an experimental sample of bodily fluid with the threshold values thereby allowing a comparison that results in diagnosing a subject with one or more metabolic diseases or a change in severity of one or more metabolic diseases.

Reference Electrode:

As will be understood from context, a reference electrode or control electrode is an electrically conductive support such as an electrode placed in a circuit with an at least one electrically conductive support comprising hydrogel and/or immobilized enzymes disclosed herein, to permit a relevant comparison of voltage difference between the reference or control electrode and the at least one electrically conductive support comprising hydrogel and/or immobilized enzymes disclosed herein.

Sample:

As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises bodily fluid. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. in some embodiments, the methods disclosed herein do not comprise a processed sample.

In some embodiments, the system, test strip, device, biosensor, and/or cartridge comprises a concentration of any one or combination of the reagents disclosed on pages 78-84 of this disclosure.

TABLE 2

| Enzyme | Gene Sequence | Accession Numbers |
|---|---|---|
| Phenylalanine Dehydrogenase | ATGGAAATCTTCGAGGAAATCAAACGGCGGGGACACGAGCAAATTCTGTT | AEW06037.1 |
| | CAATTATGATCGGGCTTCCGGTTTGAAAGCAATTATCGCCATTCACAATA | YP_005257709.1 |
| | CTACGTTGGGGCCGGCGTTGGGCGGGTGCCGAATGTTACCGTATCAAACG | AEH47572.1 |
| | GAAGAGGCGGCCCTCGAGGATGCGCTGCGGTTGTCGGAAGGGATGACCTA | YP_004587653.1 |
| | TAAAGCGGCCGCCGCCGGGCTCGATTTCGGCGGGGGCAAAACGGTGATTA | YP_004581770.1 |
| | TCGGGGATCCGATGAAAGACAAGTCCGAGGCCCTGTTTCGTGCGCTCGGG | AEH07849.1 |
| | CGTTTTATCGAGACCTTGAAAGGCCGTTACCTTACGGGAGAAGACGTAGG | ACF96938.1 |
| | AACCAACGAAGAAGATTTTGTCTGGGCTCGTCGGGAAACCCGTTATGTTG | YP_007466124.1 |
| | TCGGATTGCCGCCGGCTTATGGCGGGTCCGGCGATACGGGTGACAATACC | EZP75760.1 |
| | GCGCGCGGCGTCATTCAAGCGATGCGCGCCGCGTTGATGCACCGGTACGG | AGT95551.1 |
| | TTCGCCGGATCTCCAGGGCCGGCGGATTGCCGTCCAAGGGCTGGGCAAAG | EWG09095.1 |
| | TAGGCTATCATGTGGCGCGACGGGCCATCGAGGCCGGCGCTCGAGTGATT | YP_008456272.1 |
| | GCGGCCGATATCAATCCGCATGTAGTCGGCCGAGTGGCGTCCGCTTGGGG | EME23486.1 |
| | GATTGAAGCCACCGATCCGTGGGCTGTGGTGGAAACCCCCTGCGATATTT | EJS99791.1 |
| | TCGCCCCCTGTGCGTTGGGTAACGTCATTACGGAACGGACCGTGTCCGCC | EIT85807.1 |
| | CTCCAATGTCAGGTGGTGGCCGGTTCGGCCAACAATCAGCTGGCGGATGA | AAA22646.1 |
| | TCGACTGGCCGATGATTTAGCTGCCCGCGGCATTCTCTATGCGCCGGATT | EDL64419.1 |
| | TTATTGCGAATGCCGGCGGATTGATTCAGGTGGCGGATGAAATTCGGGGA | EAR66050.1 |
| | TATCATGAAGAACGGGTCCGTCATCAAATAGACGGGATTTATGACGTCCT | BAA08816.1 |
| | GCTCGAGATTTTTCGGAAGGCGGACGCCTCCGGCCGATCAACCGTGGCGG | |
| | TTGCGGTAGACGAGGCGCGTCGCCGTTTGGACACCATTCAGGCCATCCAC | |
| | CGCCTGTACGGATCATAG | |
| Phenylalanine Ammonia-Lyase | CTGCAGGTCAACGGATCATATTCTACACATATATAATGCACTCCAATTGA | AAA34179.2 |
| | CATAATACATAACGTGACATATGATACATTTATTAATATTAATTGTCACA | ADR78835.1 |
| | TTTACACTTCACATATTAAAATACTCTCGTATGAATGCAATTTGAAACAT | AAA99500.1 |
| | ATTTTAAATTAATTGATTGATATATATTGAACAAAACCTATTCACAAAGA | AAC18871.1 |
| | AACTTTCTTCTATTTCTCACTTATTTCTGCTAGTGTCTTTCCTATTCAAA | AAC18870.1 |
| | GCCATCATTTCCATCAACCTTCACAATACCATGTTTAAAAAGTCATTAAA | AAA33805.1 |
| | AATCAATTTTTTAAATAGAAAAAAACAAGAAGATGGAAATCACTTGGTTG | AIC66437.1 |
| | GTACTATATATTTAGTTGTTAAGTTTGACTCATACCGTGTATTGACCAAT | AGY49231.1 |
| | ATAAATAAAATCTTATTTCAAATAAATTCAAAAGTTCAATAAATATATAT | AEW43005.1 |
| | TCGTTCATAACTTATAATAAAATTGATTATACATAGTCCTCCCCCATTCA | AFP24940.1 |
| | CTTTTACTGATCAATTATTTCTAAAATATATTATTACTTTTACTTGTTAT | AER58180.1 |
| | TTTTAATAAATTAAGAAAATATAATACTCCCTTCGTTTTTAAAAAAATAC | ADD12041.1 |
| | CTAGTTTGACTTGAAACGGAGTTTAATAAAAGAAAGAAGACTTGTTAATC | AEE81750.1 |
| | TTGTGATTCTAAATTAAAGTTATGTCAAATGTACCAAAATGTCCTTTAAT | AAP59440.1 |
| | CTTGTGGTCTTAAACATGTCACATGAAAAATTAAAGTGTTTCCAAAAAAA | AAP59439.1 |
| | GAAAGGGGTCAATGTCATTCTTTTTAAACAGACTAAAAAAGAAATAAAC | AAP59438.1 |
| | TCATTCTTTTTGAAACGGAGAGAGTAATTTTTTCCACGTTTTACTCATTA | ACG80829.1 |
| | ATATTAAATATTATTCTCTAGATCATCCTATAAGATCTAATAGTGGACAT | ACG80828.1 |
| | CAATTAATACCTATGTCACTTATTATTATTTTAATAATTGTATCAAGTCA | ACG56648.1 |
| | AATAATAACAAGTAAAAATGGAGTACCTACTATTAATCTTCAACAACCAC | ACG56647.1 |
| | AATTTACTAGTTTTTTCCTAGCAACCCCCTCTCACATATTTCACCATTTA | |
| | CTGGTTTTTTCCTAGCAACCCCCTCTCACATATTTTGTTTACCAACCATC | |
| | ATTTGTTCCTCTATATACTCACCACATGATAGATACATATATATACCACA | |
| | ACCAAAACAAAGGTTTTATAAGTTCACAACATTTTTTATATACATACAA | |
| | ATAAACTCTAACCATTTTCTCTTCACTAAAAATTTCTTCATTACAAATCT | |
| | AACAATTTACTTGATCCAATGGCACCATCAATTGCACAAAATGGACATAT | |
| | TAATGGAGAAGTAGCTATGGATTTGTGCAAGAAATCAATCAATGATCCAT | |

TABLE 2-continued

| Enzyme | Gene Sequence | Accession Numbers |
|---|---|---|
| | TGAATTGGGAAATGGCTGCTGATTCTTTAAGAGGCAGCCATTTGGATGAA<br>GTGAAAAAGATGGTGGATGAATTTAGAAAGCCAATTGTGAAACTTGGGG<br>TGAAACTTTGTCAGTTGCACAAGTTGCATCCATTGCAAATGTTGATGACA<br>AAAGTAATGGGGTTAAAGTGGAACTTTCTGAAAGTGCAAGGGCTGGTGTG<br>AAAGCTAGTAGTGATTGGGTTATGGATAGTATGAGTAAAGGTACAGATAG<br>TTATGGTGTTACTGCTGGATTTGGAGCAACATCTCATAGAAGAACAAAAA<br>ATGGTGGTGCTCTTCAAAAAGAACTTATTAGGTAAACAAACTATTTTTTT<br>TCGTTATATATACTAACAATGTAAAGAATTTAATATTTTTTGTTATATA<br>TACTAACAATGTAAAAAATTTAATATTTTTTGTTATATATACTAACAAT<br>GTAAGAATTTAATATTTTTTGTTATACATAGCTTATCGACTACTTAAGT<br>GCTCCATTGATAAAGATTTTTTTTGTTTTTACGCGAAGGGGATTCGGAT<br>GAATTCAGTTAAAATGTGATCTTAATGAATTATGATATTTTTTGTAGGT<br>TCTTGAATGCTGGAGTTTTTGGTAATGGAATAGAATCATTTCACACATTG<br>CCACATTCAGCAACAAGGGCAGCTATGCTTGTTAGGATCAACACTCTGCT<br>TCAAGGCTACTCTGGCATTAGATTTGAGATCTTGGAAGCAATCACTAAGT<br>TGATCAATAGCAACATCACCCCGTGTTTGCCTCTCCGTGGCACGATCACT<br>GCCTCGGGTGATCTCGTCCCTTTGTCCTATATTGCTGGTTTGCTCACTGG<br>CAGACCTAATTCCAAGGCTGTTGGACCCAATGGTGAGAAACTTAATGCTG<br>AGGAAGCTTTCTGCGTGGCTGGTATTAGTGGTGGATTTTTCGAGTTGCAG<br>CCTAAGGAAGGACTTGCACTTGTGAATGGCACAGCAGTTGGTTCTGCTAT<br>GGCATCAATAGTCCTGTTTGAGTCCAATATCTTTGCTGTTATGTCTGAAG<br>TTTTATCAGCGATTTTTACTGAAGTGATGAACGGAAAGCCCGAATTCACT<br>GACTATTTGACACACAAGTTGAAGCATCACCCTGGTCAGATTGAGGCTGC<br>TGCTATTATGGAACACATTTTGGATGAAGCTCTTATGTGAAGGTAGCTC<br>AGAAGCTCCATGAAATGGATCCTCTTCAAAAACCAAAGCAAGATCGTTAT<br>GCTCTCCGAACATCTCCACAATGGCTTGGACCTCAGATTGAAGTCATTCG<br>TGCTGCAACTAAGATGATCGAGAGGGAGATTAACTCAGTGAACGACAATC<br>CATTGATCGATGTTTCAAGAAACAAGGCCTTACATGGTGGCAACTTCCAA<br>GGAACCCCTATTGGTGTCTCCATGGATAATACAAGATTGGCCCTTGCATC<br>AATTGGTAAATTGATGTTTGCCCAATTCTCAGAGCTTGTCAACGACTATT<br>ACAACAACGGGTTGCCATCTAATCTGACAGCAGGAAGGAATCCAAGCTTG<br>GACTATGGTTTCAAGGGCGCTGAAATCGCGATGGCTTCTTACTGCTCGGA<br>ACTTCAATTCTTGGCAAATCCAGTGACTAACCATGTCTAAAGTGCTGAGC<br>AACACAACCAAGATGTGAATTCCTTGGGCTTAATTTCAGCCAGGAAAACA<br>GCTAAGGCTGTTGATATCTTGAAGATAATGTCATCAACCTATCTCGTGGC<br>TCTTTGCCAAGCTATTGACTTACGACATTTGGAGGAAAACTTGAAGAGTG<br>TTGTCAAGAACACAGTTAGCCAAGTAGCTAAGAGAACTTTGACAATGGGT<br>GCTAATGGTGAACTTCATCCAGCAAGATTCAGCGAAAAAGAATTGCTTCG<br>AGTCGTGGATAGAGAATACTTGTTTGCCTATGCTGATGATCCCTGCAGCT<br>CCAACTACCCTTTGATGCAGAAGCTGAGCACAAGTCCTTGTTGATCAAGCA<br>ATGAAGAATGGTGAAAGTGAGAAGAATGTCAACAGCTCAATCTTCCAAAA<br>GATTGGAGCTTTCGAGGACGAATTAATCGCTGTGTTGCCTAAGAAGTTG<br>AGAGTGTAAGAGCTGTTTTTGAAAGTGGCAACCCTTTAATTCGTAACAGG<br>ATCACAGAATGCAGATCATATCCATTGTACAGGTTGGTGAGAGAAGAACT<br>TGGAACAGAATTGTTGACGGGTGAAAAAGTTCGATCACCTGGTGAGGAGA<br>TTGATAAGTGTTTACAGCAATATGTAATGGACAGATTATTGATCCATTGT<br>TGGAGTGTCTGAAGAGCTGGAATGGTGCTCCTCTTCCAATCTGCTAAATG<br>TGTTATTCTTTCAAGTTCTTTTTTTGTACCTTTTAGTGAATTACTAGAAT<br>TATAATGATGTTATGAACTTATATTAAAAAAAAAATATTTTTGACTATAAA<br>ATTTAGTTTTGTTATTGAAATTAAAGGCTCAATCTGTGTTCTTTCCTTCT<br>GTTATCTGAATATTATAAGAATTCAAGTAATCTTTTAGCTTTGTGAACAT<br>GATGACATGCTTTCTT | |
| Histidine<br>Ammonia-Lyase | ATGATCACGCTTACCCCCGGCCACCTGACCCTCCCGCAACTGCGCCAGAT<br>CGCGCGCGAGCCCGTGCAGCTGACGCTGGATCCGGCCAGCTTCGCGAAGA<br>TCGACGCGGGCGCGAAGGCCGTGTCCGACATCGCCGCGAAGGGCGAGCGC<br>GCGTACGGCATCAACACGGGCTTCGGTCGTCTGGCCAGCACGCATATCCC<br>GCACGATCAGCTCGAATTGCTGCAGAAGAACCTCGTGCTGTCGCATGCAG<br>TCGGTGTCGGCGAGCCGATGGCGCGTTCGTCGGTGCGTCTGCTGATCGCG<br>CTGAAGCTGTCGAGCCTCGGCCGCGGCCATTCGGGCATTCGCCGCGAAGT<br>GATGACGCGCTGATCAAGCTGTTCAACGCCGACGTGCTGCCGCTGATTC<br>CGGTGAAGGGCTCGGTCGGCGCATCGGGCGACCTCGCGCCGCTCGCGCAC<br>ATGTCGGCCGTGCTGCTCGGCGTCGGCGAAGTGTTCATTCGCGGCGAGCG<br>CGCGAGCGCGGTGGACGGGTTGCGCGTCGCGGGCCTCGCGCCGCTGACGC<br>TGCAGGCGAAGGAAGGCCTCGCGCTGCTGAAGGCAGGCGTCGACG<br>GCGCTCGCGCTCGACAACCTGTTCGCGTACGAAGACCTGTACCGCACGGC<br>GCTCGTCGCCGGCGCGCTGTCGGTCGATGCGGCGGCCGGCTCGGTGAAGC<br>CGTTCGACGCGCGCATCCACGAACTGCGCGGCCATCGCGGCCAGATCGAT<br>GCGCGCGGCCGCGTATCGCGAGCTGCTCGAAGGGCTCGGCGATCAACCTCTC<br>GCATCGCGACTGCGGCAAGGTGCAGGATCCGTACAGCCTGCGCTGCCAGC<br>CGCAGGTGATGGGCGCGTGCCTGGACCAGATGCGTCATCGGCCGACGTG<br>CTGCTCGTCGAGGCGAACGCGGTATCGGACAACCCGCTGATCTTCCCGGA<br>TACCGGCAAGTGCTGTGGGCGGCAATTTCCATGCGGAGCCGCGT<br>TCGCGGCCGACAACCTCGCGCTCGCGGCTGCGGAAATCGGCGCGCTGGCC<br>GAGCGCCGCATCGCGCTGCTGATCGACGCGACGCTGTCGGGCCTGCCGCC<br>GTTCCTCGTGAAGGATGGCGGCGTGAACTCGGGCTTCATGATTGCGCACG<br>TGACGGCAGCTGCGCTCGCATCGGAGAACAAGACGCTCGCGCATCCGGCG<br>TCGGTCGATTCGCTGCCGACCTCGGCGAACCAGGAAGACCACGTGTCGAT | BAG44062.1<br>YP_005225923.1<br>CDF52938.1<br>ABR76232.1<br>AAL19728.1<br>AEW60321.1<br>AEW51583.1<br>ABQ54772.1<br>AAX64695.1<br>AAU27462.1<br>WP_021000087.1<br>YP_005185682.1<br>YP_001250118.1<br>EFC47317.1<br>AAH89809.1<br>BAH62483.1<br>XP_002680061.1<br>AAO73411.1<br>CAI79696.1<br>CAI79696.1 |

TABLE 2-continued

| Enzyme | Gene Sequence | Accession Numbers |
|---|---|---|
| | GGCGACGTTCGCGGCACGCAAGCTGGCCGACATCGCCGACAAGACGAAGC<br>ACATCCTCGCGATCGAACTGCTCGCGGCCGCGCAGGGCGTCGATCTGCGC<br>GAGAACGAGACGAGCCCGAAGCTCGCGGAAGTGATGAAGACGATTCGCAG<br>CAAGGTCGCGCATTACGAGCTCGACCACTACTTTGCGCCGGACATCGCCG<br>TGATCGCGAAGCTCGTCGTCGAGCGCGCGTTCGCGAAGCACTGCCCGTTC<br>GCCTTCGCATCGGAGCAGTAA | |
| Tyrosine<br>Ammonia-Lyase | GTGACGCAGGTCGTGGAACGTCAGGCTGATCGGCTCAGCAGCAGGGAGTA<br>CCTGGCCCGGGTCGTGCGCAGCGCCGGGTGGGACGCCGGTCTCACCTCGT<br>GCACCGACGAGGAGATCGTCCGGATGGGCGCCGAGCGCGCGCACCATCGAG<br>GAGTACCTGAAGTCCGACAAGCCCATCTACGGCCTGACGCAGGGCTTCGG<br>TCCGCTGGTGCTGTTCGACGCCGACTCGGAGCTGGAGCAGGGCGGCTCGC<br>TGATCTCGCACCTGGGCACCGGCCAGGGCGCGCCACTGGCCCCGGAGGTG<br>TCGCGGCTGATCCTCTGGCTGCGCATCCAGAACATGCGCAAGGGGTACTC<br>GGCGGTCTCGCCGGTGTTCTGGCAGAAGCTCGCCGACCTGTGGAACAAGG<br>GGTTCACCCCGGCGATCCCCCGGCACGGCACGGTCAGCGCGAGCGGCGAC<br>CTGCAACCGCTGGCGCACGCCGCGCTCGCCTTCACCGGTGTCGGCGAGGC<br>GTGGACCCGGGACGCCGACGGCCGGTGGTCCACCGTGCCGGCCGTGGACG<br>CGCTCGCCGCGCTGGGGGCGGAGCCGTTCGACTGGCCGGTGCCGGAGGCG<br>CTGGCGTTCGTCAACGGGACCGGCGCGAGCCTCGCGGTGGCCTGTGCTCAA<br>CCACCGGTCCGCCCTGCGGCTGGTCCGCGCCTGCGCCGTGCTCTCCGCGC<br>GGCTGGCGACCCTGCTGGGGGCCAATCCCGAGCACTACGACGTGGGGCAC<br>GGTGTCGCGCGCGGCCAGGTCGGTCAGCTGACCGCCGGCGGAGTGGATCCG<br>GCAGGGGCTGCCCCGGGGCATGGTGCGCGACGGCAGCCGCCCGCTCCAGG<br>AGCCGTACAGCCTGCGGTGCGCGCCGCAGGTGCTCGGCGCGGTGCTCGAC<br>CAGCTCGACGGCGCGGGCGACGTGCTGGCGCGGGAGGTCGACGGCTGCCA<br>GGACAACCCGATCACCTACGAGGGCGAGCTGCTGCACGGCGGCAACTTCC<br>ACGCCATGCCGGTGGGTTTCGCCTCCGACCAGATCGGGTTGGCCATGCAC<br>ATGGCCGCCTACCTGGCCGAGCGCCAGCTGGGTCTGCTGGTCAGCCCGGT<br>GACCAACGGCGACCTGCCGCCCATGCTCACCCCGCGCGCCGGGCGCGGTG<br>CCGGGCTGGCCGGGGTGCAGATCAGCGCGACCTCGTTCGTCTCGCGGATC<br>CGGCAGCTGGTGTTCCCCGCCTCGCTGACCACCCTGCCGACCAACGGCTG<br>GAACCAGGACCACGTGCCGATGGCGCTCAACGGGGCGAACTCGGTGTTCG<br>AGGCGTTGGAGCTCGGCTGGCTGACGGTCGGGTCGCTGGCGGTGGGCGTC<br>GCGCAGCTCGCGGCCATGACCGGCCACGCCGCGGAGGGCGTCTGGGCGGA<br>GCTGGCCGGGATCTGCCCGCCGCTGGACGCCGACCGCCCGCTGGGCGCCG<br>AGGTGCGCGCCGCGCGCGACCTGCTGTCCGCGCACGCGGACCAACTGCTC<br>GTCGACGAGGCAGACGGGAAGGATTTCGGATGA | YP_007039999.1<br>Q8GMG0.1<br>WP_015103237.1<br>CCH33126.1<br>AGZ04575.1<br>GAK34477.1<br>AIG26365.1<br>WP_030814263.1<br>WP_030592622.1<br>WP_030583802.1<br>WP_030225885.1<br>WP_030107056.1<br>WP_010261615.1<br>WP_009065811.1<br>WP_029043904.1<br>WP_029027607.1<br>WP_029025670.1<br>WP_029023988.1<br>WP_029020280.1<br>WP_028673581.1 |
| Glutamate<br>Dehydrogenase | ATGTCAGCAAAGCAAGTCTCGAAAGATGAAGAAAAAGAAGCTCTTAACTT<br>ATTTCTGTCTACCCAAACAATCATTAAGGAAGCCCTTCGGAAGCTGGGTT<br>ATCCGGGAGATATGTATGAACTCATGAAAGAGCCGCAGAGAATGCTCACT<br>GTCCGCATTCCGGTCAAAATGGACAATGGGAGCGTCAAAGTGTTCACAGG<br>CTACCGGTCACAGCACAATGATGCTGTCGGTCCGACAAAGGGGGCGTTC<br>GCTTCCATCCAGAAGTTAATGAAGAGGAAGTAAAGGCATTATCCATTTGG<br>ATGACGCTCAAATGCGGGATTGCCAATCTTCCTTACGGCGGCGGGAAGGG<br>CGGTATTATTTGTGATCCGCGGACAATGTCATTTGGAGAACTGGAAAGGC<br>TGAGCAGGGGTATGTCCGTGCCATCAGCCAGATCGTCGGTCGACAAAG<br>GATATTCCAGCTCCCGATGTGTACACCAATTCGCAGATTATGGCGTGGAT<br>GATGGATGAGTACAGCCGGCTGCGGGAATTCGATTCTCCGGGCTTTATTA<br>CAGGTAAACCGCTTGTTTTGGGAGGATCGCAAGGACGGGAAACAGCCACG<br>GCACAGGGCGTCACGATTTGTATTGAAGAGGCGGTGAAGAAAAAGGGAT<br>CAAGCTGCAAAACGCGCGCATCATCATACAGGGCTTTGGAAACGCGGGTA<br>GCTTCCTGGCCAAATTCATGCACGATGCGGGCGCGAAGGTGATCGGGATT<br>TCTGATGCCAATGGCGGGCTCTACAACCCAGACGGCCTTGATATCCCTTA<br>TTTGCTCGATAAACGGGACAGCTTTGGTATGGTCACCAATTTATTTACTG<br>ACGTCATCACAAATGAGGAGCTGCTTGAAAAGGATTGCGATATTTTAGTG<br>CCTGCCGCGATCTCCAATCAAATCACAGCCAAAAACGCACATAACATTCA<br>GGCGTCAATCGTCGTTGAAGCGGCGAACGGCCCGACAACCATTGATGCCA<br>CTAAGATCCTGAATGAAAGAGGCGTGCTGCTTGTGCCGGATATCCTAGCG<br>AGTGCCGGCGGCGTCACGGTTTCTTATTTTGAATGGGTGCAAAACAACCA<br>AGGATATTATTGGTCGGAAGAAGAGGTTGCAGAAAAACTGAGAAGCGTCA<br>TGGTCAGCTCGTTCGAAACAATTTATCAAACAGCGGCAACACATAAAGTG<br>GATATGCGTTTGGCGGCTTACATGACGGGCATCAGAAAATCGGCAGAAGC<br>ATCGCGTTTCCGCGGATGGGTCTAA | P39633.3<br>KEG08275.1<br>NP_001233850.1<br>NP_001268039.1<br>AEW04907.1<br>YP_007161255.1<br>YP_005256579.1<br>YP_004932652.1<br>YP_004442444.1<br>YP_004412348.1<br>YP_004410986.1<br>YP_004372731.1<br>YP_004367667.1<br>YP_004366366.1<br>YP_004343968.1<br>YP_004343356.1<br>YP_004261766.1<br>YP_004270382.1<br>YP_004099961.1<br>YP_003967811.1 |
| Glutamate<br>Ammonia-Lyase | ATGTCCATCAAAGACGCTGTAAAACTGATTGAAGAAAGCGAAGCCCGCTT<br>TGTCGATTTGCGCTTTACCGATACCAAAGGCAAGCAGCACCACTTTACCG<br>TGCCTGCGCGCATCGTGTTGGAAGACCCCGAAGAGTGGTTCGAAAACGGA<br>CAGGCGTTTGACGGTTCGTCCATCGGCGGCTGGAAAGGCATTCAGGCTTC<br>CGATATGCAGCTTCGCCCCGATCCCGCCACGGCGTTTATCGATCCTTTTT<br>ATGATGATGTTACCGTCGTCATTACCTGCGACGTTATCGATCCCGCCGAC<br>GGTCAGGGTTACGACCGCGACCCCGCTTCCATCGCACGCCGCGAAGC<br>CTATTTGAAATCTTCCGGTATCGGCGACACGGCATACTTCGGTCCCGAAC<br>CCGAGTTTTTCGTCTTCGACGGCTAGAATTTGAAACCGATATGCACAAA<br>ACCCGTTACGAAATCACGTCCGAAAGCGGCGCATGGGCCAGCGGCCTGCA<br>TATGGACGGTCAAAACACCGGCCACCGCCCTGCCGTCAAAGGCGGTTACG<br>CGCCCGTCGCGCCGATTGACTGCGGTCAGGATTTGCGTTCCGCGATGGTA | CBX22311.1 |

TABLE 2-continued

| Enzyme | Gene Sequence | Accession Numbers |
|---|---|---|
| | AACATTTTGGAAGGACTCGGCATCGAAGTCGAAGTGCACCACAGCGAAGT<br>CGGTACCGGCAGCCAAATGGAAATCGGCACGCGCTTCGCCACCTTGGTCA<br>AACGCGCCGACCAAACCCAAGACATGAAATATGTGATTCAAAATGTCGCC<br>CACAACTTCGGCAAAACCGCCACCTTCATGCCCAAACCCATTATGGGCGA<br>CAACGGCAGCGGTATGCACGTTCACCAATCCATCTGGAAGACGGTCAAAA<br>CCTGTTCGCAGGCGACGGCTATGCCGGCTTGAGCGACACCGCGCTCTACT<br>ACATCGGCGGCATCATCAAACACGCCAAAGCCCTGAACGCGATTACCAAT<br>CCGTCCACCAACTCCTACAAACGCCTTGTGCCGCACTTTGAAGCGCCGAC<br>CAAACTGGCATATTCCGCCAAAAACCGTTCCGCTTCCATCCGTATTCCGT<br>CTGTGAACAGCAGCAAGGCGCGCCGCATCGAAGCGCGTTTCCCCGACCCG<br>ACCGCCAACCCGTACTTGGCGTTCGCTGCCCTGCTGATGGCGGGTTTGGA<br>CCGGCATTCAAAACAAAATCCATCCGGGCGATCCTGCCGATAAAAATCTC<br>TACGACCTGCCGCCGGAAGAAGACGCGCTCGTCCCGACCGTTTGCGCTTC<br>TTTAGAAGAAGCCCTCGCCGCGCTCAAAGCCGACCACGAATTCCTCTTAC<br>GCGGCGGCGTGTTCAGCAAAGACTGGATCGACAGCTACATCGCCTTTAAA<br>GAGGAAGATGTCCGCCGCATCCGTATGGCGCCGCATCCGCTGGAATTTGA<br>AATGTATTACAGCCTGTAA | |
| Threonine<br>Dehydrogenase | AGGAGGTGTTTTAATAATGAAAGGTTTTGCAATGCTCAGTATCGGTAAAG<br>TCGGTTGGATTGAAAAAGAAAAGCCTACTCCCGGCCCTTTTGACGCTATT<br>GTAAGACCTCTAGCTGTGGCCCCTTGCACTTCGGACGTTCATACCGTTTT<br>TGAAGGTGCTATTGGCGAAAGACATAACATGATACTCGGTCACGAAGCTG<br>TAGGTGAAGTAGTTGAAGTAGGTAGTGAGGTAAAAGATTTTAAACCTGGT<br>GATCGCGTTGTGGTACCAGCTATTACCCCTGATTGGCGAACCTCTGAAGT<br>GCAAAGAGGATATCACCAACACTCTGGTGGAATGCTGGCAGGCTGGAAAT<br>TTTCGAATATAAAAGATGGTGTTTTTGGTGAATTTTTTCATGTGAACGAT<br>GCTGATATGAATTTAGCACATCTGCCTAAGGAAATTCCATTGGAAGCTGC<br>AGTTATGATTCCCGATATGATGACTACTGGCTTTCACGGAGCCGAACTGG<br>CAGATATAGAATTAGGTGCGACGGTAGCGGTTTTGGGTATTGGCCCAGTA<br>GGTCTTATGGCAGTCGCTGGTGCCAAATTGCGGGGTGCTGGAAGGATTAT<br>CGCAGTAGGCAGTAGACCAGTTTGTGTAGATGCTGCAAAATACTATGGAG<br>CTACTGATATTGTAAACTATAAAGATGGTCCTATCGACAGTCAGATTATG<br>GATTTAACGGAAGGCAAAGGTGTTGATGCTGCCATCATCGCTGGAGGAAA<br>TGTTGACATCATGGCTACAGCAGTTAAGATTGTTAAACCTGGTGGCACCA<br>TCGCTAATGTAAATTACTTTGGCGAAGGAGATGTTTTGCCTGTTCCTCGT<br>CTTGAATGGGGTTGCGGCATGGCTCATAAAACTATAAAAGGCGGGCTATG<br>CCCCGGTGGACGTCTAAGAATGGAAAGACTGATTGACCTTGTTGTTTATA<br>AGCGTGTCGATCCTTCTAAGCTCGTCACTCACGTTTTCCGGGGATTTGAC<br>AATATTGAAAAAGCCTTTATGTTGATGAAAGACAAACCAAAAGACCTAAT<br>CAAACCTGTTGTAATATTAGCATAA | NP_622353.1<br>EPX86072.1<br>AFT82159.1<br>YP_006796158.1<br>EJZ15419.1<br>YP_001727630.1<br>ACA82186.1<br>AGZ44086.1<br>AEB44998.1<br>YP_008737139.1<br>EPX87740.1<br>YP_004405598.1<br>BAN60779.1<br>EPE39095.1<br>EPC57128.1<br>EME23086.1<br>ACI75705.1<br>ACI75704.1<br>ACI75703.1<br>ACI75702.1 |
| Threonine<br>Ammonia-Lyase | ATGGCTGACTCGCAACCCCTGTCCGGTACCCCGGAAGGTGCCGAATATTT<br>AAGAGCGGTGCTGCGCGCGCCGGTCTACGAAGCGGCGCAGGTCACGCCGC<br>TACAGAAAATGAAAAACTGTCGTCGCGTCTCGATAACGTGATTCTGGTG<br>AAGCGCGAAGATCGCCAGCCAGTTCATAGCTTTAAGTTGCGCGGCGCATA<br>CGCCATGATGGCGGGCCTGACGGAAGAACAAAAAGCACACGCGTGATTA<br>CCGCTTCTGCAGGTAACCACGCGCAGGGCGTCGCGTTTTCTTCCGCACGG<br>TTAGGCGTGAAGGCGCTGATCGTCATGCCAACCGCCACCGCCGATATCAA<br>AGTTGATGCGGTGCGCGGCTTTGGCGGCGAAGTGCTGCTTCACGGCGCAA<br>ATTTCGATGAAGCGAAAGCGAAAGCGATCGAACTGTCACAGCAGCAGGGT<br>TTCACCTGGGTACCGCCGTTCGATCATCCGATGGTGATCGCCGGGCAAGG<br>CACGCTGGCGCTGGAACTTCCAGCAGGACGCCCATCTCGACCGCGTAT<br>TTGTACCGGTCGGCGGCGGCGGTCTGGCAGCGGGTGTGGCGGTGCTGATC<br>AAACAACTGATGCCGCAAATCAAAGTAATCGCCGTGGAAGCGGAAGATTC<br>CGCCTGCCTGAAAGCGGCGCTGGATGCGGGTCATCCCGTTGATCTGCCCC<br>GCGTGGGCGTGTTTGCTGAAGGCGTCGCGGTAAAACATCGGCGATGAA<br>ACCTTCCGTTTGTGCCAGGAGTATCTTGACGACATCATCACCGTCGATAG<br>CGATGCCATCTGTGCGGCGATGAAAGATCTGTTCGAAGATGTGCGCGCGG<br>TGGCGGAACCTTCCGGCGCGCTGGCGCTGGCGGGGATGAAAAAATACATC<br>GCCCAGCACAACATTCGCGGTGAACGGCTGGCGCATATTCTTCCGGTGC<br>TAACGTGAACTTTCACGGTCTGCGCTACGTCTCGGAACGCTGCGAACTGG<br>GCGAACAGCGTGAAGCGTTGTTGGCGGTGACCATTCCGGAAGAAAAAGGC<br>AGCTTCCTCAAATTCTGCCAACTGCTTGGCGGGCGTTCGGTCACCGAGTT<br>CAACTACCGTTTTGCCGATGCCAAAAACGCCTGCATCTTTGTCGGCGTGC<br>GCTTAAGCCGTGGCCTCGAAGAGCGCAAAGAAATTTTGCAGATGCTCAAC<br>GACGGTGGCTACGCGTGGTTGATCTCTCCGACGACGAAATGGCGAAGCTG<br>CATGTGCGCTATATGGTTGGCGGCGTCCATCGCATCCGTTGCAGGAACG<br>CCTATACAGCTTCGAATTCCCGGAATCACCGGGCGCGCTGCTGCGCTTCC<br>TCAACACGCTGGGTACGCACTGGAACATCTCGCTGTTCCATTATCGCAGC<br>CACGGTACCGACTACGGGCGCGTACTGGCGGCGTTCGAGCTTGGCGATCA<br>TGAACCGGATTTTGAAACCCGGTTGAATGAACTGGGCTACGATTGCCACG<br>ACGAAACCAATAACCCGGCGTTCAGGTTCTTTTTGGCGGGTTAG | EGP22802.1<br>AIL15845.1<br>KFJ14411.1<br>B22317<br>ESE06785.1<br>ESD87895.1<br>ESD77040.1<br>ESD56952.1<br>ESD26867.1<br>ESD18649.1<br>ESC98561.1<br>ESA95751.1<br>ESA86931.1<br>ESA78951.1<br>ESA72735.1<br>ESA67809.1<br>ERL21545.1<br>ERK40933.1<br>ERJ97484.1<br>ERH28800.1 |
| Serine<br>Dehydrogenase | ATGAGCGGTACCATCCTCATCACCGGCGCCACGTCCGGCTTCGGACAGGC<br>CACGGCGCGGCGTTTCGTCAAGGAAGGCTGGAAGGTCATCGGCACAGGTC<br>GGCGGGCGGAACGGCTGGAGGCGCTGGCGCAAGAACTCGCTCCGCCTTTC<br>ACGGCGCTGCCTTCGATGTTACCGACGAAGATGCCACTAGAAAGGCACTT<br>GCGGCTTTGCCGGAAGGTTTCCGGGACATCGATATTCTCGTCAACAATGC | ADY67207.1<br>YP_004444298.1<br>EAZ63492.1<br>XP_001387515.1<br>BAB07807.1 |

TABLE 2-continued

| Enzyme | Gene Sequence | Accession Numbers |
|---|---|---|
| | GGGGCTTGCGCTCGGCACCGCACCTGCACCGCAGGTGCCGCTGAAAGACT<br>GGCAGACCATGGTGAACACCAACATCACCGGTCTTTTGAACATCACCCAC<br>CATCTTTTGCCCACGTTGATCGACCGCAAGGGCATTGTCATCAACCTTTC<br>CTCGGTAGCTGCGCACTGGCCCTATGCGGGCGGCAATGTCTATGCCGGAA<br>CGAAAGCCTTCCTGCGGCAATTCTCGCTCGGTCTGCGCTCCGACCTGCAT<br>GGCAAGGGCGTGCGCGTCACCTCGATCGAACCGGGCATGTGCGAAACGGA<br>ATTCACGCTTGTTCGCACCGGCGGCAATCAGGATGCCTCGGACAATCTTT<br>ACAAGGGCGTCAATCCGATCACGGCCGAGGATATCGCCAATACGATCCAT<br>TGGGTCGCCTCGCAGCCCAAACATATCAACATCAACAGCCTCGAACTCAT<br>GCCGGTCAACCAGTCCTTTGCCGGTTTCCAAGTGCATCGGGAAAGTTGA | EMS96834.1<br>EKJ96295.1<br>EHJ96027.1<br>EHH03760.1<br>WP_028707025.1<br>NP_356536.1<br>AEQ50417.1<br>AAK89321.1<br>YP_004898167.1<br>YP_064393.1<br>WP_003522480.1<br>EGP55658.1<br>EGL63994.1<br>KFC62486.1<br>WP_031354348.1 |
| Serine<br>Ammonia-Lyase | ATGATGACCAAAAACGAAATCCAAAAGTGGGTAAAGGAATTCCCGCTGCT<br>TGAAACGATCATGGCGGCCGAAGAGGTATTTTGGCGCAATCCAAAATATC<br>ACGCGTTTGCGCAAGCTATTCGAACGATTCCTTTACGCGAAGCGATGTC<br>AAGGAGGCCGAAGAGCGATTGCGCCGCTTTGCCCCCTACATCGCGAAAGT<br>GTTTCCCGAGACGCGAACGGCCCACGGTATCATCGAATCCCCTTTAGTGC<br>GGATTCCGAACATGAAACAGCGTTTGGAAAAGATGTTTCAGACCAACATC<br>GAGGGGGATCTGTTGCTAAAATGCGACAGCCATCTTCCCATCTCCGGATC<br>GATCAAGGCGAGAGGGGGAATCTACGAGGTTCTGAAACATGCGGAAGAAC<br>TCGCTCTGGCAAACCATATGATCACCATGGGGGATGACTATGCGGTCATG<br>GCCAGCGAAGAATTCCGGCAGTTCTTTTCCCGCTATTCGCTTGTCGTTGG<br>TTCGACGGGAAATTTAGGCTTGAGTATCGGCATCATCGGGGCGCAGCTTG<br>GGTTCCGCGTTACCGTTCATATGTCAGCCGATGCGAAACAATGGAAAAAA<br>GACTTGTTGCGAAGCAAAGGGGTTGCGGTCATCGAACATCTCACCGACTA<br>CAACAAGGTGGTGGAAGAGGCGCGAAGACAGTCCGCCGAGGATCCAACGT<br>CGTATTTTATCGATGATGAGAACTCGATCCATCTGTTTTTAGGCTATGCG<br>GTGGCGGCGTTTCGGCTGAAAAAGCAATTAGAGGACATGAACATCACGGT<br>TGATGAAAACCACCCGCTCTTTGTATATCTTCCTTGCGGCGTCGGCGGCG<br>GTCCGGGCGGGGTGACGTTTGGGCTGAAGCTCGTGTACGGCGATCATGTC<br>CATTGCTTTTTCGCTGAGCCGACGCATTCGCCTTGCATGTTGCTCGGCCT<br>GATGACGGGACAGCACGACCGCGTGTCGGTGCAAGATTTTGGCCTCGACA<br>ATAAGACCGAAGCGGACGGGCTAGCGGTGGGGCGGCCGTCAAGGTTGGTG<br>GGGAACATGCTTGAGAACGTCATCAGCGGCGTCTATACGGTGGACGATGC<br>GACGCTTTACCGCTTGCTCGCGGCGATGGTGGAAACGGAGGAAATCTATT<br>TAGAGCCGTCCGCCTTGGCGGGGGTGGCGGGGCCTGTTCGGCTGTTTCGT<br>GATTTGGCGGGGCAAACGTACGGTAGAGGCAAACGGTTTGAAAGAAAAGAT<br>GAAAAACGCCGTCCATATTGGCTGGGCGACAGGCGGAAGCATGGTGCTAA<br>AGGATGTGATGGAGGCCTATTATCGGGAAGGCGTGCGCATCGAAACGATG<br>ACAGGGAACGGTTTTTCTGAAGGACGATAA | KFL14920.1<br>AIF56070.1<br>KFI03369.1<br>KFH36969.1<br>KFH35774.1<br>KFH56112.1<br>WP_031409141.1<br>KFC30598.1<br>KEZ84476.1<br>KEY95863.1<br>KER46054.1<br>WP_030024949.1<br>KEK24273.1<br>KEK22892.1<br>KEK18491.1<br>KEK12402.1<br>WP_029761212.1<br>WP_029758174.1<br>WP_029714078.1<br>WP_029598316.1 |
| Leucine<br>Dehydrogenase | ATGCTGATGTTCGAAGAAATCCAGGCGCGCGGCCACGAGAGCGTCACGCT<br>GCTGCACCACGCCCCAGCGGCCTGCGCGCCGTGCTCGCCGTGCACTCCA<br>CCGTGCTCGGCCCTGCCATTGCCGGCTGCCGCTGATGCCCTGCACCGAG<br>GAACGCGCCGTGCGCGACGCCCTCGCCCTCAGCGAGTCCGTCACGCTCAA<br>GGCCGCCCTCGCGGGCCTGAACTACGGCGGGGCGCGTGCGTCATGCTCC<br>CCCCGGAAGGCGGCGACATCGACGGGCACGCCCGCGAGGCGCTGTTCCGC<br>GCGCTCGGCCGGCAGATCCGTTACCGCGGTGGCCGTCATCCTCACCGA<br>GGACGTCGGCGTGACCGGCCGCGACATCGCCTTCGCCGCGCAGGAAACCG<br>ACAGCACCATGGGCATGCACACCGACACGCCCACCGTCACCGCGTACGGC<br>GTGTACCGCGGCATCAAGGCCGCCGCGCGCGCCTACCTCGGCGGCGAGAG<br>CATGCGCGGCGTGCGCGTCGCGTGCTCGGCGCGGCAGTCGGGCGCA<br>CCCTCGCGCAGCACCTGCACCGCGAGGGCGCGCGCCTCACCGTCGCAGAC<br>CTGATGTCTGAGCGCGCGCAGGCCCTCGCGGACGACCTCGGCGAGCGCGT<br>CACCGTCGTGAGCGCCGCTGACATCTTCGACGTGCCGTGCGACGTATTCG<br>CGCCGTGCGCGTTCGGGCACAGCATCAAAAGCGCCGACGTGCCCCGCTTG<br>CAGTGCCGGGTGATCGCCGGCAGCGAACACCACCCGCTCAGCCACAACGG<br>CGAGACGTCGTGCGCGAAGCGGGCATCATACACATCCCGGACTTCGCCA<br>TCAACAGCGCCGGCCTGATGAGCGCCGCGCAGAACCTCAGCATCGAAACG<br>GCGGCGGAACGCGTGTACGAGAGCGTCGCGCAGATCTGCGCGACCGCGCA<br>GAAGTACGAGAAGCCGCCACGTCGTCGCCCGTCAAACTCGCTGCGCC<br>GCATCGAACTGATCGGCTCCATCAGCGGCCAGTACGCCGGCCAGTAA | YP_004169785.1<br>ADV66120.1<br>ADY26991.1<br>AEW05136.1<br>YP_005256808.1<br>YP_004256608.1<br>YP_004346245.1<br>AEA45407.1<br>YP_004101992.1<br>YP_004101991.1<br>YP_003825932.1<br>ADU51265.1<br>ADU51264.1<br>ADU08309.1<br>AFY88585.1<br>YO_004054007.1<br>YP_007092454.1<br>YP_003825216.1<br>ADR21899.1<br>ADL07593.1 |
| Asparte<br>Dehydrogenase | TCATGTGCCAACACGTATGTTATCACTTAAAATTTTTAGTAAAGTGACTG<br>CTGAATATGCTGCCAAAACACTTGTTTTGGATTTAATTCACACACAGTG<br>TTTTTTGTTATAGATTTAAACTCTCCAAAATCTCCTTTAACATGGACTTC<br>ATGGATATTGTGTTCAACTTCAGGATCTGCAATTATCTTTACATCCGCAT<br>CTATTCCAGAGGCTAGACTTAATGCCGCAGCAACGTTAATATTCACTGGA<br>AATTTTTTAACAGCTTCTGAGGATTTCCCTTTAAACACGACCTCTTTTT<br>TTGGTCTTAACACCTAACGAAGTAGGTGATTTTCTCGTTATAAGTTTTA<br>TTTCTTTTATCTTACCTAAGGATCGGCTTTTACACCATCTAAACCAATT<br>ATTGCACCGAAGGTATGTATATATTAGCTCCTGATTCTCTAGATTCCTT<br>TATCAATCTTCTTCTAACTTTCTCATCTAATAGTGCACCCACACTCATAA<br>TCAAAACATCTATACCTCTACTAATATATTGGGCACAATTTCTTTTACT | ADP76847.1<br>YP_004003609.1<br>ADE37476.1<br>AEH60264.1<br>AEH50568.1<br>YP_004615483.1<br>YP_004659664.1<br>YP_003543121.1<br>YP_003895891.1<br>ADN37453.1<br>ADV47603.1 |

TABLE 2-continued

| Enzyme | Gene Sequence | Accession Numbers |
|---|---|---|
| | GCCTCTTGAGAAGCAGATTCAATTATCAAATCAACTCCATTGAACATTTC TTCTACCTTTTTTACGGCAGTGCCATTTGTTAAATTTGCTAGCTTCTTAG CTTTTCTAAAATTTCTGTCATAAAAATATTTTAATTTTATTTTTTTGATA TCTTGTTTTAAGACAAGGTTAACTATTGTATTTGCAATTGCACCACATCC TATAATCCCACATCTCAT | YP_004163101.1 ADY50896.1 ABX33598.1 YP_004272718.1 ADN60949.1 ACL18032.1 ACL16745.1 ADD08173.1 |
| Aspartate Ammonia-Lyase | ATGTCCTCGCCTGCATCATCGCGCATCGAAAAAGACCTGCTTGGTGTTCT CGAAGTACCTGCCAACGCGTATTACGGCATCCAGACCCTGCGAGCGGTGA ACAACTTTCACCTCTCCGGCGTGCCGCTTTCGCACTACCCGAAACTGGTA GTCGCGCTGGCCATGGTCAAGCAGGCGGCAGCGGATGCAAACCATCAGCT CGGACACCTCAATGACGCCAAGCATGCGGCGATCAGCGAGGCCTGTGCCC GCCTGATCCGCGGCGACTTCCACGATCAGTTCGTGGTCGACATGATCCAG GGCGGCGCTGGCACGTCGACCAACATGAATGCCAACGAAGTCATCGCCAA CATCGCTCTGGAAACCATGGGTTTCGAGAAAGGCGCATACAAACACCTGC ACCCCAACAACGATGTCAACATGGCGCAGTCGACCAACGACGCCTACCCC ACGGCGATCCGCTTGGGTCTGCTGCTGGGTCACGACGCTCTGCTCGCCAG CCTTTCCAGCCTGATTCAGGCCTTCGCCGCCAAGGGCGAAGAATTCAACC ATGTGCTGAAGATGGGCCGCACCCAGTTGCAGGACGCCGTTCCAATGACC CTGGGTCAGGAATTCCGCGCCTTCGCCACCACCCTGACAGAAGACCTGAA CCGCCTGCGCAGCCTGGCGCCAGAGCTGTTGACCGAAGTGAACCTCGGCG GAACCGCCATCGGCACCGGCATCAACGCCGACCCTGGCTATCAGAAGCTG GCAGTCGATCGTCTGGCACTCATCAGCGGCCAGCCTCTGGTGCCAGCAGC CGACCTGATCGAAGCGACCTCCGACATGGGCGCCTTCGTGTTGTTCTCGG GCATGCTCAAGCGTACTGCGGTCAAGCTGTCGAAAATCTGCAACGACCTG CGCCTGCTGTCCAGCGGCCCACGCACCGGCATCAACGAAATCAACCTGCC GGCACGTCAGCCAGGCAGCTCGATCATGCCCGGCAAGGTCAACCCGGTGA TCCCGGAAGCGGTCAATCAGGTTGCCTTCGAAATCATCGGCAACGACCTG TCGCTGACCATGGCAGCCGAAGGAGGACAATTGCAGCTCAACGTGATGGA GCCGCTGATCGCCTACAAGATCTTCGACTCGATCCGCCTGCTGCAGCGCG CCATGGACATGTGCGCGAGCACTGCATCGTCGGCATCACAGCCAACGAA CAGCGCTGCCGAGCTGGTCGAGCATTCGATCGGTCTGGTCACCGCCCT GAACCCTTACATCGGTTACGAGAACTCCACCCGTATCGCCCGCATCGCGC TGGAAACCGGCCGCGGCGTGCTGGAACTGGTGCGTGAGGAAGGTCTGCTC GACGACGCCATGCTCGACGACATCCTGCGCCCCGGAAAACATGATCGCTCC GCGTCTGGCCCCCTTGAAGGCCTGA | ELS44542.1 EXL32019.1 EPF69098.1 EDZ32290.1 ACC77466.1 ET009916.1 ETN58394.1 AGZ94384.1 EGU12843.1 AGQ54567.1 BAN21048.1 ELU36465.1 ELU36464.1 EDS31003.1 BAM20634.1 ACO48312.1 XP_001828833.2 EAU92840.2 XP_001849880.1 XP_001658988.1 |
| Valine Dehydrogenase | TCAGCGACCGCGGGCCTCGGCCATCCGCTGCTCGGCGATCCGGTCGGCCG CCGCGGCGGGCGGAATGCCGTCCGCCTTCGCACGTGCGAATATTTCCAGC GTGGTGTCGAAGATCTTCGTCGCCTTCGCCTTGCACCGGTCGAAGTCGAA CCCGTGCAGCTCGTCGGCGACCTGGATCACGCCGCCGGCGTTGACCACAT AGTCGGGTGCGTAGAGGACCGACCGGTCGGCCAGGTCCTTCTCGACACCC GGGTGGGCCAGCTGGTTGTTGGCGCGCCGCCGCACACCACCTTCGCCGTGAG CACCGGAACGGTCGCGTCGTTGAGCGCGCCGCCGAGCGCGCAGGGCGCGT AGATGTCGAGACCCTCGGTGCGGATCAGCGTCTCGGTGTCCGCCACCACG GTGACCTCGGGGTGCAGATCGGTGATCCGGCGCACCGACTCCTCGCGTAC GTCGGTGATCACGACCTCGGCCCCGTCGGAGAGCAGGTGCTCGACGAGGT GGTGGCCCACCTTGCCGACCCCGGCGACGCCGACCTTGCGGCCGCGCAGC GTCGGGTCGCCCCACAGGTGCTGGGCCGAGGCCCGCATGCCCTGGAAGAC ACCGAACGCGGTGAGGACGGAGGAGTCGCCGGCCGCCGTTCTCGGGGG AGCGGCCGGTGGTCCAGCGGCACTCCCTGGCGACGACGTCCATGTCGGCG ACGTAGGTGCCGACATCGCAGGCGGTGACGTACCGGCCGCCGAGCGAGGC GACGAACCGGCCGTAGGCCAGGAGGAGTTCCTCCGTCTTGATCTTCTCCG GGTCGCCGATGATGACGGCCTTGCCGCCACCGTGGTCGAGTCCGGCCAGG GCGTTCTTGTACGACATCCCGCGCGACAGGTTCAGCGCGTCGGCGACGGC CTCGGCCTCGGTCGCGTACGGGTAGAAGCGGGTGCCGCCGAGGCCGGGGC CCAGGGCGGTGGAGTGGAGGGCGATGACGGCCTTGAGGCCGGTGGCACGG TCCTGGCAGATCACGACTTGCTCGTGACCCCCCTGATCCGAGTGGAACAG GGTGTGCAGGACGCCGTTAGTCACATCGGTCAC | YP_007932652.1 AGK78767.1 NP_628270.1 YP_001973234.1 AIJ14557.1 YP_007523209.1 WP_015659426.1 CCK29082.1 CAR62534.1 AGT93561.1 AEK45617.1 ADI08852.1 YP_008454282.1 ESQ05180.1 ESP98677.1 YP_005535074.1 YP_004963983.1 EOD63988.1 EME98953.1 EME52779.1 |
| Glycine Dehydrogenase | CTAGTTGTAAAAGTCGAGGGAGGCGCAACTGCACATGAGGTGACGATCTC CGTAAACCCGTCAATGCGACCCACAGTCGGCCAGTACTTTTCAACGTAC GAGTAAGGATAAGGGAATGCCGCCAAACGCCGATCATATGGTTTGTCCCA TTTATCATCGGTGACACATCTTGCCGTGTGTGGTGCATTCTTCAAAACAT TGTTATCCACTGGTTGTTCACCTTTTTCAATGGCGGCAATCTCACCTCGA ATGGAAATTAGTGCATCTGCCAAGCGATCCAACTCCCGCTTGGGTTCTGA TTCGGTGGGTTCAATCATTAAAGTCCCGGGTACAAGGAAACGCCAGTGTTG GCGAGTGAATTCCGTAGTCCATCAACCGTTTGGCCACGTCCTCCGCCTCA ATATGAGCTGTCTTCTTGAACCGTCGAAGATCAACGATAAACTCATGAGC GCAGTAGTTTTCTCCACCCAGGAAAAGAATCGTATAATGGTTCTCTAGGC GCTTCTTCAAGTAGTTTGCATTCAAAACGGCGTACTCTGTACAAGTTTTG AGCCCGTGTGATCCAAGCATTAACATCAACATGTACGATATCGGAAGAAT TGATGCTGATCCGTACGCTGATTGTGAGACTTGGCCAATGGCTGTGAAC CGCCAACTTTTTGGTTGAAAACAGAATTTGGCAAAAGGGGGCCAGATGT TGACGGACAGCTATAGGGCCCATTCCGGGGCCGCCACCACCATGGGGAAT TGAAAACGTCTTGTGGAGATTAATGTGGCACACGTCGCCACCGATATATC | KEG12217.1 ADH66904.1 YP_003679410.1 YP_003507491.1 ADN74845.1 ADD28471.1 YP_004445203.1 YP_003911919.1 ADQ81869.1 AEH88507.1 YP_007138219.1 YP_004612601.1 YP_004170318.1 YP_004163559.1 YP_004045375.1 YP_004787190.1 |

TABLE 2-continued

| Enzyme | Gene Sequence | Accession Numbers |
|---|---|---|
| | CAGGGCCTGTATAGCCAACCATGGCGTTAAGATTTGCCCCATCAATGTAG | YP_001742361.1 |
| | CATTGTCCACCGTAGTAGTGCGCCATTGATGTAATGATAAAATATCCTT | YP_007067896.1 |
| | GTCAAACAAGCCATACGTACTTGGATATGTTATCATGATACACGACAACT | YP_007100788.1 |
| | CCTTTGCGTGTTTTTGGCAAGATTTCTCCAGGTCATTGATATCAACCCTG | YP_004773043.1 |
| | CCGTTAGACAAGCATTTCACCAAGACAATATTCATTCCTGCCAATGTTGC | |
| | CGAAGCTGGATTCGTACCATGCGCACTCTCTGGAATCAAACAGACGTTGC | |
| | GGTGTCCTTCCTTCATTGATAGATGGTACGCACGAATAACACGAAGCCCA | |
| | GCGTATTCACCTTGGGCGCCACTATTAGGCTGAAGCGATACCGCATCCAG | |
| | ACCGGTAATTTCCCTTAACTTTTGCTCAAGATCTAGACACAACGCACTGT | |
| | ACCCTCGCACTTGGTCCACTGGGGCAAGGGGATGCACATTGGTGAATTCT | |
| | GGCCAAGAGAGTGGTAACATAGCAGCGGCAGGGTTAAGCTTCATGGTGCA | |
| | AGATCCCAACGGGACGCAACCATGCGTAAGGCCGTAATCCTTTCGTTGTA | |
| | GACGATGAATATAGCGCATCAGTTCACTTTCACTCTTGTACTTTTGAAAC | |
| | GTTGAGTGTTTCAGGAAATCAGACTTCCGCACCAGATCCAACGGTAGTAC | |
| | CGATTTCTGATCGGCTATTTTGGAAAGGGCTGCGACGACGGGAAGCTTCA | |
| | ACCCTGCAGCCTCCAAAAGTGACACAATGTGTCCATCCGTTGTTGCCTCA | |
| | TCCACAGAAATGGAGACAGTCCCATTACTGTAATCAACAAAAACATTAAT | |
| | ACCCTTCTCAACACATCGTGTCTTGTAATCCTCCGCTGTAATGCCTTTTA | |
| | GGTTCACAGTAACAGTGTCGAAAAATGCACTGTTTACCACAGAGTGTCCT | |
| | ACTGATTCCATACCAACAGCGAGCACTTTCGCCTTGCCGTGTATCTCATT | |
| | GGCAATCTCATTTAGACCATCTGGACCATGGTAGGCGGCATAAAACCCAC | |
| | TCACGTTGGCCAATAACGCTTGTGCAGTACAGATATTTGATGTGGCGCGC | |
| | TCACGCTTAATATGTTGTTCACGTGTCTGCAGCGCCATGCGTATGGATGG | |
| | CTCTCCGGCAGAATCCTTACTGACGCCGATCACACGTCCCGGCATCAACC | |
| | TCTTAAACTGCTCCTTGACAGCAAAGAACGCGGCGTGAGGACCTCCATAT | |
| | CCTAGTGGAACACCAAAACGCTGGGAGGATCCCACAACCACATCTGCATT | |
| | CATTTCACCAGGTGGCTTGACAAGAACACAAGCCATCAAGTCGGTCCCAC | |
| | AGCAACTAATGACACCGTGCTTCTTTGCATTCTCGAACAGTGGTGAGAAG | |
| | TCATGAAGCATGCCCATCGCATCTGGTGTTTGTACAAGGATACCAAACAA | |
| | GGAACTGTCAGTCCAGTCAATCAGATTCGTGTCGCCCACGACGACGTTTA | |
| | TCTTGAGCGGTTCGGCTCTTGTCTTAACCATCTCAATGCAGGATGGAAAA | |
| | ACAGTTTTGATACGAAGAACGTATTCCGCTTTCGTTGACCATGCTGAAAA | |
| | GCAAGATGCATCGCCTCGGATGATGTCTGTCGCTTGGTCAAGAAGAGATG | |
| | CATTTGCCACATCCATCTTTGTCAAATCCATAACCATGGTTTGGAAATTC | |
| | AAAAGGGACTCCAGACGTCCTTGTGCAATCTCAGCTTGGTATGGTGTGTA | |
| | GGGTGTGTACCATCCAGGATTTTCAATGACGTTGCGAAGTATGACAGGAG | |
| | GAGTAATGGACTCGTAGTACCCCTGACCAATCATGCTTTTTAGTACCTTG | |
| | TTTCGCGCACCAAGAGAGCGACGAGTGCGAGAGCATCCATCTCACTCATA | |
| | GCCGCCACCTCCGTCAAGGGTGGGCGTACAATATCCCTGGAATAGCAGC | |
| | CGTCATCAAATCAGAGACTCTCTTTTCCAACCGTTCGAAGCATCGACATT | |
| | GTCTCAGCCGTTGTTGGACCAATATGGCGGTTAATATAGCTGTCCGTGGC | |
| | AGTCCATCGAACAAATGTCACGCATGGCAAAGAGCCACGAAACAAACGAC | |
| | GGTACAT | |
| Alanine Dehydrogenase | ATGGATCATTGGCCTGCCGAAAGAGATCAAAGTTAAGGAAAACCGCGTTGGC | YP_004171395.1 |
| | ACTCACGCCCGGGGGCGTCGCCAGCCTCGTGCGCCGCGGCCACACCGTCA | ADV67730.1 |
| | TCGTGGAACGCAGCGCCGGCGTGGGCAGCGGCATCCAGGACACCGAGTAC | ADV25885.1 |
| | GAGCAGGCCGGCGCGCAGCTCGGCAGCGCCGCCGAGGCGTGGGCCGCGCA | ADV48359.1 |
| | GATGGTCGTGAAGGTCAAGGAGCCCATCAAGAGCGAATACGGGTACCTCC | AFZ35417.1 |
| | GCCCGGACCTGCTGCTGTTCACGTACCTGCACCTCGCTGCGGACCAGCCC | AFZ05172.1 |
| | CTCACGGACGCCCTGCTGAGCGCCGGCACGACCGCCGTTGCGTACGAGAC | AEW05285.1 |
| | GGTGCAGCTCGACGACCGCAGCCTGCCGCTGCTCACGCCCATGAGTGAGG | AEW04533.1 |
| | TCGCGGGCCGCCTGAGCGTGCAGGCCGGCGCGTACCACCTGCAAAAGCCC | AEM70054.1 |
| | ATCGGCGGGCGCGGCGTGCTGCTCGGCGGCGTGCCGGGCGTGCAGGCGGG | YP_005256957.1 |
| | CCACGTCGTCGTGATTGGCGGCGGCGTCGTCGGCACGAACGCCGCGAAAA | YP_005256205.1 |
| | TGGCCATGGGCCTCGGCGCGAAGGTCACGGTGCTGGACGTGAACCACGGG | YP_004450492.1 |
| | CGCCTCTCGTACCTCGACGACGTGTTCTTCGGGAAGCTCACCACCATGAT | YP_004368103.1 |
| | GAGCAACGAGGCGAACATCCGCTCCATCCTGCCCGAAGCGGACCTCGTGA | YP_004340432.1 |
| | TCGGCGGCGTGCTGATCCCCGGGCGAAGGCGCCGCACCTTGTCACGCGC | YP_004261609.1 |
| | GACATGCTGGCGACCATGCAGGAAGGCAGCGTCATCGTCGACGTGGCGGT | YP_004255502.1 |
| | GGACCAGGGCGGATGCGTGGAGACCATTCACGCGACGACGCACGACGATC | YP_004163857.1 |
| | CCACGTACATCGTGGACGGCGTGATCCACTCACGGCGTGGCGAACATGCCG | YP_004787486.1 |
| | GGCGCGGTGCCGCGCACCAGCACGTTCGCGCTCACGAACCAGACCATTGG | YP_007132437.1 |
| | GTACGTGCTGCAGCTCGCGGACAAGGGCGTGGAGGCACTCAGCGCCAGCA | YP_007113588.1 |
| | AGCCGCTGCTGCGTGGCCTGAACACCATCGGCGGGAAGCTGACGTACGCG | |
| | GGCGTCGCGGAAGCGTTCGGCCTGACGTACACCGCGCCTGAAGTGGCGCT | |
| | GGCGTAA | |
| Proline Dehydrogenase | ATGGAGCCCACTATGAGCCAATTCGAACAGCTGTACCGCCAGGTGGCCCT | ADY26965.1 |
| | CAGTGTCGCCGGCAACCCGGTCGTGGAAAAGTCTTGAGCAAGCAGGGCT | ADI14966.1 |
| | GGGCGCTGGCGCAGCGTTTTGTATCGGGCGAGACGGCGCAGGACGCCATC | YP_004437470.1 |
| | AAGGCCATCAAGCGGCTGGAAGCCCAGGGCATCTCCGGCAACCTCGACCT | YP_004368974.1 |
| | GCTGGGCGAGTTCGTGAACACCCCGGAACCCGCCAATGCTACCGCCGAGA | YP_004345744.1 |
| | TGATTCTGGCGACCATTGACCAGGTGCACGCGGCGGGCCTCACGCCCTAC | YP_004340684.1 |
| | AACAGCGTGAAAATGTCGGCGCTGGGCCAAGGGCAGACCGCGCCGGACGG | YP_004256582.1 |
| | CCAGGACCTCGGCTACGTCAACACCCGCCGCGTCGTGGAGCGGGCCAAGC | YP_004170680.1 |
| | GCTACGCGCGCTTCGTCAATCTGGACATGGAAGACCACACCCGCGTGGAC | YP_003705539.1 |
| | TCGACTCTGCAGATTTTCCGCCGCCTGGTCAAGGAGTTCGGCCACCAGCA | AEA44906.1 |

TABLE 2-continued

| Enzyme | Gene Sequence | Accession Numbers |
|---|---|---|
| | TGTGGGAACGGTGTTGCAGGCCTACCTGCACCGCTCGGAAGACGACCGCC | AEB12864.1 |
| | GCAGCCTGGACGACCTGCGCCCCAACCTCCGCATGGTGAAGGGCGCCTAC | ADV67015.1 |
| | CTGGAGCCCGCCTCCGTCGCCCTGCAGAGCAAAACCGACATTGACGCCGC | AEE14339.1 |
| | CTACCGCCGCCTGGTCTACGAGCACCTCAAGGCCGGCAACTACTGCAACG | AEA34625.1 |
| | TGGCCACCCACGACCACCACATCATCTACGACGTGATGCACTTTGCGCTG | EFH82753.1 |
| | GCCCACGGCATCCCTAAGGACCAGTTCGAATTCCAGCTGCTGTACGGCAT | NP_868270.1 |
| | CCGCGAGGACCTGCAGCGCGAATTGGCCGAGGCCGGCTACACGGTGCGCT | ADQ16526.1 |
| | CGTACATTCCTTTCGGCAAGGACTGGTACGGCTACTACTCGCGCCGCATC | AEL26370.1 |
| | GCCGAGCGCCCGCAGAACGTGATGTTCGTGCTGCGCGGCCTGCTGTAA | AFK04422.1 |
| | | AEM71761.1 |
| Lysine Dehydrogenase | ATGAAAAACATTGTGGTTATCGGCGCGGGCAATATCGGTTCGGCAATCGC | BAH80102.1 |
| | CTGGATGCTGGCCGCATCAGGCGATTATCGCATCACGGTTGCCGATCGTT | AAV93559.1 |
| | CAGCCGATCAGCTGGCCAATGTGCCGGCGCATGAACGGGTCGACATCGTC | YP_165503.1 |
| | GACATTACCGACCGTCCCGCTCTGGAAGCACTGCTAAAAGGCAAATTCGC | AIA01810.1 |
| | CGTGCTCTCCGCCGCCCCCACCGAATTCCACCTGACGGCGGGTATTGCCG | AIA03878.1 |
| | AAGCGGCCGTTGCCGTCGGCACGCATTATCTCGATCTCACCGAAGACGTG | AIA03881.1 |
| | GAATCCACCCGCAAGGTCAAGGCGCTGGCGGAAACGGCCGAAACCGCGCT | AIA00889.1 |
| | CATTCCGCAATGCGGCCTCGCCCCCGGCTTCATCTCCATCGTCGCTGCCG | EXU92064.1 |
| | ATCTCGCCGTCAAGTTCGACAAGCTGGACAGCGTGCGCATGCGCGTCGGC | EOT00338.1 |
| | GCTCTGCCGCAATATCCGTCCAATGCGCTCAACTACAACCTCACCTGGAG | NP_882461.1 |
| | TACCGACGGGCTGATCAACGAATATATCGAGCCCTGCGAAGGATTCGTCG | EIJ80893.1 |
| | AAGGCCGCCTCACCGCCGTTCCGGCCCTTGAGGAGCGCGAGGAGTTCTCG | AIA06975.1 |
| | CTCGATGGCATCACCTACGAGGCGTTCAACACCTCGGGCGGTCTCGGTAC | AIA05885.1 |
| | GCTTTGCGCGACGCTGGAAGGCAAGGTGCGGACCATGAACTACCGCACTA | EXU88317.1 |
| | TCCGTTATCCCGGCCATGTGGCGATCATGAAGGCGCTTTTGAACGACCTC | EOT04629.1 |
| | AACCTGCGCAACCGCCGCGATGTGCTGAAGGACCTGTTCGAAAACGCCCT | AIA07859.1 |
| | GCCCGGCACCATGCAGGATGTGGTCATCGTCTTCGTCACCGTCTGCGGCA | AIA04644.1 |
| | CCCGCAACGGCCGCTTCCTGCAGGAAACCTATGCCAACAAGGTCTATGCC | AIA04440.1 |
| | GGCCCGGTTTCCGGCCGGATGATGAGCGCCATCCAGATCACTACCGCCGC | AIA03522.1 |
| | CGGCATCTGCACGGTTCTCGACCTGCTCGCGGAAGGCGCCCTGCCGCAGA | AIA02686.1 |
| | AGGGCTTCGTTCGACAGGAGGAAGTGGCGCTGCCGAAGTTCCTCGAAAAC | |
| | CGGTTTGGCCGGTATTATGGCTCGCATGAGCCGCTGGCGCGGGTTGGGTG | |
| | A | |

The disclosure relates to an ammonia or ammonium ion biosensor for measuring a total concentration of a ammonia in the blood. The ammonia bio sensor comprises a measuring electrode which include as components, a mediator and an enzyme, which selectively act on the plurality of specific amino acids each serving as a substrate, and a counter electrode. In the amino-acid biosensor, the enzyme has a substrate affinity to each of the plurality of specific amino acids. The enzyme is operable to catalyze a reaction in each of the plurality of specific amino acids as a substrate so as to form a reaction product. The mediator is operable, during amino-acid concentration measurement, to carry electrons between the reaction product and the measuring electrode. Further, the amino-acid bio sensor is designed to apply a voltage between the measuring electrode and the counter electrode at a measurement point in such a manner that, in an analytical curve representing a relationship between an applied voltage and a current value in a specific concentration for each of the plurality of specific amino acids, the applied voltage is a voltage allowing the variety of the current values for the amino acids in the same concentration and at the same applied voltage.

In some embodiments, the measuring electrode (at least a first electrode) further comprises a a hydrogel that comprises a coenzyme or reduction agent as a component. In some embodiments, the enzyme consists of a dehydrogenase. Further, the reaction product consists of a reduced coenzyme derived by reduction of the coenzyme, and the mediator is operable, during the amino-acid concentration measurement, to carry electrons from the reduced coenzyme to the measuring electrode.

In some embodiments, a biosensor or system disclosed herein is used in conjunction with one or a combination of the following:

1. a power source in electrical connection with the electrodes and capable of supplying an electrical potential difference between the electrodes sufficient to cause diffusion limited electro-oxidation of the reduced form of the mediator at the surface of the working electrode; and 2. at least one meter, (such as a spectrophoteomter, voltmeter and/or amperometer) in electrical connection with the electrodes and capable of measuring the diffusion limited current produced by of the reduced form of the mediator with the above-stated electrical potential difference is applied.

The meter will normally be adapted to apply an algorithm to the current measurement, whereby an ammonia or ammonium ion concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are hereby expressly incorporated by reference.

Ammonia or ammonium ion concentrations from a plurality of samples may be analyzed in parallel. For example, human and non-human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues from humans and non-human animals can also be assayed, along with foods, water samples, fermentation products and environmental substances, which potentially contain environmental contaminants. In some embodiments, human serum is assayed with the disclosed biosensor. In some embodiments, the biosensor comprises or is configured to assay whole blood.

After reaction is complete, a power source (e.g., a battery) applies a potential difference between electrodes. When the potential difference is applied, the amount of oxidized form of the mediator at the auxiliary electrode and the potential difference must be sufficient to cause diffusion-limited electro-oxidation of the reduced form of the at least one mediator at the surface of the working electrode. In some embodiments, the working electrode comprises a hydrogel disclosed herein. A current measuring meter (not shown) measures the diffusion-limited current generated by the oxidation of the reduced form of the mediator at the surface of the working electrode. The measured current may be accurately correlated to the concentration of ammonia or ammonium ion and/or one or more amino acids in sample when the following requirements are satisfied:

1. The rate of the indophenol reaction based upon the concentration of indophenol reagents is governed by the rate of diffusion of the ammonia from the sample in a first vessel to the second vessel comprising a surface of the working electrode.

To manufacture biosensor a roll of metallized film is fed through guide rolls into an ablation/washing and drying station. A laser system capable of ablating bottom plate element 14 is known to those of ordinary skill in the art. Non-limiting examples of which include excimer lasers, with the pattern of ablation controlled by mirrors, lenses, and masks. A non-limiting example of such a system is the LPX-300 or LPX-200 both commercially available from LPKF Laser Electronic GmbH, of Garbsen, Germany.

In the laser ablator, the metallic layer of the metallized film is ablated in a pre-determined pattern, to form a ribbon of isolated electrode sets. The metallized film is further ablated, after the isolated electrode sets are formed to create recesses positioned adjacent the electrochemical area. The ribbon is then passed through more guide rolls, with a tension loop and through an optional inspection camera. The camera is used for quality control in order to check for defects.

Reagent is compounded and applied in a liquid form to the center of the electrochemical area at a dispensing and drying station. Reagent application techniques are well known to one of ordinary skill in the art as described in U.S. Pat. No. 5,762,770, the disclosure of which is expressly incorporated herein by reference. It is appreciated that reagent may be applied to array in a liquid or other form and dried or semi-dried onto the center of the electrochemical area in accordance with this disclosure.

In addition, a roll or top plate element material is fed into an assembly station along with a roll of spacer material. Liners on either side of the spacer material are removed in that station and the top plate element or surface scaffold is applied to one side of the spacer material to form a top plate element/spacer subassembly. The top plate element/spacer subassembly is slit into the appropriate width for a row of biosensors. Next, a new release liner is added to the side of the spacer material opposite the cover and the subassembly is wound into a roll.

The ribbon of the reagent-coated bottom plate element is unwound and fed into a sensor assembly station along with the top plate element/spacer subassembly. The liner is removed from the spacer and the subassembly is placed on bottom plate element to cover reagent. Next, the assembled material is cut to form individual biosensors, which are sorted and packed into vials, each closed with a stopper, to give packaged sensor test strips.

Although ablating recesses is described herein, it is appreciated that the method of forming recesses in bottom plate element is also not limited. For example, the recesses may be formed by etching (e.g., using photoligographic methods) or otherwise removing a portion of the surface of top plate element. The nearest electrode edge is approximately about 10 μm to about 500 μm from the recess, or about 100 μm to about 400 μm from the recess, or from about 200 μm to about 300 μm from the recess. Biosensors that are formed with recesses in accordance with this disclosure yield a reagent profile with generally uniform thickness of chemistry. A generally uniform thickness of chemistry allows for more accurate sample analysis.

The processes and products described above include a disposable biosensor, especially for use individually as a diagnostic device or in combination with other components such as a pump system or spectrophotometer configured to diagnose hyperammonemia, abnormal function, or abnormally high or low amounts of ammonia in a sample.

Variations on the Indophenol Reaction

The disclosure relates to contacting a sample with one or a plurality of reagents in independently variable phases of dried, powdered or aqueous phases. The reaction has four major components: a compound comprising a phenyl group, a hypohalite, a catalyst and an alkali buffer. When these reagents are exposed to ammonia, an indophenol compound is produced that, when exposed to a light source at a particular wavelength, absorbs and/or emits a particular wavelength of light. in some embodiments, any of the methods disclosed herein make comprise a step of detecting the presence, absence, or quantity of ammonia or ammonium ion by measuring the absorbance of the contents of at least the first vessel or the second vessel.

Family of Phenols

Different compounds comprising a phenyl group can be used as long as the compound comprises a 4, 5, or 6-membered ring with at least one carbon atom and a unsubstituted 'para-position.'

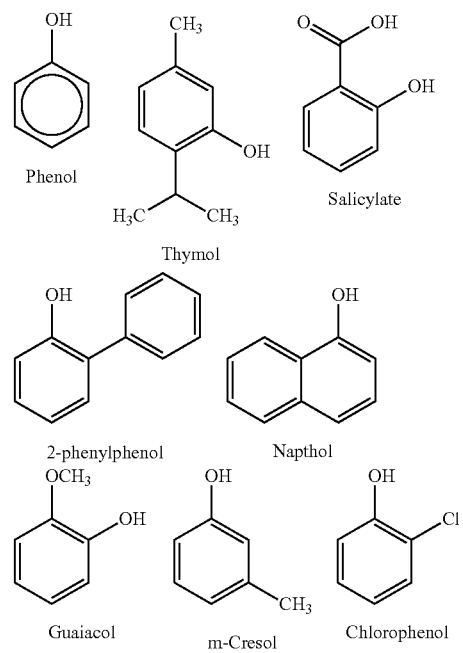

-continued

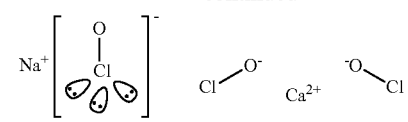

Family of Hypohalites
Hypochlorite

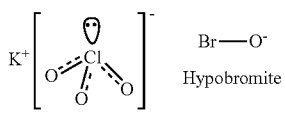

Hypobromite

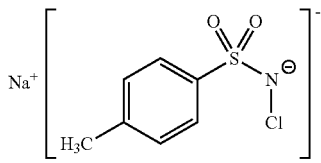

Chloramine T

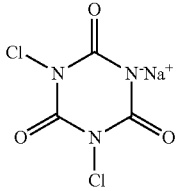

Sodium dichloroisocyanurate

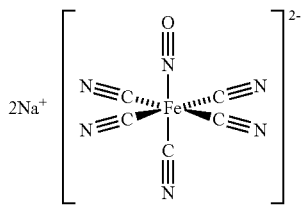

Family of Catalysts/Coupling Agents
Sodium Nitroprusside
Chrominum
Iron
Maganese Alkali Conditions Any buffer capable of creating an alkali microenvironment for the reaction to take place with ammonia from a sample may be used. In some embodiments, a vessel comprising an alkali buffer with pH from about 8.5 to about 13 can be used in the biosensor, test strip, or system disclosed herein. Any compound that can create these alkali conditions can be used including sodium and potassium hydroxide, or sodium or potassium acetate. In some embodiments, the alkali buffer is in a powdered form, lyophilized, or aqueous solution in a vessel located within the biosensor or kit disclosed herein.

Electrode

In some embodiments, the biosensor, system or test strip disclosed herein comprise one or more electrodes. In some embodiments, the one or more electrodes transmit current variation generated by the reaction between the indophenol reagents and ammonia or ammonium ion from a sample and/or transmit current variation generated by a battery source to the light source or other equipment necessary to provide a readout of the levels of ammonia in a sample, for instance, in the case of a spectrophotometer to measure absorbance of a reactant vessel in the biosensor. In some embodiments, the electrodes comprise metal. In some embodiments, the electrodes comprise a carbon scaffold upon which a metal is deposited. In some embodiments, the electrodes comprise a carbon scaffold of carbon nanotubes.

Electrode structures which are suitable for the present disclosure and methods for the production of such structures have already been suggested in biosensor technology for other purposes. In this regard, reference is made to U.S. Pat. No. 6,645,359 and its content is incorporated herein by reference in its entirety. Electrodes or Electrically conductive tracks are created or isolated on first surface. Tracks represent the electrodes of biosensor. As used herein, the phrase "electrode set" is a set of at least two electrodes, for example 2 to 200, or 3 to 20, electrodes. These electrodes may, for example, be a working (or measuring) electrode and an auxiliary electrode. In some embodiments, tracks cooperate to form an interdigitated electrode array positioned within the periphery of recesses and leads that extend from array and between recesses toward end.

Tracks are constructed from electrically conductive materials. Non-limiting examples of electrically-conductive materials include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, tracks include gold, platinum, palladium, iridium, or alloys of these metals, since such noble metals and their alloys are unreactive in biological systems. In some embodiments, the track is a working electrode made of silver and/or silver chloride, and track is an auxiliary electrode that is also made of silver and/or silver chloride and is substantially the same size as the working electrode.

Tracks are isolated from the rest of the electrically conductive surface by laser ablation. Techniques for forming electrodes on a surface using laser ablation are known. Techniques for forming electrodes on a surface using laser ablation are known. See, for example, U.S. patent application Ser. No. 09/411,940, filed Oct. 4, 1999, and entitled "LASER DEFINED FEATURES FOR PATTERNED LAMINATES AND ELECTRODE", the disclosure of which is expressly incorporated herein by reference. Tracks are preferably created by removing the electrically conductive material from an area extending around the electrodes. Therefore, tracks are isolated from the rest of the electrically-conductive material on a surface by a gap having a width of about 5 µm to about 500 µm, preferably the gap has a width of about 100 µm to about 200 µm. Alternatively, it is appreciated that tracks may be created by laser ablation alone on bottom substrate. Further, tracks may be laminated, screen-printed, or formed by photolithography.

Multi-electrode arrangements are also possible in accordance with this disclosure. For example, it is contemplated that a biosensor may be formed that includes an additional electrically conductive track. In a three-electrode arrangement such as the arrangement depicted in FIG. 4, the first track is a working electrode, the second is a counter electrode, and the third electrode is a reference electrode. It is also appreciated that an alternative three-electrode arrangement is possible where tracks are working electrodes and a third electrode is provided as an auxiliary or reference electrode. It is appreciated that the number of tracks, as well as the spacing between tracks in array may vary in accordance with this disclosure and that a number of arrays may be formed as will be appreciated by one of skill in the art.

in some embodiments, the electrodes are embedded on or attached to a solid support, such as a test strip comprising a plastic and/or paper material.

Micro-electrode arrays are structures generally having two electrodes of very small dimensions, typically with each electrode having a common element and electrode elements or micro-electrodes. If "interdigitated" the arrays are arranged in an alternating, finger-like fashion (See, e.g., U.S. Pat. No. 5,670,031). These are a sub-class of micro-electrodes in general. Interdigitated arrays of micro-electrodes, or IDAs, can exhibit desired performance characteristics; for example, due to their small dimensions, IDAs can exhibit excellent signal to noise ratios.

Interdigitated arrays have been disposed on non-flexible substrates such as silicon or glass substrates, using integrated circuit photolithography methods. IDAs have been used on non-flexible substrates because IDAs have been considered to offer superior performance properties when used at very small dimensions, e.g., with feature dimensions in the 1-3 micrometer range. At such small dimensions, the surface structure of a substrate (e.g., the flatness or roughness) becomes significant in the performance of the IDA. Because non-flexible substrates, especially silicon, can be processed to an exceptionally smooth, flat, surface, these have been used with IDAs. In some embodiments, the at least one electrode is a component of any IDA disclosed herein.

Membrane

In some embodiments, the membrane positioned at a fluid exchange opening comprises an ionomer. In some embodiments, the membrane comprises one or a combination of the following polymers:

1.

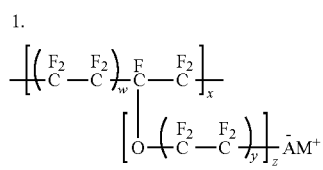

2.

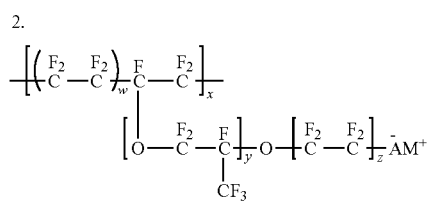

3.

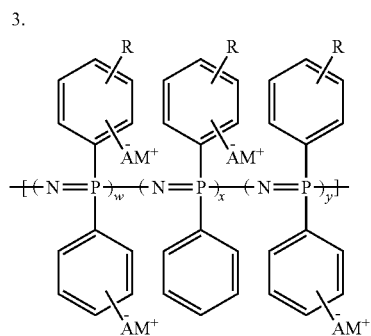

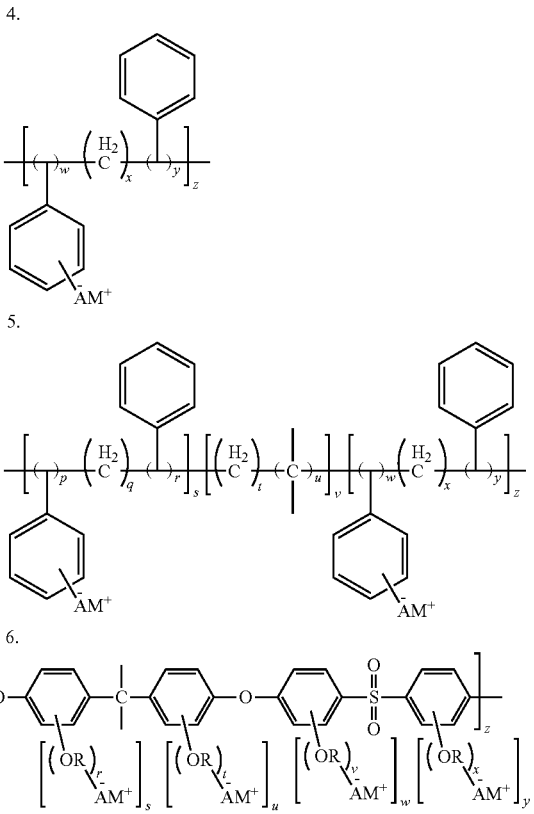

wherein each of the variables p, q, r, s, t, u, v, w, x, y, and z are independently variable and are 0 or any positive integers; and wherein R is independently selected from an amine, hydroxy, hydroxyl, carbonyl, H, =O, —OH, —COOH, —N, —CH$_3$, —CH$_2$—X, halo, aryl, arylalkoxy, arylalkyl, alkynyl, alkenyl, alkylene, alkyl, akyl-halo, arylamido, alkylheterocycle, alkylamino, alkylguanidino, alkanol, alkylcarboxy, cyclo alkyl, heteroaryl, heteroarylalkyl, heteroarylalkoxy, or heterocyclyl; or any salt thereof.

In some embodiments, the R group is acidic or an electronegative substituent. In some embodiments, the variables p, q, r, s, t, u, v, w, x, y, z are independently variable and are 0 or positive integers from about 1 to about 200. In some embodiments, the variables p, q, r, s, t, u, v, w, x, y, z are independently variable and are 0 or positive integers from about 10 to about 100. In some embodiments, the variables p, q, r, s, t, u, v, w, x, y, z are independently variable and are 0 or positive integers from about 10 to about 100 across many species within a matrix of material comprising many species of polymer. A− represents the anionic or acidic groups that can include sulfonate, carboxylate, or other similar functional group. M+ represents the counter ion and may include H+, Li+, Na+, or similar cation. Letters (p-z) accompanied by parenthesis or brackets represent repeat units that can range from 0 to any integer value. Any polymer containing any combination of Carbon (C), Fluorine (F), Sulfur (S), Oxygen (O), Hydrogen (H), Nitrogen (N), Phosphorous (P), or any similar element, which may be used to create an ionic exchange membrane may also be utilized.

Ion exchange membranes can be constructed from polymers including perfluorinated ionomers (1&2), polyphosphazene based ionomers (3), polystyrene based ionomers (4), polystyrene based block-co-polymer ionomers (5), and poly (arlyene ether sulfone) based ionomers (6).

Total acid content for ionic exchange membranes may range from about 0.57 to about 3.5 meq/g. In some embodiments, the total acid content for ionic exchange is from about 0.57 to about 4.0 meq/g. In some embodiments, the total acid content for ionic exchange is from about 0.57 to about 3.0 meq/g. In some embodiments, the total acid content for ionic exchange is from about 0.57 to about 2.9 meq/g. In some embodiments, the total acid content for ionic exchange is from about 0.57 to about 2.8 meq/g. In some embodiments, the total acid content for ionic exchange is from about 0.57 to about 2.7 meq/g. In some embodiments, the total acid content for ionic exchange is from about 0.57 to about 2.6 meq/g. In some embodiments, the total acid content for ionic exchange is from about 0.57 to about 2.5 meq/g. In some embodiments, the total acid content for ionic exchange is from about 0.57 to about 2.4 meq/g. In some embodiments, the total acid content for ionic exchange is from about 0.57 to about 2.3 meq/g. In some embodiments, the total acid content for ionic exchange is from about 0.57 to about 2.2 meq/g. In some embodiments, the total acid content for ionic exchange is from about 0.57 to about 2.1 meq/g. In some embodiments, the total acid content for ionic exchange is from about 0.57 to about 2.0 meq/g.

Membranes constructed from these ionomers may range in thickness from about 0.025 to about 0.69 mm in thickness. In some embodiments the membrane is from about 0.001 to about 069 mm in thickness. In some embodiments the membrane is from about 0.001 to about 068 mm in thickness. In some embodiments the membrane is from about 0.001 to about 067 mm in thickness. In some embodiments the membrane is from about 0.001 to about 066 mm in thickness. In some embodiments the membrane is from about 0.001 to about 065 mm in thickness. In some embodiments the membrane is from about 0.001 to about 064 mm in thickness. In some embodiments the membrane is from about 0.001 to about 063 mm in thickness. In some embodiments the membrane is from about 0.001 to about 062 mm in thickness. In some embodiments the membrane is from about 0.001 to about 061 mm in thickness. In some embodiments the membrane is from about 0.001 to about 060 mm in thickness. In some embodiments the membrane is from about 0.001 to about 059 mm in thickness. In some embodiments the membrane is from about 0.001 to about 058 mm in thickness. In some embodiments the membrane is from about 0.001 to about 050 mm in thickness. In some embodiments the membrane is from about 0.001 to about 040 mm in thickness. In some embodiments the membrane is from about 0.001 to about 030 mm in thickness. In some embodiments the membrane is from about 0.001 to about 020 mm in thickness. In some embodiments the membrane is from about 0.001 to about 010 mm in thickness. In some embodiments the membrane is from about 0.025 to about 065 mm in thickness. In some embodiments the membrane is from about 0.025 to about 064 mm in thickness. In some embodiments the membrane is from about 0.025 to about 063 mm in thickness. In some embodiments the membrane is from about 0.025 to about 062 mm in thickness. In some embodiments the membrane is from about 0.025 to about 061 mm in thickness. In some embodiments the membrane is from about 0.025 to about 060 mm in thickness. In some embodiments the membrane is from about 0.025 to about 059 mm in thickness. In some embodiments the membrane is from about 0.025 to about 058 mm in thickness. In some embodiments the membrane is from about 0.025 to about 050 mm in thickness. In some embodiments the membrane is from about 0.025 to about 040 mm in thickness. In some embodiments the membrane is from about 0.025 to about 030 mm in thickness. In some embodiments the membrane is from about 0.025 to about 020 mm in thickness. In some embodiments the membrane is from about 0.025 to about 010 mm in thickness.

Higher total acid content and smaller membrane thickness leads to faster diffusion times. Membranes may be formed through extrusion casting, drop casting, hot pressing, or similar method.

Cartridges and Disposable Devices

The bio sensor, device, system, and or test strip may be or comprise a cartridge. In some embodiments, the cartridge is disposable after one use or can be used more than once per ammonia or ammonium ion detection event. In some embodiments, the cartridge comprises a plurality of microfluidic conduits in fluid communication with a storage portion, a mixing portion and a readout portion of the cartridge. The storage portion comprises a plurality of compartments that store one or a combination of indophenol reagents either crystallized, dried, lyophilized or in solution. In some embodiments, the compartments may be partitioned from an adjacent conduit by plastic wall or other inert material. The mixing portion of the cartridge comprises a trunk-shaped conduit where one or more reagents being stored mix after they are released from the storage portion of the device. The reagents may mix with a sample and/or each other at different points in the microfluidic channels adjacent to the storage portion of the device. In some embodiments of the device the readout portion of the microfluidic conduits is adjacent to the mixing portion of the device. In some embodiments of the device, the cartridge comprises only a storage portion and a readout portion, wherein the readout portion comprises a microfluidic conduit configured to align to an instrument that measures the amount of ammonia or ammonium in a sample but also allows mixing of samples prior to any detection or quantification step takes place through the instrument. In some embodiments, the cartridge does not comprise an instrument for detection of the amount of ammonia or ammonium ion in an sample (spectrophotometer), but is configured to align the readout portion of the cartridge to a instrument capable of determining the amount of ammonia or ammonium ion in a sample. In some embodiments, the cartridge comprises an instrument for detection of the amount of ammonia or ammonium ion in an sample, such as a photodiode. In some embodiments, the cartridge comprises readout portion comprising microfluidic conduits for detection or quantification adjacent to the mixing portion of the device. In some embodiments, the cartridge comprises an instrument for detection of the amount of ammonia or ammonium ion in an sample, such as a photodiode, such instrument comprising a light source aligned to or with the readout portion of the device such that light from the light source may penetrate the readout portion and such instrument may detect the presence, absence or absorbance of wavelength of light in the readout portion.

In some embodiments, the cartridge comprises a microfluidic circuit comprising a storage portion in fluid communication with a mixing portion which is also in fluid communication with a readout portion. Fluid in such an embodiment is designed to flow from the storage portion to the mixing portion, and from the mixing portion to the readout portion of the cartridge. In some embodiments the storage portion comprises one compartment for each indophenol reagent. In some embodiments, the storage portion comprises a first compartment comprising a hypohalite (such as hypochlorite), a second compartment comprising an basic buffer (such as NaOH), and a third compartment comprising at least one indophenol reagent or indophenol related compound (such as 2-phenylphenol). In some embodiments, the storage portion comprises a fourth compartment comprising a catalyst or coupling reagent (such as Sodium Nitroprusside). In some embodiments, the storage portion comprises a fifth compartment comprising an alkali buffer (such as sodium acetate or calcium acetate or zinc acetate). In some embodiments, the cartridge comprises a fluid exchange opening between a microfluidic conduit the compartment comprising a an alkali buffer (such as sodium acetate or calcium acetate or zinc acetate). In some embodiments, a membrane disclosed herein is positioned over at least a portion of the fluid exchange opening such that when a sample comes in contact with the alkali buffer, ammonia can be transported across the membrane into the adjacent microfluidic conduit.

In some embodiments, the storage portion comprises a compartment optionally comprising an electrode. In some embodiments the compartment optionally comprising an electrode is adjacent to a compartment comprising the alkali buffer in solid or liquid phase, such compartment having an opening through which a sample may be deposited into the cartridge from a point exterior to the cartridge. In some embodiments, the cartridge comprises a sixth compartment comprising an opening and optionally comprising an electrode, such compartment having an opening through which a sample may be deposited into the cartridge from a point exterior to the cartridge. In some embodiments, the cartridge comprises a sixth compartment comprising an opening and optionally comprising an electrode, such compartment having an opening through which a sample may be deposited into the cartridge from a point exterior to the cartridge; wherein the cartridge further comprises a a compartment comprising an alkali buffer that is positioned at or substantially near the compartment comprising the opening, such that, upon inserting a sample into the compartment with an opening, the alkali buffer is transported to the compartment comprising the opening and mixes with the sample.

In some embodiments, a compartment has a volume of no more than about 100 microliters of fluid. In some embodiments, one or more compartments in the cartridge has a volume of no more than about 100 microliters of fluid. In some embodiments, one or more compartments in the cartridge has a volume of no more than about 90 microliters of fluid. In some embodiments, one or more compartments in the cartridge has a volume of no more than about 80 microliters of fluid. In some embodiments, one or more compartments in the cartridge has a volume of no more than about 70 microliters of fluid. In some embodiments, one or more compartments in the cartridge has a volume of no more than about 60 microliters of fluid. In some embodiments, one or more compartments in the cartridge has a volume of no more than about 50 microliters of fluid. In some embodiments, one or more compartments in the cartridge has a volume of no more than about 40 microliters of fluid. In some embodiments, one or more compartments in the cartridge has a volume of no more than about 30 microliters of fluid. In some embodiments, one or more compartments in the cartridge has a volume of no more than about 20 microliters of fluid. In some embodiments, one or more compartments in the cartridge has a volume of no more than about 10 microliters of fluid.

Figure 24:
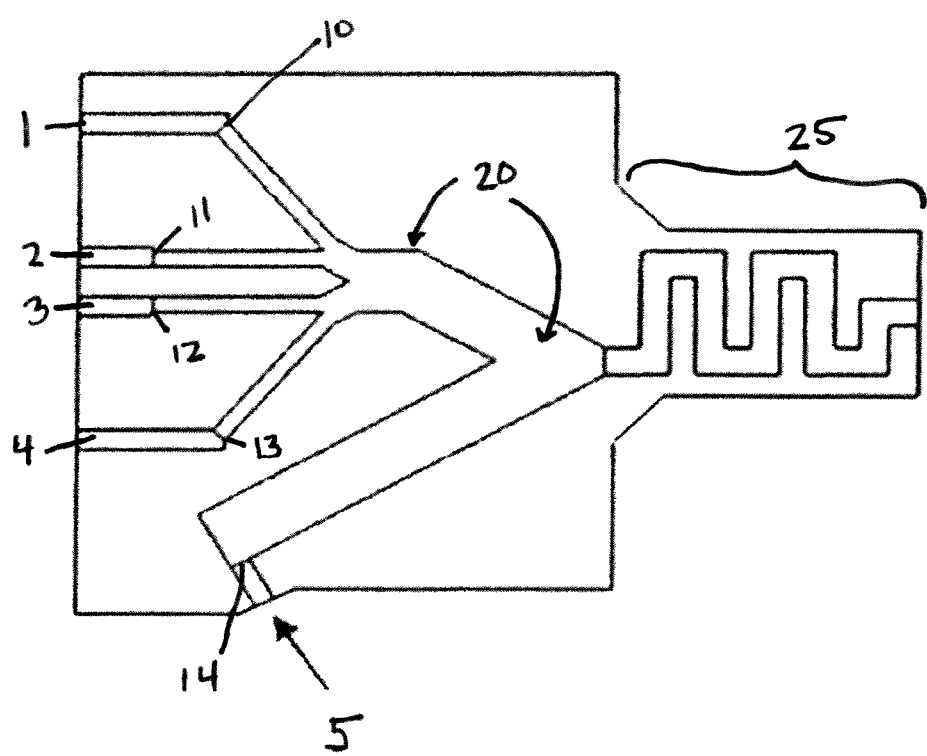
FIG. 24 depicts a CAD sketch of the top piece of a disposable cartridge, with dimensions in mm. Channels 1 through 5 are labeled.
Figure 25:
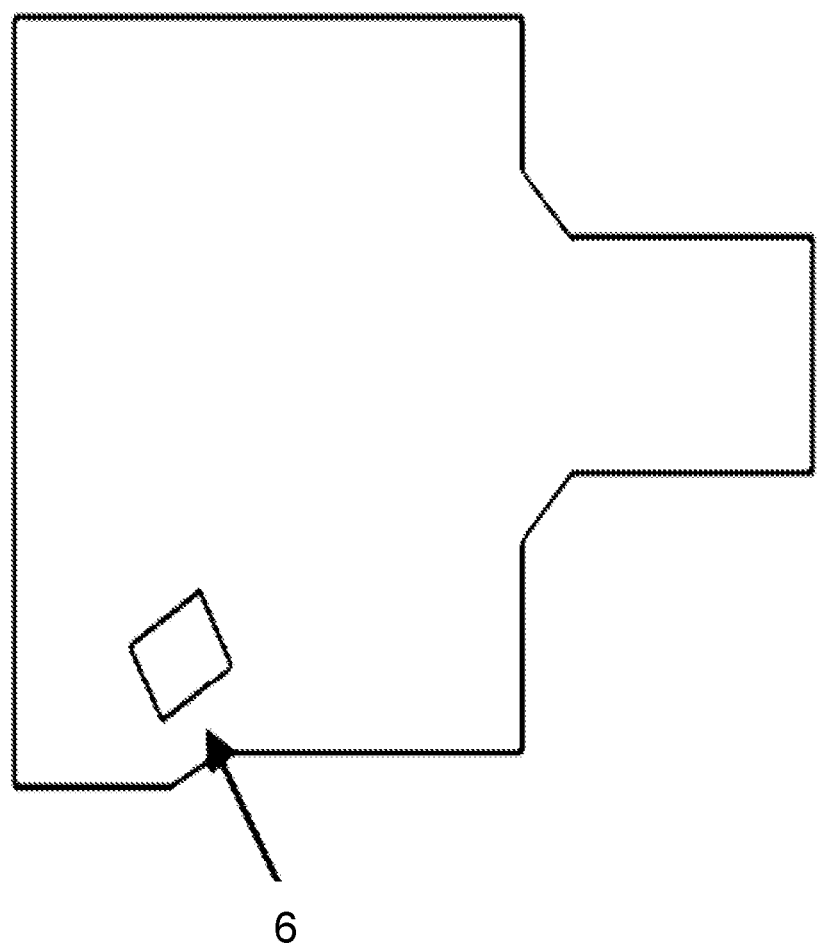
FIG. 25: CAD sketch of the bottom piece of the chip with channel 6 labeled.

FIGS. 24 through 28 depict an embodiment of the invention that is a cartridge. one half of the cartridge is depicted in FIG. 24 while the opposite facing half of the cartridge is depicted in FIG>25. The two halves of the cartridge may be secured together by one or a plurality of microscrews, dowels or fasteners. The two halves of the cartridge may be made out of one or a plurality of inert materials such as a plastic and/or glass.

Figure 26:
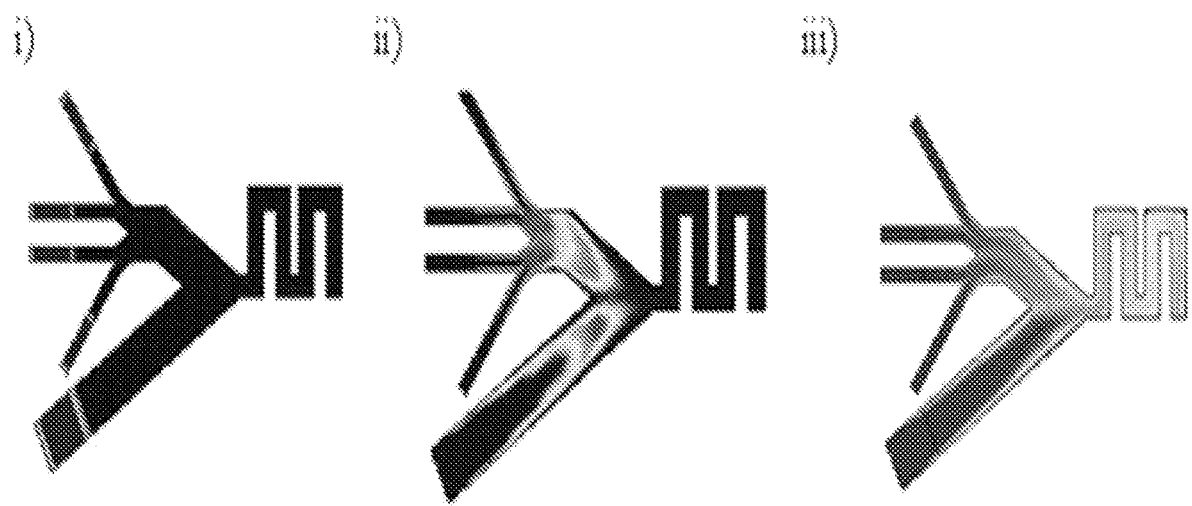
FIG. 26: depicts the representations of a concentration profile at i) t=0 seconds (s); ii) t=13 s, and iii) t=24 s after a whole blood sample in 40 microliters is loaded into well number 6.
Figure 27:
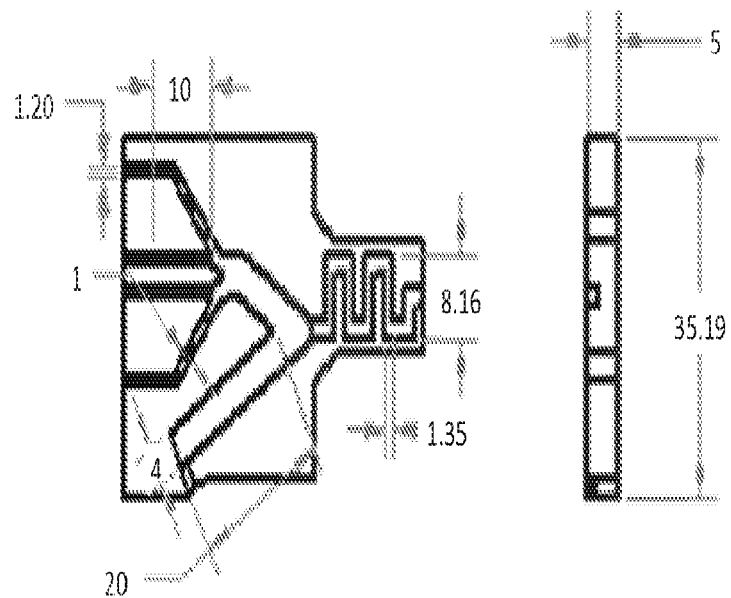
FIG. 27 depicts the top half of an embodiment comprising a microfluidic device used to quantify ammonia levels in whole blood.
Figure 27:
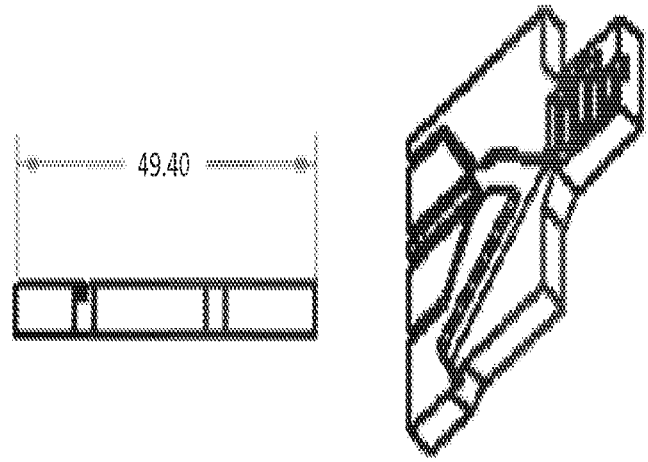
Figure 28:
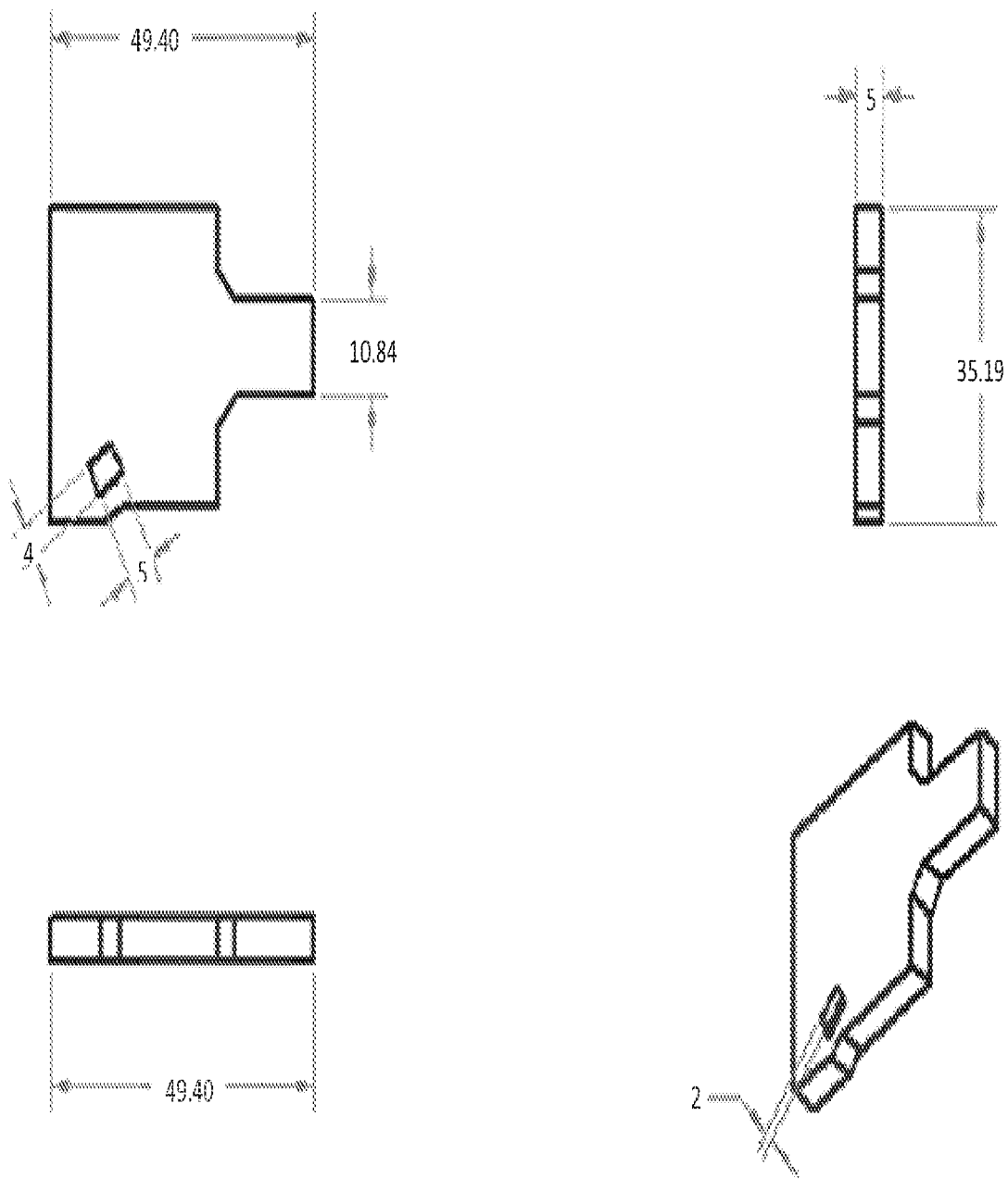
FIG. 28 depicts the bottom half of an embodiment comprising a microfluidic device used to quantify ammonia levels in whole blood.

The cartridge half disclosed in FIG. 24 comprises a first, second, third, fourth and fifth storage compartment. FIG. 24 depicts a first, second, third, fourth and fifth compartment (labeled 1, 2, 3, 4, and 5 respectively) that define a volume immediately adjacent to, but partitioned from, a microfluic conduit on a bottom half of the cartridge. The partition is delineated by the small solid dash bisecting the space between the compartment and the microfluidic conduit (labeled 10, 11, 12, 13, and 14 for each of the compartments 1, 2, 3, 4, and 5 respectively. In this embodiment, the first compartment comprises hypohalite, the second compartment comprises an basic buffer, the third compartment comprises a catalyst, the fourth compartment comprises a indophenol reagent (such as a phenolic compound), and the fifth compartment comprises an alkali buffer, which, if in aqueous solution, may be at a concentration from about 500 mM to about 1 M sodium acetate. The storage portion of the microfluidic circuit comprises the storage points 1, 2, 3, 4, 5, and 6. Any membrane disclosed herein may be placed at or near position 14 such that, upon introduction of a sample such as whole blood in the compartment 6 of FIG. 25, mixing of the reagents can occur. Fluid from compartment 5 is mixed with the sample and ammonia ions in solution may be transferred from 5 and 6 into the mixing portion of the device 20 across the membrane. The reagents in compartments 1 through 4 are also released such that after a period of about 4-5 seconds, all reagents have entered the mixing portion of the device 20. The upper branched portion of the mixing portion 20 mixes the indophenol reagents contained in the compartments 1, 2, 3 and 4 while the ammonia from the sample and to buffer in 5 and 6 mix in the lower trunk of the cartridge. Once in use, FIG. 26 depicts the anticipated flow of fluid from each compartment to the mixing portion of the cartridge. Lighter shades of grey show the bolus of reagents from each compartment as they travel at 0 seconds (i); at 13 second (ii); and 24 seconds (iii) through the microfluid circuit. After mixing is complete in the mixing portion of the device, all reagents mix in the portion of the mixing portion closest proximate to the readout portion 25 of the circuit. At the readout portion of the device, the cartridge may have an opening though which light may travel and expose the fluid to a certain measurable wavelength of light. An instrument such as a photodiode may be present near or adjacent to the readout portion of the device so that measurements of absorbance may be taken.

In some embodiments, the cartridge comprises at least one electrode that detects the presence or absence of ammonia or ammonium ion in a sample in a vessel configured to receive a sample from a point external to the cartridge. Once the electrode is activated by the presence of a sample, the storage portion of the cartridge open and release their contents such that a solution from each compartment is released into the mixing portion of the microfluidic conduits. The microfluidic conduits are of a length sufficient to mix all of the reagents from each compartment such that, by the time total fluid volume of reactants reach the readout portion of the cartridge, an indophenol reaction has taken place and an indophenol reaction product (such as indophenol or an indophenol related compound) have formed in the microfluidic conduits.

TABLE 3

Examples of Indophenol Reagent Concentration Ranges

| Reagent | Range |
| --- | --- |
| 2-phenylphenol | From about 50 to about 70 mmol/liter |
| Sodium Nitroprusside | About 7 micromoles/liter |
| Sodium Hydroxide | From about 50 to about 500 mmol/liter |
| Sodium Hypochlorite | From about 50 to about 120 mmol/liter |
| Sodium/Calcium Acetate | From about 0.5 to about 1 mol/liter |

Hydrogel

The bio sensor comprises a hydrogel in some embodiments. The hydrogel may be a cross-linked polymeric material that swells in water but does not dissolve. It is envisioned that the hydrogel may be capable of absorbing at least about 1 to about 10 times, and in one embodiment at least about 100 times, its own weight of a liquid. The hydrogel chosen for use in the biosensor should depend directly on the method of functionalization. It is envisioned that the hydrogel may be biocompatible. In some embodiments, the hydrogel comprises sodium alginate. In some embodiments, the hydrogel comprises from about 0.1% to about 5% alginate weight/volume. In some embodiments, the hydrogel comprises from about 0.1% to about 4% alginate weight/volume. In some embodiments, the hydrogel comprises from about 0.1% to about 3% alginate weight/volume. In some embodiments, the hydrogel comprises from about 0.1% to about 2% alginate weight/volume. In some embodiments, the hydrogel comprises from about 0.1% to about 1% alginate weight/volume. In some embodiments, the hydrogel comprises from about 0.1% to about 1% alginate weight/volume. In some embodiments, the hydrogel comprises from about 0.2% to about 1% alginate weight/volume. In some embodiments, the hydrogel comprises sodium alginate. In some embodiments, the hydrogel comprises from about 0.3% to about 1% alginate weight/volume. In some embodiments, the hydrogel comprises from about 0.4% to about 1% alginate weight/volume In some embodiments, the hydrogel comprises from about 0.5% to about 1% alginate weight/volume. In some embodiments, the hydrogel comprises from about 0.6% to about 1% alginate weight/volume. In some embodiments, the hydrogel comprises from about 0.7% to about 1% alginate weight/volume. In some embodiments, the hydrogel comprises from about 0.8% to about 1% alginate weight/volume. In some embodiments, the hydrogel comprises from about 0.9% to about 1% alginate weight/volume. In some embodiments, the hydrogel comprises from about 1.0% to about 3.0% alginate weight/volume. In some embodiments, the hydrogel comprises from about 1.0% to about 2.0% alginate weight/volume. In some embodiments, the hydrogel comprises from about 1.0% to about 1.5% alginate weight/volume. In some embodiments, the hydrogel comprises about 1%, about 2%, or about 3% alginate weight/volume. In some embodiments, the hydrogel comprises sodium alginate. The aliginate may be any individual polymer of alginate used in bulk form or repetitive pattern of monomers, G blocks, M blocks, and/or GM blocks. In some embodiments the alignate comprises the formula:

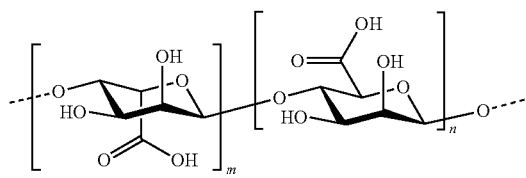

where m and n are any positive integer. In some embodiments m and n are independently variable and any positive integer from about 1 to about 1000. In some embodiments, the hydrogel may be polymerized from acrylic monomers. The acrylic monomer may be one or a combination of the following: acrylamido-glycolic acid, acrylamido-methyl-propa-ne-sulfonic acid, acrylamido-ethylphosphate, diethyl-aminoethyl-acrylamide-, trimethyl-amino-propyl-methacrylamide, N-octylacrylamide, N-phenyl-acrylamide and tert-butyl-acrylamide. In embodiments in which the device contains a cross-linking agent, exemplary cross-linking agents may be N,N'-methylene-bis-acrylamide, N,N'-methylene-bismethacrylamide, diallyltatardiamide and poly(ethylene glycol)dimethacrylate. Examples of suitable hydrogels may also include silicon wafers, borosilicate glass substrates, 2-hydroxyethyl methacrylate (HEMA), N-Isopropylacrylamide (NIPAAm), and polyethylene glycol (PEG).

The hydrogel may include any number of molecules. For example, the hydrogel may include a polymerized monomer or hydrogel a cross linking agent and optionally a chemical or UV-light activated inducer agent. Examples of such monomers or dimers include vinyl acetates, vinyl pyrrolidones, vinyl ethers, olefins, styrenes, vinyl chlorides, ethylenes, acrylates, methacrylates, nitriles, acrylamides, maleates, epoxies, epoxides, lactones, ethylene oxides, ethylene glycols, ethyloxazolines, amino acids, saccharides, proteins, anhydrides, amides, carbonates, phenylene oxides, acetals, sulfones, phenylene sulfides, esters, fluoropolymers, imides, amide-imides, etherimides, ionomers, aryletherketones, amines, phenols, acids, benzenes, cinnamates, azoles, silanes, chlorides, and epoxides, N,N'-methylenebisacrylamide, methylenebismethacrylamide ethyleneglycol-dimethacrylate, N,N'-methylenebisacrylamide, polyethyleneglycoldiacrylate (PEGDA), polyethyleneglycoldimethacrylate (PEGDMA), polyethyleneglycoldiacrylate (PEGDA), polyethyleneglycoldimethacrylate (PEGDMA), poly(vinyliden fluoride) (PVdF) based polymer, a polyacrylonitrile (PAN) based polymer, a polymethylmethacrylate (PMMA) based polymer, a polyvinyl chloride (PVC) based polymer, and a mixture of the poly(vinyliden fluoride) (PVdF) based polymer, polyacrylonitrile (PAN) based polymer, polymethylmethacrylate (PMMA) based polymer, and polyvinyl chloride (PVC) based polymer, and mixtures of any two or more thereof. IN some embodiments, the hydrogel does not comprise 3,4-dihydroxybenzoic acid (3, 4-DHB) or an analog thereof.

Cross linking agents and optionally the chemical or UV-light activated inducer agent may include N,N'-methylenebisacrylamide, methylenebismethacrylamide ethyleneglycol-dimethacrylate and agent N,N'-methylenebisacrylamide. Irgacure 2959 (Ciba); 2,2-dimethoxy-2-phenylacetophenone, 2-methoxy-2-phenylacetone, benzyl-dimethyl-ketal, ammonium sulfate, benzophenone, ethyl benzoin ether, isopropyl benzoin ether, .alpha.-methyl benzoin ether, benzoin phenyl ether, 2,2-diethoxy acetophenone, 1,1-dichloro acetophenone, 2-hydroxy-2-methyl-1-phenylpropane 1-on, 1-hydroxy cyclohexyl phenyl ketone, antraquinone, 2-ethyl antraquinone, 2-chloroantraquinone, tioxantone, isopropyltioxantone, chloro tioxantone, 2,2-chlorobenzophenone, benzyl benzoate, and benzoyl benzoate, TEMED, and ammonium persulfate (APS). In some embodiments, hydrogel comprises a protein, peptide, glycoprotein, proteoglycans, glycosaminoglycans, and/or carbohydrate that is secreted by cells into the extracellular environment. In some embodiments, the secreted protein, peptide, glycoprotein, proteoglycans, glycosamainoglycans, and/or carbohydrate, or structures composed thereof.

In some embodiments, the disclosure relates to a coated biosensor device comprising at least one coating, wherein the biosensor comprises a metabolic enzyme covalently bound or immobilized to the coating, wherein the metabolic enzyme shares at least 70% sequence identify to SEQ ID NO:1 or SEQ ID NO:2 or shares at least 70% sequence identify to functional fragments of SEQ ID NO:1 or SEQ ID NO:2. In some embodiments, the disclosure relates to a coated biosensor device comprising at least one coating, wherein the biosensor comprises a metabolic enzyme covalently bound or immobilized within the coating, wherein the coating comprises a composition comprising a hydrogel matrix, said matrix comprising any one or combination of: alginate, trehalose, at least one electron mediator, and at least one reduction agent. In some embodiments, the disclosure relates to a coated biosensor device comprising at least one coating, wherein the biosensor comprises a metabolic enzyme covalently bound or immobilized to the coating, wherein the coating comprises a composition comprising a hydrogel matrix, said matrix comprising any one or combination of: poly(ethylene glycol) dimethyacrylate with a molecular weight of about 1000 (PEGDMA-1000), 2-hydroxy-2 methyl propiophenone (HMPP) and at least one acrylate, wherein the acrylate is selected from the group consisting of methacrylic acid (MAA) and methyl methacrylate (MMA), wherein the ratio of PEGDMA:Acrylate is from about 10:90 mol % to about 70:30 mol %, and said HMPP is at a concentration of from about 0.2% to about 0.6%, total weight.

In some embodiments, the hydrogel solution prior to curing comprises trehalose or an analog thereof at a concentration from about 1 nM to about 999 mM. In some embodiments, the hydrogel solution prior to curing comprises trehalose at a concentration from about 1 µM to about 10 mM. In some embodiments, the hydrogel solution prior to curing comprises trehalose at a concentration from about 1 µM to about 9 mM. In some embodiments, the hydrogel solution prior to curing comprises trehalose at a concentration from about 1 µM to about 8 mM. In some embodiments, the hydrogel solution prior to curing comprises trehalose at a concentration from about 1 µM to about 7 mM. In some embodiments, the hydrogel solution prior to curing comprises trehalose at a concentration from about 1 µM to about 6 mM. In some embodiments, the hydrogel solution prior to curing comprises trehalose at a concentration from about 1 µM to about 5 mM. In some embodiments, the hydrogel solution prior to curing comprises trehalose at a concentration from about 1 µM to about 4 mM. In some embodiments, the hydrogel solution prior to curing comprises trehalose at a concentration from about 1 µM to about 3 mM. In some embodiments, the hydrogel solution prior to curing comprises trehalose at a concentration from about 1 µM to about 2 mM. In some embodiments, the hydrogel solution prior to curing comprises trehalose at a concentration from about 1 µM to about 1 mM. In some embodiments, the hydrogel solution prior to curing comprises trehalose at a concentration from about 10 µM to about 1 mM. In some embodiments, the hydrogel solution prior to curing comprises trehalose at a concentration from about 100 µM to about 1 mM. In some embodiments, the hydrogel solution prior to curing comprises trehalose at a concentration from about 200 µM to about 1 mM. In some embodiments, the hydrogel solution prior to curing comprises trehalose at a concentration from about 300 µM to about 1 mM. In some embodiments, the hydrogel solution prior to curing comprises trehalose at a concentration from about 400 µM to about 1 mM. In some embodiments, the hydrogel solution prior to curing comprises trehalose at a concentration from about 500 µM to about 1 mM. In some embodiments, the hydrogel solution prior to curing comprises trehalose at a concentration from about 600 µM to about 1 mM. In some embodiments, the hydrogel solution prior to curing comprises trehalose at a concentration from about 700 µM to about 1 mM. In some embodiments, the hydrogel solution prior to curing comprises trehalose at a concentration from about 800 µM to about 1 mM. In some embodiments, the hydrogel solution (prior to contacting with the electrode) comprises trehalose at a concentration from about 900 µM to about 1 mM.

Enzymes

Any one or more metabolic enzymes may be chosen to used with the present disclosure. Metabolic enzymes that can be used individually or in combination with the biosensor, system or test strip disclosed herein include: any bacterial clone of phenylalanine dehydrogenase, histidine ammonia lyase, mistidine oxidase. phenylalanine lyase, glutamate dehydrogenase. In some embodiments the enzyme is chosen from any one or combination of enzymes disclosed below or their respective functional fragments that are at least 70%, 80%, 85%, 90%, 95%, 96%, 97%, 98%, or 99% homologous to the full-length enzyme or nucleic acid encoding such enzyme.

| Organism | Enzyme | GenBank Accession No | SEQ ID NO |
|---|---|---|---|
| Thermoactinomyces intermedius | phenylalanine dehydrogenase | D00631.1 | 2 |
| Solanum lycopersicum | phenylalanine ammonia-lyase | XM_004246602 | 7 |
| Thermoactinomyces intermedius | phenylalanine dehydrogenase | DD421709.1 | 8 |
| Caenorhabditis remanei | phenylalanine dehydrogenase | XM_003102740 | 9 |

-continued

| Arabidopsis thaliana | glutamate dehydrogenase | NM_121822.3 | 10 |
| Spirochaeta africana | Hisitidine ammonia lyase | NC_017098.1 | |

SEQ ID NO: 2

MRDVFEMMDRYGHEQVIFCRHPQTGLKAIIALHNTTAGPALGGCRMIPYASTDEALEDVLRLSKGMTYKCSLADVD
FGGGKMVIIGDPKKDKSPELFRVIGRFVGGLNGRFYTGTDMGTNPEDFVHAARESKSFAGLPKSYGGKGDTSIPTA
LGVFHGMRATARFLWGTDQLKGRVVAIQGVGKVGERLLQLLVEVGAYCKIADIDSVRCEQLKEKYGDKVQLVDVNR
IHKESCDIFSPCAKGGVVNDDTIDEFRCLAIVGSANNQLVEDRHGALLQKRSICYAPDYLVNAGGLIQVADELEGF
HEERVLAKTEAIYDMVLDIFHRAKNENITTCEAADRIVMERLKKLTDIRRILLEDPRNSARR

SEQ ID NO: 7

MASSIVQNGHVNGEAMDLCKKSINVNDPLNWEMAAESLRGSHLDEVKKMVDEFRKPIVKLGGETLTVAQVASIANV
DNKSNGVKVELSESARAGVKASSDWVMDSMGKGTDSYGVTTGFGATSHRRTKNGGALQKELIRFLNAGVFGNGTES
SHTLPHSATRAAMLVRINTLLQGYSGIRFEILEAITKLINSNITPCLPLRGTITASGDLVPLSYIAGLLTGRPNSK
AVGPNGEKLNAEEAFRVAGVTSGFFELQPKEGLALVNGTAVGSGMASMVLFESNILAVMSEVLSAIFAEVMNGKPE
FTDYLTHKLKHHPGQIEAAAIMEHILDGSSYVKAAQKLHEMDPLQKPKQDRYALRTSPQWLGPQIEVIRAATKMIE
REINSVNDNPLIDVSRNKALHGGNFQGTPIGVSMDNTRLALASIGKLMFAQFSELVNDYYNNGLPSNLTAGRNPSL
DYGLKGAEIAMASYCSELQFLANPVTNHVQSAEQHNQDVNSLGLISARKTAEAVDILKLMSSTYLVALCQAIDLRH
LEENLRSAVKNTVSQVAKRTLTMGANGELHPARFCEKELLRVVDREYVFAYADDPCSSTYPLMQKLRQVLVDHAMK
NGESEKNVNSSIFQKIVAFEDELKAVLPKEVESARAVVESGNPAIPNRITECRSYPLYRLVRQELGSELLTGEKVR
SPGEEIDKVFTAMCNGQIIDPLLECLKSWNGAPLPIC

SEQ ID NO: 8

```
     atgcgcgacg tgtttgaaat gatggaccgc tatggccacg agcaggtcat tttttgccgt
  61 catccgcaaa ccggtctcaa agcgatcatc gccttgcata atacaaccgc ggggccggct
 121 ttgggtggat gccgcatgat cccgtatgct tcgacggacg aagccttgga ggatgttttg
 181 cggttgtcca aaggcatgac ctataaatgc agtctggcgg atgtggactt tggcgggggga
 241 aaaatggtta tcatcggcga tccgaaaaaa gataaatcgc cggagttgtt tcgcgtgatc
 301 ggccgttttg tgggcgggtt aaacggccgt ttctataccg gaaccgacat gggaaccaat
 361 ccggaagatt ttgtccatgc cgccaggaa tcgaaatctt ttgccggatt gccgaaatcg
 421 tacggcggaa aggggacac atccattccc accgcgctcg gggtgtttca cggaatgcgg
 481 gccaccgccc ggttttatg ggggacggat cagctgaaag ggcgtgtggt tgccatccaa
 541 ggagtcggca aggtgggaga gcgcttgttg cagcttttgg tcgaagtggg ggcttactgc
 601 aaaattgccg acatcgattc ggtcgcgatgc aacagctga aagaaaagta tggcgacaag
 661 gtccaattgg tggatgtgaa ccggattcac aaggagagtt gcgatatttt ctcgccttgc
 721 gccaaaggcg gcgtggtcaa tgatgacacc attgacgagt tccgttgcct ggccattgtc
 781 ggatccgcca acaaccaact ggtggaagac cggcatgggg cactgcttca aaaacggagc
 841 atttgttatg caccgatta tctggtgaat gccggcgggc tgattcaagt ggctgatgaa
 901 ctggaaggct tccatgaaga gagtgctc gccaaaaccg aagcgattta tgacatggtc
 961 ctggatattt tcaccgggc gaaaatgag aatattacca cttgtgaggc agcggaccgg
1021 atcgtgatgg agcgtttgaa aaagttaacc gatattcgcc ggatcttgtt ggaggatccc
1081 cgcaacagcg caaggaggta a
```

SEQ ID NO: 9

MDFKAKLLAEMAKKRKAVSGLEVKEGGAKFVRGADLESKRTQEYEAKQEELAIKKRKADDEILQESTSRAKIVPEV
PEAEFDEKTPMPEIHARLRQRGQPILLFGESELSVRKRLHQLEIEQPELNEGWENEMQTAMKFIGKEMDKAVVEGT
ADSATRHDIALPQGYEEDNWKSIEHASTLLGVGDEMKRDCDIILSICRYILARWARDLNDRPLDVKKTAQGMHEAA
HHKQTTMHLKSLMTSMEKYNVNNDIRHHLAKICRLLVIERNYLEANNAYMEMAIGNAPWPVGVTRSGIHQRPGSAK
AYVSNIAHVLNDETQRKYIQAFKRLMTKLQEYFPTDPSKSVEFVKKSV

SEQ ID NO: 10

MNALAATNRNFKLAARLLGLDSKLEKSLLIPFREIKVECTIPKDDGTLASFVGFRVQHDNARGPMKGGIRYHPEVD
PDEVNALAQLMTWKTAVAKIPYGGAKGGIGCDPSKLSISELERLTRVFTQKIHDLIGIHTDVPAPDMGTGPQTMAW
ILDEYSKFHGYSPAVVTGKPIDLGGSLGRDAATGRGVMFGTEALLNEHGKTISGQRFVIQGFGNVGSWAAKLISEK
GGKIVAVSDITGAIKNKDGIDIPALLKHTKEHRGVKGFDGADPIDPNSILVEDCDILVPAALGGVINRENANEIKA
KFIIEAANHPTDPDADEILSKKGVVILPDIYANSGGVTVSYFEWVQNIQGFMWEEEKVNDELKTYMTRSFKDLKEM
CKTHSCDLRMGAFTLGVNRVAQATILRGWGA (SEQ ID NO: 1)

MNTVTNQWKAVDIFTQIRDHEQVVFCNDKNTGLKAIIAIHDTTLGPALGGCRMYPYATVEDALFDVLRLSKGMTYK
CLAADVDFGGGKAVIIGDPHKDKTPELFRAFGQFVESLNGRFYTGTDMGTTPDVFVHAMKETNCIVGVPEEYGGSG
DSSVPTALGVIYGIQATNKVIWGSDELHGKTYAIQGLGKVGRKVAERLLKEGADLYVCDIHPTAIEAIVSYAKKLG
ANVKVVQGTEIYRTDADIFVPCAFGNVVNDNTIHVLKVKAIVGSANNQLLDVRHGQLLKEKGILYAPDYIVNAGGL
IQVADELYGLNKERVLQKTKAIYSTLLHIYSRAEADHITTIEAANRFCEERLQQRSRRNDFFTHRKQPKWDIRR.

Solid Support

There are many forms of ammonia- or ammonium ion-measuring devices; one common type is represented by hand-held electronic meters which receive blood samples via enzyme-based test strips. In using these systems, the patient may for example lances a finger or alternate body site to obtain a blood sample, the strip is inserted into a test strip opening in the meter housing, the sample is applied to the test strip and the electronics in the meter convert a current generated by the enzymatic reaction in the test strip to a amino acid concentration value.

Solid supports of the disclosure may be solid state but are a flexible substrate. According to the disclosure, the inter-digitated array or at least one electrode is disposed proximal to, e.g., on, a flexible substrate. To act as a flexible substrate, a material must be flexible and also insulating, and is typically relatively thin. The substrate should be capable of adhering components of an IDA, or additional components of a sensor, to its surface. Such thin, insulative, flexible substrates are known in the art of flexible circuits and flex circuit photolithography. "Flexible substrates" according to the present disclosure can be contrasted to non-flexible substrates used in integrated circuit (IC) photolithography but not in flexible circuit photolithography. Examples of non-flexible substrates used in IC photolithography include silicon, aluminum oxide, and other ceramics. These non-flexible substrates are chosen to be processable to a very flat surface. Typical flexible substrates for use in the disclosure are constructed of thin plastic materials, e.g., polyester, especially high temperature polyester materials; polyethylene naphthalate (PEN); and polyimide, or mixtures of two or more of these. Polyimides are available commercially, for example under the trade name Kapton®, from I.E. duPont de Nemours and Company of Wilmington, Del. (duPont). Polyethylene naphthalate is commercially available as Kaladex®, also from duPont. A particularly preferred flexible substrate is 7 mil thick Kaladex® film.

Interdigitated arrays of the disclosure can be used in applications generally known to incorporate electrodes, especially applications known to involve interdigitated arrays of electrodes. Various applications are known in the arts of electronics and electrochemistry, including applications relating to process and flow monitoring or control, and chemical analytical methods. The arrays may be particularly useful as a component of an electrochemical sensor, where there is added value, benefit, or cost efficiency, to the use of a flexible substrate, or where there is value, benefit, or cost efficiency in having an interdigitated array of dimensions relatively larger than the dimensions of interdigitated arrays conventionally disposed on non-flexible substrates.

An interdigitated array of the disclosure can, for example, be included in an electrochemical sensor (sometimes referred to as a "biosensor" or simply "sensor") used in electrochemical detection methods. Electrochemical detection methods operate on principles of electricity and chemistry, or electrochemistry, e.g., on principles of relating the magnitude of a current flowing through a substance, the resistance of a substance, or a voltage across the substance given a known current, to the presence of a chemical species within the substance. Some of these methods can be referred to as potentiometric, chronoamperometric, or impedance, depending on how they are practiced, e.g., whether potential difference or electric current is controlled or measured. The methods and sensors, including sensors of the disclosure, can measure current flowing through a substance due directly or indirectly to the presence of a particular chemical compound (e.g., an analyte or an electroactive compound), such as a compound within blood, serum, interstitial fluid, or another bodily fluid, e.g., to identify levels of amino acids, blood urea, nitrogen, cholesterol, lactate, and the like. Adaptations of some electrochemical methods and electrochemical sensors, and features of their construction, electronics, and electrochemical operations, are described, for example, in U.S. Pat. Nos. 5,698,083, 5,670,031, 5,128,015, and 4,999,582, each of which is incorporated herein by reference.

In some embodiments, any of the above biosensor cartridges, devices, or methods comprise a volume of anticoagulant. In some embodiments, the volume of the anticoagulant disclosed herein in a volume of about 10 microliters. In some embodiments, the volume of the anticoagulant disclosed herein in a volume of about 20 microliters. In some embodiments, the volume of the anticoagulant disclosed herein in a volume of about 30 microliters. In some embodiments, the volume of the anticoagulant disclosed herein in a volume of about 40 microliters. In some embodiments, the volume of the anticoagulant disclosed herein in a volume of about 50 microliters. In some embodiments, the volume of the anticoagulant disclosed herein in a volume of about 100 microliters.

In some embodiments, the methods disclosed herein comprise a step of mixing a sample comprising blood with an anticoagulant such as heparin, Acenocoumarol, phenprocoumon, Atromentin, Brodifacoum, Phenindione, Coumadin or the like. In some embodiments the biosensor, cartridge, device, or test strip comprise a mechanical shaker mechanism configured to shake one or more volumes within the at least one vessel, microfluidic conduit, or mixing portion of the biosensor, cartridge, device, or test strip.

Methods

The disclosure relates to a method of diagnosing or prognosing a clinical outcome of a subject with hyperammonemia or a hyperammonia related disorder, comprising contacting a sensor, system, or test strip disclosed herein with a sample of bodily fluid, and quantifying a level of ammonia or ammonium ion in the sample; and comparing the level of amino acid in the sample to a threshold value of what is considered normal level of amino acid level in the bodily fluid. In some embodiments, the method relates to to a method of diagnosing or prognosing a clinical outcome of a subject suspected of having or having been previously diagnosed with hyperammonemia or a hyperammonemia-related disorder and/or at least one aminoacidopathy.

In some embodiments, the method relates to to a method of diagnosing or prognosing a clinical outcome of a subject suspected of having or having been previously diagnosed with at least one hyperammonemia or a hyperammonemia-related disorder. The ranges of what ammonia or ammonium ion levels are considered normal for each age type are below in Table 4. If, after performing the quantification steps provided herein, the amount of ammonia or ammonium ion in the sample solution exceeds or falls below the ranges provided, diet regimen, exercise regimen, and/or medical treatment may be initiated or changed such that ammonia or ammonium ion levels are monitored until the subject's levels have stabilized or fall within what is considered a healthy range.

TABLE 4

Ammonia Ranges

| Case | Range |
| --- | --- |
| Newborn - Healthy | Less than 110 micromoles/liter |
| Newborn - Suspected Metabolic Disorder | Greater than 200 micromoles/liter |
| Older than Newborn - Healthy | 50-80 micromoles/liter |
| Older than Newborn - Suspected Metabolic Disorder | Greater than 100 micromoles/liter |
| Hepatic Encephalopathy | Greater than 70 micromoles/liter |

The disclosure relates to a method of detecting the presence or absence or quantity of ammonia or ammonium related disorder in bodily fluids. The disclosure also relates to a method of quantifying the concentration of ammonia or ammonium ion in bodily fluids of a subject. Quantification can occur at the point-of-care due to the quick enzymatic reaction readout caused by the generation of a detectable current within a circuit after exposure of a sample from a subject to one or a plurality of vessels comprising any one or combination of indophenol reagents disclosed herein. In some embodiments, the device or system described herein may be utilized to detect if a person has abnormally high or low levels of ammonia in the blood, after which an electronic message or display may then be provided to the user of the device or system or activated on a display by one or more processors or microchips that remotely or directly access one or more storage memories comprising one or more concentration values of ammonia or ammonium ion in sample of the subject. In some embodiments, multiple concentration values may be obtained either simultaneously or in series, compared or analyzed by the one or more processors operably connected to the device or system disclosed herein. In some embodiments, multiple concentration values of a subject over a time period may be compared or analyzed by the one or more processors operably connected to the device or system disclosed herein, after which a message comprising the concentration value and/or threshold values are displayed. In some embodiments, the message optionally includes a signal indicating that the subject should seek medical treatment or alter diet to control ammonia or ammonium ion levels in the subject.

The disclosure also relates to a method of diagnosing a subject with a liver dysfunction comprising: (a) contacting a sample of bodily fluid from a subject to the to the biosensor, system or test strip disclosed herein;
(b) quantifying one or more concentration values of ammonia in the sample;
(c) comparing the one or more concentration values of ammonia in the sample to a threshold value of ammonia concentration identified as being in a healthy range; and
(d) identifying the subject as having a metabolic disease if the one or more concentration values of ammonia in the sample exceed or fall below the threshold value. In some embodiments, if the sample is blood or whole blood, the method comprises contacting the sample with an anticoagulant before or simultaneously with step (a).

The disclosure also relates to a method of diagnosing a subject with hyperammonemia comprising: (a) contacting a sample of bodily fluid from a subject to the to the biosensor, system or test strip disclosed herein;
(b) quantifying one or more concentration values of ammonia in the sample;
(c) comparing the one or more concentration values of ammonia in the sample to a threshold value of ammonia concentration identified as being in a healthy range; and
(d) identifying the subject as having a metabolic disease if the one or more concentration values of ammonia in the sample exceed or fall below the threshold value. In some embodiments, if the sample is blood or whole blood, the method comprises contacting the sample with an anticoagulant before or simultaneously with step (a).

The disclosure also relates to a method of quantifying the amount of amino acid in sample comprising: (a) contacting a sample of bodily fluid from a subject to the to the biosensor, system or test strip disclosed herein;
(b) quantifying one or more concentration values of ammonia in the sample;
(c) comparing the one or more concentration values of ammonia in the sample to a threshold value of ammonia concentration identified correlating to amino acid quantity; and
(d) identifying the amino acid levels if the one or more concentration values of ammonia in the sample exceed or fall below the threshold value. Any amino acid may be detected using the reference information from FIG. 14 wherein the biosensor, system or test strip disclosed herein comprises an enzyme disclosed herein or a functional fragment that has 70, 75, 80, 85, 90, 91, 92, 93, 94, 95, 96, 97, 98, or 99% sequence identity to any enzyme disclosed herein. One of ordinary skill in the art would know, for instance, that to detect the presence, absence, or quantity of amino acids listed on Table 5, one or more recombinant or synthetic enzymes disclosed herein or a functional fragment thereof that has 70, 75, 80, 85, 90, 91, 92, 93, 94, 95, 96, 97, 98, or 99% sequence identity to any sequence (either nucleic acid or encoded amino acid) disclosed herein.

In some embodiments, the phenolic reagent or indophenol reagent is used in a range from about 50 to about 70 mmol/liter. In some embodiments, the phenolic reagent or indophenol reagent is used in a range from about 52 to about 70 mmol/liter. In some embodiments, the phenolic reagent or indophenol reagent is used in a range from about 54 to about 70 mmol/liter. In some embodiments, the phenolic reagent or indophenol reagent is used in a range from about 56 to about 70 mmol/liter. In some embodiments, the phenolic reagent or indophenol reagent is used in a range from about 58 to about 70 mmol/liter. In some embodiments, the phenolic reagent or indophenol reagent is used in a range from about 60 to about 70 mmol/liter. In some embodiments, the phenolic reagent or indophenol reagent is used in a range from about 62 to about 70 mmol/liter. In some embodiments, the phenolic reagent or indophenol reagent is used in a range from about 64 to about 70 mmol/liter. In some embodiments, the phenolic reagent or indophenol reagent is used in a range from about 66 to about 70 mmol/liter. In some embodiments, the phenolic reagent or indophenol reagent is used in a range from about 68 to about 70 mmol/liter. In some embodiments, the phenolic reagent or indophenol reagent is used in a range from about 50 to about 68 mmol/liter. In some embodiments, the phenolic reagent or indophenol reagent is used in a range from about 50 to about 66 mmol/liter. In some embodiments, the phenolic reagent or indophenol reagent is used in a range from about 50 to about 64 mmol/liter. In some embodiments, the phenolic reagent or indophenol reagent is used in a range from about 50 to about 62 mmol/liter. In some embodiments, the phenolic reagent or indophenol reagent is used in a range from about 50 to about 60 mmol/liter. In some embodiments, the phenolic reagent or indophenol reagent is used in a range from about 50 to about 58 mmol/liter. In some embodiments, the phenolic reagent or indophenol reagent is used in a range from about 50 to about 56 mmol/liter. In some embodiments, the phenolic reagent or indophenol reagent is used in a range from about 50 to about 54 mmol/liter. In some embodiments, the phenolic reagent or indophenol reagent is used in a range from about 50 to about 52 mmol/liter. In some embodiments, the phenolic reagent or indophenol reagent is used in concentration about 59 mmol/liter. In some embodiments, the phenolic reagent or indophenol reagent is 2-phenylphenol.

In some embodiments, the catalyst is used in a concentration of about 7 micromoles/liter. In some embodiments, the catalyst is sodium nitroprusside.

In some embodiments, the basic buffer is used in a range from about 50 to about 500 mmol/liter. In some embodiments, the basic buffer is used in a range from about 120 to about 500 mmol/liter. In some embodiments, the basic buffer is used in a range from about 140 to about 500 mmol/liter. In some embodiments, the basic buffer is used in a range from about 160 to about 500 mmol/liter. In some embodiments, the basic buffer is used in a range from about 180 to about 500 mmol/liter. In some embodiments, the basic buffer is used in a range from about 200 to about 500 mmol/liter. In some embodiments, the basic buffer is used in a range from about 220 to about 500 mmol/liter. In some embodiments, the basic buffer is used in a range from about 240 to about 500 mmol/liter. In some embodiments, the basic buffer is used in a range from about 260 to about 500 mmol/liter. In some embodiments, the basic buffer is used in a range from about 280 to about 500 mmol/liter. In some embodiments, the basic buffer is used in a range from about 300 to about 500 mmol/liter. In some embodiments, the basic buffer is used in a range from about 320 to about 500 mmol/liter. In some embodiments, the basic buffer is used in a range from about 340 to about 500 mmol/liter. In some embodiments, the basic buffer is used in a range from about 360 to about 500 mmol/liter. In some embodiments, the basic buffer is used in a range from about 380 to about 500 mmol/liter. In some embodiments, the basic buffer is used in a range from about 400 to about 500 mmol/liter. In some embodiments, the basic buffer is used in a range from about 420 to about 500 mmol/liter. In some embodiments, the basic buffer is used in a range from about 440 to about 500 mmol/liter. In some embodiments, the basic buffer is used in a range from about 460 to about 500 mmol/liter. In some embodiments, the basic buffer is used in a range from about 480 to about 500 mmol/liter. In some embodiments, the basic buffer is used in a range from about 100 to about 480 mmol/liter. In some embodiments, the basic buffer is used in a range from about 100 to about 460 mmol/liter. In some embodiments, the basic buffer is used in a range from about 100 to about 440 mmol/liter. In some embodiments, the basic buffer is used in a range from about 100 to about 420 mmol/liter. In some embodiments, the basic buffer is used in a range from about 100 to about 400 mmol/liter. In some embodiments, the basic buffer is used in a range from about 100 to about 380 mmol/liter. In some embodiments, the basic buffer is used in a range from about 100 to about 360 mmol/liter. In some embodiments, the basic buffer is used in a range from about 100 to about 340 mmol/liter. In some embodiments, the basic buffer is used in a range from about 100 to about 320 mmol/liter. In some embodiments, the basic buffer is used in a range from about 100 to about 300 mmol/liter. In some embodiments, the basic buffer is used in a range from about 100 to about 280 mmol/liter. In some embodiments, the basic buffer is used in a range from about 100 to about 260 mmol/liter. In some embodiments, the basic buffer is used in a range from about 100 to about 240 mmol/liter. In some embodiments, the basic buffer is used in a range from about 100 to about 220 mmol/liter. In some embodiments, the basic buffer is used in a range from about 100 to about 200 mmol/liter. In some embodiments, the basic buffer is used in a range from about 100 to about 180 mmol/liter. In some embodiments, the basic buffer is used in a range from about 100 to about 160 mmol/liter. In some embodiments, the basic buffer is used in a range from about 100 to about 140 mmol/liter. In some embodiments, the basic buffer is used in a range from about 100 to about 120 mmol/liter. In some embodiments, the basic buffer is used in a concentration about 50 mmol/liter. In some embodiments, the basic buffer is sodium hydroxide. In some embodiments, the basic buffer is used in a concentration about 100 mmol/liter. In some embodiments, the basic buffer is sodium hydroxide. In some embodiments, the basic buffer is used in a concentration about 200 mmol/liter. In some embodiments, the basic buffer is sodium hydroxide. In some embodiments, the basic buffer is used in a concentration about 300 mmol/liter. In some embodiments, the basic buffer is sodium hydroxide. In some embodiments, the basic buffer is used in a concentration about 400 mmol/liter. In some embodiments, the basic buffer is sodium hydroxide. In some embodiments, the basic buffer is used in a concentration about 500 mmol/liter. In some embodiments, the basic buffer is sodium hydroxide.

In some embodiments, the hypohalite is used in a range from about 50 to about 120 mmol/liter. In some embodiments, the hypohalite is used in a range from about 52 to about 120 mmol/liter. In some embodiments, the hypohalite is used in a range from about 54 to about 120 mmol/liter. In some embodiments, the hypohalite is used in a range from about 56 to about 120 mmol/liter. In some embodiments, the hypohalite is used in a range from about 58 to about 120 mmol/liter. In some embodiments, the hypohalite is used in a range from about 58 to about 120 mmol/liter. In some embodiments, the hypohalite is used in a range from about 60 to about 120 mmol/liter. In some embodiments, the hypohalite is used in a range from about 62 to about 120 mmol/liter. In some embodiments, the hypohalite is used in a range from about 64 to about 120 mmol/liter. In some embodiments, the hypohalite is used in a range from about 66 to about 120 mmol/liter. In some embodiments, the hypohalite is used in a range from about 68 to about 120 mmol/liter. In some embodiments, the hypohalite is used in a range from about 70 to about 120 mmol/liter. In some embodiments, the hypohalite is used in a range from about 72 to about 120 mmol/liter. In some embodiments, the hypohalite is used in a range from about 74 to about 120 mmol/liter. In some embodiments, the hypohalite is used in a range from about 76 to about 120 mmol/liter. In some embodiments, the hypohalite is used in a range from about 78 to about 120 mmol/liter. In some embodiments, the hypohalite is used in a range from about 80 to about 120 mmol/liter. In some embodiments, the hypohalite is used in a range from about 82 to about 120 mmol/liter. In some embodiments, the hypohalite is used in a range from about 82 to about 120 mmol/liter. In some embodiments, the hypohalite is used in a range from about 84 to about 120 mmol/liter. In some embodiments, the hypohalite is used in a range from about 86 to about 120 mmol/liter. In some embodiments, the hypohalite is used in a range from about 90 to about 120 mmol/liter. In some embodiments, the hypohalite is used in a range from about 92 to about 120 mmol/liter. In some embodiments, the hypohalite is used in a range from about 94 to about 120 mmol/liter. In some embodiments, the hypohalite is used in a range from about 96 to about 120 mmol/liter. In some embodiments, the hypohalite is used in a range from about 98 to about 120 mmol/liter. In some embodiments, the hypohalite is used in a range from about 100 to about 120 mmol/liter. In some embodiments, the hypohalite is used in a range from about 102 to about 120 mmol/liter. In some embodiments, the hypohalite is used in a range from about 104 to about 120 mmol/liter. In some embodiments, the hypohalite is used in a range from about 106 to about 120 mmol/liter. In some embodiments, the hypohalite is used in a range from about 108 to about 120 mmol/liter. In some embodiments, the hypohalite is used in a range from about 110 to about 120 mmol/liter. In some embodiments, the hypohalite is used in a range from about 112 to about 120 mmol/liter. In some embodiments, the hypohalite is used in a range from about 114 to about 120 mmol/liter. In some embodiments, the hypohalite is used in a range from about 116 to about 120 mmol/liter. In some embodiments, the hypohalite is used in a range from about 118 to about 120 mmol/liter. In some embodiments, the hypohalite is used in a range from about 50 to about 118 mmol/liter. In some embodiments, the hypohalite is used in a range from about 50 to about 116 mmol/liter. In some embodiments, the hypohalite is used in a range from about 50 to about 114 mmol/liter. In some embodiments, the hypohalite is used in a range from about 50 to about 112 mmol/liter. In some embodiments, the hypohalite is used in a range from about 50 to about 110 mmol/liter. In some embodiments, the hypohalite is used in a range from about 50 to about 108 mmol/liter. In some embodiments, the hypohalite is used in a range from about 50 to about 106 mmol/liter. In some embodiments, the hypohalite is used in a range from about 50 to about 104 mmol/liter. In some embodiments, the hypohalite is used in a range from about 50 to about 102 mmol/liter. In some embodiments, the hypohalite is used in a range from about 50 to about 100 mmol/liter. In some embodiments, the hypohalite is used in a range from about 50 to about 98 mmol/liter. In some embodiments, the hypohalite is used in a range from about 50 to about 96 mmol/liter. In some embodiments, the hypohalite is used in a range from about 50 to about 94 mmol/liter. In some embodiments, the hypohalite is used in a range from about 50 to about 92 mmol/liter. In some embodiments, the hypohalite is used in a range from about 50 to about 90 mmol/liter. In some embodiments, the hypohalite is used in a range from about 50 to about 88 mmol/liter. In some embodiments, the hypohalite is used in a range from about 50 to about 86 mmol/liter. In some embodiments, the hypohalite is used in a range from about 50 to about 84 mmol/liter. In some embodiments, the hypohalite is used in a range from about 50 to about 82 mmol/liter. In some embodiments, the hypohalite is used in a range from about 50 to about 80 mmol/liter. In some embodiments, the hypohalite is used in a range from about 50 to about 78 mmol/liter. In some embodiments, the hypohalite is used in a range from about 50 to about 76 mmol/liter. In some embodiments, the hypohalite is used in a range from about 50 to about 74 mmol/liter. In some embodiments, the hypohalite is used in a range from about 50 to about 72 mmol/liter. In some embodiments, the hypohalite is used in a range from about 50 to about 70 mmol/liter. In some embodiments, the hypohalite is used in a range from about 50 to about 68 mmol/liter. In some embodiments, the hypohalite is used in a range from about 50 to about 66 mmol/liter. In some embodiments, the hypohalite is used in a range from about 50 to about 64 mmol/liter. In some embodiments, the hypohalite is used in a range from about 50 to about 62 mmol/liter. In some embodiments, the hypohalite is used in a range from about 50 to about 60 mmol/liter. In some embodiments, the hypohalite is used in a range from about 50 to about 58 mmol/liter. In some embodiments, the hypohalite is used in a range from about 50 to about 56 mmol/liter. In some embodiments, the hypohalite is used in a range from about 50 to about 54 mmol/liter. In some embodiments, the hypohalite is used in a range from about 50 to about 52 mmol/liter. In some embodiments, the hypohalite is used in a concentration about 100 mmol/liter. In some embodiments, the hypohalite is sodium hypochlorite.

In some embodiments, the alkali buffer is used in a range from about 0.5 to about 1.0 mol/liter. In some embodiments, the alkali buffer is used in a range from about 0.6 to about 1.0 mol/liter. In some embodiments, the alkali buffer is used in a range from about 0.7 to about 1.0 mol/liter. In some embodiments, the alkali buffer is used in a range from about 0.8 to about 1.0 mol/liter. In some embodiments, the alkali buffer is used in a range from about 0.9 to about 1.0 mol/liter. In some embodiments, the alkali buffer is used in a range from about 0.5 to about 0.9 mol/liter. In some embodiments, the alkali buffer is used in a range from about 0.5 to about 0.8 mol/liter. In some embodiments, the alkali buffer is used in a range from about 0.5 to about 0.7 mol/liter. In some embodiments, the alkali buffer is used in a range from about 0.5 to about 0.6 mol/liter. In some embodiments, the alkali buffer is used in a concentration about 1.0 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a range from about 0.5 to about 0.6 mol/liter. In some embodiments, the alkali buffer is used in a concentration about 1.0 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a range from about 0.5 to about 0.6 mol/liter. In some embodiments, the alkali buffer is used in a concentration about 1.0 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a range from about 0.5 to about 0.6 mol/liter. In some embodiments, the alkali buffer is used in a concentration about 1.0 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a range from about 0.5 to about 0.6 mol/liter. In some embodiments, the alkali buffer is used in a concentration about 1.0 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a range from about 0.5 to about 0.6 mol/liter. In some embodiments, the alkali buffer is used in a concentration about 0.5 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a concentration about 0.6 mol/liter. In some embodiments, the alkali buffer is used in a concentration about 0.7 mol/liter. In some embodiments, the alkali buffer is used in a concentration about 0.8 mol/liter. In some embodiments, the alkali buffer is used in a concentration about 0.9 mol/liter. In some embodiments, the alkali buffer is used in a concentration about 0.75 mol/liter.

The disclosure relates to a method of diagnosing liver dysfunction or hyperammonemia in a subject comprising:
(a) contacting a sample of the subject to a system, cartridge, test strip, biosensor or device disclosed herein;
(b) detecting the presence, absence, or quantity of ammonia;
(c) correlating the quantity of ammonia to the levels of amino acid in the sample;
(d) diagnosing the subject as having liver dysfunction or hyperammonemia if the ammonia levels are quantified as above about 100 micromoles/liter of sample.

The disclosure relates to a method of diagnosing liver dysfunction or hyperammonemia in a subject comprising:
(a) contacting a sample of the subject to a system, cartridge, test strip, biosensor or device disclosed herein;
(b) detecting the presence, absence, or quantity of ammonia;

(c) correlating the quantity of ammonia to the levels of amino acid in the sample;
(d) diagnosing the subject as having liver dysfunction or hyperammonemia if the ammonia levels are quantified as above about 90 micromoles/liter of sample.

The disclosure relates to a method of diagnosing liver dysfunction or hyperammonemia in a subject comprising:
(a) contacting a sample of the subject to a system, cartridge, test strip, biosensor or device disclosed herein;
(b) detecting the presence, absence, or quantity of ammonia;
(c) correlating the quantity of ammonia to the levels of amino acid in the sample;
(d) diagnosing the subject as having liver dysfunction or hyperammonemia if the ammonia levels are quantified as above about 80 micromoles/liter of sample.

The disclosure relates to a method of diagnosing liver dysfunction or hyperammonemia in a subject comprising:
(a) contacting a sample of the subject to a system, cartridge, test strip, biosensor or device disclosed herein;
(b) detecting the presence, absence, or quantity of ammonia;
(c) correlating the quantity of ammonia to the levels of amino acid in the sample;
(d) diagnosing the subject as having liver dysfunction or hyperammonemia if the ammonia levels are quantified as above about 70 micromoles/liter of sample.

A method of treating a subject with liver dysfunction or hyperammonemia comprising:
(a) contacting a sample of the subject to a system, cartridge, test strip, biosensor or device disclosed herein;
(b) diagnosing the subject as having liver dysfunction or hyperammonemia if the ammonia levels are quantified as above about 70 micromoles/liter of sample; and
(c) treating the subject by administering steroids, arginine supplements, sodium benzoate, phenylacetate, and/or a glucose solution.

A method of treating a subject with liver dysfunction or hyperammonemia comprising:
(a) contacting a sample of the subject to a system, cartridge, test strip, biosensor or device disclosed herein;
(b) diagnosing the subject as having liver dysfunction or hyperammonemia if the ammonia levels are quantified as above about 80 micromoles/liter of sample; and
(c) treating the subject by administering steroids, arginine supplements, sodium benzoate, phenylacetate, and/or a glucose solution.

A method of treating a subject with liver dysfunction or hyperammonemia comprising:
(a) contacting a sample of the subject to a system, cartridge, test strip, biosensor or device disclosed herein;
(b) diagnosing the subject as having liver dysfunction or hyperammonemia if the ammonia levels are quantified as above about 90 micromoles/liter of sample; and
(c) treating the subject by administering steroids, arginine supplements, sodium benzoate, phenylacetate, and/or a glucose solution.

A method of treating a subject with liver dysfunction or hyperammonemia comprising:
(a) contacting a sample of the subject to a system, cartridge, test strip, biosensor or device disclosed herein;
(b) diagnosing the subject as having liver dysfunction or hyperammonemia if the ammonia levels are quantified as above about 100 micromoles/liter of sample; and
(c) treating the subject by administering steroids, arginine supplements, sodium benzoate, phenylacetate, and/or a glucose solution.

In any of the above methods, the method comprises detecting the ammonia or ammonium ion levels in whole blood, water, or a sample taken from a microenvironment such as a test solution reconstituted from a swab taken from a microenvironment.

The disclosure relates to a method of diagnosing a metabolic disorder in a subject comprising:
(a) contacting a sample of the subject to a system, cartridge, test strip, biosensor or device disclosed herein;
(b) detecting the presence, absence, or quantity of ammonia;
(c) correlating the quantity of ammonia to the levels of amino acid in the sample;
(d) diagnosing the subject as having a metabolic disorder if the amino acid levels are quantified as above those levels set forth in Table 1.

In some embodiments, any methods disclosed herein comprises taking multiple steps of detecting the presence, absence, or quantity of ammonia in a sample by performing 1, 2, 3, or more tests simultaneously or in series.

In some embodiments, the step of detecting the presence, absence, or quantity of ammonia comprises detecting the wavelength emitted or absorbed by a indophenol reaction product. In any of the above methods, the step of detecting the presence, absence, or quantity of ammonia comprises detecting the wavelength emitted or absorbed by a indophonel reaction product by looking at the visible light in one or more vessels. In some embodiments, the step of detecting the presence, absence, or quantity of ammonia comprises detecting the wavelength absorbed by a indophenol reaction product wherein the wavelength from about 500 nm to about 700 nm.

In some embodiments, any of the above methods, the step of detecting the presence, absence, or quantity of ammonia comprises detecting the wavelength emitted or absorbed by a indophonel reaction product.

In some embodiments, any of the above methods do not comprise a step of converting liquid to a gas or any step involving gas chromatography.

In some embodiments, any of the above biosensor cartridges, devices, or methods comprise mixing a volume of any of the reagents disclosed herein in a volume of from about 10 microliters to about 150 microliters. In some embodiments, any of the above biosensor cartridges, devices, or methods comprise comprise mixing a volume of any of the reagents disclosed herein in a volume of from about 10 microliters to about 100 microliters. In some embodiments, any of the above biosensor cartridges, devices, or methods comprise a volume of any of the reagents disclosed herein in a volume of from about 10 microliters to about 150 microliters. In some embodiments, any of the above biosensor cartridges, devices, or methods comprise a volume of any of the reagents disclosed herein in a volume of about 10 microliters. In some embodiments, any of the above bio sensor cartridges, devices, or methods comprise a volume of any of the reagents disclosed herein in a volume of about 20 microliters. In some embodiments, any of the above biosensor cartridges, devices, or methods comprise a volume of any of the reagents disclosed herein in a volume of about 30 microliters. In some embodiments, any of the above biosensor cartridges, devices, or methods comprise a volume of any of the reagents disclosed herein in a volume of about 40 microliters. In some embodiments, any of the above biosensor cartridges, devices, or methods comprise a volume of any of the reagents disclosed herein in a volume of about 50 microliters.

In some embodiments, the disclosure relates to a computer-implemented method of quantifying ammonia or ammonium ions and/or amino acid concentration in a sample.

In some embodiments, the disclosure relates to a system comprising a processor that performs a computer-implemented method of quantifying amino acid concentration in a sample of a subject. In some embodiments, the system comprises a processor optionally located at a remote location and accessible by internet connection, operably connected to a computer storage memory that stores subject's concentration values over time. In some embodiments, the subject or the subject's healthcare provider may accesses the internet to communicate with a server linked to the computer storage memory. Subject data reports may be generated and obtained by the subject after initiating a retrieve command through the processor. In some embodiments, the system comprises a computer program-product that performs a function convert current signals generated by a biosensor disclosed herein to concentration of a particular amino acid and/or ammonia in a sample. In some embodiments, the disclosure relates to a system including at least one processor and a computer readable memory, said computer readable memory having stored thereon program code for quantifying amino acid concentration in a sample of bodily fluid comprising: means for storing data associated with a subject; means for, responsive to receiving a level of current response from a biosensor or its computer storage memory, presenting a concentration value to a user as part of a user interface. In some embodiments, the user is the subject or healthcare provider of the subject. In some embodiments, the disclosure relates to a system that comprises at least one processor, a program storage, such as memory, for storing program code executable on the processor, and one or more input/output devices and/or interfaces, such as data communication and/or peripheral devices and/or interfaces. In some embodiments, the user device and computer system or systems are communicably connected by a data communication network, such as a Local Area Network (LAN), the Internet, or the like, which may also be connected to a number of other client and/or server computer systems. The user device and client and/or server computer systems may further include appropriate operating system software.

The present disclosure relates generally to definition and/or use of concentration values that characterize a subject's modification of behavior. in some embodiments, the concentration values corresponding to the concentration of amino acids in a sample of bodily fluid may characterize the degree to which a subject is advised to modify a diet or seek medical treatment.

In some embodiments, the present disclosure provides biosensors or test strips for use in diagnostic assays. In some embodiments the biosensor and/or test strips are provided as part of a diagnostic or detection kit. In certain embodiments, kits for use in accordance with the present disclosure may include one or more reference samples; instructions (e.g., for processing samples, for performing tests, for interpreting results, etc.); media; and/or other reagents necessary for performing tests.

The disclosure provides a test strip comprising: a solid support, a at least a first vessel in fluid communication with at least one conduit, wherein the test strip comprises a hydrogel disclosed herein. In some embodiments, the solid support is a slide optionally coated with a polymer. In some embodiments, the solid support is coated with a polymer. In some embodiments, the polymer is polyacrylamide. In some embodiments, the solid support is a material chosen from: polysterene (TCPS), glass, quarts, quartz glass, poly(ethylene terephthalate) (PET), polyethylene, polyvinyl difluoride (PVDF), polydimethylsiloxane (PDMS), polytetrafluoroethylene (PTFE), polymethylmethacrylate (PMMA), polycarbonate, polyolefin, ethylene vinyl acetate, polypropylene, polysulfone, polytetrafluoroethylene, silicones, poly(meth) acrylic acid, polyamides, polyvinyl chloride, polyvinylphenol, and copolymers and mixtures thereof. In some embodiments, the test strip is a paper product. In some embodiments, the at least one electrode is attached to the solid support.

According to some embodiments, the disclosure provides a software component or other non-transitory computer program product that is encoded on a computer-readable storage medium, and which optionally includes instructions (such as a programmed script or the like) that, when executed, cause operations related to the calculation of amino acid concentration values. In some embodiments, the computer program product is encoded on a computer-readable storage medium that, when executed: quantifies one or more ammonia or ammonium ion concentration values; normalizes the one or more ammonia or ammonium ion concentration values over a control set of data; creates an amino acid profile or signature of a subject; and displays the profile or signature to a user of the computer program product. In some embodiments, the computer program product is encoded on a computer-readable storage medium that, when executed: calculates one or more ammonia or ammonium ion concentration values, normalizes the one or more ammonia or ammonium ion concentration values, and creates an amino acid signature, wherein the computer program product optionally displays the amino acid signature and/or one or more ammonia or ammonium ion concentration values on a display operated by a user. In some embodiments, the disclosure relates to a non-transitory computer program product encoded on a computer-readable storage medium comprising instructions for: quantifying one or more ammonia or ammonium ion concentration values; and displaying the one or more ammonia or ammonium ion concentration values to a user of the computer program product.

In some embodiments, the step of calculating one or more ammonia or ammonium ion concentration values comprises quantifying an average and standard deviation of counts on replicate trials of contacting the device or test strip with one or more samples of bodily fluids.

In some embodiments, the one or more hydrogel coated electrodes are attached to a solid phase support. In some embodiments, a solid phase support comprises any solid or semi-solid surface. In some embodiments, a solid phase comprises any traditional laboratory material for growing or maintaining cells in culture including petri dishes, beakers, flasks, test tubes, microtitre plates, and/or culture slides. In some embodiments, a solid phase comprises a glass slide, a plastic slide, a paper test strip, or combination thereof.

In some embodiments, the one or more hydrogel coated electrodes are attached to discrete addressable sites on a solid phase support. In some embodiments, a solid phase comprises polyamides, polyesters, polystyrene, polypropylene, polyacrylates, polyvinyl compounds (e.g. polyvinylchloride), polycarbonate, polytetrafluoroethylene (PTFE), nitrocellulose, cotton, polyglycolic acid (PGA), cellulose, dextran, gelatin, glass, fluoropolymers, fluorinated ethylene propylene, polyvinylidene, polydimethylsiloxane, polystyrene, silicon substrates (such as fused silica, polysilicon, or single silicon crystals) or combinations thereof.

In some embodiments, the disclosure relates to a catalogue of medical records relating to a subject comprising test results from the one or plurality of methods described herein. Such catalogue, in some embodiments, being stored on a computer readable medium being accessible remotely through a wireless internet connection.

As described above, certain embodiments of the present disclosure may be used to distinguish between samples of bodily fluid obtained from a subject who does or is suspected of having an hyperammonemia and a subject who does not have a metabolic disease. This system is potentially useful, for example, when testing whole blood samples of a subject to determine whether disease is present. Diagnosing a patient using one or more ammonia or ammonium ion concentration values would include, for example, comparing one or more ammonia or ammonium ion concentration values of a sample from a subject with the measured reference values or threshold values of a subject.

Kits

In some embodiments, kits in accordance with the present disclosure may be used to quantify amino acid concentration is samples of bodily fluid.

The disclosure further provides for a kit comprising one or a plurality of containers that comprise one or a plurality of the polypeptides or fragments disclosed herein. In some embodiments, the kit comprises a test strip and/or a biosensor comprising a test strip, or any animal-based derivative of serum that enhances the culture or proliferation of cells. In some embodiments, the kit comprises: a biosensor disclosed herein, any test strip disclosed herein, and a computer program product disclosed herein optionally comprising instructions to perform any one or more steps of any method disclosed herein. In some embodiments, the kit does not comprise cell media. In some embodiments, the kit comprises a solid support comprising a membrane disclosed herein and/or embedded with at least one electrode disclosed herein optionally comprising any one or combination of a hypohalite, an aqueous basic solution, and at least one compound comprising a phenyl group in one or a a plurality of containers. In some embodiments, the kit comprises a device to affix a hydrogel to a solid support.

The kit may contain two or more containers, packs, or dispensers together with instructions for preparation of an array. In some embodiments, the kit comprises at least one container comprising the bio sensor or system described herein and a second container comprising a solution for maintenance, use, and/or storage of the biosensor such as storage buffer. In some embodiments, the kit comprises a composition comprising any molecule disclosed herein in solution or lyophilized or dried and accompanied by a rehydration mixture. In some embodiments, the molecules and rehydration mixture may be in one or more additional containers. In some embodiments, the kit comprises a composition comprising any one or combination of The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

The kit may contain a bio sensor described herein and/or a test strip comprising hypohalite, an aqueous basic solution, and at least one compound comprising a phenyl group. The kit may also contain a sold support such as a test strip comprising any membrane disclosed herein.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

The disclosure also provides a kit comprising: a biosensor comprising: a solid support and a plurality of electrodes, wherein at least one electrode comprises a hydrogel disclosed herein. in some embodiments, the hydrogel comprises an immobilized metabolic enzyme or a functional fragment thereof; and optionally comprising at least one vessel comprising a hypohalite, an aqueous basic buffer, in liquid or solid phase, and at least one compound comprising a phenyl group. In some embodiments, the kit further comprises at least one of the following: a sample, and a set of instructions, optionally accessible remotely through an electronic medium.

Generally referring to FIGS. 1-7, a system, method, and apparatus for point of care hyperammonemia sensors may be described. In the exemplary embodiments described by the figures, samples may be tested for ammonia levels, amino acid levels, or other compound levels by being in concert with certain reagents to utilize an indophenol reaction. Color change in the reaction may be measured and correspond to certain concentrations of specific compounds and molecules by manual comparison to an extensive color-matching sheet or automated electronic analysis with the use of calibration curves.

FIG. 1 shows one exemplary embodiment of a system demonstrating the ability to detect ammonia levels in various samples. A well 100 may be made of plastic, wood, metal, composite materials, or a combination thereof. Additionally, well 100 may be comprised of synthetic compounds or polymers, such as silicone. Well 100 may further be divided into two or more sections, and may be separated by a membrane filter 105 interposed in or near the center of well100. Membrane filter 105 may be made of a cation exchange filter such as Nafion, shown in Supplementary Fig. A, or similar perfluorinated ionomers to allow for only the passage of small positively charged and neutral molecules between sections. Therefore, membrane filter 105 may be selected to allow for the passage of various molecules or biological components based on charge, size, or similar characteristics. Other membrane filters may consequently be used for desired functionality, such as acrylamide, poly(ethylene glycol) diacrylate, poly(2-hydroxylethyl methacrylate), poly(vinyl alcohol), or other similar polymeric hydrogels. The selection of membrane filter 105 for a hyperammonemia sensor may depend on the membranes ability to allow for the passage of molecules such as ammonia, and the ability to limit the passage of proteins, amino acids, and other molecules or compounds.

Still referring to FIG. 1, reagent section 101 may contain reagents such as phenol, 2-phenylphenol, sodium salicylate, other phenolic reagents or polymers, or a combination thereof. Further, reagent section 101 may also contain bleach, hypochlorite, chloramine T, a similar anion, or a combination thereof, catalysts such as nitroprusside, and a basic buffer such sodium hydroxide or potassium hydroxide to maintain alkali conditions. Sample section 102 may contain serum, blood, plasma, or other liquid desired to be tested. Membrane filter 105 may only allow the passage of ammonia from section 102 to section 101. A chemical reaction, described in FIG. 3, may take place upon reception of ammonia or similar molecule into section 101, turning the reagents a blue color, as shown in section 103. Section 104 may describe the tested sample after the reaction takes place. Color sheets may be available for a qualitative comparison between colors representing specific ammonium concentrations.

In order for the cation exchange membrane, such as Nafion, to be useable for this application, a certain washing procedure and method may be disclosed. The membrane may be washed in a hydrogen peroxide aqueous solution, which may be at boiling temperatures. Additionally, the membrane may be washed in deionized water, ethylenediaminetetraacetic acid or other chelating agents, sulfuric acid, and other similar aqueous materials. The membrane may be exposed to extreme temperatures and pressures to further ensure washing.

Figure 2:
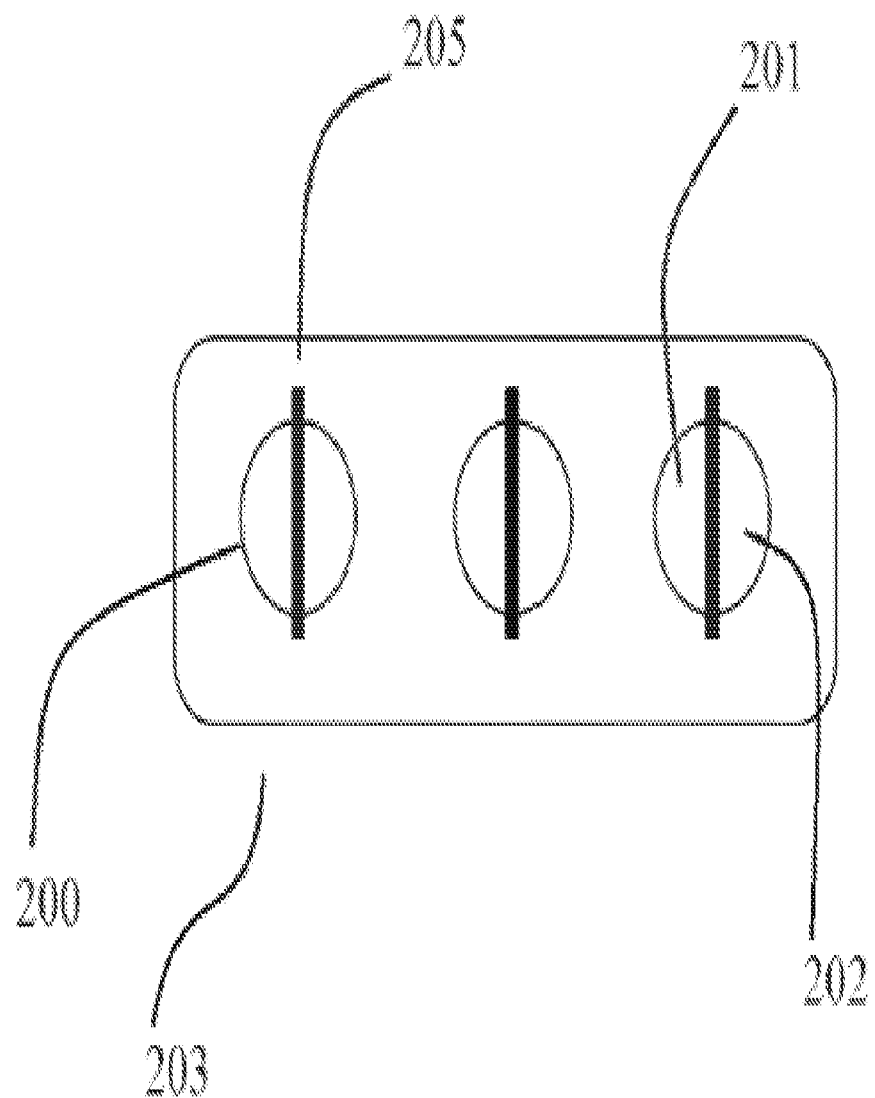
FIG. 2 is an exemplary view of a system comprising multiple vessels within which more than one indophenol reaction mat be performed in parallel.

FIG. 2 shows an exemplary embodiment of a device fitted with multiple wells. Wells 200 may be depressions or fossa in a mounting plate 203. Mounting plate 203 may be comprised of plastic, wood, metals, composite materials, or a combination thereof. Additionally, mounting plate 203 may be comprised of synthetic compounds or polymers, such as silicone. As shown, mounting plate 203 carries three wells 200, yet those skilled in the art may appreciate the ability for a mounting plate 203 to carry substantially more or fewer wells as desired. Membrane filter 205 may be made of Nafion or similar membranes, and may be disposed of in any angle, such as a vertical placement as shown in FIG. 2, a horizontal placement, or a different angle as desired. Reagent section 201 may be filled with phenol, 2-phenylphenol, other phenolic reagents, or a combination thereof; bleach, hypochlorite, chloramine T, a similar anion, or a combination thereof; sodium hydroxide, potassium hydroxide, or a similar basic buffer to maintain alkali conditions; and one or more catalysts, such as nitroprusside. Sample section 202 may be filled with serum, blood, plasma, or similar material desired to be tested. The various wells 200 may be interconnected to facilitate the fluid flow between respective sections in order to test samples multiple times to further accuracy, or to test samples with multiple different membrane filters or reagents. Generally, if sample section 202 contains sufficient levels of ammonia, the ammonia may diffuse through membrane filter 205 and into reagent section 202, which may allow the reaction to be described in FIG. 3 to take place.

Figure 3:
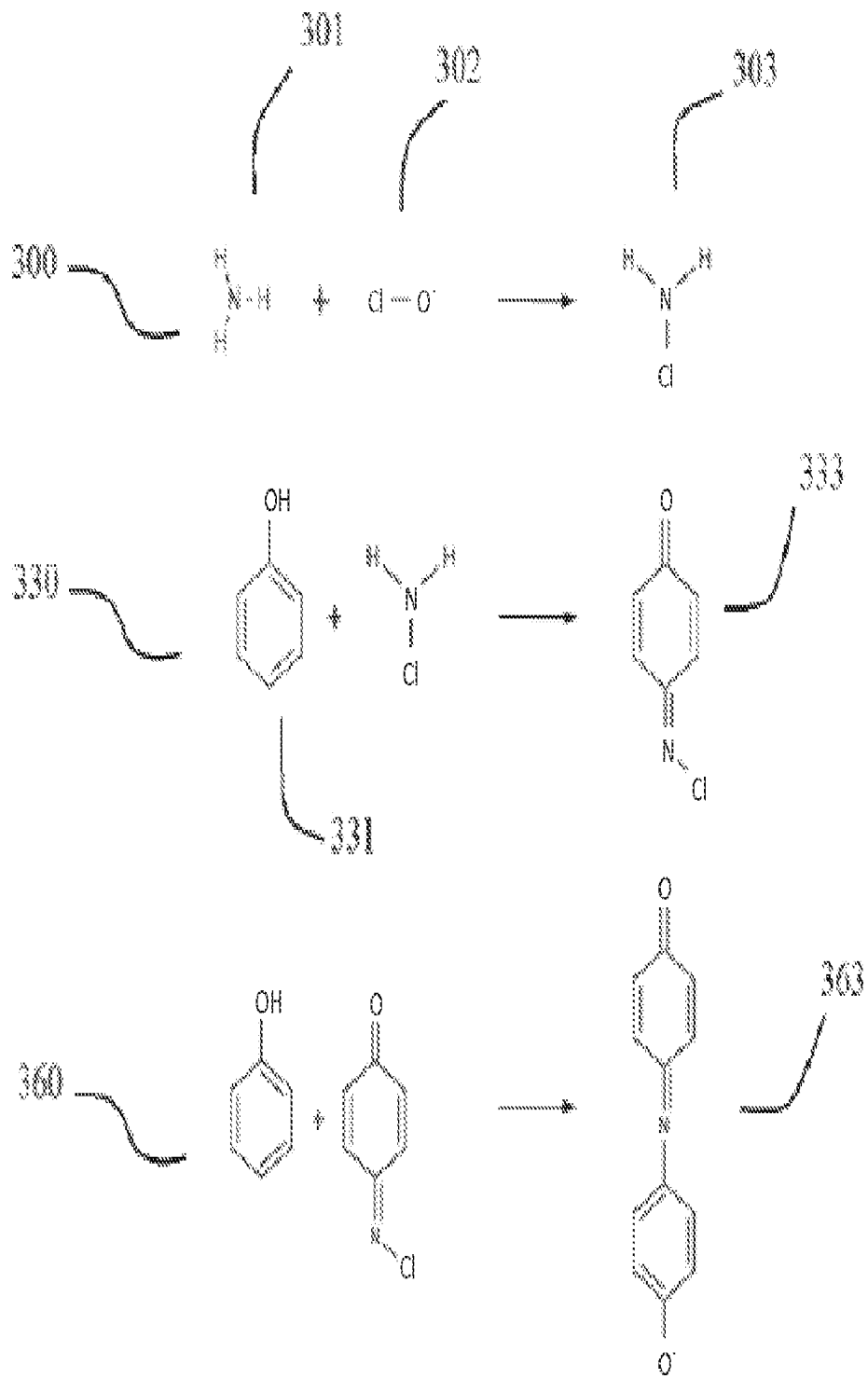
FIG. 3 shows exemplary reaction otherwise known as Berthelot's Reaction or an indophenol reaction.

FIG. 3 shows exemplary reactions that may take place in a point of care hyperammonemia sensor, sometimes known as an indophenol reaction or Berthelot's Reaction. Reactions 300, 330, and 360 may take place upon diffusion of ammonia from one section of a well to another through a membrane filter, as described in FIGS. 1-2. Anion 302 may be hypochlorite, as shown, bleach, calcium hypochlorite, sodium hypochlorite, or other similar anions. Anion 302 may then react with ammonia 301, and produce chloramine 303, or similar ammonia derivative. Chloramine 303 may then react with further reagents, such as phenol 331. A phenol-cholarmine intermediate 333 may further react with additional phenol 331 molecules, producing indophenol 363 which may appear visibly blue in color. Phenol 331 may also be replaced with 2-phenylphenol for further efficacy, with other phenolic reagents such as sodium salicylate, with phenol polymers, or with a combination thereof. The color change in the reagent section of the well or depression may demonstrate the presence of ammonia in the sample section.

Figure 4:
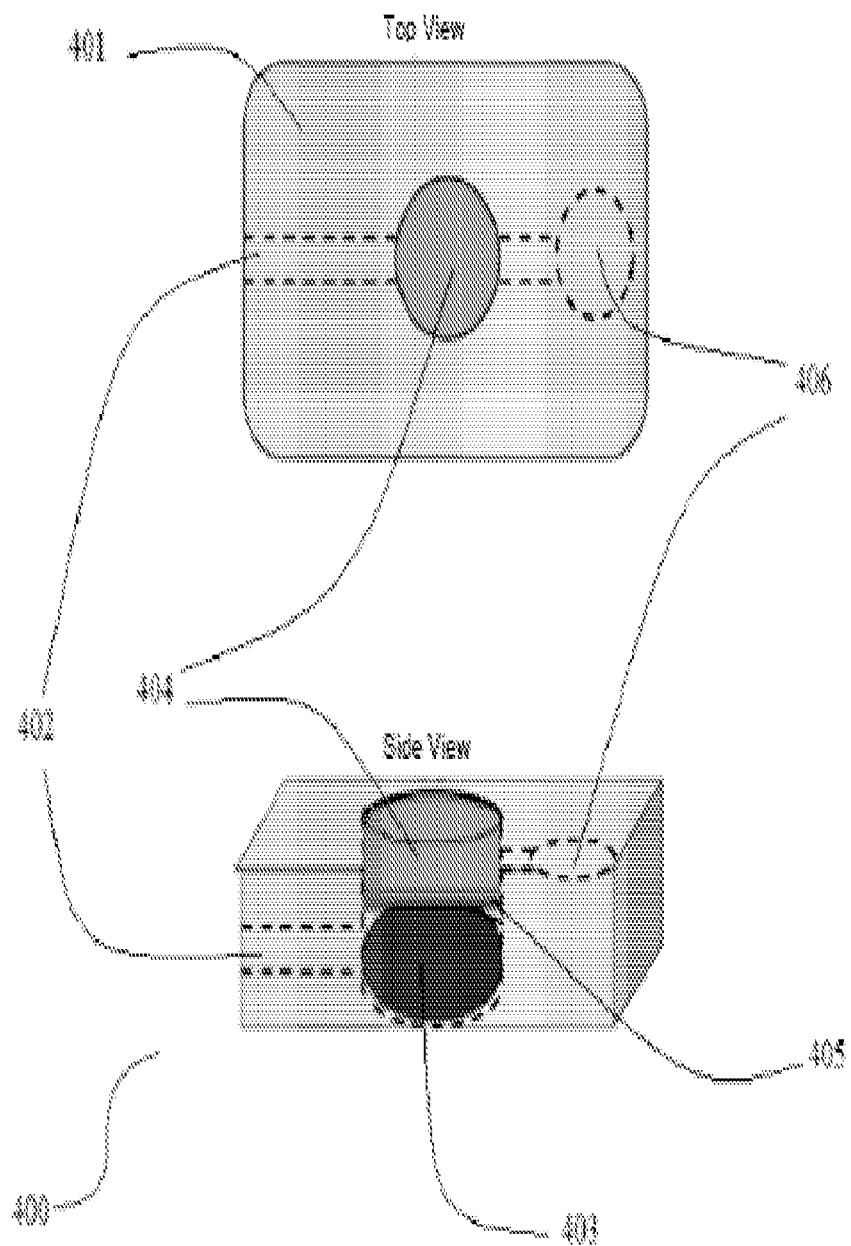
FIG. 4 shows an exemplary embodiment of a microfluidic testing device.

FIG. 4 shows a further exemplary embodiment of a testing device, comprising of a microfluidic. The microfluidic 400 may be suitable for home use in a similar fashion to blood glucose meters to provide ongoing, rapid, reliable testing for hyperammonemia, various aminoacidopathies, and other similar applications. The device 401 may be manufactured of plastic, wood, metal, composites, or a combination thereof, or a synthetic polymer or compound, such as silicone. A user may use a lancet to excrete a small amount of blood from the tip of a finger or other location on the body, and apply a small amount of blood, serum, plasma, or similar component at opening of a conduit channel 402. The sample may be transported through conduit channel 402 by capillary action and reach sample section 403. Sample section 403 may be separated from reagent section 404 by a cation exchange membrane 405, such as Nafion, whereby allowing ammonia to diffuse through membrane 405 into reagent section 404. Prior to the application of a blood sample, a squeezable reservoir 406 containing either dry or liquid bleach, hypochlorite, chloramine T, or similar anion may be manually or electronically stimulated, allowing for the flow of bleach into interposed reagent section 404. The bleach may be separate from reagents in reagent section 404 to ensure accurate and timely chemical reactions. Reagent section 404 may contain liquid or dry components of reagents disclosed in FIGS. 1-3, such as phenol, 2-phenylphenol, other phenolic reagents, or a combination thereof; sodium hydroxide, potassium hydroxide, or a similar basic buffer to maintain alkali conditions; and may also contain one or more catalysts, such as nitroprusside. Upon the presence of a certain level of ammonium in the sample, the reagent section 404 may turn into a blue color, which may be compared to a separate or included color schematic for the user to identify.

Still referring to FIG. 4, the microfluidic 400 may be used multiple times or manufactured to be a single-use device. Additionally, changes may be implemented to the design and range of chemicals used to determine amino acid levels in samples. Those skilled in the art may also appreciate the ability for a device or similar device to conform to various biological or non-biological samples, such as saliva, urine, waste water, or perhaps various chemicals to be used in a laboratory or medical setting.

In addition to the qualitative methods of determining presence or levels of ammonia in applicable samples, a quantitative apparatus, system, and method may be disclosed.

Figure 5:
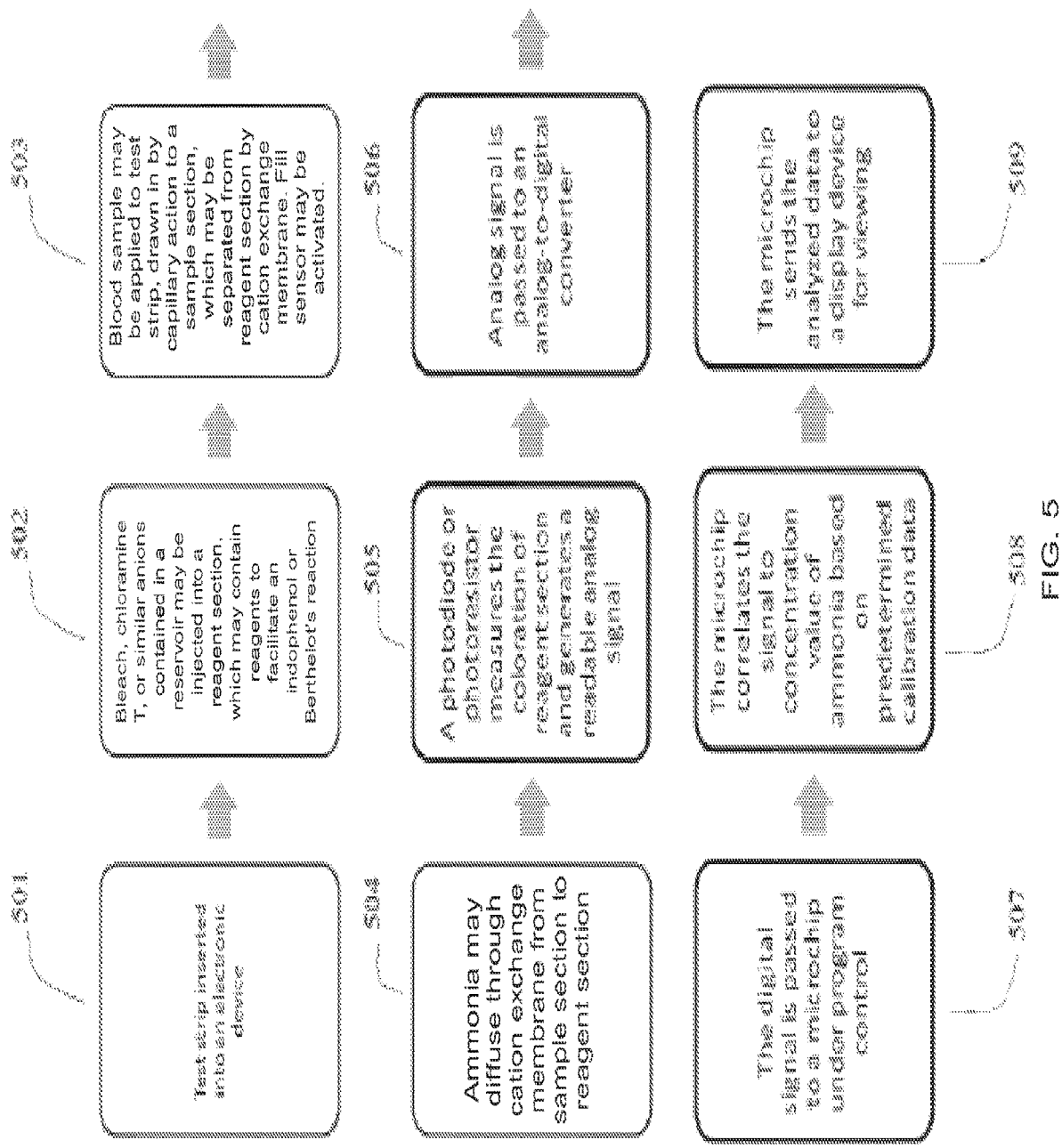
FIG. 5 shows an exemplary flowchart for a method of quantitative point of care hyperammonemia sensing using embodiments of the disclosure.
Figure 6:
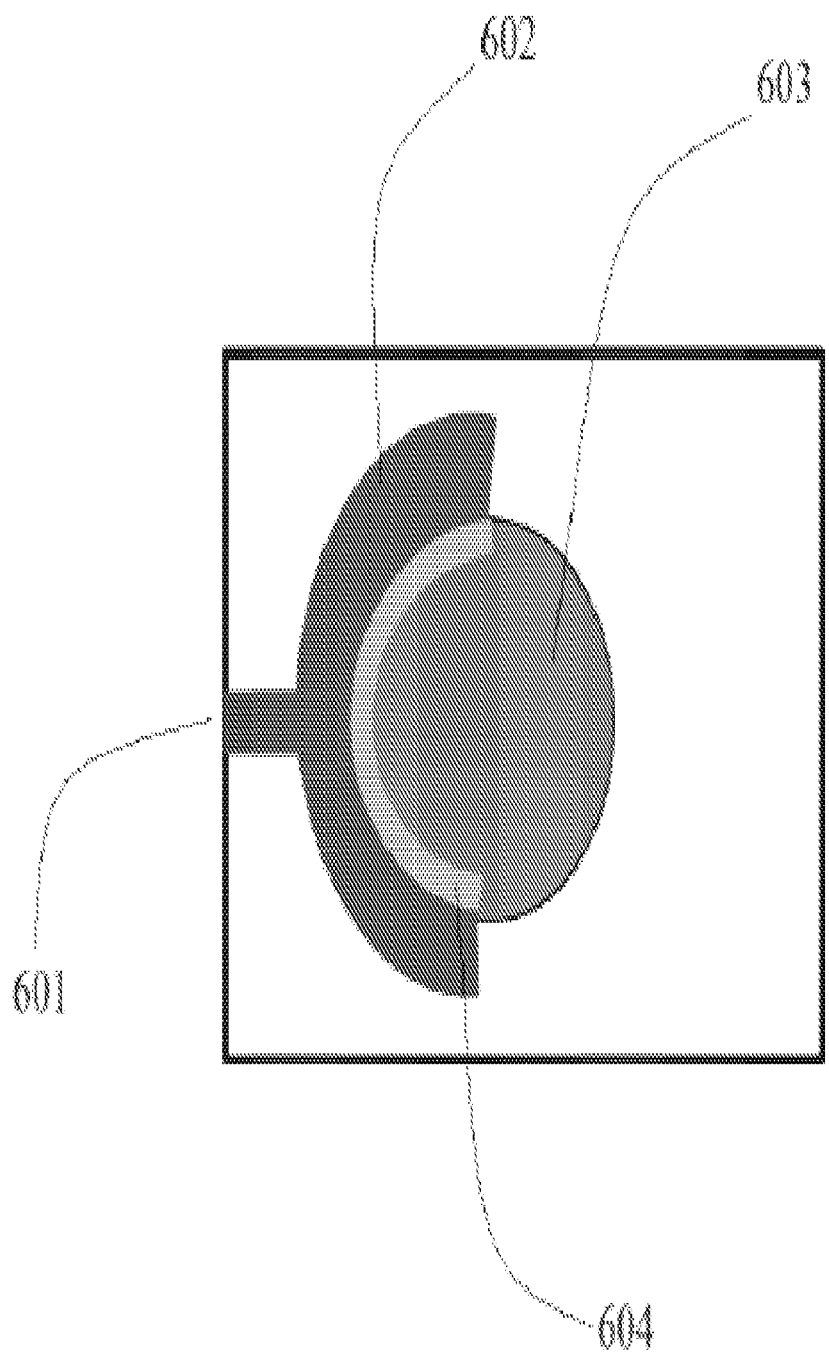
FIG. 6 shows an exemplary embodiment of a blood test strip for use with an electronic testing device.
Figure 7:
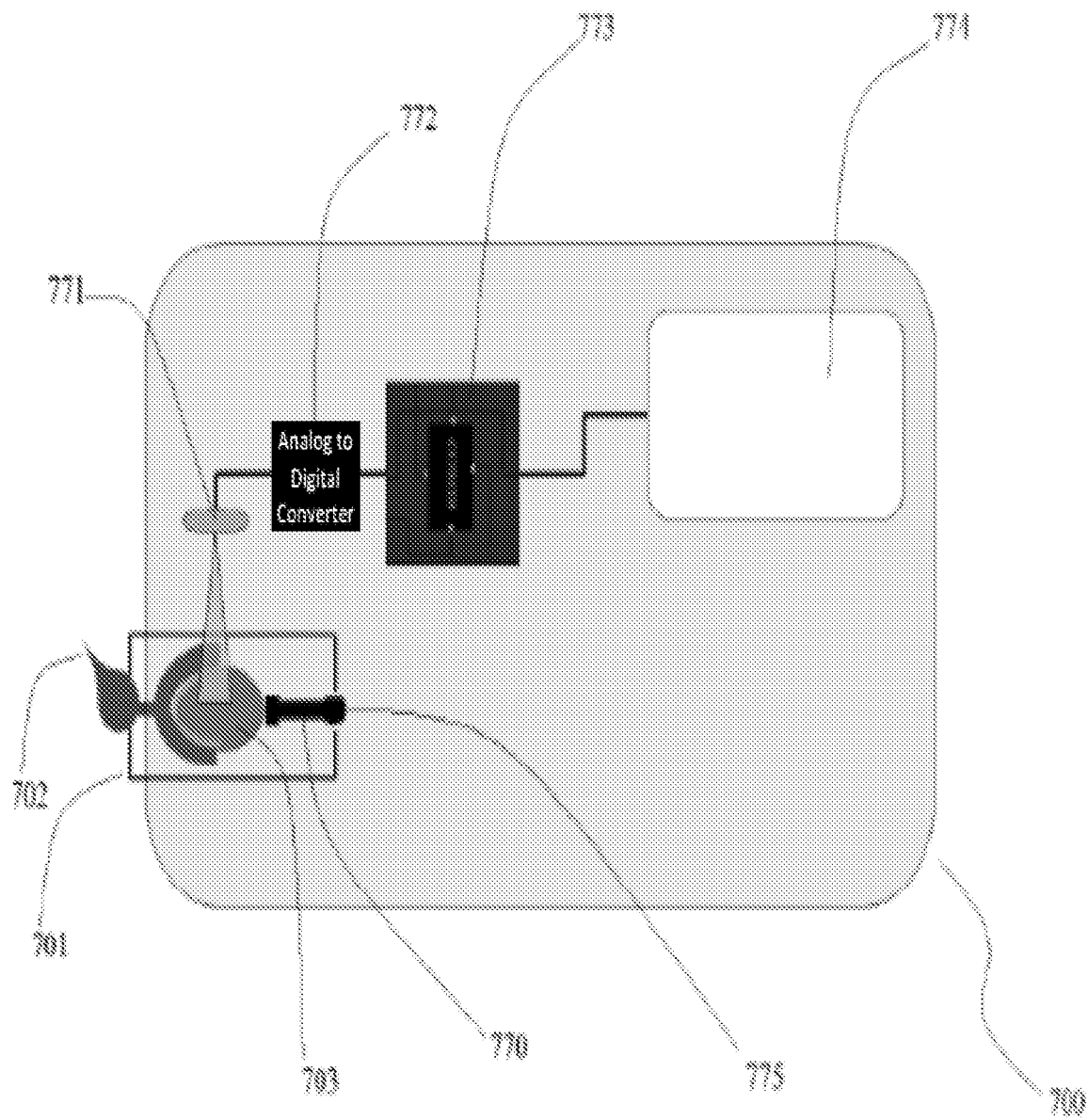
FIG. 7 shows an exemplary embodiment of a device comprising an electronic circuit comprising an electrode exposed to a vessel configured for performance of the indophenol reaction; an analog to digital convertor, a microchip in electronic communication with a display.

FIG. 5 shows an exemplary flowchart of a sequence of events that may take place to accurately and quantitatively identify the amount of ammonia in a sample, and is closely related to the exemplary apparatus and system disclosed in FIGS. 6-7. Additionally, those skilled in the art may appreciate that quantitative analysis in this, or a similar fashion, be added to any of the apparatuses or systems disclosed in FIGS. 1-4.

FIG. 5 therefore shows an exemplary flowchart of steps for a quantitative point of care hyperammonemia sensor. It may be appreciated that these steps may be interchangeable chronologically, may be altered significantly, or eliminated while receiving similar results. Block 501 may refer to a test strip of any size, similar to sizing of the testing strips of blood glucose meters. The insertion mechanism block 501 test strip may be manual or automated. Upon insertion into a device, block 502 may further disclose the initiation of a series of events that may take place under program control. A bleach reservoir may be opened, manually or automatically, into a reagent section within the device. The reagent section, sample section, or both may contain reagents necessary for an indophenol reaction, or reagents used for diagnosing aminoacidopathies or similar diseases and conditions. Block 503 may further disclose the application of a blood sample by way of lancet excretion. The blood sample may be substituted for other biological samples, which may then be transported through a conduit channel to a sample section separated by a reagent section by a cation exchange membrane, such as Nafion. Block 503 may further initiate a microchip under program control which may serve as a timing device, allowing for consistent timing between various steps. This microchip may direct a photodiode or photoresistor to remain inactive for a desired duration to allow for an adequate period of time for certain reactions to take place.

Still referring to FIG. 5, Block 504 may further disclose the diffusion of ammonia or similar compound from sample section to reagent section to initiate any reaction. After a determined period of time, the reagent section may turn blue in the presence of ammonia. The degree of coloration may be dependent on the amount of ammonia in the sample section, which will allow for accurate quantitative analysis. Block 505 may further disclose the initiation of a photodiode or photoresistor near the reagent section to measure the degree of coloration. The photodiode or photoresistor may change the current of the system based on the coloration, whereby block 506 may disclose the step of converting photodiode or photoresistor signal from an analog to a digital signal. Block 507 may further disclose the reception of a digital signal to a microchip under program control. Upon reception, a microchip of block 507 may utilize a predetermined calibration curve in order to correlate a signal to an accurate ammonia concentration value, as further disclosed in block 508. Block 509 may further disclose a transmission of data from the microchip to a display device, which may be either physically or wirelessly connected to microchip, for user accessibility. This method may include the use of fewer or significantly more microchips and controllers under additional program control. Further microchips may be useful for various tests, display mechanisms, data analysis, and both visual and auditory aesthetics. Microchips may also facilitate communication between an exemplary device and an at-home computer, cell phone, TV, or other common display and communication devices.

FIG. 6 shows an exemplary embodiment of a blood test strip for use with an electronic device further disclosed in FIG. 7. The testing strip may be large or small in nature, for use in either laboratory settings or personal home use. Conduit channel 601 may be the reception point of a sample to be tested. A blood droplet, excreted by lancet, may be placed on distal edge of conduit channel 601, where capillary action may transport sample into sample section 602. Sample section 602 may be U-shaped to increase surface area with a cation exchange membrane 604, such as Nafion. On the opposing side of membrane 604, a reagent section 603 may be filled with reagents commonly used with an indophenol or Berthelot's reaction. Bleach, or a similar anion, may be located in a separated reservoir either on the testing strip or within the electronic device in order to ensure the reactivity of certain reagents.

FIG. 7 shows an exemplary embodiment of a testing device under program control and a display device for the presentation of quantitative analysis. A blood test strip 701, such as a strip disclosed in FIG. 6, may be inserted into a port or aperture located on testing device 700, and a blood droplet 702 may be dispensed onto a conduit located distally on blood test strip 701. Upon insertion, an injection mechanism 770 may either automatically or manually add bleach or a similar anion to a reagent section 703. Bleach, chloramine T, or similar dry or liquid anion may be stored in reservoir 775, and may be refillable as desired. A photodiode or photoresistor 771 may remain inactive for a predetermined period of time until a fill sensor within microchip 773 directs the photodiode or photoresister to generate a signal corresponding to the coloration of reagent section 703. Photodiode or photoresistor 771 may then alter the current or voltage of the system with or without the means of an instrumentational amplifier and emit a signal sent to an analog-to-digital converter 772. Upon conversion to a digital signal, this may be sent to microchip 773 for analysis and further program control. Microchip 773 may compute signal and equate to a concentration of ammonium, or specific amino acids, within sample section 702 by means of pre-programmed calibration curves. Microchip 773 may then send data and information to display device 774 for user readability. Display device 774 may be wholly integrated into testing device 700, or may be connected to testing device 700 physically or wirelessly. Additionally, an alternate embodiment of testing device 700 may incorporate multiple microchips for further program control, and may be connected wirelessly or physically to an external display device, such as a computer, cell phone, TV, LCD screen, printer, or similar display and communication devices. Testing device 700 may also be in communication with devices at hospitals or laboratories for ease of information transfer to a user's doctor or medical facility.

Figure 8:
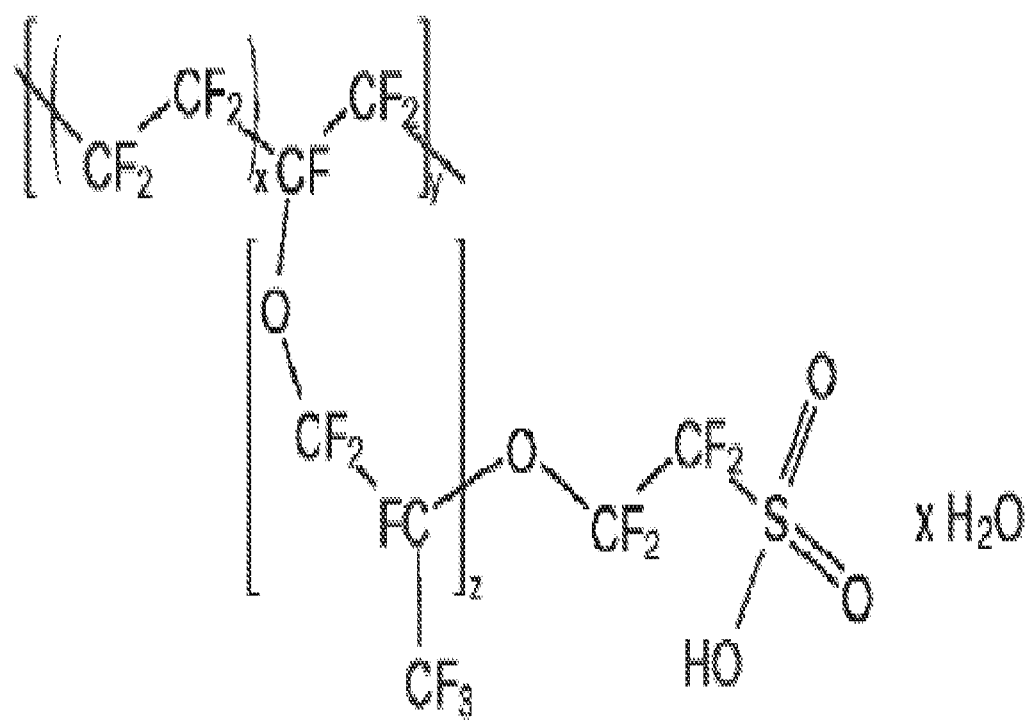
FIG. 8 shows the chemical composition of Nafion.
Figure 9:
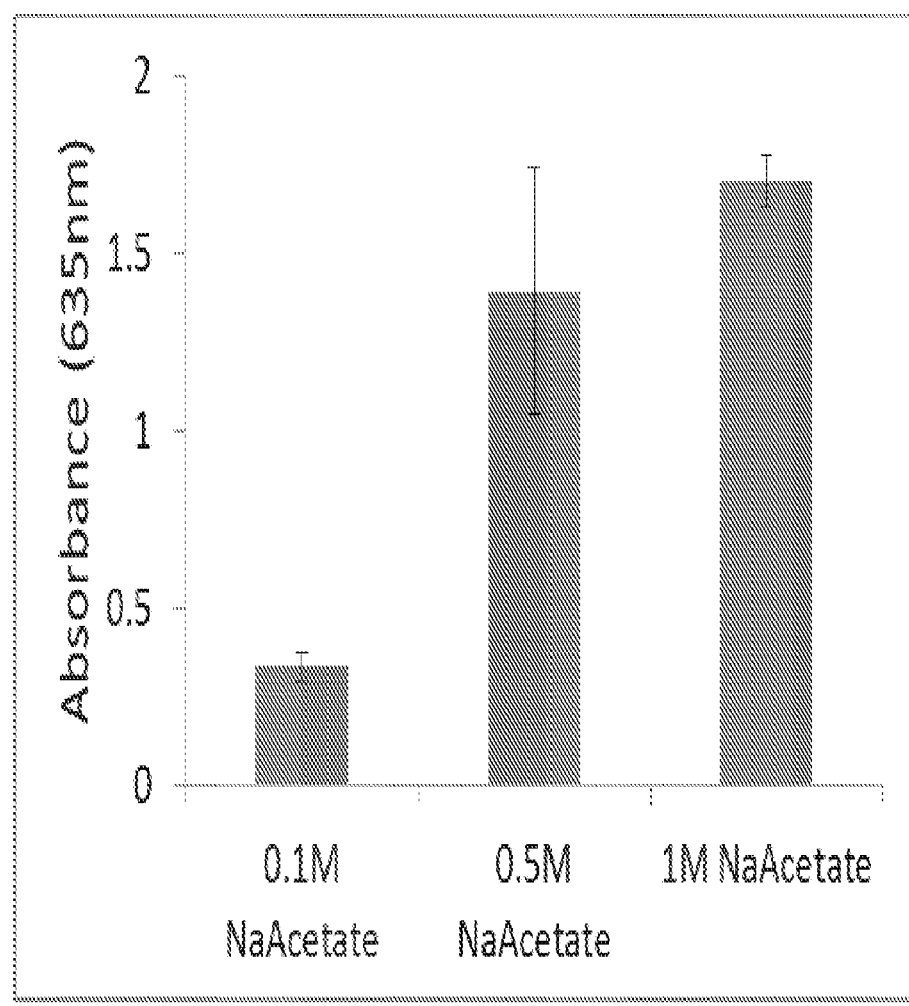
FIG. 9 shows experimental data demonstrating how the concentration of sodium salt yields high recovery and transfer of ammonia from a sample.
Figure 10:
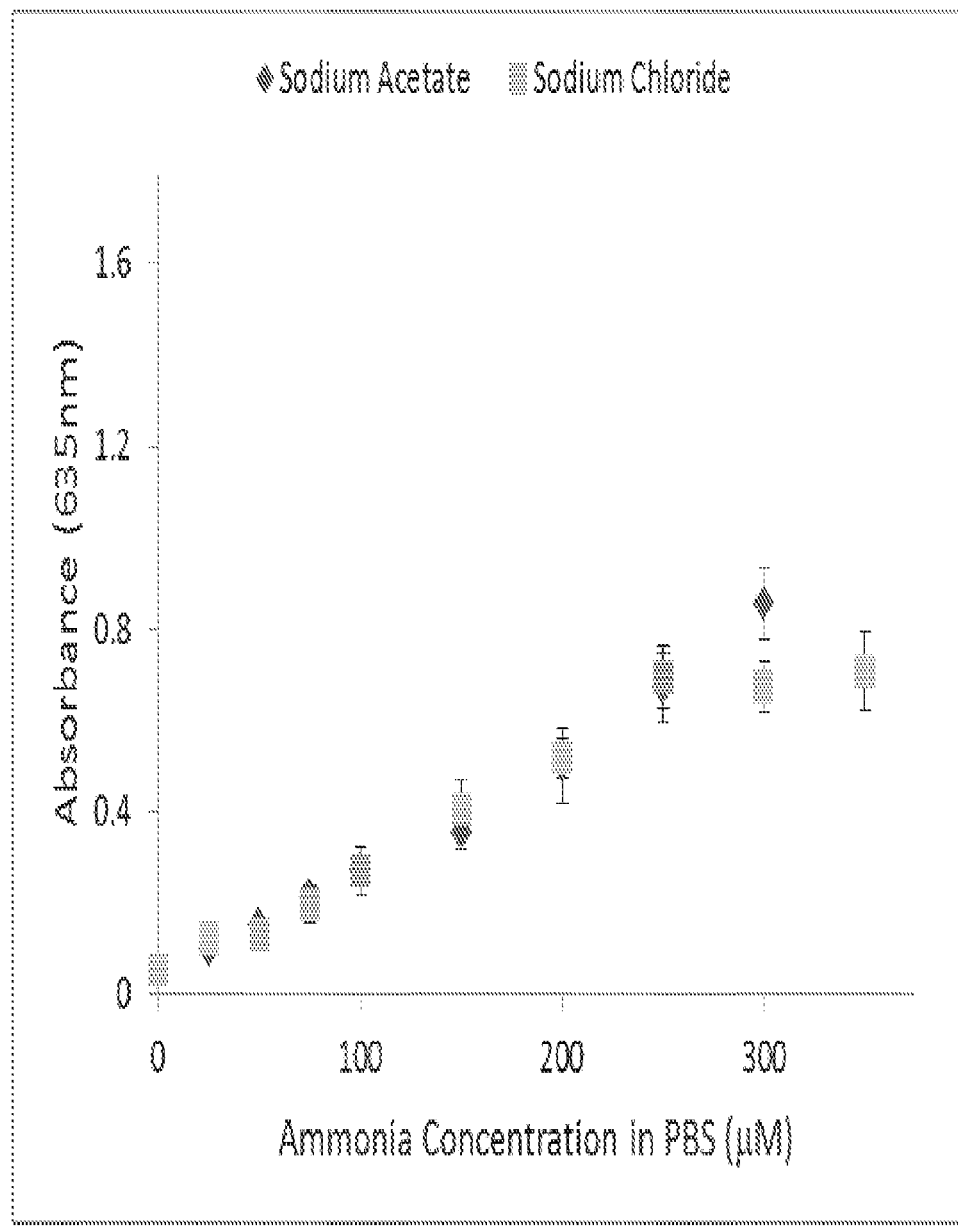
FIG. 10 shows experimental data demonstrating the differences in device performance when using sodium acetate versus sodium chloride as a basic buffer.

FIG. 8 shows the chemical composition of Nafion. Other similar cation exchange membranes or perfluorinated ionomer membranes may also be used interchangeably.

The foregoing description and accompanying figures illustrate the principles, preferred embodiments and modes of operation of the invention. However, the invention should not be construed as being limited to the particular embodiments or applications discussed above. Additional variations, modifications, and applications of the embodiments discussed above will be appreciated by those skilled in the art. Additional variations and modifications may include, but are not limited to, the detection of a variety of different amino acids, such as phenylalnine, histidine, tyrosine, glutamate, threonine, serine, leucine, isoleucine, aspartate, valine, glycine, alanine, tryptophan, proline, lysine, arginine, or others. Detection of these amino acids may involve placing dehydrogenase enzymes or other ammonia lyase enzymes in the sample section of the well, along with the blood, serum, or plasma. Possible applications for the detection of the presence of amino acids is to diagnose phenylketonuria or other aminoacidopathies or aminoacidemia.

Any and all journal articles, patent applications, issued patents, or other cited references disclosed herein are incorporated by reference in their respective entireties.
PCT Application Serial No. PCT/US2013/065548.
1. J. Zschocke, G. F. Hoffmann, Vademecum Metabolicum (Milupa Metabolics, Friedrichsdorf, Germany, ed. 3rd, 2011).
2. B. C. Lanpher, A. L. Gropman, K. A. Chapman, U. Lichter-Konecki, M. L. Summar, Urea Cycle Disorders Overview (NCBI Bookshelf, 2003).
3. M. L. Summar, S. Koelker, D. Freedenberg, C. Le Mons, J. Haberle, H.-S. Lee, B. Kirmse, The incidence of urea cycle disorders., Mol. Genet. Metab. 110, 179-80 (2013).
4. R. H. Singh, Nutritional management of patients with urea cycle disorders., J. Inherit. Metab. Dis. 30, 880-7 (2007).
5. M. Msall, Neurological Outcome in Children with Inborn Errors of Urea Synthesis.pdf, N. Engl. J. Med. 310, 1500-1505 (1984).
6. A. L. Gropman, M. L. Batshaw, Cognitive outcome in urea cycle disorders., Mol. Genet. Metab. 81 Suppl 1, S58-62 (2004).
7. M. L. Batshaw, S. Brusilow, L. Waber, W. Blom, A. M. Brubakk, B. K. Burton, H. M. Cann, D. Kerr, P. Mamunes, R. Matalon, D. Myerberg, I. A. Schafer, Treatment of Inborn Errors of Urea Synthesis, N. Engl. J. Med. 306, 1387-1392 (1982).
8. F. F. Poordad, Review article: the burden of hepatic encephalopathy., Aliment. Pharmacol. Ther. 25 Suppl 1, 3-9 (2007).
9. R. F. Butterworth, J. F. Giguere, J. Michaud, J. Lavoie, G. P. Layrargues, Ammonia: key factor in the pathogenesis of hepatic encephalopathy, Neurochem Pathol 6, 1-12 (1987).
10. R. F. Butterworth, Pathophysiology of hepatic encephalopathy: a new look at ammonia., Metab. Brain Dis. 17, 221-7 (2002).
11. J. Stahl, Studies of the Blood Ammonia in Liver Disease, Ann. Intern. Med. 58 (1963).
12. I. Eijgelshoven, S. Demirdas, T. A. Smith, J. M. T. van Loon, S. Latour, A. M. Bosch, The time consuming nature of phenylketonuria: A cross-sectional study investigating time burden and costs of phenylketonuria in the Netherlands, Mol. Genet. Metab. 109, 237-242 (2013).
13. P. V. D. Burg, H. W. Mook, A simple and rapid method for the determination of ammonia in blood, Clin. Chim. Acta 8, 162-164 (1962).
14. Y. Murawaki, K. Tanimoto, C. Hirayama, Y. Ikuta, N. Watabe, A simple and rapid microdiffusion method for blood ammonia using a reflectance meter and a reagent plate, and its clinical evaluation for liver diseases., Clin. Chim. Actal 144 (1984).
15. R. J. Barsotti, Measurement of ammonia in blood, J. Pediatr. 138, S11-S20 (2001). 16. J. Buttery, R. Ratnaike, B. Chamberlain, The measurement of erythro-cyte ammonia using the Hyland ammonia kit, J Clin Chem Clin Biochem 20 (1982).
17. S. Dienst, An ion exchange method for plasma ammonia concentration, J. Lab. Clin. Med. 58 (1961).
18. J. Huizenga, C. Gips, Determination of blood ammonia using the Ammonia Checker, Ann Clin Biochem 20 (1983).
19. H. van Anken, M. Schiphorst, A kinetic determination of ammonia in plasma, Clin Chim Acta 56 (1974).
20. L. Rover Junior, J. C. Fernandes, G. de Oliveira Neto, L. T. Kubota, E. Katekawa, S. H. Serrano, Study of NADH stability using ultraviolet-visible spectrophotometric analysis and factorial design., Anal. Biochem. 260, 50-5 (1998).
21. M. Berthelot, B, Repert. Chim. Appl., 254 (1859).
22. E. D. Rhine, G. K. Sims, R. L. Mulvaney, E. J. Pratt, Improving the Berthelot Reaction for Determining Ammonium in Soil Extracts and Water, Soil Sci. Soc. Am. J. 62 (1998).
23. T. T. Ngo, A. P. H. Phan, C. F. Yam, H. M. Lenhoff, Interference in Determination of Ammonia with the Hypoehlorite-Alkali Phenol Method of Berthelot, 46-49 (1981).

The foregoing description and accompanying figures illustrate the principles, preferred embodiments and modes of operation of the disclosure. However, the disclosure should not be construed as being limited to the particular embodiments or applications discussed above. Additional variations, modifications, and applications of the embodiments discussed above will be appreciated by those skilled in the art. Additional variations and modifications may include, but are not limited to, the detection of a variety of different amino acids, such as phenylalnine, histidine, tyrosine, glutamate, threonine, serine, leucine, isoleucine, aspartate, valine, glycine, alanine, tryptophan, proline, lysine, arginine, or others. Detection of these amino acids may involve placing dehydrogenase enzymes or other ammonia lyase enzymes in the sample section of the well, along with the blood, serum, or plasma. Possible applications for the detection of the presence of ammonia or ammonium ion is to diagnose phenylketonuria or other aminoacidopathies.

Therefore, the above-described embodiments should be regarded as illustrative rather than restrictive. Accordingly, it should be appreciated that variations to those embodiments can be made by those skilled in the art without departing from the scope of the disclosure as defined by the following claims.

EXAMPLES

Example 1

The presented work demonstrates how the systematic investigation of previously known technologies yielded the fabrication of an effective blood ammonia sensor. The indophenol reaction, in tandem with a polyelectrolyte membrane, was explored as a means to quantify ammonia concentrations in whole blood.

The ammonia-indophenol standard curve was produced using a range of ammonium chloride concentrations in 1× phosphate buffered saline (PBS) of 0 to 750 μM. The following concentrations were utilized in the indophenol reaction: 59 mM 2-phenylphenol in ethanol, 7 μM sodium nitroprusside in water, 500 mM sodium hydroxide in water, and 0.2-0.25% aqueous hypochlorite. These concentrations were mixed in a 1:1:1:0.5 ratio with an equal volume of the ammonium solution of interest and allowed to react at room temperature for 10 minutes. The absorbance of the resulting solution was measured at a wavelength of 635 nm.

Example 2

Stability Studies

The reagents utilized in the indophenol reaction were investigated for long term stability. Aqueous solutions of hypochlorite, sodium nitroprusside, sodium hydroxide and a solution of 2-phenylphenol in ethanol were stored in separate 50 mL falcon tubes, with limited exposure to light. At intervals of 3, 5, 7, 15, 21, 28, 35, 50, 75 and 100 days the hypochlorite, sodium nitroprusside, sodium hydroxide and 2-phenylphenol were utilized to develop a standard curve using ammonia concentrations ranging from 0-750 µM. Significant deviations from the original standard curve indicated the degradation of the stored reagents. It should be noted that fresh ammonia samples were utilized at each test interval.

Response to Amino Acids

Primary amines can also undergo the indophenol reaction. Total amino acid concentrations in blood can be as high as 2.5 mM, therefore the selectivity of 2-phenylphenol was determined in the indophenol reaction. 1 mM solutions of each of the 21 amino acids was prepared in 1×PBS. The same protocol utilized with the indophenol reagents for the ammonia standard curve was utilized with each amino acid solution. 10 minutes after the indophenol reagents and amino acid solution was mixed, its absorbance at 635 nm was measured using a plate reader. The response was directly compared to the response seen from a 1 mM solution of ammonium chloride and expressed as a percentage of the ammonium response.

Sensor Design

Figure 11:
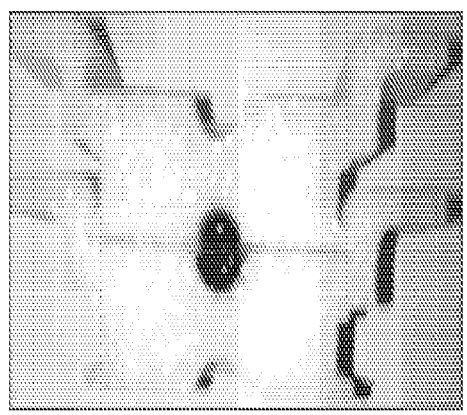
FIG. 11 depicts a photograph of the 3D printed modular pieces snapped together around Nafion to form the bisected well utilized for the sensing experiments

A bisected well containing blood in one section and a concentrated alkali solution in the other would provide a means for cation exchange of the whole blood to occur, yielding a strong recovery of the ammonium. A computer-aided design of the well that is both reusable and modular was 3D printed. As seen in FIG. 11, two modular pieces were 3D printed from acrylonitrile-butadiene-styrene thermoplastic. The pieces will snap together with the membrane in the middle, forming a Nafion bisected well. This design was chosen to provide a uniform platform for all future experiments involving this sensing mechanism. Silicone gasketing material, at a 1/64" thickness, was glued to the inner face of each well-half to ensure a water tight seal. The wells were then back-filled with polydimethylsiloxane to improve their mechanical properties.

FIG. 11 Photograph of the 3D printed modular pieces snapped together around Nafion to form the bisected well utilized for the sensing experiments.

Sensor Response to Ammonia in Phosphate Buffered Saline and Whole Blood

The 3D printed wells were constructed with 1 cm$^2$ pieces of Nafion membrane. In one bisection of the well a range of 0-500 µM concentrations of ammonium chloride in 1×PBS was added. In the opposing bisection a 1M alkali solution was added. Ion-exchange of ammonium was allowed to occur for 20 minutes. The alkali solution, now containing ammonia, was then extracted and utilized in the indophenol reaction. The absorbance of the resulting indophenol reaction was measured at 635 nm after 10 minutes using a microplate reader.

Whole human blood was spiked using ammonium chloride to generate concentrations of ammonia of 25, 50, 75, 100, 150, 200, 250, 300, 400 and 500 µM. This method of producing ammonia-spiked blood was verified utilizing a Siemens RXL to determine the true ammonia concentrations of the resulting whole blood. The ammonia-spiked whole blood was pipetted into the sensor in a protocol identical to the one used in the case of the ammonium in 1×PBS. In one section of the well the ammonia-spiked blood was added. In the other section was the concentrated alkali solution. After 20 minutes the ion-exchange has taken placed and the ammonia is extracted into the alkali solution. The ammonia-containing alkali solution was then mixed with the hypochlorite, sodium hydroxide, sodium nitroprusside, and 2-phenylphenol. The resulting indophenol reaction's absorbance was measured at 635 nm after 10 minutes.

Hypochlorite Concentrations Effect on Indophenol Response to Blood Ammonia

To reduce interference from reducing species in blood, higher concentrations of hypochlorite than conventionally utilized were employed in the indophenol reaction with ammonia extracted from whole sheep's blood. 1, 2, 3, 5, and 10× concentrations of hypochlorite were utilized and the resulting absorbance at 635 nm was recorded.

Ammonia-Indophenol Standard Curve

Figure 12:
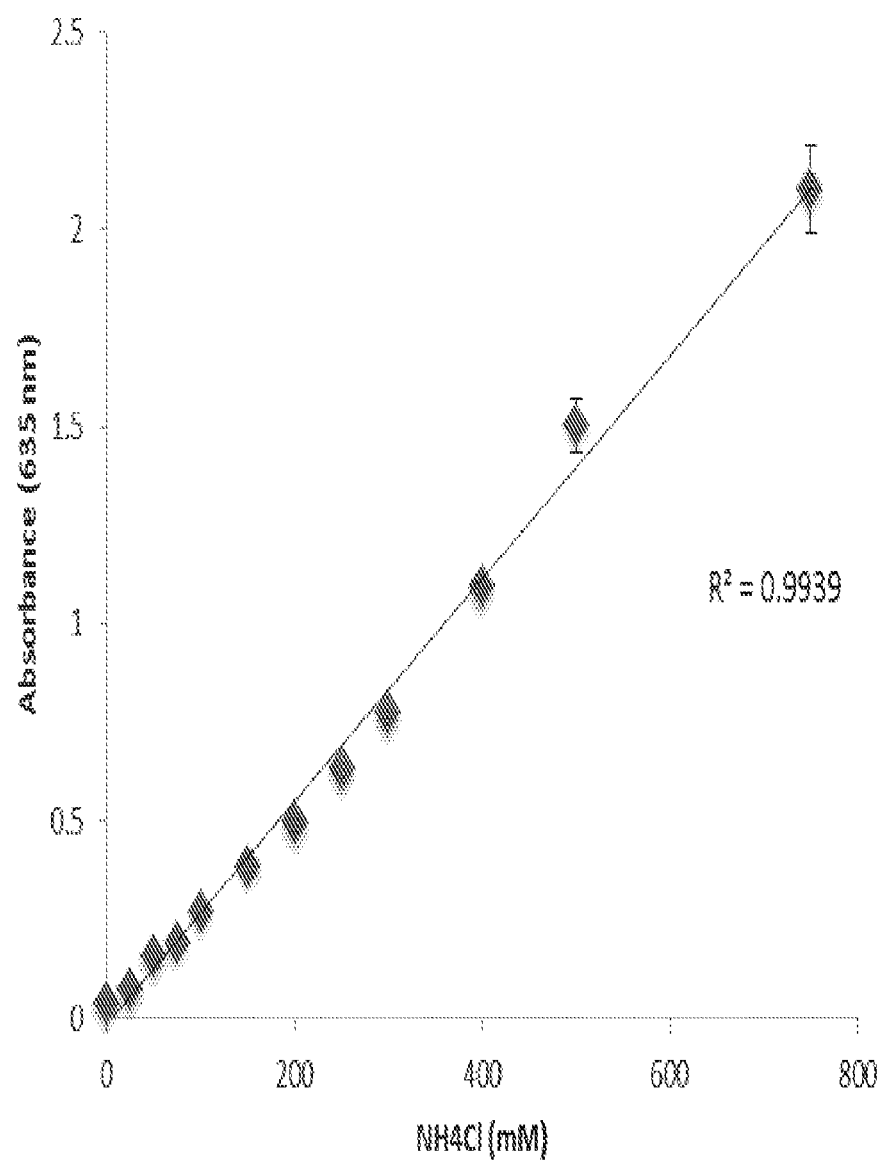
FIG. 12 depicts an indophenol reaction produces a linear curve with concentrations of ammonium chloride ranging from 0-750 µM with a COD of 0.9939.

FIG. 12. The indophenol reaction produces a linear curve with concentrations of ammonium chloride ranging from 0-750 µM with a COD of 0.9939.

The efficacy of the indophenol reaction was initially evaluated for its lower limit of quantification (LLoQ), resolution, range and, response time. The utilized reagents were optimized to produce a response from 25-1000 µM ammonium chloride demonstrated in FIG. 12. An LLoQ of 25 µM was recorded with an average error of ~15%, therefore the sensor's resolution in terms of concentration is higher at lower ammonium concentrations.

Stability Studies

Figure 13:
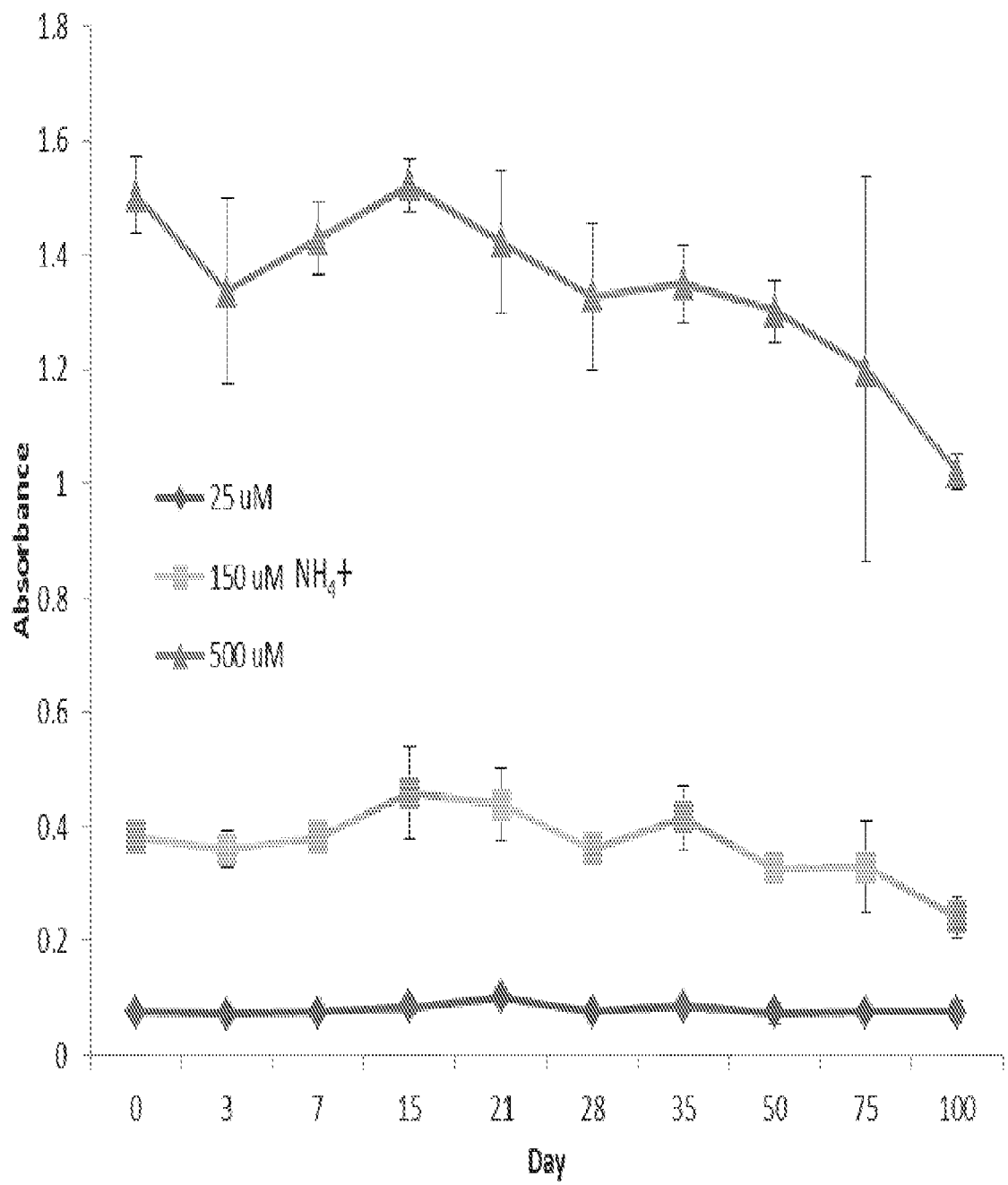
FIG. 13 depicts reagents for the indophenol reaction were stored at room temperature and used to generate an ammonia standard curve at regular intervals for 100 days. The response to 500 µM ammonia began to degrade at day 75. The reagents of the indophenol reaction are stable at room temperature for up to 50 days before its response to different concentrations of ammonia begins to deteriorate.

One major advantage of using the indophenol reaction for determining ammonia concentrations is that it does not require any biological components such as enzymes, which are prone to stability issues. The shelf-life of the solutions used for the indophenol reaction was examined over the course of 100 days. The components of the indophenol reaction are not stable when mixed together, potentially due to the hypochlorite and the coupling agent's, sodium nitroprusside, reactivity. The response to the range of ammonium chloride concentrations was stable for up to 50 days. As seen in FIG. 13, the response to 25, 150 and 500 µM ammonium chloride does not change significantly until day 75.

FIG. 13 The reagents for the indophenol reaction were stored at room temperature and used to generate an ammonia standard curve at regular intervals for 100 days. The response to 500 µM ammonia began to degrade at day 75. The reagents of the indophenol reaction are stable at room temperature for up to 50 days before its response to different concentrations of ammonia begins to deteriorate.

Response to Amino Acids

The mechanism for the indophenol reaction is also applicable to other primary amine containing compounds. For whole blood applications this is problematic due to the presence of small amine containing molecules such as amino acids which would cause interference when measuring blood ammonia. The phenol compound utilized in the indophenol reaction, 2-phenylphenol, is thought to introduce some form of selectivity due the large phenyl group adding a degree of steric hindrance to the reaction. The selectivity of the reaction was tested with a large array of different amino acids. Since the response to the amino acids was so low, a concentration of 500 µM was utilized for ammonia and 1 mM for the amino acids. The absorbance values recorded for the amino acids were normalized with the ammonia acting as 100%. The radar graph in FIG. 14 shows the response of each amino acid, the highest of which was threonine that was just 7% of the ammonia response.

Figure 14:
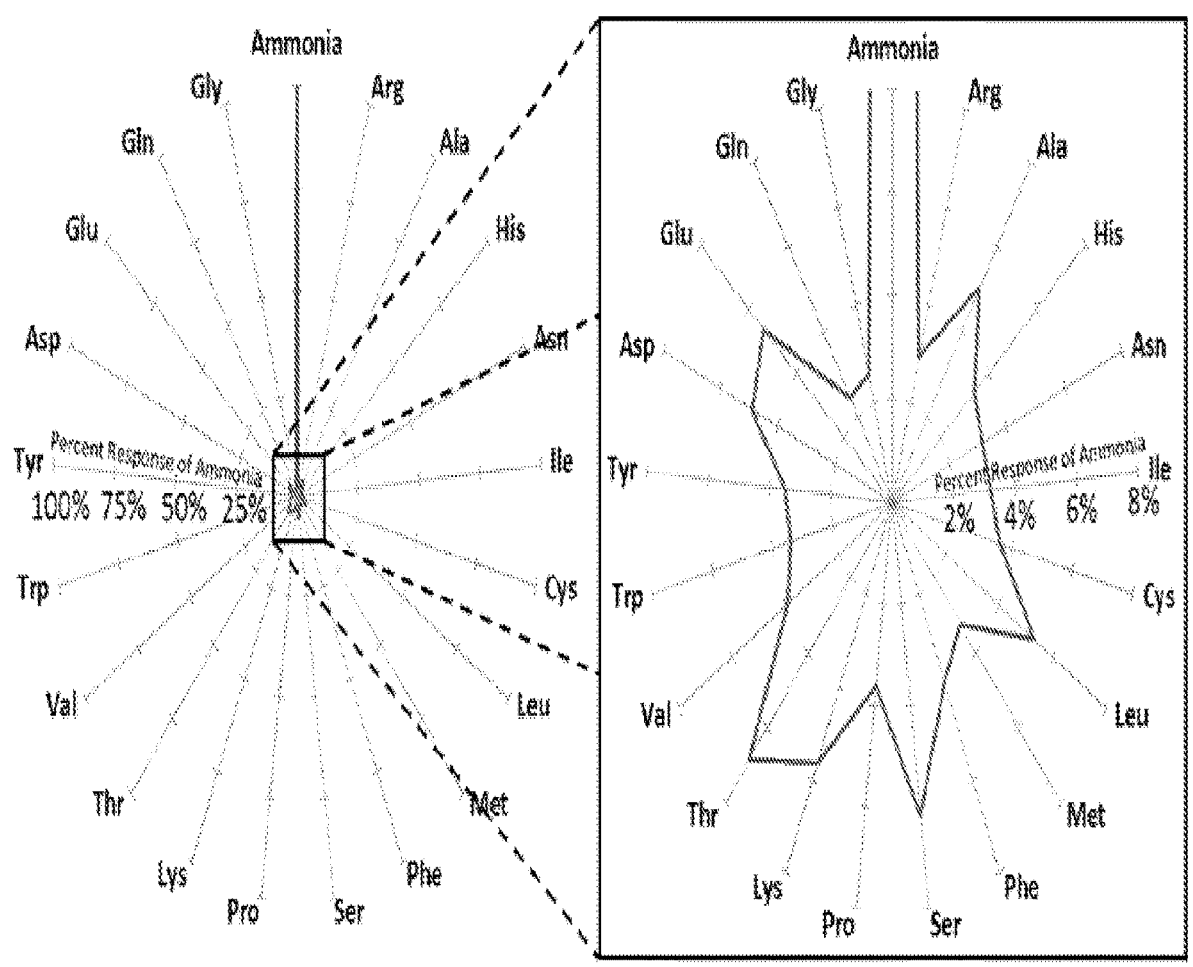
FIG. 14 depicts 1 mM concentrations of each of the 21 amino were tested using the indophenol reaction. The absorbance measured at 635 nm for each amino acid after the indophenol reaction was calculated as percentage of the response from indophenol reaction with 1 mM ammonium chloride. The radar graph displays the percent response as compared to ammonium chloride. The highest response was threonine which produced an absorbance value that was just 7% of ammonia's response.

FIG. 14 1 mM concentrations of each of the 21 amino were tested using the indophenol reaction. The absorbance measured at 635 nm for each amino acid after the indophenol reaction was calculated as percentage of the response from indophenol reaction with 1 mM ammonium chloride. The radar graph displays the percent response as compared to ammonium chloride. The highest response was threonine which produced an absorbance value that was just 7% of ammonia's response.

Cation Exchange of Whole Blood

The other major source of interference for the indophenol reaction is proteins. Small quantities of proteins can completely disable the reaction from proceeding. In order to rapidly separate ammonium from whole blood while excluding any proteins, Nafion, a cation exchange membrane, was utilized. Nafion has had previous application in biosensors but almost entirely for protection of electrodes in electrochemical sensors. In this case Nafion is being operated as a cation exchange membrane rather than a nanoporous form of Teflon, as used in electrochemical sensors. Nafion is a fluorinated ionomer block copolymer. When cast into films, usually from solution in a hot press, the ionomeric block aggregate into long-range pores of the sulfones surrounded by a matrix of the fluoropolymer. The pores are highly negatively charged due to the sulfonic acids groups and are generally 1-4 nm in size. These pores allow for the rapid diffusion of hydroxyl containing molecules and cations through the Nafion while inhibiting anions and completely preventing macromolecules. This would allow for the rapid diffusion of ammonia while reducing amino acid diffusion and completely eliminating proteins from passing and disabling the indophenol reaction.

The ion-exchange of ammonium through the use of the Nafion is the main mechanism of recovery of the analyte. Ammonium will diffuse across the membrane passively as well, but at a rate that is not sufficient for a beneficial point-of-care sensor. Alkali solutions of different ionic strength were tested for their effectiveness in exchanging with the ammonium from a PBS solution. It was expected that higher concentrations of salt would yield larger recoveries of ammonium. Bisected wells were prepared with Nafion membranes. A 500 mM solution of ammonium chloride in PBS was placed on the 'analyte' side of the bisected well and solutions of a concentrated aqueous alkali in the opposing bisection. Distilled water resulted in a 10% recovery, in the control case, while the concentrated aqueous alkali resulted in a 75% recovery of the ammonium. The larger concentration of ammonium in the alkali solution versus the analyte is indicative of the ion exchange mechanism occurring, as the concentration would be equal if the mechanism was simply passive diffusion.

Sensor Response to Ammonia in PBS

The sensor was initially challenged with ammonium chloride solution in PBS, before introducing an environment as complex as whole blood. Concentrations ranging from 0-500 µM were analyzed. In healthy adults ammonia levels are generally 50-80 µM whereas concentrations greater than 100 µM are suspect. These numbers are higher in neonates in which case less than 110 µM is normal, up to 180 µM could be attributed to other illnesses and greater than 200 µM is cause for concern. In severe cases ammonia levels can be as high as 500 µM(1).

FIG. 5 The constructed sensor's response to a range of ammonia concentrations in 1×PBS. The COD is 0.9758 with n=5 samples.

Figure 15:
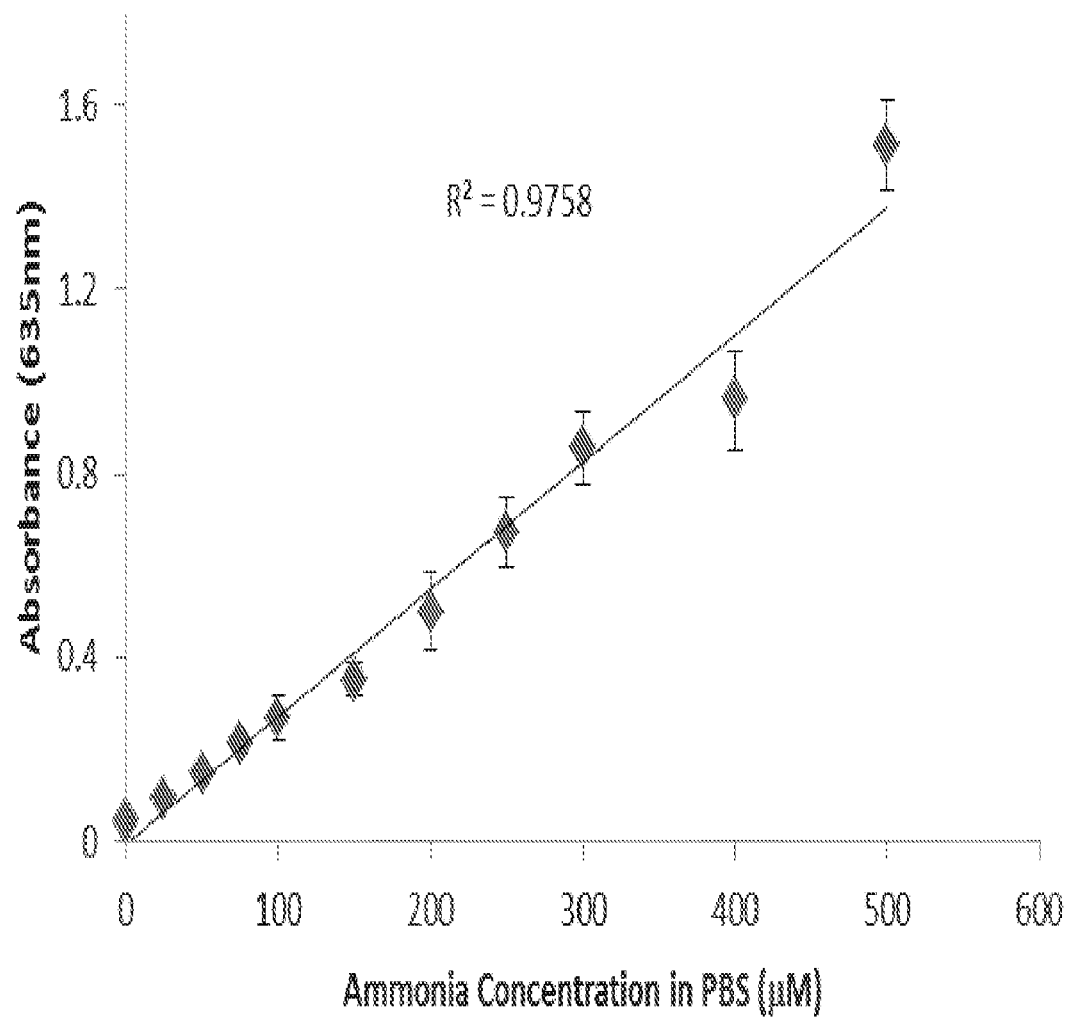
FIG. 15: The constructed sensor's response to a range of ammonia concentrations in 1×PBS. The COD is 0.9758 with n=5 samples.
Figure 16:
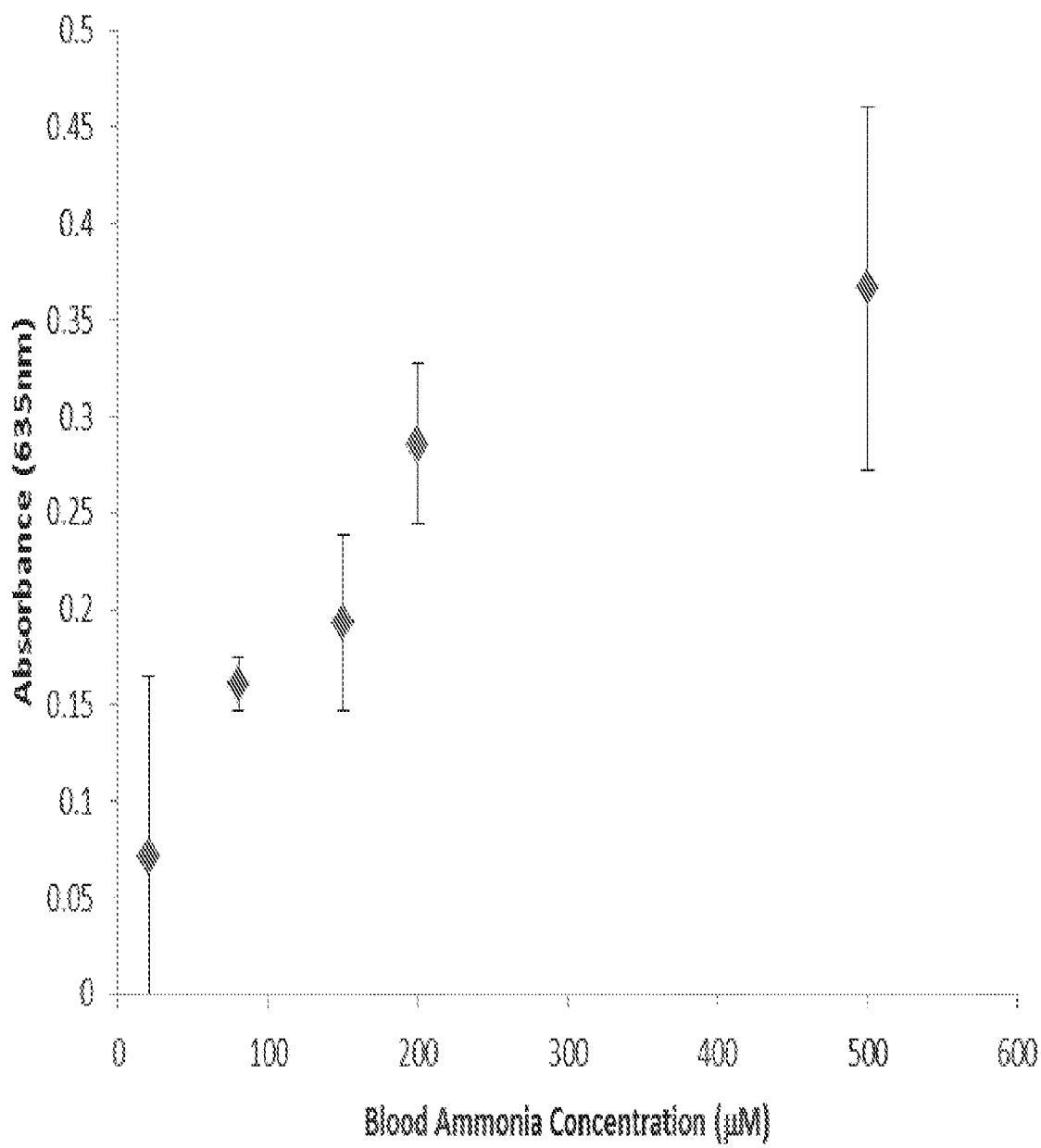
FIG. 16: Initial experiments of determining blood ammonia concentration demonstrated a limited response. Responses were hindered and would not exceed an absorbance of 0.35 indicating some degree of interference.

The sensor reliably extracted the ammonia in 20 minutes time. The extracted solution was then tested using the indophenol reaction and the developed color analyzed using a plate reader measuring absorbance at 635 nm. This process produced the standard curve seen in FIG. 15. The COD for detection in PBS was 0.97, with an error of 5-15%. In the range of 0-100 mM, there was a resolution of ~30 µM ammonium. The sensor was efficacious over the entire clinically relevant range of ammonia levels in PBS.

Initial Sensor Response to Ammonia in Whole Blood

Figure 17:
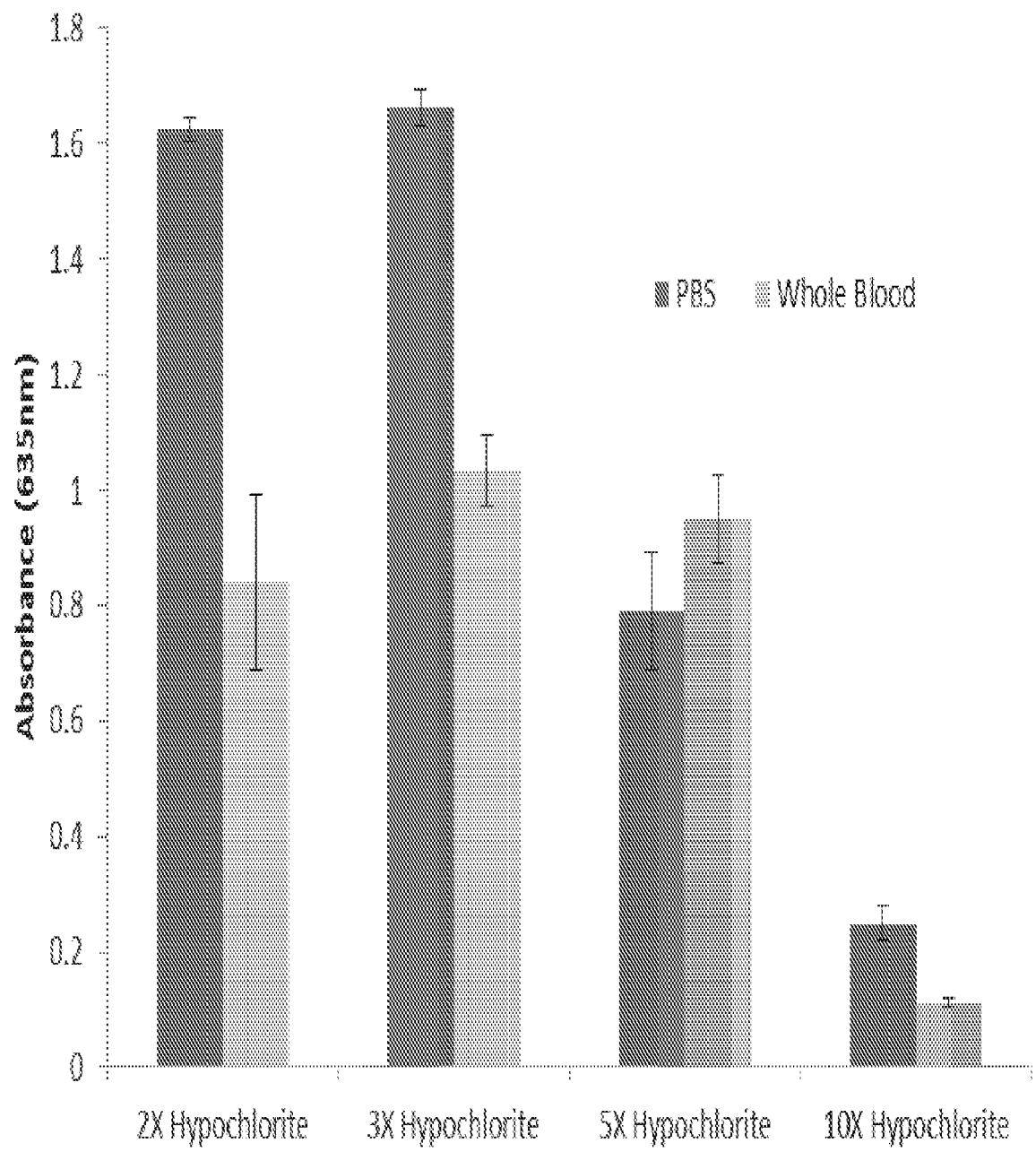
FIG. 17: Concentrations of 2-10× hypochlorite were utilized in the analysis of 500 mM ammonia in 1×PBS and whole sheep's blood. Increasing the concentration of hypochlorite utilized in the indophenol reaction reduced the negative interference small blood molecules had on the indophenol reaction. At concentrations higher than 3×, reaction itself began to degrade. A 3-fold increase in hypochlorite concentration was optimal.

Initial studies in blood produced a non-linear relationship between ammonia concentration and absorbance. The response was limited at an absorbance of 0.35 at a blood ammonia concentration of 500 mM. These responses are markedly reduced from the same concentrations of ammonia in PBS. This suggests that the ammonia is either inhibited from diffusing across the Nafion membrane or small molecules from blood are interfering with the indophenol reaction. Negative interference of the indophenol reaction can also occur from the presence of certain small molecules. It has been previously reported that high concentrations of amines, thiols and reducing agents will disrupt the indophenol reaction, all of which are present in blood(23). Reducing agents will readily react with hypochlorite, an oxidizing agent, effectively disabling the indophenol reaction. To determine if this was the case, ammonia extract from whole sheep blood was exposed to a modified indophenol reaction using 2, 3, 5 and 10× more concentrated hypochlorite than conventionally utilized. As seen in FIG. 17, increasing the hypochlorite concentration up to 3× improved the reaction's response to the ammonia extracted from the whole blood. At 5 and 10× concentrated hypochlorite, the reactions response to ammonia began to degrade, indicating that 3× hypochlorite is optimal for reducing the interference introduced by reducing agents found in blood.

Modified Sensor Response to Ammonia in Whole Blood

The 3× hypochlorite-modified indophenol reaction was examined in conjunction with the Nafion based separation technique for its effectiveness in distinguishing blood ammonia concentrations ranging from 25 to 500 µM, representing healthy to diseased levels. The resulting standard curve, in FIG. 18, demonstrated the response in this range. There was a significant correlation, with a COD of 0.9573, between blood ammonia concentrations and the resulting absorbance at 635 nm after the indophenol reaction.

Figure 18:
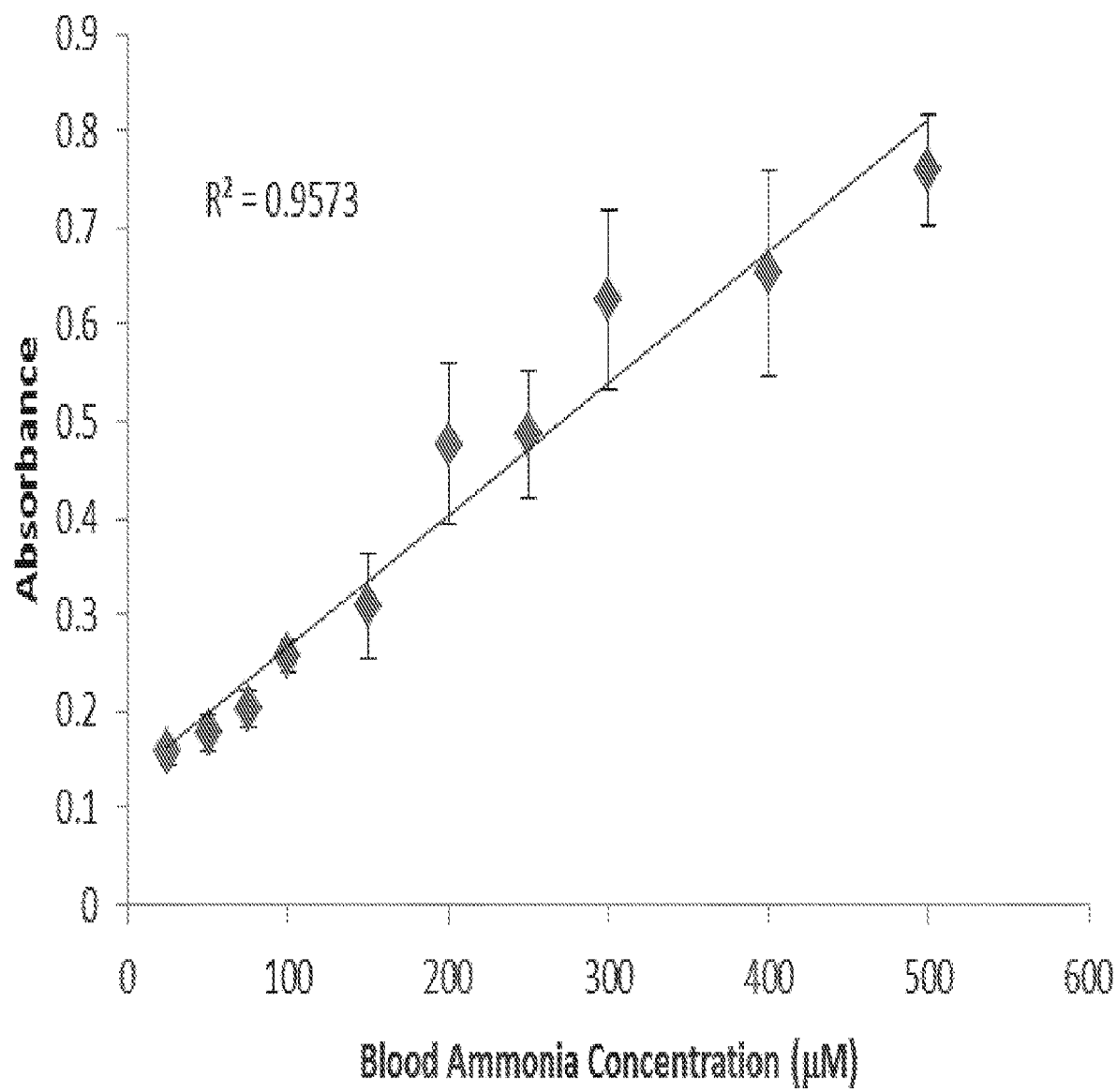
FIG. 18: The bisected well sensor was again used to extract ammonia in whole human blood. The extracted ammonia solutions were tested with the 3× hypochlorite-modified indophenol reaction and the absorbance measured at 635 nm. In the range of 0-500 µM the COD was 0.9573 with n=5 samples.

FIG. 18. The bisected well sensor was again used to extract ammonia in whole human blood. The extracted ammonia solutions were tested with the 3× hypochlorite-modified indophenol reaction and the absorbance measured at 635 nm. In the range of 0-500 µM the COD was 0.9573 with n=5 samples.

Figure 19:
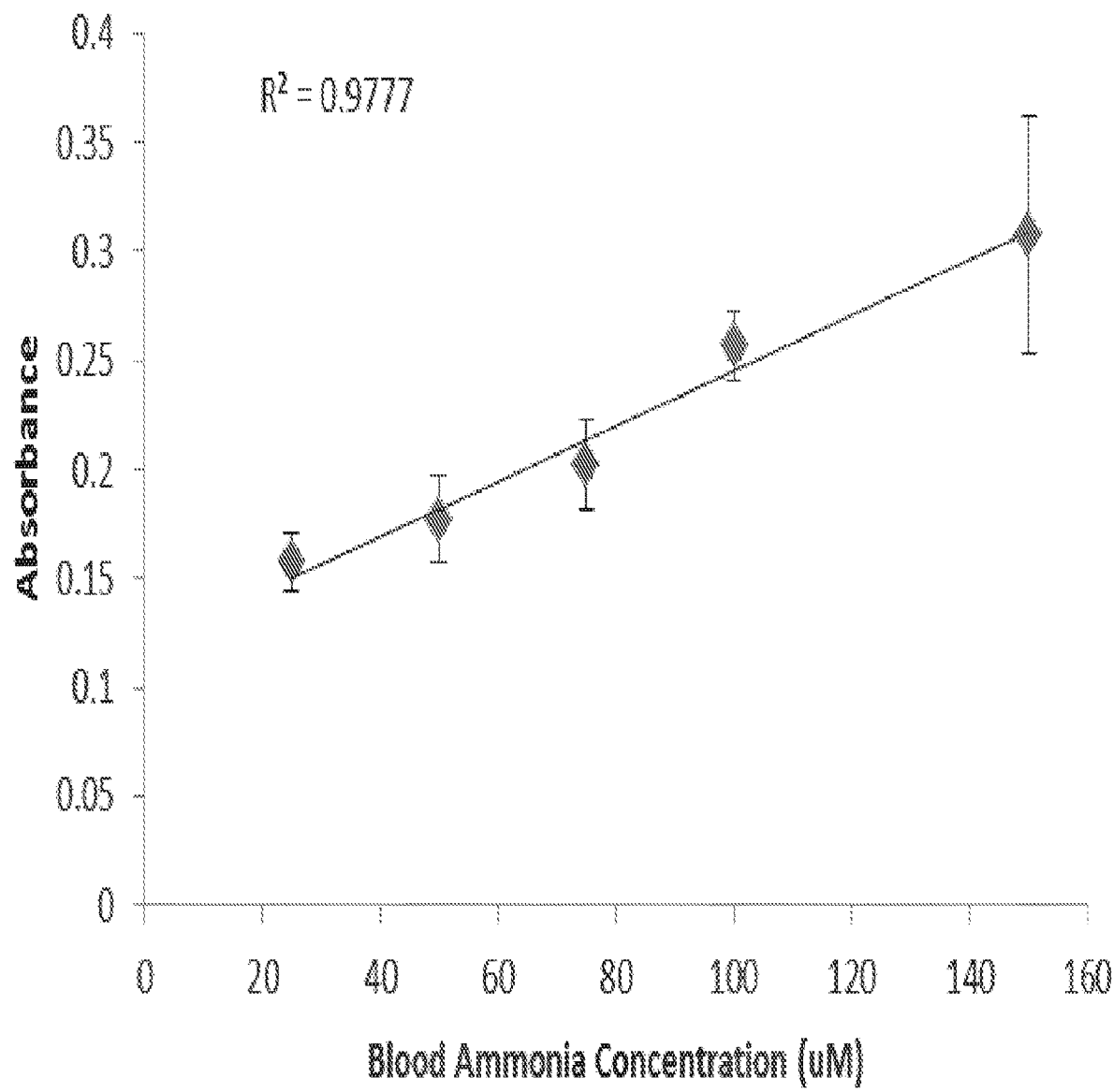
FIG. 19: The sensor's response to blood ammonia concentrations ranging from 0-150 µM. The relative standard deviation is ~10% with a COD of 0.9777 with n=5 samples.

In the range of 25-150 µM, where high resolution measurements are critical for examining treatment effectiveness, the COD was 0.9777, seen in FIG. 19. The error in this range was ~10%, giving a preliminary resolution of 15 µM. The relative standard deviation of 10% percent falls within the FDA guide for validation of a bioanalytical method which requires an relative standard deviation of 15% at n=5 samples. The LLoQ, 25 µM, is at least 3σ above the mean background reading of 0.04483+/−0.00117 absorbance. Additionally, the sensor can reliably differentiate between 50 and 100 µM blood ammonia with a p=0.0001.

FIG. 19 depicts the sensor's response to blood ammonia concentrations ranging from 0-150 µM. The relative standard deviation is ~10% with a COD of 0.9777 with n=5 samples.

The investigated bioanalytical method for evaluating blood ammonia levels demonstrated a high degree of correlation between blood ammonia and sensor response. In the range of from about 25 to about 150 mM, the relative standard deviation was approximately 10%. The sensor has about a twenty-minute response time, and the interference from other small molecules was greatly reduced. The components used are stable at room temperature for up 50 days and inexpensive.

Validation of the functionality of the biosensor will also be performed using the following experimental design. The evaluation of the efficacy of the phenylalanine sensor requires the construction of a three carbon electrode modified with an alginate hydrogel consisting of alginate, CaCl2, Toluidine Blue, Phenylalanine Dehydrogenase, and NAD (P)+. The hydrogel will act as a filter to prevent interference from small molecules and proteins in whole blood. Initially 32 whole blood samples will be tested with phenylalanine concentrations ranging from about 35 µM to about 2000 µM. Specifically the following Phe concentrations will be tested on the enzyme electrode: 35, 100, 250, 500, 1000, 1250, 1500, 2000 µM. In this experiment 35 µM will represent a physiologically normal concentration and each other concentration above 100 µM will represent a variety of different diseased concentrations. These concentrations will be generated by doping whole blood of a concentration lower than 35 µM. Additionally, subject samples will be tested to ensure the sensor operates without issues form unforeseen abnormalities with patient whole blood. All phenylalanine concentration will be verified by the use of high performance liquid chromatography (HPLC), which is the gold standard for determining phenylalanine levels in blood. The samples will not require preprocessing. The blood will be taken using sodium heparin vacuum tubes and then used unmodified outside of doping the blood with higher phenylalanine concentrations. The expected detection limit is 35 µM with a range of 35-2000 µM and a resolution of 20 µM. Statistical Evaluations will be performed to assess the reliability of the concentration measurements. The concentration measurements will be analyzed using ANOVA single factor analysis to demonstrate differences between groups assuming a normal data distribution. Confidence intervals will be assessed and the sensitivity and the reproducibility of the method demonstrated. Concentration measurements ranging from normal physiological conditions to diseased conditions with a confidence 95% ($p<0.05$) or higher will be deemed statistically significant. Statistical differences between diseased concentration levels and healthy, physiological concentration levels will first be demonstrated. Subsequent experimentation will be used to validate quantification of over the full range of discrete concentration values.

Example 3

Figure 20:
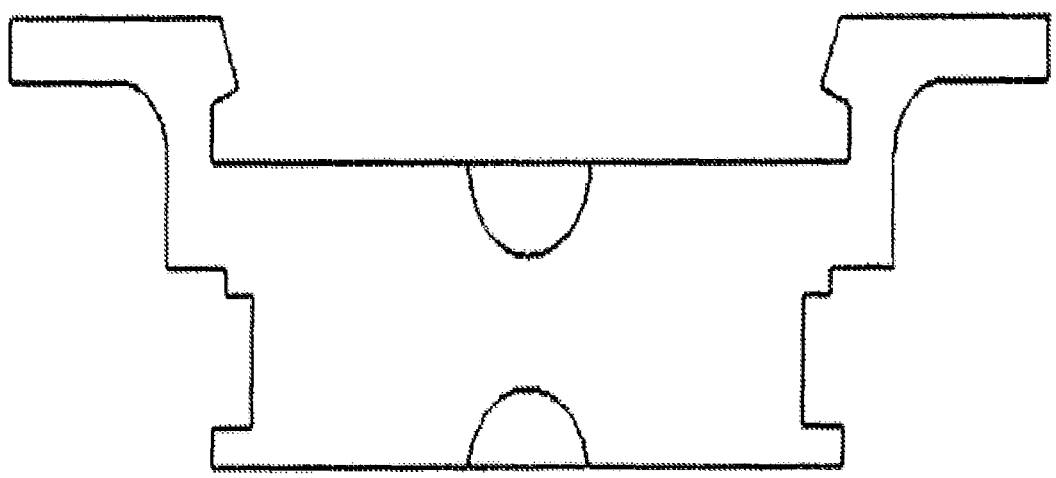
FIG. 20: depicts a CAD sketch of the front face of the well plate of an embodiment.
Figure 21:
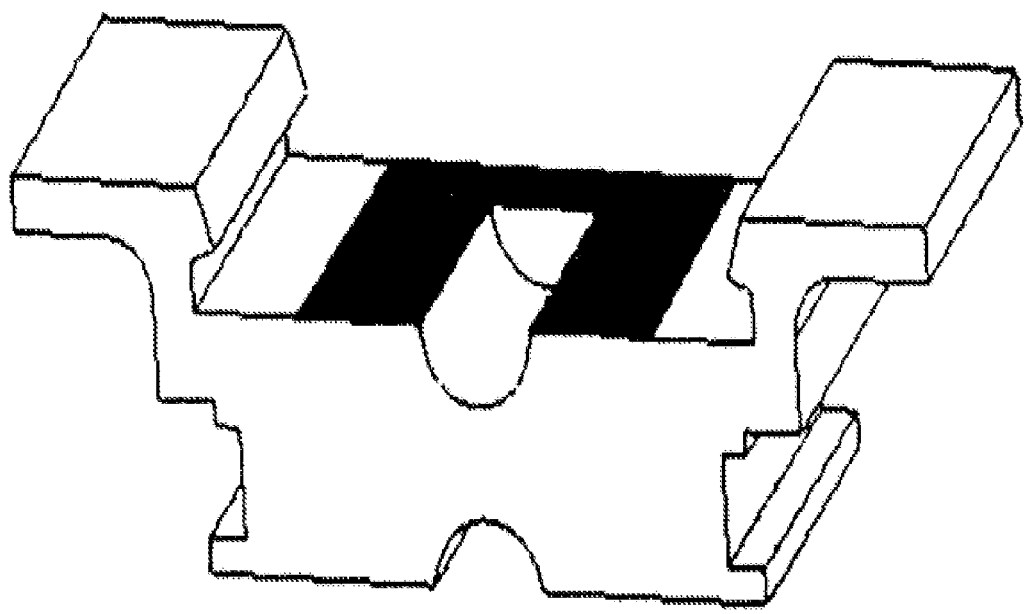
FIG. 21: depicts a CAD sketch demonstrating the area of the well plate of an embodiment that the adhesive silicone should be attached to (black area) prior to completing the manufacturing of the device.
Figure 22:
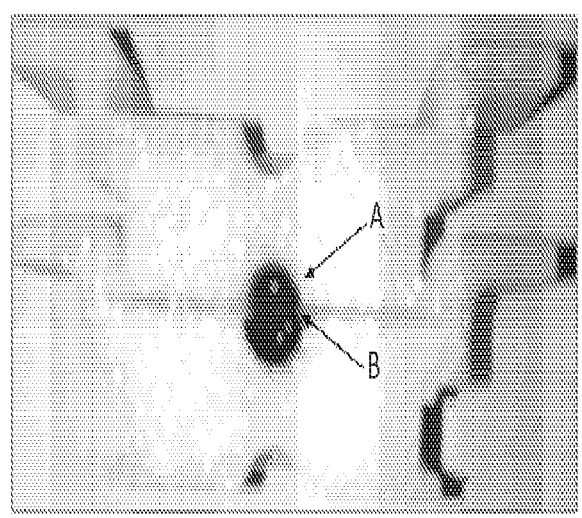
FIG. 22 depicts a photograph of the 3D-printed modular left and right sides pieces snapped together around Nafion® to divide the well into two sections.
Figure 23:
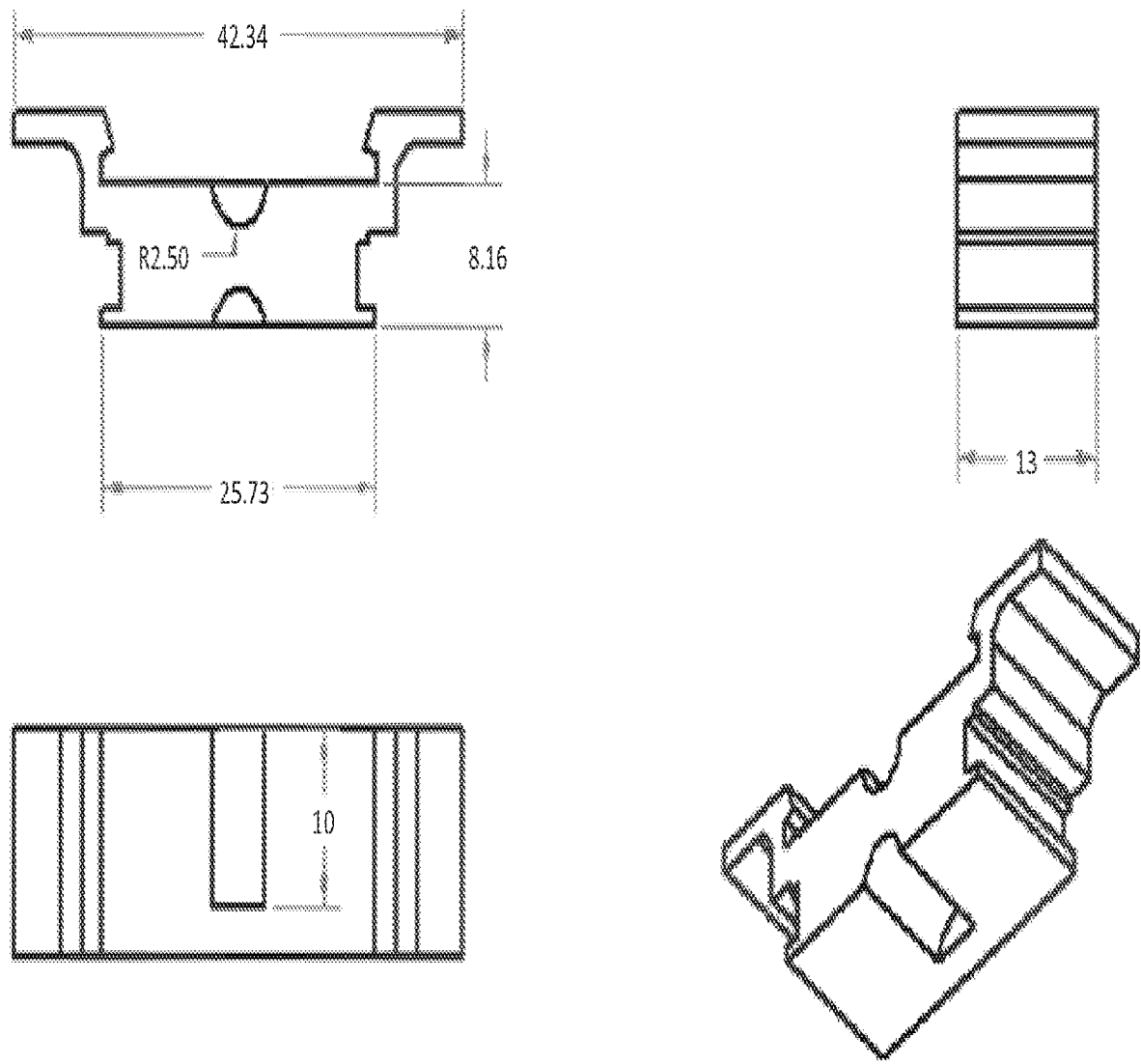
FIG. 23 depicts an engineering drawing of 3D printed well.

Measuring Ammonia in Whole Blood with a Modular Well Plate
Materials
2-phenylphenol, sodium nitroprusside, sodium hydroxide, sodium hypochlorite, sodium acetate, and ammonium chloride were purchased from Sigma-Aldrich. Nafion 111 was purchased from Ion-Power. 1/64" silicone gasket with adhesive backing was purchased from McMaster-Carr, Acrylonitrile Butadiene Styrene Resin.
Methods
   Preparation of Sample
   Prepare stock solutions of 59 mM 2-phenylphenol in ethanol, 7 µM sodium nitroprusside in water, 500 mM sodium hydroxide in water and 0.6-0.75% sodium hypochlorite in water.
   Prepare a stock solution of 1M sodium acetate in water.
   3D printed wells are produced from fused deposition modeling using acrylonitrile butadiene styrene based on the model seen in FIG. 21.
   Attach a layer of the 1/64" silicone to the area of the well shaded in FIG. 21.
   Remove the 25 µm thick Nafion 111 from plastic backing and cut it into 1.5×1.5 cm squares.
Ammonia Exchange
   Snap two of the modular 3D printed pieces around one of the Nafion Squares, creating a Bisected Well. The final configuration is shown in FIG. 22.
   Pipette 45 µl of the sodium acetate solution into section B of the well.
   Pipette 100 µM of the ammonia containing sample (whole blood) into section A of the well.
   Wait 20 minutes for ion exchange to occur.
Collection of Data
   Pipette 35 µl of the sodium acetate/ammonia solution from section B into a 384 well plate.
   Pipette 10 µl each of the 2-phenylphenol, sodium nitroprusside and sodium. hydroxide stock solutions into the same well as the sodium acetate.
   Add 5 microliters of the sodium hypochlorite solution to the well and mix thoroughly by pipette.
   Wait ten minutes for the indophenol reaction to proceed.
   Measure the absorbance of the well at 635 nm using a 384 plate reader.
   Compare the measured absorbance to a standard curve to determine unknown ammonia concentration.
FIG. 20 CAD sketch of the front face of the well plate.
FIG. 21 CAD sketch demonstrating the area of the well plate that the adhesive silicone should be attached to (black area).
FIG. 22 Photograph of the 3D printed modular pieces snapped together around Nafion to divide the well into two sections.
FIG. 23 Engineering Drawing of 3D printed well.

Example 4

Measuring Ammonia in Whole Blood with a Fluidic Device
Materials
2-phenylphenol, sodium nitroprusside, sodium hydroxide, sodium hypochlorite, sodium acetate, and ammonium chloride were purchased from Sigma-Aldrich. Nafion 111 was purchased from Ion-Power.
Methods
Preparation of Sample
   Prepare stock solutions of 59 mM 2-phenylphenol in ethanol, 7 µM sodium nitroprusside in water, 500 mM sodium hydroxide in water and 0.75% sodium hypochlorite in water.
   Prepare a stock solution of 1M sodium acetate in water.
   Molds are produced from a 3D printer for the 2 individual pieces of the device.
   Fill each mold with the PDMS elastomer and heat at 60° C. for one hour.
   Remove each side of the device from the mold with a spatula.
   Remove the 25 µm thick Nafion 111 from plastic backing and cut it into a 1.5×1.5 cm square.
   Glue the square of Nafion over the well in the channel 6 using PDMS.
   Glue the top piece of the device to the bottom piece using PDMS, ensuring channel 6 lines up with channel 5.
   Heat the device to 60° C. for one hour.
Ammonia Exchange
   Insert a needle through the bottom of the device into well 6, and fill with 40 µl of blood.

Fill channels 1-4 with 5 μl of 2-phenylphenol, sodium nitroprusside, sodium hydroxide and sodium hypchlorite respectively.

Fill channel 5 with 20 μl of sodium acetate solution.

Wait 20 minutes for ion exchange to occur.

Collection of Data

Apply a flow rate of 1 mm/sec to channels 1 through 5 for 24 seconds.

Wait ten minutes for the indophenol reaction to proceed.

Insert the device into the custom photo-spectrometer to acquire absorbance data.

Compare the measured absorbance to a standard curve to determine unknown ammonia concentration.

Figure 29:
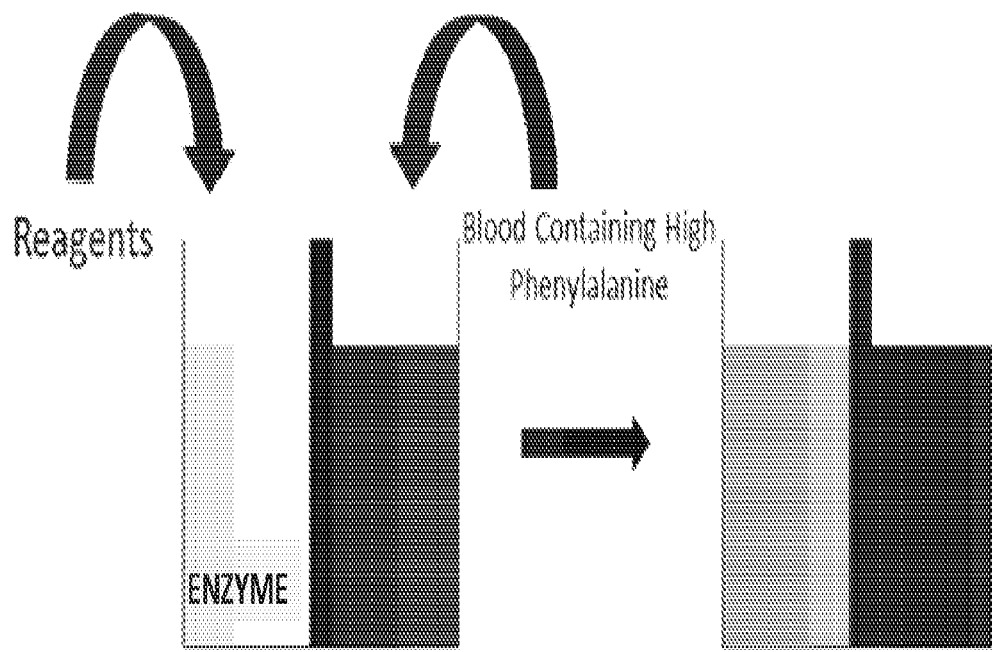
FIG. 29: is an exemplary view of a system having the ability to detect ammonia or ammonium ion levels and amino acids in a given sample applied to a first and second vessel separated by a membrane positioned at an fluid exchange opening, wherein the reaction is catalyzed by an enzyme.

An embodiment depicting a method of detecting amino acids based upon ammonia levels is depicted in FIG. 29. After addition of blood as depicted on the left handside of FIG. 29, ammonia levels are visualized by a color change of ammonia reaction with indophenol reagents in the left well of the device depicted on the righthand side. The left well is more grey (an indication of blue color) than the left well in the device depicted on the lefthand side (before the indophenol reaction takes place).

Example 5

Detection of Amino Acids in Whole Blood Through Use of Ammonia Producing Enzymes with a Modular Well Plate Dehydrogenases and ammonia-lyases generally affect amino acids by cleaving off the primary amine thereby generating ammonia. Using the ammonia detection modular well plate system described herein, the ammonia generated, measured via the color change produced, can then be correlated to the concentration of a given amino acid. This example tests for the presence of phenylaline using phenylalanine ammonia-lyase, although other amino acids can be tested by using the appropriate enzyme(s) listed on Table 5.

phosphate buffered saline (optional), 0.1M CaCl2 solution (optional).

Methods

Preparation of Sample

Prepare stock solutions of 59 mM 2-phenylphenol in ethanol, 7 μM sodium nitroprusside in water, 500 mM sodium hydroxide in water and 0.6-0.75% sodium hypochlorite in water.

Prepare a stock solution of 1M sodium acetate in water.

3D printed wells are produced from fused deposition modeling using acrylonitrile butadiene styrene based on the model seen in FIG. 210.

Attach a layer of the 1/64" silicone to the area of the well shaded in FIG. 21.

Remove the 25 μm thick Nafion 111 from plastic backing and cut it into 1.5×1.5 cm squares.

The enzyme can be added to the amino acid containing sample (whole blood) in two ways. Either by adding in the enzyme directly to the sample, or by immobilizing the enzyme in a gel placed inside the sample well, introducing greater enzyme stability.

Ammonia Exchange with Free Enzyme (Option 1)

Snap two of the modular 3D printed pieces around one of the Nafion Squares, creating a Bisected Well. The final configuration is shown in FIG. 22.

Pipette 45 μl of the sodium acetate solution into section B of the well.

Pipette 100 μM of the amino acid containing sample (whole blood) into section A of the well.

Add 40 units of phenylalanine ammonia-lyase to the sample.

Wait 20 minutes for ion exchange to occur.

Ammonia Exchange with Gel-Immobilized Enzyme (Option 2)

Snap two of the modular 3D printed pieces around one of the Nafion Squares, creating a Bisected Well. The final configuration is shown in FIG. 22.

TABLE 5

| Phenylalnine | Histidine | Tyrosine | Glutamate | Threonine | Serine |
|---|---|---|---|---|---|
| Phenylalanine Ammonia Lyase, Phenylalanine Dehydrogenase | Histidine Ammonia Lyase | Tyrosine Ammonia Lyase | Glutamate Dehydrogenase | Threonine Ammonia Lyase, Threonine Dehydrogenase | Serine Ammonia Lyase, Serine Dehydrogenase |
| Leucine | Isoleucine | Aspartate | Valine | Glycine | Alanine |
| Leucine Dehydrogenase | Isoleucine Dehydrogenase | Aspartate Ammonia Lyase, Aspartate Dehydrogenase | Valine Dehydrogenase | Glycine Dehydrogenase | Alanine Dehydrogenase |
| Tryptophan | | Proline | | Lysine | Arginine |
| Tryptophan Dehydrogenase | | Proline Dehydrogenase | | Lysine Dehydrogenase | Arginine Dehydrogenase |

Materials 2-phenylphenol, sodium nitroprusside, sodium hydroxide, sodium hypochlorite, sodium acetate, and ammonium chloride were purchased from Sigma-Aldrich. Nafion 111 was purchased from Ion-Power. 1/64" silicone gasket with adhesive backing was purchased from McMaster-Carr, Acrylonitrile Butadiene Styrene Resin, phenylalanine ammonia-lyase, sodium alginate from brown algae (optional), -

Prepare a pre-gel solution of 40 units of phenylalanine ammonia-lyase, and 1% weight/volume sodium alginate from brown algae in 1 mL 1× phosphate buffered saline.

Place 10 μL of the pre-gel solution into section A of the well (where the whole blood will go).

Spray the pre-gel solution in the well with 0.1M CaCl2 solution using a Badger 200N airbrush at 7.5 psi for 1 second, depositing ~5 µL of the CaCl2 solution. The gel will be allowed to cure for 30 minutes in a humid environment.

Pipette 45 µl of the sodium acetate solution into section B of the well.

Pipette 100 µM of the amino acid containing sample (whole blood) into section A of the well.

Wait 20 minutes for ion exchange to occur.

Collection of Data

Pipette 35 µl of the sodium acetate/ammonia solution from section B into a 384 well plate.

Pipette 10 µl each of the 2-phenylphenol, sodium nitroprusside and sodium. hydroxide stock solutions into the same well as the sodium acetate.

Add 5 microliters of the sodium hypochlorite solution to the well and mix thoroughly by pipette.

Wait ten minutes for the indophenol reaction to proceed.

Measure the absorbance of the well at 635 nm using a 384 plate reader.

Compare the measured absorbance to a standard curve to determine unknown ammonia concentration.

Example 6

Detection of Amino Acids in Whole Blood Through Use of Ammonia Producing Enzymes with a Fluidic Device Dehydrogenases and ammonia-lyases generally affect amino acids by cleaving off the primary amine thereby generating ammonia. Using the ammonia detection modular well plate system described herein, the ammonia generated, measured via the color change produced, can then be correlated to the concentration of a given amino acid. This example tests for the presence of phenylaline using phenylalanine ammonia-lyase, although other amino acids can be tested by using the appropriate enzyme(s) listed on Table 5.

Materials 2-phenylphenol, sodium nitroprusside, sodium hydroxide, sodium hypochlorite, sodium acetate, and ammonium chloride were purchased from Sigma-Aldrich. Nafion 111 was purchased from Ion-Power, phenylalanine ammonia-lyase, sodium alginate from brown algae (optional), phosphate buffered saline (optional), 0.1M CaCl2 solution (optional).

Methods

Preparation of Sample

Prepare stock solutions of 59 mM 2-phenylphenol in ethanol, 7 µM sodium nitroprusside in water, 500 mM sodium hydroxide in water and 0.75% sodium hypochlorite in water.

Prepare a stock solution of 1M sodium acetate in water.

Molds are produced from a 3D printer for the 2 individual pieces of the device.

Fill each mold with the PDMS elastomer and heat at 60° C. for one hour.

Remove each side of the device from the mold with a spatula.

Remove the 25 µm thick Nafion 111 from plastic backing and cut it into a 1.5×1.5 cm square.

Glue the square of Nafion over the well in the channel 6 using PDMS.

Glue the top piece of the device to the bottom piece using PDMS, ensuring channel 6 lines up with channel 5.

Heat the device to 60° C. for one hour.

The enzyme can be added to the amino acid containing sample (whole blood) in two ways. Either by adding in the enzyme directly to the sample, or by immobilizing the enzyme in a gel placed inside the sample well, introducing greater enzyme stability.

Ammonia Exchange with Free Enzyme (Option 1)

Insert a needle through the bottom of the device into well 6, and fill with 40 µl of blood.

Add 40 units of phenylaline ammonia-lyase to the blood sample.

Fill channels 1-4 with 5 µl of 2-phenylphenol, sodium nitroprusside, sodium hydroxide and sodium hypchlorite respectively.

Fill channel 5 with 20 µl of sodium acetate solution.

Wait 20 minutes for ion exchange to occur.

Ammonia Exchange with Gel-Immobilized Enzyme (Option 2)

Prepare a pre-gel solution of 40 units of phenylalanine ammonia-lyase, and 1% weight/volume sodium alginate from brown algae in 1 mL 1× phosphate buffered saline.

Place 10 µL of the pre-gel solution into section A of the well (where the whole blood will go).

Spray the pre-gel solution in the well with 0.1M CaCl2 solution using a Badger 200N airbrush at 7.5 psi for 1 second, depositing ~5 µL of the CaCl2 solution. The gel will be allowed to cure for 30 minutes in a humid environment.

Insert a needle through the bottom of the device into well 6, and fill with 40 µl of blood.

Add 40 units of phenylaline ammonia-lyase to the blood sample.

Fill channels 1-4 with 5 µl of 2-phenylphenol, sodium nitroprusside, sodium hydroxide and sodium hypchlorite respectively.

Fill channel 5 with 20 µl of sodium acetate solution.

Wait 20 minutes for ion exchange to occur.

Collection of Data

Apply a flow rate of 1 mm/sec to channels 1 through 5 for 24 seconds.

Wait ten minutes for the indophenol reaction to proceed.

Insert the device into the custom photo-spectrometer to acquire absorbance data.

Compare the measured absorbance to a standard curve to determine unknown ammonia concentration.

EQUIVALENTS

Those skilled in the art will recognize, or be able to ascertain using no more than routine experimentation, many equivalents to the specific embodiments of the disclosure described herein.

The scope of the present disclosure is not intended to be limited to the above description, but rather is as set forth in the following claims:

1. A method of quantifying a concentration of ammonia or ammonium ion in a sample comprising contacting a sample of bodily fluid to a biosensor, wherein the biosensor comprises:

(i) at least a first and second vessel;

(ii) a fluid exchange opening positioned between the first and the second vessel;

(iii) at least one conduit in fluid communication with the at least first vessel, the at least one conduit configured to receive a fluid from a point external to the biosensor; and (iv) a membrane positioned at the fluid exchange opening;

wherein the membrane comprises an ionomer;

wherein the at least one conduit is configured to hold a sample volume from about 5 µl to about 100 µl; and wherein the first vessel or the second vessel comprises, individually or in combination: a hypohalite, an alkali buffer, and at least one phenolic reagent or indophenol related compound;

wherein the sample is in contact with the biosensor for a sufficient period of time to allow modification of the phenolic reagent or indophenol related compound to become modified into a phenolic or indophenol reaction product.

2. The method of claim 1, wherein the method does not comprise exposing the sample of bodily fluid to any external stimuli or reagent prior to contacting the sample to the biosensor.

3. The method of claim 1, wherein the sample of bodily fluid is whole blood from a subject.

4. The method of claim 1, further comprising comparing a concentration value obtained by the contacting step to a threshold value associated with one or more metabolic diseases.

5. The method of claim 4, wherein the metabolic disease is hyperammonemia.

* * * * *